US012637521B2

(12) United States Patent
Huh et al.

(10) Patent No.: US 12,637,521 B2
(45) Date of Patent: May 26, 2026

(54) LOW-VISCOSITY ANTIGEN BINDING PROTEINS AND METHODS OF MAKING THEM

(71) Applicant: AMGEN INC., Thousand Oaks, CA (US)

(72) Inventors: Joon Hoi Huh, Culver City, CA (US); Riki Stevenson, Ventura, CA (US); Pavel Bondarenko, Thousand Oaks, CA (US); Andrew Nichols, Calabasas, CA (US); Da Ren, Thousand Oaks, CA (US); Neeraj Jagdish Agrawal, Natick, MA (US); Richard Smith, Belmont, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/644,757

(22) Filed: Apr. 24, 2024

(65) Prior Publication Data

US 2024/0343832 A1      Oct. 17, 2024

Related U.S. Application Data

(62) Division of application No. 17/346,156, filed on Jun. 11, 2021, now Pat. No. 11,993,663, which is a division of application No. 16/338,292, filed as application No. PCT/US2017/053967 on Sep. 28, 2017, now Pat. No. 11,059,908.

(60) Provisional application No. 62/546,469, filed on Aug. 16, 2017, provisional application No. 62/430,773, filed on Dec. 6, 2016, provisional application No. 62/401,770, filed on Sep. 29, 2016.

(51) Int. Cl.
*C07K 16/40* (2006.01)
*C07K 16/28* (2006.01)
*G01N 11/14* (2006.01)

(52) U.S. Cl.
CPC .......... *C07K 16/40* (2013.01); *C07K 16/2869* (2013.01); *C07K 2317/21* (2013.01); *C07K 2317/24* (2013.01); *C07K 2317/52* (2013.01); *C07K 2317/55* (2013.01); *C07K 2317/90* (2013.01); *C07K 2317/92* (2013.01); *C07K 2317/94* (2013.01); *G01N 11/14* (2013.01)

(58) Field of Classification Search
CPC ................ C07K 16/40; C07K 16/2869; C07K 2317/21; C07K 2317/24; C07K 2317/52; C07K 2317/90; C07K 2317/94
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 8,545,849 B2 | 10/2013 | Borras et al. | |
| 9,695,233 B2 | 7/2017 | Duerr et al. | |
| 10,294,303 B2 | 5/2019 | Yie et al. | |
| 10,570,198 B2 | 2/2020 | Borras et al. | |
| 2013/0064825 A1 | 3/2013 | Chan et al. | |
| 2013/0189277 A1* | 7/2013 | Walsh ............. | A61K 39/39591 424/158.1 |
| 2014/0017244 A1 | 1/2014 | Duerr et al. | |
| 2017/0275370 A1 | 9/2017 | Yie et al. | |
| 2019/0276546 A1 | 9/2019 | Yie et al. | |
| 2020/0095310 A1 | 3/2020 | Regula et al. | |
| 2021/0047434 A1 | 2/2021 | Chan et al. | |

FOREIGN PATENT DOCUMENTS

| | | |
|---|---|---|
| EP | 0173494 A2 | 3/1986 |
| EP | 0171496 B1 | 5/1993 |
| EP | 3026061 A1 | 6/2016 |
| GB | 2177096 B | 5/1989 |
| JP | 2015527064 A | 1/2000 |
| WO | 2014009465 A1 | 1/2000 |
| WO | 2011017330 | 2/2011 |
| WO | 2012125495 A2 | 9/2012 |
| WO | 2012154999 A1 | 11/2012 |
| WO | 2017112824 A2 | 6/2017 |

OTHER PUBLICATIONS

Yadav. Establishing a Link Between Amino Acid Sequences and Self-Associating and Viscoelastic Behavior of Two Closely Related Monoclonal Antibodies, Pharm Res., 28(7):1750-1764. (Year: 2011).*
Armstrong, G.B., et al., "A framework for the biophysical screening of antibody mutations targeting solvent-accessible hydrophobic and electrostatic patches for enhanced viscosity profiles", Computational and Structural Biotechnology Journal, vol. 23, pp. 2345-2357, XP093261050, Dec. 1, 2024.
EPO Communication issued to EP Application No. 17794111.9, dated Mar. 27, 2025.
Written Opinion issued to Singapore Application No. 10201912565Q, Intellectual Property Office of Singapore, dated Mar. 10, 2025.
BR Application 112019006486-9 Office Action, 6 pages, (Oct. 5, 2022).
Chaudhri, et al., Antibodies: Insights from Coarse-Grained Modeling, The Journal of Physical Chemistry B, vol. 117, No. 5, 7 (Feb. 2013).
CN Application No. 201780073880.7, Office Action (Jul. 22, 2022).
Dudgeon, et al. General strategy for the generation of human antibody variable domains with increased aggregation resistance; Proceedings of the National Academy of Sciences of the United States of America, Early Edition (Jul. 24, 2012).

(Continued)

*Primary Examiner* — Daniel E Kolker
*Assistant Examiner* — Maureen Varina Driscoll
(74) *Attorney, Agent, or Firm* — Melissa E. Karabinis

(57) ABSTRACT

The present invention concerns a method for preparing antigen binding proteins specific for PCSK9 with reduced viscosity. The method proceeds by replacing residues in high viscosity variable domain subfamilies with residues in correlating low viscosity subfamilies. The method further comprises substituting residues in the Fc domain with residues associated with low viscosity and adding charged residues to the C-terminus of the Fc domain. The present invention further concerns antigen binding proteins produced by this method.

12 Claims, 28 Drawing Sheets

Specification includes a Sequence Listing.

(56) References Cited

OTHER PUBLICATIONS

IN Application 201917016348, Office Action, Mar. 27, 2023.

JP Application 2019-516945 Office Action (Nov. 4, 2022) 5 pages.

Office Action BR 202103596 (Aug. 4, 2023).

Office Action JP 2022-043944 (Jul. 24, 2023).

Yamauchi, Shape and size of proteins in hydrodynamics, Kagaku To Seibutsu, 1982, vol. 20, No., 5, pp. 296-304.

Ye, J. et al., "Characterization of a Silencer Regulatory Element in the Human Interferon-γ Promoter," J Biol Chem., 269(41):25728-25734 (1994).

Carraway, K. L. and Koshland, Jr., D. E., "Carbodiimide modification of proteins," Methods Enzymol., 25:616-623 (1972).

Chaudhri et al., "The Role of Amino Acid Sequence in the Self-Association of Therapeutic Monoclonal Antibodies: Insights from Coarse-Grained Modeling," J. Phys. Chem. B, vol. 117 (5), pp. 1269-1279 (2013).

Cheng et al., Linking the Solution Viscosity of an IgG2 Monoclonal Antibody to its Structure as a Function of pH and Temperature, J. Pharm Sci. (2013), 102:4291-4304.

Chothia et al., "Canonical structures for the hypervariable regions of immunoglobulins," J. Mol. Biol., vol. 196 (4), pp. 901-917 (1987).

Chothia, C. et al., "Structural repertoire of the human VH segments," J. Mol. Biol., 227(3):799 817 (1992).

Connolly et al., Weak Interactions Govern the Viscosity of Concentrated Antibody Solutions: High-Throughput Analysis Using the Diffusion Interaction Parameter, Biophys. J. (2012), 103:69-78.

Diebolder, C. A. et al., "Complement is Activated by IgG Hexamers Assembled at the Cell Surface," Science, 343(6176):1260-1263 (2014).

Edelman, G. M. et al., "The covalent structure of an entire gamma immunoglobulin molecule," Proc. Natl. Acad. Sci. U.S.A., 63(1):78-85 (1969).

Ewert, S. et al., "Biophysical properties of human antibody variable domains," J. Mol. Biol., 325:531-553 (2003).

Ewert, S. et al., "Stability improvement of antibodies for extracellular and intracellular applications: CDR grafting to stable frameworks and structure-based framework engineering," Methods, 34(2):184-199 (2004).

Ewert, S. et al., "Structure-based improvement of the biophysical properties of immunoglobulin VH domains with a generalizable approach," Biochemistry, 42:1517-1528 (2003).

Ford, C. F. et al., "Fusion tails for the recovery and purification of recombinant proteins," Protein Expression and Purification, 2(2-3):95-107 (1991).

Grussenmeyer et al., "Complexes of polyoma virus medium T antigen and cellular proteins", Proc. Natl. Acad. Sci. USA, vol. 82 (23), pp. 7952-7954 (1985).

Guo et al., Structure-Activity Relationship for Hydrophobic Salts as Viscosity-Lowering Excipients for Concentrated Solutions of Monoclonal Antibodies, Pharm Res (2012), 29(11):3102-3109.

Honegger et al., "Yet Another Numbering Scheme for Immunoglobulin Variable Domains: An Automatic Modeling and Analysis Tool", J. Mol. Biol., vol. 309 (3), pp. 657-670 (2001).

Hopp et al., "A Short Polypeptide Marker Sequence Useful For Recombinant Protein Identification And Purification", Biotechnology, vol. 6, pp. 1204-1210 (1988).

Horton et al., "Molecular Biology of PCSK9: Its Role in LDL Metabolism", Trends in Biochemical Sciences, vol. 32 (2), pp. 71-77 (2006).

Jefferis, R. and Lefranc, M-P., Human immunoglobulin allotypes: possible implications for immunogenicity, mAbs, 1:332-338 (2009).

JP Patent Application No. 2019-516945 Office Action (Jun. 7, 2022).

JP-2019-516945 Office Action issued Sep. 14, 2021.

Kabat et al., "Sequences of proteins of immunological interest", 5th Ed., U.S. Dept. of Health and Human Services, Table of Contents (1991).

Kanai et al., "Reversible self-association of a concentrated monoclonal antibody solution mediated by Fab-Fab interaction that impacts solution viscosity", Journal of Pharmaceutical Sciences, vol. 97 (10), pp. 4219-4227 (2008).

Ketchem et al., Mitigation of monoclonal antibody viscosity by modification of protein surface charge, Ninth Annual PEGS Summit, Apr. 29-May 3, 2013, Boston, MA (2013).

Ketchem, R. R. et al., "Mitigation of monoclonal antibody viscosity by modification of protein surface charge," Abstracts of Papers; ACS National Meeting & Exposition, American Chemical Society, US, 243rd , p. 1, (2012) URL:http://abstracts.acs.org/chem/243nm/program/view.phpobj_id=122153&terms=abstract.

Lemaigre et al., "Transcriptional control of genes that regulate glycolysis and gluconeogenesis in adult liver", Biochem J., vol. 303, pp. 1-14 (1994).

Li et al., Concentration Dependent Viscosity of Monoclonal Antibody Solutions: Explaining Experimental Behavior in Terms of Molecular Properties, Pharm. Res. 31 (2014), 3161-3178.

Loeken, "Effects of mutation of the CREB binding site of the somatostatin promoter on cyclic AMP responsiveness in CV-1 cells", Gene Expr., vol. 3 (3), pp. 253-264 (1993).

Mcgehee Jr. et al., "Differentiation-specific element: a cis-acting developmental switch required for the sustained transcriptional expression of the angiotensinogen gene during hormonal-induced differentiation of 3T3-L1 fibroblasts to adipocytes", Mol End.

Morrison et al., "Chimeric human antibody molecules: mouse antigen-binding domains with human constant region domains", Proc. Natl. Acad. Sci. USA, vol. 81 (21), pp. 6851-6855 (1984).

Neergaard et al., Viscosity of High Concentration Protein Formulations of Monoclonal Antibodies of The IgG1 And IgG4 Subclass—Prediction Of Viscosity Through Protein-Protein Interaction Measurements, Eur. J. Pharm Sci. (2013), 49(3):400-410.

Nilsson et al., "Expression and Purification of Recombinant Insulin-like Growth Factors from *Escherichia coli*", Methods in Enzymology, vol. 198, pp. 3-16 (1991).

Nilsson et al., "Immobilization and Purification of Enzymes with Staphylococcal Protein A Gene Fusion Vectors", The EMBO Journal, vol. 4 (4), pp. 1075-1080 (1985).

O'Reilly, M. A. et al., "Identification of an activating transcription factor (ATF) binding site in the human transforming growth factor-beta 2 promoter," J. Biol. Chem., 267(28):19938-19943 (1992).

Paul, William E. (Ed.), Fundamental Immunology, 2nd Ed., Raven Press, New York, Ch. 7, pp. TOC, 139-165 (1989).

Piper et al., "The crystal structure of PCSK9: a regulator of plasma LDL-cholesterol", Structure, vol. 15 (5), pp. 545-552 (2007).

Ropartz, C., Schanfield, M. S., Steinberg, A. G., "Review of the notation for the allotypic and related markers of human immunoglobulins," WHO meeting on human immunoglobulin allotypic markers, Held Jul. 16-19, 1974, Rouen, France, Report Amended Jun. 1976, J. Immunogenet, 3:357-362 (1976).

Rothlisberger, D. et al., "Domain interactions in the Fab fragment: a comparative evaluation of the single-chain Fv and Fab format engineered with variable domains of different stability," J. Mol. Biol., 347:773-789 (2005).

Seidah et al., The proprotein convertases are potential2011 targets in the treatment of dyslipidemia, J Mol Med (Berl) (2007), 85(7), 685-696.

Shukla et al., "Downstream processing of monoclonal antibodies—application of platform approaches," J Chromatogr B Analyt Technol Biomed Life Sci., vol. 848 (1), pp. 28-39 (2007).

Singh et al., Dipole-Dipole Interaction in Antibody Solutions: Correlation with Viscosity Behavior at High Concentration, Pharm Res (2014), 31(9):2549-2558.

Smith et al., "Single-step purification of polypeptides expressed in *Escherichia coli* as fusions with glutathione S- transferase", Gene, vol. 67 (1), pp. 31-40 (1988).

Takeda et al., "Construction of chimaeric processed immunoglobulin genes containing mouse variable and human constant region sequences", Nature, vol. 314, pp. 452-454 (1985).

Tomlinson et al., "The structural repertoire of the human Vk domain", EMBO J., vol. 14 (18), pp. 4628-4638 (1995).

Treisman, R. "The SRE: a growth factor response transcriptional regulator, Seminars in Cancer Biol.," 1(1):47-58 (1990).

Tseng, C. C. et al., "Postprandial stimulation of insulin release by glucose-dependent insulinotropic polypeptide (GIP). Effect of a

(56) References Cited

OTHER PUBLICATIONS specific glucose-dependent insulinotropic polypeptide receptor antagonist in the rat," J. Clin. Invest., 98 (11):2440-2445 (1996).

Van Den Bremer, E. T. J. et al., "Human IgG is produced in a pro-form that requires clipping of C-terminal lysines for maximal complement activation," mAbs, 7(4):672-680 (2015).

Vidarsson, G. et al., "IgG subclasses and allotypes: from structure to effector functions," Front. Immunol., 5:1-17 (2014).

Yadav et al., "Establishing a Link Between Amino Acid Sequences and Self-Associating and Viscoelastic Behavior of Two Closely Related Monoclonal Antibodies", Pharm Res., vol. 28 (7), pp. 1750-1764 (2011).

Yadav et al., "The Influence of Charge Distribution on Self-Association and Viscosity Behavior of Monoclonal Antibody Solutions", Mol. Pharmaceutics, vol. 9, pp. 791-802 (2012).

Yadav et al., Viscosity Behavior of High-Concentration Monoclonal Antibody Solutions: Correlation with Interaction Parameter and Electroviscous Effects, J. Pharm Sci. (2012), 101(3):998-1011.

Chilean Application No. 201900835, Office Action (Aug. 23, 2021).

Chilean Application No. 201900835, Office Action (Feb. 15, 2021).

Eurasian Application No. 201990837, Office Action (Mar. 26, 2021).

European Application No. 17794111.9, Office Action (Aug. 27, 2021).

Geoghegan, J.C. et al., Mitigation of reversible self-association and viscosity in a human IgG1 monoclonal antibody by rational, structure-guided Fv engineering. MAbs, Apr. 6, 2016, vol. 8, No. 5, pp. 941-950.

Japanese Application No. 2019-516945, Office Action (Sep. 21, 2021).

JP Application 2019516945 Office Action (Jun. 7, 2022).

Nichols, P. et al., Rational design of viscosity reducing mutants of a monoclonal antibody: Hydrophobic versus electrostatic inter-molecular interactions. MAbs, Jan. 14, 2015, vol. 7, No. 1, pp. 212-230.

Singaporean Application No. 11201902880Q, Written Opinion (Jul 7, 2020).

* cited by examiner

FIG. 1A

| Target (informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| anti-amyloid | A | 142.2 | 5.0 | IgG1 (f) (R;EM) | Kappa | VK2\|A23 | VH2\|2-26 | 9.0 | 168 | 166 |
| GMCSF (247) | B | 139.7 | 5.6 | IgG2 | Kappa | VK3\|A27 | VH1\|1-02 | 8.7 | 4 | 2 |
| CGRPR | C | 136.6 | 6.5 | IgG2 | Lambda | VL1\|1g | VH3\|3-15 | 8.6 | 180 | 178 |
| RANKL | D | 152.7 | 6.6 | IgG2 | Kappa | VK3\|A27 | VH3\|3-23 | 8.6 | 172 | 170 |
| Sclerostin (27H6) | E | 145.0 | 6.7 | IgG2 | Kappa | VK2\|O1 | VH3\|3-48 | 6.6 | 8 | 6 |
| IL-1R1 | F | 153.9 | 6.7 | IgG2 | Kappa | VK6\|A10 | VH5\|5-51 | 7.4 | 12 | 10 |
| Myostatin | G | 141.0 | 6.8 | IgG1 (z) (K;EM) | Kappa | VK1\|O18 | VH3\|3-07 | 8.7 | 16 | 14 |
| B7RP1 | H | 137.5 | 7.7 | IgG2 | Kappa | VK1\|L15 | VH3\|3-07 | 7.7 | 20 | 18 |
| Amyloid | I | 140.6 | 8.2 | IgG1 (za) (K;OL) | Kappa | VK2\|A17 | VH2\|2-70 | 8.7 | 24 | 22 |
| GMCSF (3.112) | J | 156.0 | 8.2 | IgG2 | Kappa | VK3\|A27 | VH1\|1-02 | 8.8 | 28 | 26 |
| CGRP (32H7) | K | 159.5 | 8.3 | IgG2 | Kappa | VK3\|A27 | VH3\|3-33 | 8.7 | 32 | 30 |
| CGRP (386.2) | L | 161.1 | 8.4 | IgG2 | Lambda | VL3\|3l | VH1\|1-02 | 8.6 | 36 | 34 |
| PCSK9 (8A3.1) | M | 150.0 | 9.1 | IgG2 | Kappa | VK2\|A19 | VH3\|3-07 | 6.7 | 40 | 38 |
| PCSK9 (492) | N | 150.0 | 9.2 | IgG2 | Kappa | VK2\|A19 | VH3\|3-07 | 6.9 | 44 | 42 |
| CGRP | O | 155.2 | 9.6 | IgG2 | Lambda | VL1\|1b | VH3\|3-33 | 8.8 | 48 | 46 |
| Hepcidin | P | 147.1 | 9.9 | IgG2 | Lambda | VL3\|3r | VH3\|3-33 | 7.3 | 52 | 50 |
| TNFR p55 ) | Q | 157.0 | 10.0 | IgG2 | Kappa | VK3\|A27 | VH3\|3-23 | 8.2 | 56 | 54 |
| OX40L | R | 144.5 | 10.0 | IgG2 | Kappa | VK2\|A23 | VH3\|3-33 | 8.7 | 60 | 58 |
| HGF | S | 155.8 | 10.6 | IgG2 | Kappa | VK3\|L16 | VH4\|4-59 | 8.1 | 64 | 62 |
| GMCSF | T | 162.5 | 11.0 | IgG2 | Kappa | VK4\|B3 | VH1\|1-02 | 8.1 | 68 | 66 |
| Glucagon R | V | 140.0 | 12.1 | IgG2 | Kappa | VK1\|A30 | VH3\|3-33 | 8.4 | 72 | 70 |
| GMCSF (4.381) | U | 144.5 | 12.1 | IgG2 | Kappa | VK3\|A27 | VH1\|1-02 | 8.4 | 76 | 74 |

FIG. 1B

| Target (informal name) | mAb | Conc. mg/ml | Visc. cP | HC Type (including allotypes) | LC Type | VL Germline | VH Germline | pI | HC SEQ ID NO | LC SEQ ID NO |
|---|---|---|---|---|---|---|---|---|---|---|
| Sclerostin (13F3) | W | 155.0 | 12.1 | IgG2 | Kappa | VK1\|L19 | VH1\|1-46 | 7.8 | 80 | 78 |
| CD-22 | X | 149.7 | 12.2 | IgG1 (f) (R;EM) | Kappa | VK1\|O18 | VH1\|1-69 | 8.8 | 84 | 82 |
| INFgR | Y | 154.2 | 12.2 | IgG1 (za) (K;DL) | Kappa | VK3\|A27 | VH5\|5-51 | 8.8 | 88 | 86 |
| Ang2 | Z | 151.5 | 12.4 | IgG2 | Kappa | VK2\|A19 | VH3\|3-48 | 7.4 | 92 | 90 |
| TRAILR2 | AA | 158.3 | 12.5 | IgG1 (f) (R;EM) | Kappa | VK3\|A27 | VH4\|4-30 | 8.7 | 96 | 94 |
| EGFR | AB | 141.7 | 14.0 | IgG2 | Kappa | VK1\|O18 | VH4\|4-61 | 6.8 | 100 | 98 |
| IL-4R | AC | 145.3 | 15.2 | IgG2 | Kappa | VK3\|A27 | VH3\|3-48 | 8.6 | 104 | 102 |
| IL-15 | AD | 149.0 | 16.3 | IgG1 (f) (R;EM) | Kappa | VK3\|A27 | VH5\|5-51 | 8.8 | 108 | 106 |
| IGF1R | AE | 159.2 | 17.3 | IgG1 (za) (K;DL) | Kappa | VK2\|A19 | VH4\|4-04 | 8.6 | 112 | 110 |
| IL-17R | AF | 150.9 | 19.1 | IgG2 | Kappa | VK3\|L16 | VH1\|1-18 | 8.6 | 116 | 114 |
| Dkk1 (6.37.5) | AG | 159.4 | 19.6 | IgG2 | Kappa | VK2\|A2 | VH3\|3-33 | 8.2 | 120 | 118 |
| Sclerostin | AH | 134.8 | 20.9 | IgG2 | Kappa | VK1\|O2 | VH1\|1-e | 7.4 | 124 | 122 |
| TSLP | AI | 134.2 | 21.4 | IgG2 | Lambda | VL3\|3h | VH3\|3-33 | 7.2 | 128 | 126 |
| Dkk1 (11H10) | AJ | 145.3 | 22.5 | IgG2 | Kappa | VK3\|L6 | VH3\|3-48 | 8.2 | 132 | 130 |
| PCSK9 | AK | 145.2 | 22.8 | IgG2 | Lambda | VL2\|2a2 | VH1\|1-18 | 8.1 | 136 | 134 |
| GIPR (2G10.006) | AQ | 150.0 | 19.1 | IgG1 (a) (K;EM) | Kappa | VK3\|L16 | VH3\|3-33 | 8.1 | 160 | 158 |
| Activin | AL | 133.3 | 29.4 | IgG2 | Lambda | VL3\|3r | VH1\|1-18 | 7.0 | 140 | 138 |
| Sclerostin (288) | AM | 150.0 | 30.0 | IgG2 | Lambda | VL6\|6a | VH3\|3-33 | 6.7 | 144 | 142 |
| Sclerostin | AN | 141.4 | 30.4 | IgG2 | Kappa | VK1\|O2 | VH1\|1-18 | 6.8 | 148 | 146 |
| c-fms | AO | 146.9 | 32.3 | IgG2 | Kappa | VK4\|B3 | VH1\|1-18 | 6.6 | 152 | 150 |
| α4β7 | AP | 154.9 | 32.7 | IgG2 | Kappa | VK1\|L19 | VH1\|1-24 | 6.5 | 156 | 154 |

FIG. 1C

| Target | mAb | SEQ ID NOS | | | | | | | |
| (Informal name) | | HC FR1 | HC FR2 | HC FR3 | HC FR4 | LC FR1 | LC FR2 | LC FR3 | LC FR4 |
|---|---|---|---|---|---|---|---|---|---|
| anti-amyloid | A | 280 | 281 | 282 | 283 | 189 | 190 | 191 | 192 |
| GMCSF (247) | B | 300 | 285 | 301 | 276 | 197 | 194 | 198 | 196 |
| CGRPR | C | 316 | 317 | 318 | 287 | 257 | 258 | 259 | 250 |
| RANKL | D | 291 | 292 | 293 | 276 | 193 | 194 | 195 | 196 |
| Sclerostin (27H6) | E | 304 | 292 | 349 | 276 | 246 | 225 | 226 | 188 |
| IL-1R1 | F | 277 | 278 | 279 | 276 | 185 | 186 | 187 | 188 |
| Myostatin | G | 304 | 289 | 346 | 287 | 205 | 206 | 219 | 231 |
| B7RP1 | H | 304 | 289 | 305 | 276 | 205 | 229 | 207 | 196 |
| Amyloid | I | 333 | 281 | 334 | 276 | 235 | 236 | 226 | 237 |
| GMCSF (3.112) | J | 344 | 285 | 345 | 283 | 193 | 194 | 201 | 196 |
| CGRP (32H7) | K | 302 | 289 | 338 | 287 | 193 | 194 | 198 | 231 |
| CGRP (3B6.2) | L | 299 | 285 | 339 | 287 | 266 | 267 | 268 | 269 |
| PCSK9 (8A3.1) | M | 304 | 289 | 315 | 287 | 227 | 225 | 226 | 188 |
| PCSK9 (492) | N | 304 | 289 | 314 | 287 | 227 | 225 | 228 | 188 |
| CGRP | O | 302 | 289 | 306 | 287 | 254 | 255 | 256 | 250 |
| Hepcidin | P | 302 | 289 | 303 | 283 | 263 | 264 | 265 | 250 |
| TNFR p55 ) | Q | 291 | 292 | 293 | 276 | 193 | 199 | 198 | 196 |
| OX40L | R | 302 | 289 | 303 | 276 | 189 | 190 | 213 | 214 |
| HGF | S | 273 | 274 | 275 | 276 | 181 | 182 | 183 | 184 |
| GMCSF | T | 299 | 285 | 301 | 276 | 215 | 211 | 216 | 217 |
| Glucagon R | V | 302 | 289 | 310 | 287 | 205 | 222 | 223 | 188 |
| GMCSF (4.381) | U | 299 | 285 | 301 | 276 | 193 | 202 | 203 | 204 |

FIG. 1D

| Target (Informal name) | mAb | SEQ ID NOS | | | | | | | |
|---|---|---|---|---|---|---|---|---|---|
| | | HC FR1 | HC FR2 | HC FR3 | HC FR4 | LC FR1 | LC FR2 | LC FR3 | LC FR4 |
| Sclerostin (13F3) | W | 347 | 285 | 348 | 276 | 208 | 245 | 207 | 214 |
| CD-22 | X | 307 | 308 | 309 | 287 | 218 | 206 | 219 | 220 |
| INFγR | Y | 329 | 330 | 331 | 332 | 193 | 194 | 198 | 214 |
| Ang2 | Z | 326 | 292 | 305 | 276 | 227 | 225 | 226 | 231 |
| TRAILR2 | AA | 319 | 320 | 321 | 287 | 193 | 200 | 198 | 196 |
| EGFR | AB | 335 | 336 | 337 | 283 | 205 | 206 | 221 | 188 |
| IL-4R | AC | 304 | 292 | 305 | 276 | 193 | 194 | 198 | 196 |
| IL-15 | AD | 322 | 323 | 324 | 276 | 193 | 194 | 198 | 230 |
| IGF1R | AE | 311 | 312 | 313 | 283 | 224 | 225 | 226 | 196 |
| IL-17R | AF | 299 | 285 | 328 | 276 | 181 | 232 | 233 | 188 |
| Dkk1 (6.37.5) | AG | 302 | 289 | 341 | 276 | 240 | 241 | 242 | 243 |
| Sclerostin | AH | 294 | 285 | 295 | 276 | 205 | 206 | 207 | 196 |
| TSLP | AI | 288 | 289 | 290 | 283 | 251 | 252 | 253 | 250 |
| Dkk1 (11H10) | AJ | 340 | 292 | 305 | 287 | 238 | 194 | 239 | 231 |
| PCSK9 | AK | 284 | 285 | 286 | 287 | 247 | 248 | 249 | 250 |
| GIPR (2G10.006) | AQ | 302 | 342 | 303 | 276 | 181 | 194 | 234 | 188 |
| Activin | AL | 299 | 285 | 325 | 283 | 260 | 261 | 262 | 250 |
| Sclerostin (2B8) | AM | 302 | 289 | 303 | 287 | 270 | 271 | 272 | 250 |
| Sclerostin | AN | 327 | 285 | 328 | 287 | 205 | 206 | 207 | 188 |
| c-fms | AO | 299 | 285 | 328 | 276 | 210 | 211 | 212 | 214 |
| α4β7 | AP | 296 | 297 | 298 | 276 | 208 | 206 | 209 | 196 |
| c-kit | BA | 299 | 285 | 295 | 276 | 210 | 211 | 212 | 188 |

FIG. 2

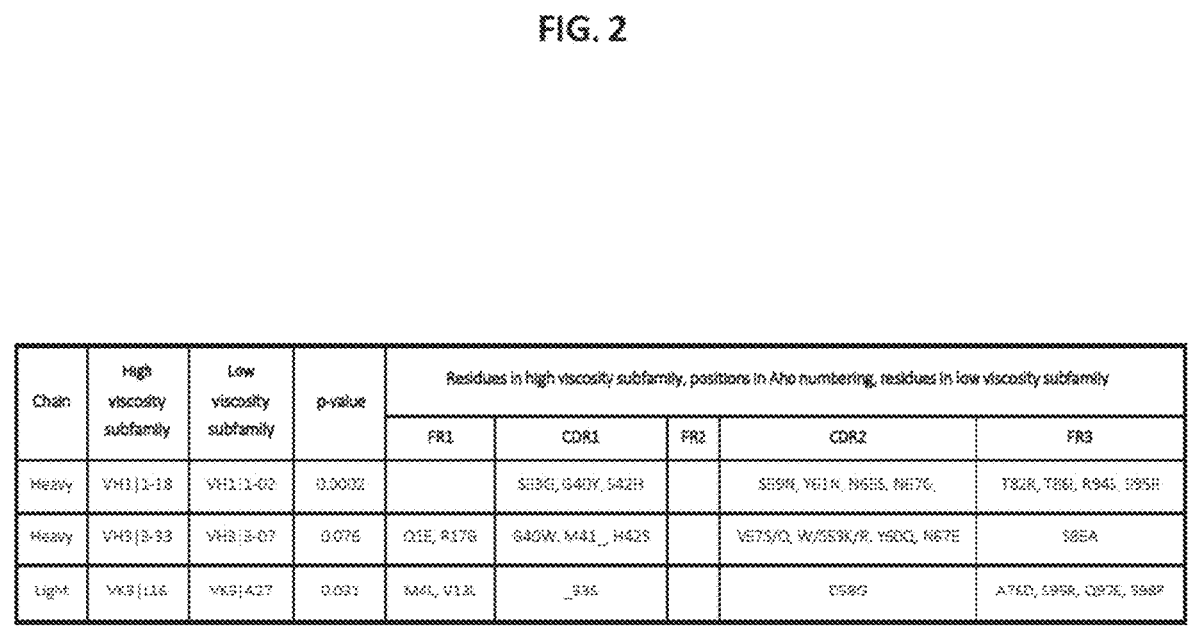

| Chain | High viscosity subfamily | Low viscosity subfamily | p-value | Residues in high viscosity subfamily, positions in Aho numbering, residues in low viscosity subfamily | | | | |
|---|---|---|---|---|---|---|---|---|
| | | | | FR1 | CDR1 | FR2 | CDR2 | FR3 |
| Heavy | VH1|1-18 | VH1|1-02 | 0.0002 | | S33G, G40Y, S42R | | S59R, Y61K, N63S, 867G, | T82R, T86I, R94S, I95H |
| Heavy | VH3|3-93 | VH3|3-07 | 0.076 | Q1E, R17G | G40W, M41_, R42S | | V67S/Q, W/G59K/R, Y60Q, K67E | S85A |
| Light | VK3|116 | VK3|427 | 0.031 | M4L, V13L | _33S | | E58G | A76D, S95R, Q97K, S98P |

FIG. 9A

| VH1|1-18 and VH1|1-02 Global sequence parameters | | | | | CDR1 | | | CDR2 | | | | | FR3 | | | | | | | | | |
|---|---|---|---|---|---|---|---|---|---|---|---|---|---|---|---|---|---|---|---|---|---|---|
| | | | | | 32 | 33 | 35 | 52 | 53 | 54 | 55 | 57 | 67 | 68 | 69 | 70 | 71 | 72 | 73 | 74 | 75 |
| | | | | | 31 | 33 | 35 | 52 | a | 53 | 54 | 56 | 66 | 67 | 68 | 69 | 70 | 71 | 72 | 73 | 74 |
| | | | | | 31 | 33 | 35 | 52 | a | 53 | 54 | 56 | 66 | 67 | 68 | 69 | 70 | 71 | 72 | 73 | 74 |
| mAbs | Visc, cP | pI | VL | VH1 | 33 | 40 | 42 | 59 | 60 | 61 | 65 | 67 | 77 | 78 | 79 | 80 | 81 | 82 | 83 | 84 | 85 |
| VBase | | | | VH1|1-02 | G | Y | H | N | P | N | S | G | R | V | T | M | T | R | D | T | S |
| B | 5.6 | 8.7 | VK3|A27 | VH1|1-02 | G | Y | H | N | P | N | S | G | R | V | T | M | T | R | D | T | S |
| J | 8.2 | 8.8 | VK3|A27 | VH1|1-02 | G | Y | H | N | P | N | S | G | R | V | T | M | T | R | D | T | S |
| L | 8.4 | 8.6 | VL3|3l | VH1|1-02 | G | Y | H | N | P | N | S | G | R | V | T | M | T | R | D | T | S |
| T | 11.0 | 8.1 | VK4|B3 | VH1|1-02 | G | Y | H | N | P | N | S | G | R | V | T | M | T | R | D | T | S |
| U | 12.1 | 8.4 | VK3|A27 | VH1|1-02 | G | Y | H | N | P | N | S | G | R | V | T | M | T | R | D | T | S |
| AF | 19.1 | 8.0 | VK3L18 | VH1|1-18 | R | G | S | S | T | Y | S | N | R | V | T | M | T | T | D | T | S |
| AK | 22.8 | 8.1 | VL2|2a2 | VH1|1-18 | S | G | S | S | F | Y | N | N | R | G | T | M | T | T | D | P | S |
| AL | 29.4 | 7.0 | VL3|3. | VH1|1-18 | S | G | S | I | P | Y | N | N | R | V | T | M | T | T | D | T | S |
| AN | 30.4 | 6.8 | VK1|O2 | VH1|1-18 | D | N | H | N | P | N | S | G | R | V | T | M | T | T | D | T | S |
| AO | 32.1 | 6.6 | VK4|B3 | VH1|1-18 | S | G | S | S | A | Y | N | N | R | V | T | M | T | T | D | T | S |
| Vbase | | | | VH1|1-18 | S | G | S | S | A | Y | N | N | R | V | T | M | T | T | D | T | S |
| p-value | 0.0002 | 0.03 | | | | | | | | | | | | | | | | | | | |

FIG. 9B

| FR3 | | | | | | | | | | | | | | | | | | | | | | | VH | VL | Schem |
|---|---|---|---|---|---|---|---|---|---|---|---|---|---|---|---|---|---|---|---|---|---|---|---|---|---|
| 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 52 | 12 | EU |
| 75 | 76 | 77 | 78 | 79 | 80 | 81 | 82 | a | b | c | 83 | 84 | 85 | 86 | 87 | 88 | 89 | 90 | 91 | 92 | 93 | 94 | 56 | 13 | Kabat |
| 75 | 76 | 77 | 78 | 79 | 80 | 81 | 82 | a | b | c | 83 | 84 | 85 | 86 | 87 | 88 | 89 | 90 | 91 | 92 | 93 | 94 | 52 | 13 | Chothia |
| 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | 59 | 13 | Aho |
| I | S | T | A | Y | M | E | L | S | R | L | R | S | D | D | T | A | V | Y | Y | C | A | R | | | |
| I | S | T | A | Y | M | E | L | S | R | L | R | S | D | D | T | A | V | Y | Y | C | A | R | N | L | |
| I | S | T | A | S | M | E | L | S | R | L | R | S | D | D | T | A | V | Y | F | C | A | R | N | L | |
| I | S | T | A | Y | M | E | L | S | R | L | R | S | D | D | T | A | V | Y | F | C | A | R | N | V | |
| I | S | T | A | Y | M | E | L | S | R | L | R | S | D | D | T | A | V | Y | Y | C | A | R | N | L | |
| I | S | T | A | Y | M | E | L | R | S | L | R | S | D | D | T | A | V | Y | Y | C | A | R | S | V | |
| I | S | T | A | Y | M | E | L | R | S | L | R | S | D | D | T | A | V | Y | Y | C | A | R | S | G | |
| I | S | T | A | Y | M | E | L | R | S | L | R | S | D | D | T | A | V | Y | F | C | A | R | I | V | |
| I | S | T | A | Y | M | E | L | R | S | L | R | S | D | D | T | A | V | Y | Y | C | A | R | N | A | |
| I | S | T | A | Y | M | E | L | R | S | L | R | S | D | D | T | A | V | Y | Y | C | A | R | S | V | |
| I | S | T | A | Y | M | E | L | R | S | L | R | S | D | D | T | A | V | Y | Y | C | A | R | | | |

FIG. 10

| mAb mutant symbols | Heavy chain mutations | Light chain mutations |
|---|---|---|
| AK | AK_HC | AK_LC |
| AK (82 94 95) | AK_HC: [T82R, R94S, S95R] | AK_LC |
| AK (59 82 94 95) | AK_HC: [S59K, T82R, R94S, S95R] | AK_LC |
| AK (82 94 95 13) | AK_HC: [T82R, R94S, S95R] | AK_LC: [G13L] |
| AK (59 82 94 95 13) | AK_HC: [S59K, T82R, R94S, S95R] | AK_LC: [G13L] |
| AO | AO_HC | AO_LC |
| AO (82 94 95) | AO_HC: [T82R, R94S, S95R] | AO_LC |
| AO (59 82 94 95) | AO_HC: [S59K, T82R, R94S, S95R] | AO_LC |
| AO (82 94 95 13) | AO_HC: [T82R, R94S, S95R] | AO_LC: [V13L] |
| AO (59 82 94 95 13) | AO_HC: [S59K, T82R, R94S, S95R] | AO_LC: [V13L] |

FIG. 11

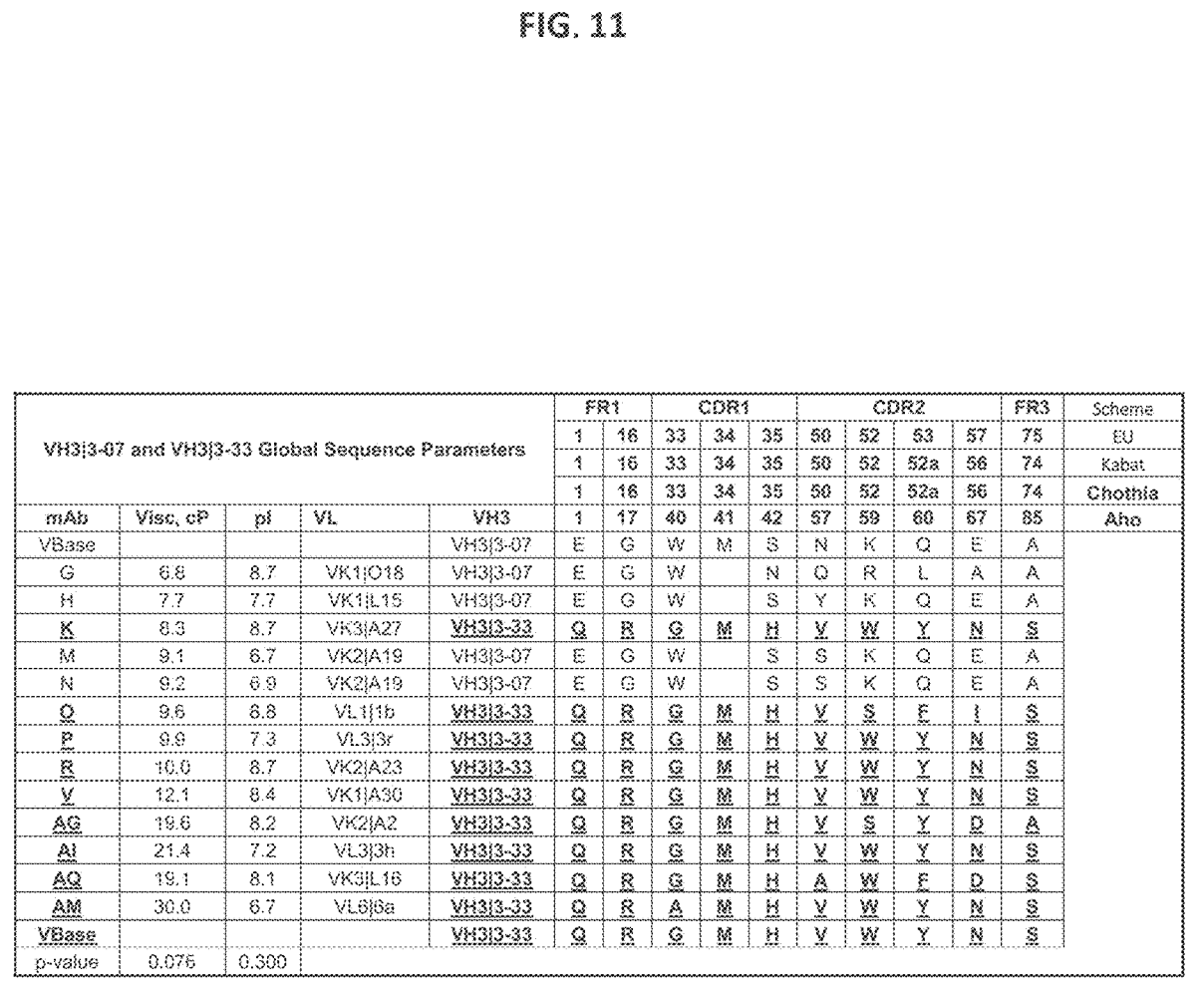

| VH3\|3-07 and VH3\|3-33 Global Sequence Parameters | | | | | FR1 | | CDR1 | | | CDR2 | | | | FR3 | Scheme |
|---|---|---|---|---|---|---|---|---|---|---|---|---|---|---|---|
| | | | | | 1 | 16 | 33 | 34 | 35 | 50 | 52 | 53 | 57 | 75 | EU |
| | | | | | 1 | 16 | 33 | 34 | 35 | 50 | 52 | 52a | 56 | 74 | Kabat |
| | | | | | 1 | 16 | 33 | 34 | 35 | 50 | 52 | 52a | 56 | 74 | Chothia |
| mAb | Visc, cP | pI | VL | VH3 | 1 | 17 | 40 | 41 | 42 | 57 | 59 | 60 | 67 | 85 | Aho |
| VBase | | | | VH3\|3-07 | E | G | W | M | S | N | K | Q | E | A | |
| G | 6.8 | 8.7 | VK1\|O18 | VH3\|3-07 | E | G | W | | N | Q | R | L | A | A | |
| H | 7.7 | 7.7 | VK1\|L15 | VH3\|3-07 | E | G | W | | S | Y | K | Q | E | A | |
| K | 8.3 | 8.7 | VK3\|A27 | VH3\|3-33 | Q | R | G | M | H | V | W | Y | N | S | |
| M | 9.1 | 6.7 | VK2\|A19 | VH3\|3-07 | E | G | W | | S | S | K | Q | E | A | |
| N | 9.2 | 6.9 | VK2\|A19 | VH3\|3-07 | E | G | W | | S | S | K | Q | E | A | |
| O | 9.6 | 6.8 | VL1\|1b | VH3\|3-33 | Q | R | G | M | H | V | S | F | I | S | |
| P | 9.9 | 7.3 | VL3\|3r | VH3\|3-33 | Q | R | G | M | H | V | W | Y | N | S | |
| R | 10.0 | 8.7 | VK2\|A23 | VH3\|3-33 | Q | R | G | M | H | V | W | Y | N | S | |
| V | 12.1 | 8.4 | VK1\|A30 | VH3\|3-33 | Q | R | G | M | H | V | W | Y | N | S | |
| AG | 19.6 | 8.2 | VK2\|A2 | VH3\|3-33 | Q | R | G | M | H | V | S | Y | D | A | |
| AI | 21.4 | 7.2 | VL3\|3h | VH3\|3-33 | Q | R | G | M | H | V | W | Y | N | S | |
| AQ | 19.1 | 8.1 | VK3\|L16 | VH3\|3-33 | Q | R | G | M | H | A | W | F | D | S | |
| AM | 30.0 | 6.7 | VL6\|6a | VH3\|3-33 | Q | R | A | M | H | V | W | Y | N | S | |
| VBase | | | | VH3\|3-33 | Q | R | G | M | H | V | W | Y | N | S | |
| p-value | 0.076 | 0.300 | | | | | | | | | | | | | |

FIG. 12

| | | | | | FR1 | | CDR1 | | CDR2 | FR3 | | | | Scheme |
|---|---|---|---|---|---|---|---|---|---|---|---|---|---|---|
| VK3\|A27 and VK3\|L Global Sequence Parameters | | | | | 4 | 12 | 31 | 33 | 51 | 66 | 85 | 87 | 88 | EU |
| | | | | | 4 | 12 | 31 | 33 | 51 | 65 | 82b | 83 | 84 | Kabat |
| | | | | | 4 | 12 | 31 | 33 | 51 | 65 | 82b | 83 | 84 | Chothia |
| mAb | Visc, cP | pI | VH | VK3 | 4 | 13 | 33 | 40 | 58 | 76 | 95 | 97 | 98 | Aho |
| VBase | | | | VK3\|A27 | L | L | S | Y | G | D | R | E | P | |
| B | 5.6 | 8.7 | VH1\|1-02 | VK3\|A27 | L | L | S | Y | G | D | R | E | P | |
| D | 6.6 | 8.6 | VH3\|3-23 | VK3\|A27 | L | L | G | Y | G | D | R | E | P | |
| J | 8.2 | 8.8 | VH1\|1-02 | VK3\|A27 | L | L | S | Y | G | D | R | E | P | |
| K | 8.3 | 8.7 | VH3\|3-33 | VK3\|A27 | L | L | S | Y | G | D | R | E | P | |
| Q | 10.0 | 8.2 | VH3\|3-23 | VK3\|A27 | L | L | S | Y | G | D | R | E | P | |
| S | 10.6 | 8.1 | VH4\|4-59 | VK3\|L16 | M | V | - | N | G | A | S | Q | S | |
| U | 12.1 | 8.4 | VH1\|1-02 | VK3\|A27 | L | L | N | Y | G | D | R | E | P | |
| Y | 12.2 | 8.8 | VH5\|5-51 | VK3\|A27 | L | L | S | Y | G | D | R | E | P | |
| AA | 12.5 | 8.7 | VH4\|4-30 | VK3\|A27 | L | L | R | Y | G | D | R | E | P | |
| AC | 15.2 | 8.6 | VH3\|3-48 | VK3\|A27 | L | L | N | Y | G | D | R | E | P | |
| AD | 16.3 | 8.8 | VH5\|5-51 | VK3\|A27 | L | L | S | Y | G | D | R | E | P | |
| AF | 19.1 | 8.6 | VH1\|1-18 | VK3\|L16 | M | V | - | N | D | A | S | Q | S | |
| AJ | 22.5 | 8.2 | VH3\|3-48 | VK3\|L6 | L | L | - | Y | D | A | S | E | P | |
| AQ | 19.1 | 8.1 | VH3\|3-33 | VK3\|L16 | M | V | - | N | G | A | S | Q | S | |
| Vbase | | | | VK3\|L16 | M | V | - | N | G | A | S | Q | S | |
| p-value | 0.007 | 0.011 | | | | | | | | | | | | |

FIG. 15

| Sample | Viscosity (cP) @ 1000s-1 @ 25C | Relative viscosity |
|---|---|---|
| Antibody AK | 43.7 | 100% |
| Fab Mutant | 25.6 | 59% |
| Fc Mutant | 34.8 | 80% |
| Double Mutant | 22.6 | 52% |

FIG. 16

Carboxylic Acid + EDC → o-Acylisourea Active Ester

Primary Amine → Crosslinked Proteins + Isourea By-product

FIG. 17

| Protein | Target | Monomer | Dimer | Other | Viscosity at 150 mg/mL at 25°C |
|---------|--------|---------|-------|-------|-------------------------------|
| ASA1 | | Yes | Yes | No | ~ 2-4 cP in A5 |
| ASA2 | | Yes | Yes | No | ~ 2-4 cP in A5 |
| Ab BA | C-kit | Yes | Yes | Yes | ~50 cP in A52Su |
| Ab AH | sclerostin | Yes | Yes | Yes | ~22 cP in A52Su |
| Ab AN | sclerostin | Yes | Yes | Yes | ~30 cP in A52Su |

| AQ mutant symbols | AQ HC mutations in Aho (Linear) numbering | AQ LC mutations in Aho (Linear) numbering | Conc, mg/mL | Visc, cP | STDEV, cP | Visc Rel to AQ |
|---|---|---|---|---|---|---|
| AQ | AQ_HC | AQ_LC | 151.1 | 19.1 | 0.6 | 1 |
| AQ (HC 1, 17, 85) | AQ_HC: Q1(1)E, R17(16)G, S85(75)A | AQ_LC | 151.7 | 15.8 | 0.8 | 0.87 |
| AQ (LC 4 13 76 95 97 98) | AQ_HC: | AQ_LC: M4(4)L, V13(13)L, A76(60)D, S95(77)R, Q97(79)L, S98(80)P | 149.1 | 12.7 | 0.4 | 0.67 |
| AQ (HC 1, 17, 85) (LC 4 13 76 95 97 98) | AQ_HC: Q1(1)E, R17(16)G, S85(75)A | AQ_LC: M4(4)L, V13(13)L, A76(60)D, S95(77)R, Q97(79)L, S98(80)P | 151.6 | 24.2 | 1 | 1.26 |

4 Abs cAMP assay in 293/huGIPR#10

| Anti-GIPR antibodies | EC50 |
|---|---|
| LC mutant | 1.53E-09 |
| HC mutant | 1.14E-09 |
| LC + HC mutant | 1.35E-09 |
| 2G10 parent | 1.27E-09 |
| control | 2.77E-11 |

FIG. 21

| Group # | Test Material | Dose Level (mg/kg) | Dose Volume (mL/kg) | Dose Concentration (mg/mL) | # Animals |
|---|---|---|---|---|---|
| 1 | Antibody AK (control) | 10 | 0.071 | 140 | 4 |
| | Diluent (procedural control) | 0 | 0.071 | 0 | |
| 2 | Antibody AK (Fab mutation) | 10 | 0.048 | 210 | 4 |
| | Diluent (procedural control) | 0 | 0.048 | 0 | |
| 3 | Antibody AK (Fc mutation) | 10 | 0.048 | 210 | 4 |
| 4 | Antibody AK (Fab and Fc double mutation) | 10 | 0.048 | 210 | 4 |

FIG. 22

| Dose Group and Level | T_max (Day) | C_max (µg/mL) | AUC_last (day*µg/mL) | AUC_last/D (day*kg*µg/mL*mg) |
|---|---|---|---|---|
| Antibody AK 10 mg/kg | 2.5 | 87.8 | 923 | 92.3 |
| Antibody AK (Fab mutation) 10 mg/kg | 2.5 | 91.1 | 807 | 80.7 |
| Antibody AK (Fc mutation) 10 mg/kg | 0.81 | 125 | 1020 | 102 |
| Antibody AK (Fab + Fc mutation) 10 mg/kg | 1 | 112 | 740 | 74.0 |

LDL-C % pretest *

Days post dose

| Animal # | pretest (Day 1 QLAB) | 1.02 | 2 | 3 | 4 | 6 | 8 | 11 | 15 | 18 | 22 | 25 | 29 | 36 | 43 |
|---|---|---|---|---|---|---|---|---|---|---|---|---|---|---|---|
| 1001 | 100.00% | 101.75% | 66.67% | 40.35% | 36.84% | 29.82% | 33.33% | 29.82% | 15.79% | 24.56% | 21.05% | 22.81% | 31.58% | 57.89% | 59.65% |
| 1002 | 100.00% | 95.00% | 52.50% | 45.00% | 37.50% | 37.50% | 47.50% | 20.00% | 7.50% | 50.00% | 32.50% | 30.00% | 42.50% | 60.00% | 70.00% |
| 1003 | 100.00% | 111.11% | 58.33% | 27.78% | 27.78% | 22.22% | 22.22% | 36.11% | 8.33% | 25.00% | 22.22% | 19.44% | 61.11% | 97.22% | 97.22% |
| 1004 | 100.00% | 105.97% | 52.24% | 35.82% | 32.84% | 29.85% | 19.40% | 14.93% | 4.48% | 4.48% | 19.40% | 19.40% | 83.58% | 98.51% | 100.00% |
| mean | 100.00% | 103.50% | 57.60% | 37.50% | 34.00% | 30.00% | 29.50% | 24.00% | 9.00% | 23.00% | 23.00% | 22.50% | 56.50% | 79.00% | 82.00% |
| 2001 | 100.00% | 106.52% | 58.70% | 34.78% | 26.09% | 28.26% | 30.43% | 28.26% | 21.74% | 52.17% | 32.61% | 39.13% | 39.13% | 54.35% | 69.57% |
| 2002 | 100.00% | 100.00% | 48.57% | 34.29% | 31.43% | 28.57% | 25.71% | 8.57% | 8.57% | 25.71% | 28.57% | 42.86% | 65.71% | 120.00% | 102.86% |
| 2003 | 100.00% | 110.34% | 63.79% | 32.76% | 32.76% | 24.14% | 13.79% | 18.97% | 5.17% | 15.52% | 18.97% | 24.14% | 41.38% | 60.34% | 67.24% |
| 2004 | 100.00% | 114.29% | 62.86% | 37.14% | 31.43% | 25.71% | 22.86% | 28.57% | 20.00% | 22.86% | 31.43% | 31.43% | 48.57% | 65.71% | 77.14% |
| mean | 100.00% | 108.05% | 59.20% | 34.48% | 30.46% | 26.44% | 22.41% | 21.26% | 13.22% | 28.74% | 27.01% | 33.33% | 47.13% | 71.84% | 77.01% |
| 3001 | 100.00% | 102.63% | 63.16% | 42.11% | 31.58% | 28.95% | 23.68% | 18.42% | 7.89% | 23.68% | 28.95% | 76.32% | 113.16% | 126.32% | 97.37% |
| 3002 | 100.00% | 104.17% | 50.00% | 29.17% | 27.08% | 29.17% | 18.75% | 14.58% | 6.25% | 16.67% | 25.00% | 52.08% | 81.25% | 89.58% | 79.17% |
| 3003 | 100.00% | 100.00% | 37.21% | 18.60% | 18.60% | 6.98% | 6.98% | 6.98% | 6.98% | 6.98% | 39.53% | 67.44% | 116.28% | 95.35% | 102.33% |
| 3004 | 100.00% | 100.00% | 55.00% | 40.00% | 32.50% | 27.50% | 25.00% | 27.50% | 20.00% | 22.50% | 25.00% | 22.50% | 32.50% | 37.50% | 50.00% |
| mean | 100.00% | 101.78% | 50.89% | 31.95% | 27.22% | 23.03% | 18.34% | 16.57% | 10.06% | 17.16% | 29.59% | 54.44% | 85.80% | 86.98% | 82.25% |
| 4001 | 100.00% | 105.88% | 76.47% | 56.86% | 47.06% | 45.10% | 35.29% | 39.22% | 25.49% | 31.37% | 31.37% | 37.25% | 64.71% | 92.16% | 96.08% |
| 4002 | 100.00% | 102.17% | 54.35% | 39.13% | 32.61% | 30.43% | 21.74% | 28.26% | 15.22% | 28.26% | 28.26% | 34.78% | 34.78% | 67.39% | 82.61% |
| 4003 | 100.00% | 94.92% | 54.24% | 35.59% | 30.51% | 20.34% | 22.03% | 27.12% | 15.25% | 23.73% | 57.63% | 45.76% | 67.80% | 74.58% | 81.36% |
| 4104 | 100.00% | 102.99% | 56.72% | 32.84% | 34.33% | 35.82% | 28.36% | 29.85% | 31.34% | 25.37% | 28.36% | 26.87% | 44.78% | 55.22% | 59.70% |
| mean | 100.00% | 101.35% | 60.09% | 40.36% | 35.87% | 32.74% | 26.91% | 30.94% | 22.42% | 26.91% | 36.77% | 35.87% | 53.36% | 71.30% | 78.48% |

LOW-VISCOSITY ANTIGEN BINDING PROTEINS AND METHODS OF MAKING THEM

CROSS REFERENCES TO RELATED APPLICATIONS

This application is divisional of U.S. Ser. No. 16/338,292, filed Mar. 29, 2019, which is a national stage application under 35 U.S.C. § 371 of International Application No. PCT/US17/53967, having an international filing date of Sep. 28, 2017, which claims the priority of U.S. Provisional Application No. 62/546,469, filed on Aug. 16, 2017; U.S. Provisional Application No. 62/430,773, filed on Dec. 6, 2016; and U.S. Provisional Application No. 62/401,770, filed Sep. 29, 2016, each of which is hereby incorporated by reference in its entirety for all purposes.

FIELD OF THE INVENTION

This invention relates to biopharmaceuticals, particularly to therapeutic antigen binding proteins, methods of use thereof, pharmaceutical compositions thereof, and processes of making them. In particular, this invention relates to antigen binding proteins, particularly antibodies, mutated to reduce viscosity.

BRIEF DESCRIPTION OF THE SEQUENCE LISTING

Incorporated herein by reference in its entirety is a Sequence Listing entitled, "A-2063-US-PSP3_SeqList_ST25.txt", comprising SEQ ID NO:1 through SEQ ID NO:379, which includes nucleic acid and/or amino acid sequences disclosed herein. The Sequence Listing has been submitted herein in ASCII text format via EFS, and thus constitutes both the paper and computer readable form thereof. The Sequence Listing was first created using PatentIn on Aug. 16, 2017, and is 4.32 MB in size.

BACKGROUND OF THE INVENTION

Currently, monoclonal antibodies (mAbs) are the most popular modality of modern therapeutic proteins on the market and under development. The differences between antibodies are predominantly in the antigen binding domains or complementary determining regions (CDRs). These differences in the CDRs are thought to result in differences in transient protein-protein interaction propensity that manifest themselves as bulk solution viscosity. Several groups have described the presence of reversible clusters of antibodies in viscous antibody solutions (predominantly dimers). Several theoretical descriptions of polymer viscosity have been proposed to explain the interactions of these clusters as a mechanism for bulk solution viscosity behavior.

Antibodies usually work as antagonists and, therefore, large amounts, often exceeding 100 mg per dose, are required to block undesirable interactions. For patient comfort, a single subcutaneous injection of a 1 mL volume is the most preferred mode of administration. The need to administer large amounts of mAbs in a relatively small volume has required high concentration formulations at or exceeding 100 mg/ml. Antibodies are large biopolymers with molecular weights of about 150 kDa, and their high concentrations result in high sheer stress and high viscosity due to protein-protein and protein-wall interactions during filtration and passage through the injection needles and in subcutaneous space. High viscosity presents challenges in the manufacture of therapeutic antigen binding proteins as well as in their administration to patients, including prohibitively high back pressure during injections leading to malfunction of injections devices, difficulty of manual administration, decreased bio-availability and patient discomfort.

The development and use of high concentration therapeutic monoclonal antibody solutions has accelerated as the cost of biopharmaceutical production has decreased. In some cases, these antibody solutions possess viscous solution attributes that can make manufacturing and administration of the intended dose challenging. The differences in the CDRs that appear to determine if an antibody is "viscous" or "not viscous" are likely related to the propensity of the CDRs to drive protein-protein interaction.

Significant efforts are underway in the industry to understand the nature of interactions leading to high viscosity and to reduce the viscosity of high viscosity antibody formulations. The most important parameters affecting viscosity of the antibody formulations include:

intermolecular interactions defined by the pI of the protein and the pH of the solution. Cheng et al. (2013), "Linking the solution viscosity of an IgG2 monoclonal antibody to its structure as a function of pH and temperature," *J. Pharm Sci.* 102:4291-4304.

Charge interactions. Yadav et al. (2012), "Viscosity behavior of high-concentration monoclonal antibody solutions: correlation with interaction parameter and electroviscous effects," *J. Pharm Sci.* 101:998-1011; Yadav et al. (2012), "The influence of charge distribution on self-association and viscosity behavior of monoclonal antibody solutions." *Mol Pharm* 9 (4): 791-802; Singh et al. (2014), "Dipole-Dipole Interaction in Antibody Solutions: Correlation with Viscosity Behavior at High Concentration," *Pharm Res.* 31 (9): 2549-2558; Chaudhri et al. (2013), "The role of amino acid sequence in the self-association of therapeutic monoclonal antibodies: insights from coarse-grained modeling," *J. Phys. Chem. B* 117:1269-1279.

Hydrophobic interactions. Guo et al. (2012), "Structure-activity relationship for hydrophobic salts as viscosity-lowering excipients for concentrated solutions of monoclonal antibodies," *Pharm Res* 29:3102-3109.

The highest solution viscosity was observed under conditions with the most negative diffusion interaction parameter kD, the highest apparent radius and the lowest net charge. Neergaard et al. (2013), "Viscosity of high concentration protein formulations of monoclonal antibodies of the IgG1 and IgG4 subclass-prediction of viscosity through protein-protein interaction measurements," *Eur. J. Pharm Sci.* 49:400-410. The diffusion interaction parameter (kD), a component of the osmotic second virial coefficient (B (2)) correlated well (R>0.9) with the viscosity of concentrated mAb solutions, while the mAb net charge correlated weakly (R<0.6), indicating that weak intermolecular interactions are important in governing the viscoelastic behavior of concentrated mAb solutions. Connolly, et al. (2012), "Weak interactions govern the viscosity of concentrated antibody solutions: high-throughput analysis using the diffusion interaction parameter," *Biophys. J.* 103:69-78. In a study reported in this specification, primary sequences linked to 3D structure were utilized. See Honegger et al. (2001), "Yet another numbering scheme for immunoglobulin variable domains: an automatic modeling and analysis tool," *J. Mol. Biol.* 309:657-670. Viscosity values of several mAb molecules were measured to develop a model for viscosity prediction of mAbs via machine learning algorithms. Structural position, charge and hydrophobicity were the main parameters of amino acids utilized for the model.

Viscosity of monoclonal antibodies was assessed using molecular information in the following articles: Li, L. et al. (2014), "Concentration dependent viscosity of monoclonal antibody solutions: explaining experimental behavior in terms of molecular properties," *Pharm. Res.* 31:3161-3178; and Sharma et al. (2014), "In silico selection of therapeutic antibodies for development: viscosity, clearance, and chemical stability," *Proc. Natl. Acad. Sci. U.S.A.* 111:18601-6.

The net result of the interactions between antibodies is either an extended transient network of interactions (a percolating network) that result in a viscous solution or the formation of larger oligomers that then somehow influence the solution rheology as larger structures. In studies reported in this specification, a small number of viscous antibodies was used as the subject for biochemical and biophysical analysis in an attempt to deduce specific protein-protein interactions that might lead to a viscous antibody solution.

The Aho numbering approach was utilized in the past to improve stability and other biophysical properties. Ewert et al. (2003), "Structure-based improvement of the biophysical properties of immunoglobulin VH domains with a generalizable approach," *Biochemistry* 42:1517-1528; Ewert et al. (2003), "Biophysical properties of human antibody variable domains," *J. Mol. Biol.* 325:531-553; Ewert et al. (2004), "Stability improvement of antibodies for extracellular and intracellular applications: CDR grafting to stable frameworks and structure-based framework engineering," *Methods* 34:184-199; and Rothlisberger et al. (2005), "Domain interactions in the Fab fragment: a comparative evaluation of the single-chain Fv and Fab format engineered with variable domains of different stability," *J Mol. Biol.* 347:773-789. The Aho numbering system was also utilized in the past to reduce propensity for aggregaton. Borras et al. (2013), U.S. Pat. No. 8,545,849.

SUMMARY OF THE INVENTION

This invention relates to methods for reducing viscosity of antigen binding proteins by modifying sequences in framework regions and/or the Fc domain that are shown to be associated with high viscosity.

In the process details which follow, all variable region amino acids are identified by Aho numbering, all amino acids from conserved regions are identified by EU numbering. Aho numbering is aligned and correlated with the other main numbering schemes including EU (Edelman et al. (1969), "The covalent structure of an entire gamma immunoglobulin molecule," *Proc. Natl. Acad. Sci. U.S.A.* 63, 78-85), Kabat (Kabat et al. (1991), *Sequences of proteins of immunological interest*, Fifth Edition. NIH Publication No. 91-3242), Chothia (Chothia et al., (1992), "Structural repertoire of the human VH segments," *J. Mol. Biol.* 227:799-817); (Tomlinson et al., (1995), "The structural repertoire of the human V kappa domain," *EMBO J* 14:4628-4638). Any of the four numbering systems can be interchangeably used to identify the preferred amino acid substitutions described in this specification.

If the antigen binding protein comprises the VH1|1-18 germline subfamily, the method comprises modifying the VH1 sequence to comprise one or more substitutions selected from $82X^1$, $94X^2$, and $95X^3$, wherein $X^1$ is a basic residues (R, K or H), $X^2$ is a polar, uncharged residue (S, T, N or Q) and $X^3$ is a basic residue (R, K, or H). All residues are identified by the Aho numbering system. Preferred mutations for the VH1|1-18 germline subfamily are 82R, 94S, and 95R. The method as applied to the VH1|1-18 germline subfamily may further comprise substitution $59X^{20}$ wherein $X^{20}$ is a basic residue (R, K or H), with the mutation 59K preferred.

If the antigen binding protein comprises the VH3|3-33 germline subfamily, the method comprises modifying the VH3 sequence to comprise one or more substitutions selected from $1X^4$, $17X^5$, and $85X^6$, wherein $X^4$ is a charged negative residue (D or E), $X^5$ is a small hydrophobic residue (G, A, V, I, L, or M), and $X^6$ is a small hydrophobic residue (G.A, V, I, L, or M). All residues are identified by the Aho numbering system. Preferred mutations for the VH3|3-33 germline subfamily are 1E, 17G, and 85A.

If the antigen binding protein comprises the VK3|L16 germline subfamily, the method comprises modifying the VK3 sequence to comprise one or more substitutions selected from $4X^{10}$, $13X^{11}$, $76X^{12}$, 78F, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E. All residues are identified by the Aho numbering system. Preferred mutations for the VK3|L16 germline subfamily are 4L, 13L, 76D, 95R, 97E, and 98P.

If the antigen binding protein comprises the VK3|L6 germline subfamily, the method comprises modifying the VK3 sequence to comprise one or more substitutions selected from $76X^{12}$ and $95X^{13}$. Preferred mutations for the VK3|L6 germline subfamily are 76D and 95R.

The methods of this invention further comprise modifying the Fc domain to comprise one or more substitutions selected from $253X^{15}$, $440X^{16}$, and $439X^{17}$, wherein $X^{15}$ is a small hydrophobic residue (G, A, V, I, L, or M), $X^{16}$ is a basic residue (R, K, or H), and $X^{17}$ is a charged negative residue (D or E), wherein the Fc domain sequence comprises only one of $440X^{16}$ and $439X^{17}$. All residues are identified by the EU numbering system. Preferred mutations of the Fc domain are 253A, 440K, and 439E.

The methods of this invention further comprise modifying the C-terminus of the Fc domain sequence to comprise $X^{18}X^{19}$ wherein $X^{18}$ is one to four amino acids selected from D and E or from H, K, and R, and $X^{19}$ is selected from P, M, G, A, V, I, L, S, T, N, Q, F, Y and W and is absent when $X^{18}$ comprises D or E, is present when $X^{18}$ comprises K or R at its C-terminal end, and is present or absent when $X^{18}$ comprises H at its C-terminal end. Preferred Fc C-terminal modifications comprise KP, KKP, KKKP, E or EE at the C-terminus.

The foregoing methods are preferably applied to the high viscosity antibodies shown in FIGS. 1A and 1B hereinafter. The part of the method involving the VH1|1-18 sequence is preferably applied to antibodies AF, AK, AL, AN, and AO from FIG. 1B. The part of the method involving the VH3|3-33 sequence is preferably applied to antibodies AQ, AM, AI, and AG from FIG. 1B. The part of the method involving the VK3|L16 sequence is preferably applied to antibodies AF and AQ from FIG. 1B. The part of the method involving the VK3|L6 sequence is preferably applied to antibody AJ.

The methods of this invention further comprise a method of preparing an antigen binding protein that reaches maximum serum concentration faster than does a parental antibody when the antigen binding protein and the parental antibody are administered at the same concentration, which comprises introducing sequence modification $440X^{16}$ in the parental antibody wherein $X^{16}$ is selected from R, K, and H. In a preferred method, the sequence-modified antigen binding protein reaches maximum serum concentration after subcutaneous injection at least twice as fast as the parental antibody. Also within this invention is a method of preparing an antigen binding protein that reaches a maximum serum concentration after subcutaneous injection that is higher than that of a parental antibody when the antigen binding protein and the parental antibody are administered at the same concentration, which comprises introducing sequence modification $440X^{16}$ in the parental antibody wherein $X^{16}$ is selected from R, K, and H. In a preferred method, the sequence-modified antigen binding protein reaches a maximum serum concentration that is at least about 25% higher than that of the parental antibody. In each of these methods, the preferred $X^{16}$ is K and the preferred parental antibody is a PCSK9 polypeptide (antibody AK most preferred).

The invention further relates to a mutant antigen binding protein, which comprises one or more sequences selected from:

a. a VH1|1-18 germline subfamily sequence comprising one or more substitutions selected from $82X^1$, $94X^2$, and $95X^3$, wherein $X^1$ is selected from R, K and H, $X^2$ is selected from S, T, N and Q and $X^3$ is selected from R, K, and H;

b. a VH3|3-33 germline subfamily sequence comprising one or more substitutions selected from $1X^4$, $17X^5$, and $85X^6$, wherein $X^4$ is selected from D and E, $X^5$ is selected from G, A, V, I, L, and M, and $X^6$ is selected from G.A, V, I, L, and M;

c. a VK3|L16 germline subfamily, comprising one or more substitutions selected from $4X^{10}$, $13X^{11}$, $76X^{12}$, 78F, $95X^{13}$, $97X^{14}$, and 98P, wherein $X^{10}$ is selected from G, A, V, I, L, and M, $X^{11}$ is selected from G, A, V, I, L, and M, $X^{12}$ is selected from D and E, $X^{13}$ is selected from R, K and H, and $X^{14}$ is selected from D and E, wherein the mutant antigen binding protein does not comprise only substitution 78F;

d. a VK3|IL6 germline subfamily, comprising one or more substitutions selected from $76X^{12}$ and $95X^{13}$;

e. an Fc domain sequence comprising one or more substitutions selected from $253X^{10}$, $440X^{11}$, and $439X^{12}$, wherein $X^{10}$ is selected from G, A, V, I, L, and M, $X^{11}$ is selected from R, K, and H, and $X^{12}$ is selected from D and E, wherein the antigen binding protein comprises at least one of $253X^{15}$ or modifications selected from subparagraphs a, b, c, d and f when $X^{16}$ is K and $X^{17}$ is E and the antigen binding protein specifically binds CD20; and f. an Fc domain sequence comprising at the C-terminus $X^{18}X^{19}$ wherein $X^{18}$ is one to four amino acids selected from D and E or from H, K, and R, and $X^{19}$ is selected from P, M, G, A, V, I, L, S, T, N, Q, F, Y and W and is absent when $X^{18}$ comprises D or E, is present when $X^{18}$ comprises K or R at its C-terminal end, and is present or absent when $X^{18}$ comprises H at its C-terminal end, and wherein the antigen binding protein comprises at least one of $253X^{15}$ or substitutions selected from subparagraphs a through e when PGKP, PGKKP, PGKKKP, or PGE appears at the C-terminus and the antigen binding protein specifically binds CD20 or CD38. Preferred Fc C-terminal modifications comprise KP, KKP, KKKP, E or EE at the C-terminus;

wherein the variable region amino acids are numbered according to the Aho numbering system and all amino acids from conserved regions including Fc are according to EU numbering.

Preferred antigen binding proteins in accordance with this invention are those wherein the foregoing modifications are applied to antibodies of FIGS. 1A and 1B hereinafter. Also preferred are antigen binding proteins wherein:

the VH1|1-18 germline subfamily sequence comprises one or more substitutions selected from 82R, 94S, and 95R, with antigen binding proteins having all such substitutions most preferred;

the VH3|3-33 germline subfamily sequence comprises one or more of substitutions 1E, 17G, and 85A, with antigen binding proteins having all such substitutions most preferred;

the VK3|L16 germline subfamily sequence comprises one or more substitutions selected from 4L, 13L, 76D, 95R, 97E, and 98P, with antigen binding proteins having all such substitutions most preferred;

the VK3|L6 germline subfamily sequence comprises one or more substitutions selected from 76D and 95R, with antigen binding proteins having both such substitutions most preferred;

the Fc domain sequence comprises one or more substitutions selected from 253A, 440K, and 439E, with antigen binding proteins having all such substitutions most preferred; and the Fc domain C-terminus comprises a sequence selected from KP, KKP, KKKP, and E.

All of the foregoing preferred amino acid substitutions in variable regions are identified by the Aho numbering system. All residues in conserved regions including Fc are identified by the EU numbering system.

Preferred antigen binding proteins in accordance with this invention include: antibodies AF, AK, AL, AN and AO from FIG. 1B having one or more, most preferably all, of the foregoing VH1|1-18 germline subfamily substitutions; antibodies AQ, AM, AI, and AG from FIG. 1B having one or more, most preferably all, of the VH3|3-33 germline subfamily substitutions; antibodies AF and AQ having one or more, most preferably all, of the VK3|L16 germline subfamily substitutions; antibody AJ from FIG. 1B having one or more, most preferably all, of the VK3|L6 germline subfamily substitutions; and antibodies BA, AH, and AN from FIG. 1B having one or more, preferably all, of the Fc substitutions noted above.

Due to the foregoing sequence modifications, the invention further relates to antigen binding proteins that specifically bind to PCSK9 comprising a heavy chain sequence selected from SEQ ID NOS: 352, 353, 354, 366, and 368, preferably also comprising a light chain sequence of SEQ ID NO: 351.

Due to the foregoing sequence modifications, the invention also relates to antigen binding proteins that specifically bind c-fms comprising a heavy chain sequence selected from SEQ ID NOS: 356, 357, and 358, preferably further comprising a light chain sequence of SEQ ID NO: 355.

Due to the foregoing sequence modifications, the invention also relates to antigen binding proteins that specifically bind GIPR comprising a heavy chain sequence selected from SEQ ID NOS: 359, 361, 362, 364, and 368, preferably further comprising a light chain sequence selected from SEQ ID NOS: 360, 363, 365, and 367.

All modified antigen binding proteins are useful for the same indications as described previously for the unmodified antibodies.

Each of the antigen binding proteins from FIGS. 1A and 1B having mutated heavy chains is preferred to further comprise a light chain sequence as noted in the unmodified parent antibody of FIGS. 1A and 1B. Each of the foregoing antigen binding proteins having a mutated light chain is preferred to further comprise a heavy chain sequence as noted above or as appearing in the unmodified parent antibody of FIGS. 1A and 1B.

The invention further comprises antigen binding proteins as described above that have improved pharmacokinetic properties. The invention comprises an antigen binding protein optionally having any of the aforementioned sequence modifications wherein:

a. the antigen binding protein comprises the sequence modification $440X^{16}$ relative to a parental antibody lacking the $440X^{16}$ sequence modification, b. the antigen binding protein reaches maximum serum concentration after subcutaneous injection faster than does the parental antibody when the antigen binding protein and the parental antibody are administered at the same concentration, and c. the antigen binding protein reaches a maximum serum concentration after subcutaneous injection that is higher than that of the parental antibody when the antigen binding protein and the parental antibody are administered at the same concentration.

The preferred parental antibody for such an antigen binding protein is a PCSK9 binding polypeptide, with antibody AK most preferred. The preferred substituent $X^{16}$ in such an antigen binding protein is K. Further within this invention is a method of treating hypercholesterolemia with such an antigen binding protein.

The invention also relates to isolated nucleic acids encoding the antigen binding proteins of the invention, as well as vectors comprising the nucleic acids, host cells comprising the vectors, and methods of making and using the antigen binding proteins.

In other embodiments, the present invention provides compositions comprising the antigen binding proteins and kits comprising the antigen binding proteins, as well as articles of manufacture comprising the antigen binding proteins.

BRIEF DESCRIPTION OF THE FIGURES

FIGS. 1A and 1B show a table of viscosity values measured for IgG1 and IgG2 monoclonal antibodies formulated at 150 mg/mL in a formulation buffer including 20 mM acetate and 9% sucrose at pH 5.2 (without polysorbate). FIGS. 1A and 1B show the targets of the antibodies studied as well as their light and heavy chain types, germline subfamilies, concentration, pI, and viscosity. Each antibody in FIGS. 1A and 1B has the amino acid sequences as noted in the figures and the Sequence Listing. The heavy and light chain amino acid sequences are encoded by nucleic acids having the SEQ ID NOS immediately preceding them in the Sequence Listing.

FIGS. 1C and 1D show the sequence identification numbers (SEQ ID NOS) for the framework regions and Fc regions of the antibodies of FIGS. 1A and 1B. FIG. 1D also shows antibody BA, which is discussed in FIG. 17.

FIG. 2 shows high viscosity and low viscosity subtype pairs identified in this specification.

FIG. 9 is a table showing global sequence parameters of mAbs high viscosity VH1|1-18 and low viscosity VH1|1-02 subtypes (germlines). The mAbs in FIG. 9 are sorted by viscosity. The table includes their mAb symbols, measured viscosity values, calculated pI values, and VL and VH germlines. For VH germlines, higher viscosity VH1|1-18 are shown in bold and underlined. Heavy chain framework 3 sequences are shown. Residues correlating with high viscosity are in bold and underlined. VBase sequences are added for VH1|1-18 and VH1|1-02 germline subfamilies for comparison to illustrate that the different residues are typical residues for the subfamilies.

FIG. 10 is a table showing produced and characterized mutants of the AK and AO antibodies.

FIG. 11 is a table showing global sequence parameters of thirteen mAbs with VH3 heavy chains. FIG. 11 includes the mAb symbols, measured viscosity values, calculated pI values, HC and LC types, and VL and VH subtypes (germlines). Higher viscosity VH3|3-33 subfamily is shown in bold and underlined. Residues correlating with high viscosity are bold and underlined. VBase sequences are added for VH3|3-33 and VH3|3-07 germline subfamilies for comparison to illustrate that the different residues are typical for those subfamilies.

FIG. 12 is a table showing global sequence parameters of fourteen mAbs with VK3 light chains. The mAbs in FIG. 12 are sorted by viscosity, including their mAb symbols, measured viscosity values, calculated pI values, HC and LC types, and VL and VH subtypes (germlines). Higher viscosity VK3|L16 and VK3|L6 subfamilies are in bold and underlined. Light chain residues that are consistently different between VK3|L16 and VK3|L6 subfamilies as compared to the VK3|A27 subfamily are shown on the right side. Residues correlating with high viscosity in the VK3|L16 and VK3|L6 subfamilies are bold and underlined. VBase sequences are added for VK3|L16 and VK3|A27 germline subfamilies for comparison to illustrate that the different residues are typical residues for the subfamilies.

FIG. 14B shows that a double mutant that restores wild type complement activity also restores wild type viscosity. The figure shows the viscosity of concentrations of antibody AK, antibody AK mutant I253A, antibody AK mutant S440K, and antibody AK double mutant K439E/S440K. The figure also shows the viscosity of antibody AK mutant K439E, antibody AK mutant H433A, and antibody AK mutant N434A which do not decrease viscosity relative to the antibody AK parent.

FIG. 15 is a table showing the absolute and relative viscosity values of parent antibody AK and various mutants. The parent antibody AK and the mutants are used in a nonhuman primate study of the pharmacokinetics and pharmacodynamics of antibody AK and low viscosity mutants.

Figure 16:
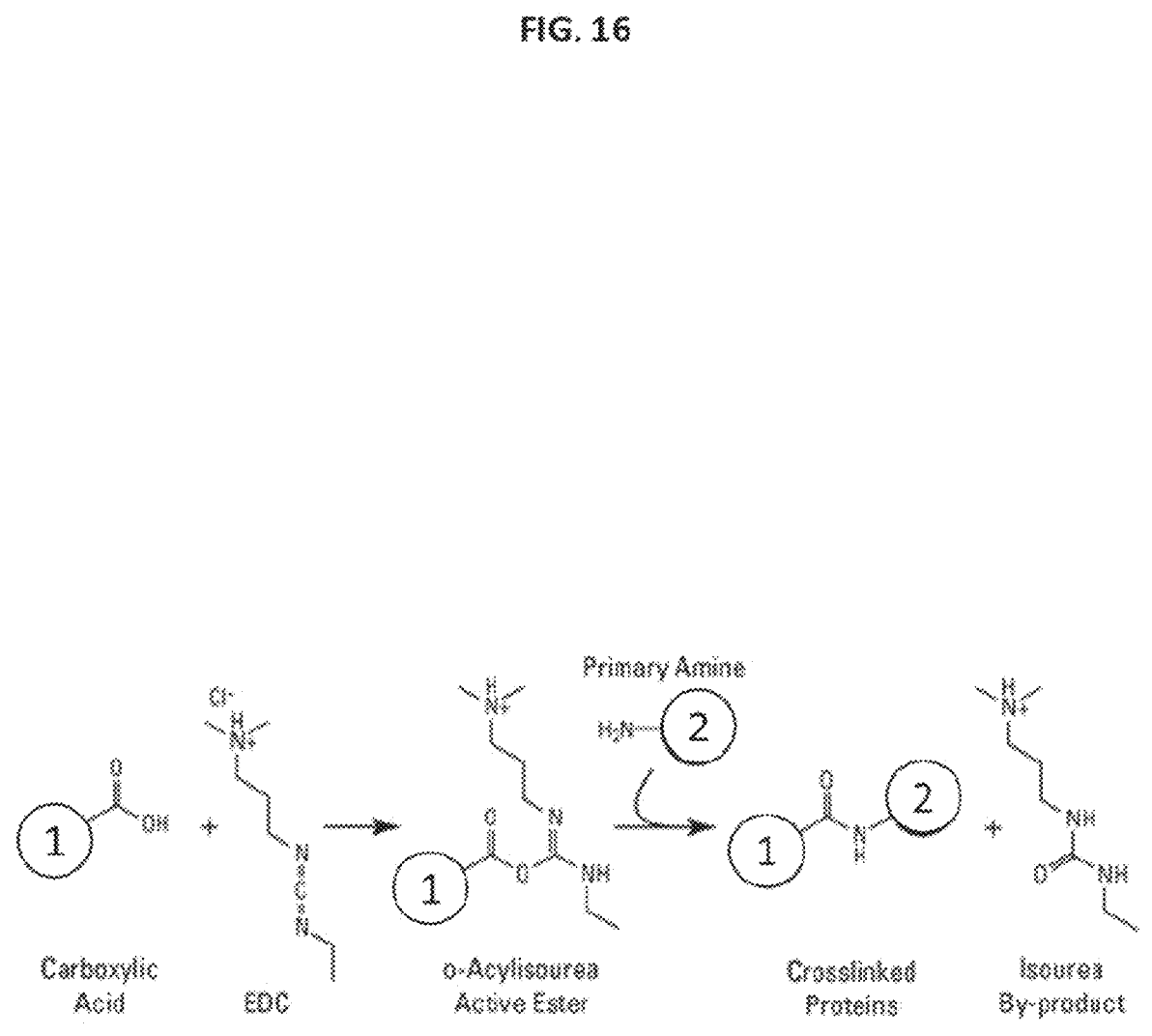

FIG. 16 is a schematic of EDC chemical cross-linking (see Example 2).

FIG. 17 is a table showing the viscosity of proteins selected for Fc mutations to lower viscosity variants.

Figure 18:
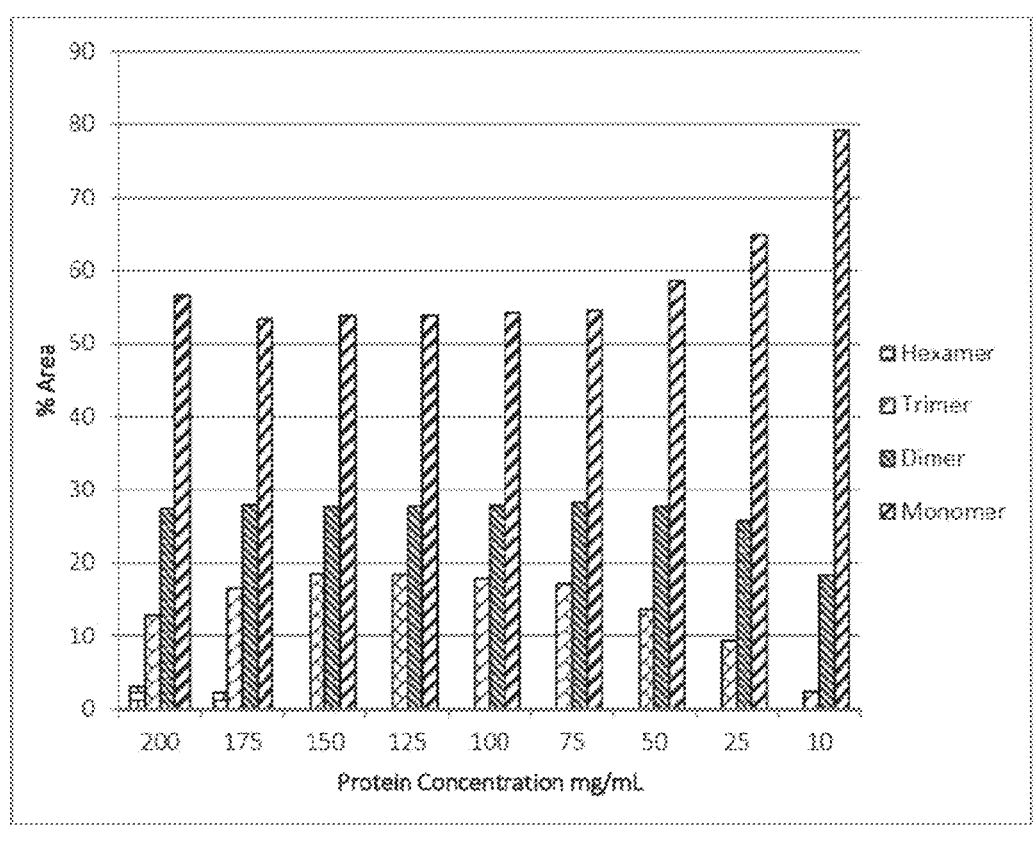

FIG. 18 shows concentration-dependent formation of antibody system oligomers by EDC chemical cross-linking of antibody AH.

Figure 19A:
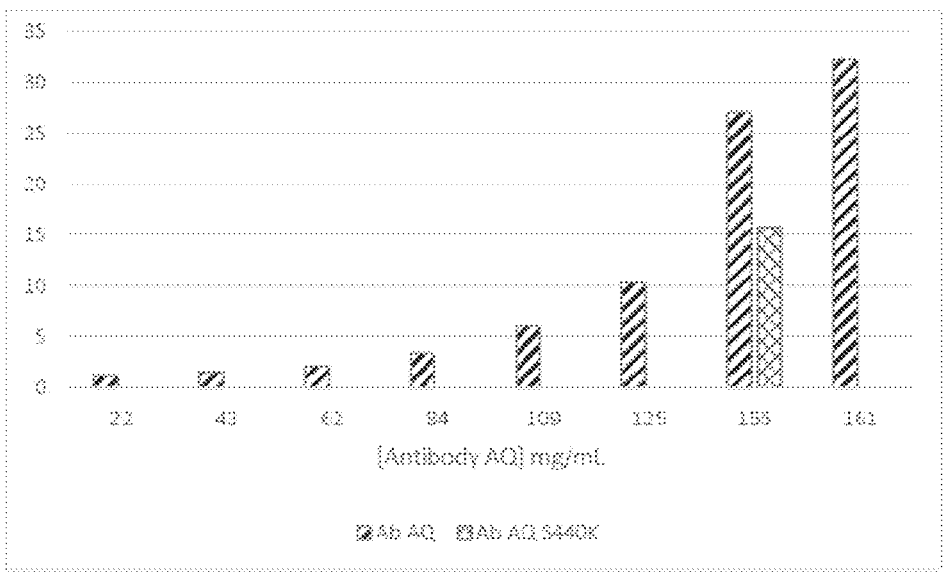
Figure 19B:
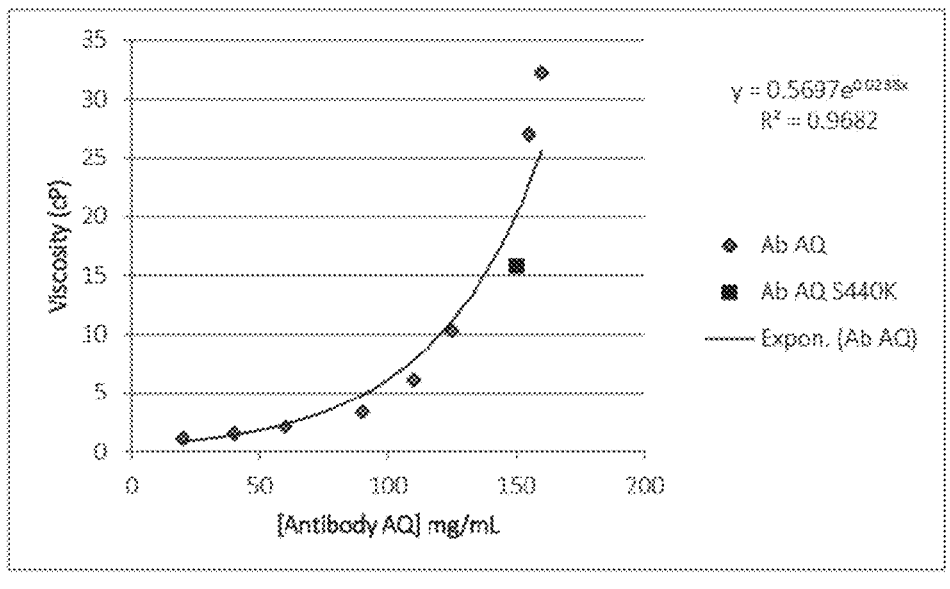

FIG. 19A shows that a S440K mutation in the Fc region reduces viscosity in antibody AQ. (Note that the concentration of the mutant is actually 150 mg/mL.) FIG. 19B is a scatter plot of the same data with an exponential fit. The diamonds in FIG. 19B denote the unmodified antibody AQ at the concentrations shown and the square shows the S440K mutant at 150 mg/mL.

Figures 20A, 20B:
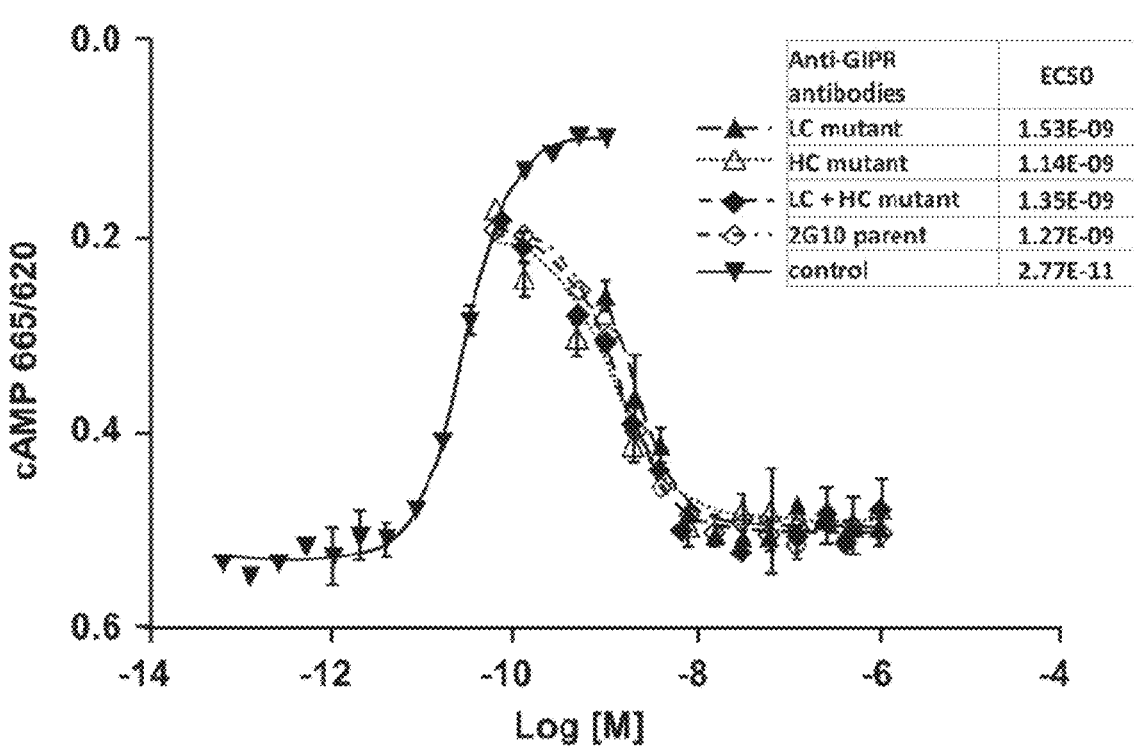

FIG. 20A is a table showing produced and characterized mutants of antibody AQ, including measured concentration and viscosity.

FIG. 20B shows cAMP response of 293/huGIPR cells expressing human GIP receptors activated by GIP and blocked by the anti-GIPR antibodies. The in vitro cAMP activity was equally unaffected by viscosity mutations. The potency remained the same within the error margin of the assay.

FIG. 21 shows a summary of the experimental design for a single-dose subcutaneous bolus pharmacokinetic study in male cynomolgus monkeys as described in further detail in a working example hereinafter.

FIG. 22 shows mean pharmacokinetic parameter estimates of antibody AK or low viscosity mutant homologues after subcutaneous administration of 10 mg/kg to male cynomolgus monkeys (N=4 males). Introduction of a mutation in the Fc region that reduces viscosity reduces Tmax and increases Cmax.

FIG. 23 shows the percentage of LDL-C compared to pretest (Day CLAB). * Percent change is expressed as the individual animal post-dose value divided by the Day 1 pretest value. All four antibodies (parent antibody AK, AK Fc mutant, AK Fab mutant and AK double Fc/Fab mutant) all induce reductions in LDL-C.

Figure 24A:
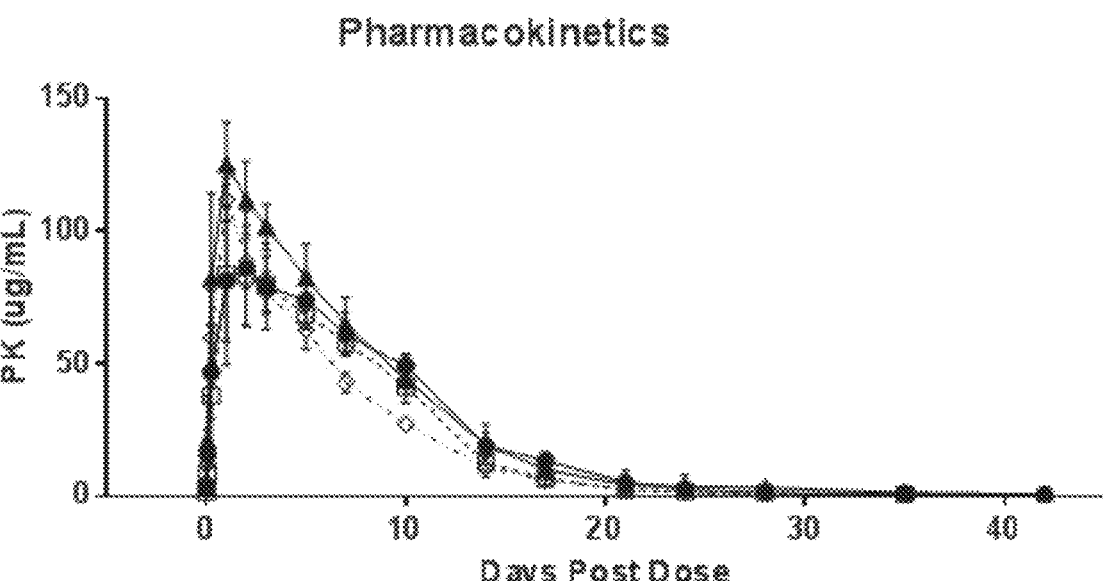
Figure 24B:
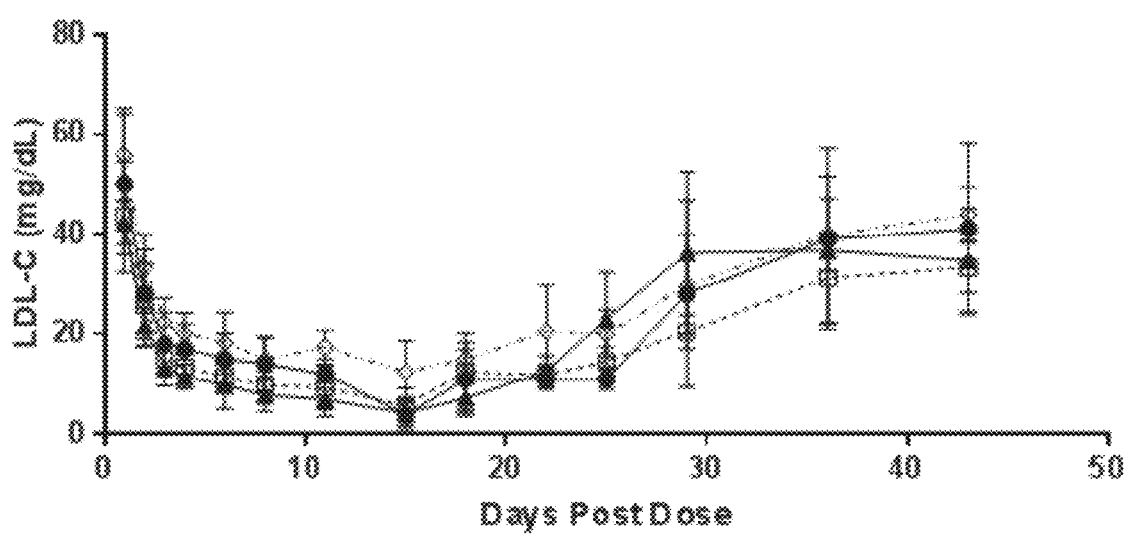

FIGS. 24A and 24B show a pharmacokinetic profile (μg/mL) with corresponding low density lipoprotein (LDL) concentration (mg/dL) profile in plasma. LDL concentrations and test article serum concentrations are presented as mean values from four animals. Solid circles with a solid line indicate the serum concentrations of the parent antibody AK. Open squares with a dashed line indicate the serum concentrations of the antibody bearing the Fab mutation. Solid triangles with a solid line indicate the serum concentrations of the antibody bearing the Fc mutation. Open diamonds with a dashed line indicate the serum concentrations of the antibody bearing both the Fab and Fc mutations. These data indicate that presence of a mutation in the Fc region that reduces viscosity of the antibody formulation results in a reduced time to Tmax and a higher Cmax. All the mutant forms of the parent antibody retain the ability to lower serum LDL-C (lower panel).

10

DETAILED DESCRIPTION OF THE INVENTION

Definition of Terms

In the description that follows, a number of terms are used extensively. The following definitions are provided to facilitate understanding of the invention.

Unless otherwise specified, "a", "an", "the", and "at least one" are used interchangeably and mean one or more than one.

"Antigen binding protein" refers to a protein or polypeptide that comprises an antigen-binding region or antigen-binding portion that has a strong affinity for another molecule to which it binds (antigen). Antigen-binding proteins encompass antibodies, peptibodies, antibody fragments (e.g., Fab, Fab', F(ab')₂, Fv, single domain antibody), antibody derivatives, antibody analogs, fusion proteins, and antigen receptors including chimeric antigen receptors (CARs).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas. Thus, as used herein, the term "antibody" or "antibody peptide(s)" refers to an intact antibody, an antibody that competes for specific binding with an antibody disclosed in this specification, or an antigen-binding fragment (e.g., Fab, Fab', F(ab')₂, Fv, single domain antibody) thereof that competes with the intact antibody for specific binding and includes chimeric, humanized, fully human, and bispecific antibodies. In certain embodiments, antigen-binding fragments are produced, for example, by recombinant DNA techniques. In additional embodiments, antigen-binding fragments are produced by enzymatic or chemical cleavage of intact antibodies. Antigen-binding fragments include, but are not limited to, Fab, Fab', F(ab)², F(ab')₂, Fv, and single-chain antibodies. Examples of antibodies suitable for use in the invention include, without limitation, the antibodies listed in FIGS. 1A and 1B as well as Abagovomab, Abciximab, Actoxumab, Adalimumab, Afclimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapincuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxctan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erenumab, Erlizumab, Ertumaxomab, Etaracizumab, Etrolizumab, Evolocumab, Exbivirumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixckizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxctumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxclumab, Ozanczumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Prezalumab, Priliximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanczumab, Solitomab, Sonepcizumab, Sontuzumab, Stamulumab, Sulesomab, Suvizumab, Tabalumab, Tacatuzumab tetraxctan, Tadocizumab, Talizumab, Tanczumab, Taplitumomab paptox, Tefibazumab, Telimomab aritox, Tenatumomab, Tefibazumab, Telimomab aritox, Tenatumomab, Teneliximab, Teplizumab, Teprotumumab, Tezepclumab, TGN1412, Tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urclumab, Urtoxazumab, Ustekinumab, Vapaliximab, Vatelizumab, Vedolizumab, Veltuzumab, Vepalimomab, Vesencumab, Visilizumab, Volociximab, Vorsctuzumab mafodotin, Votumumab, Zalutumumab, Zanolimumab, Zatuximab, Ziralimumab and Zolimomab aritox.

The term "isolated antibody" as used herein refers to an antibody that has been identified and separated and/or recovered from a component of its natural environment. Contaminant components of its natural environment are materials which would interfere with diagnostic or therapeutic uses for the antibody, and may include enzymes, hormones, and other proteinaccous or nonproteinaccous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassic blue or, preferably, silver stain. Isolated antibody includes the antibody in situ within recombinant cells since at least one component of the antibody's natural environment will not be present. Ordinarily, however, isolated antibody will be prepared by at least one purification step.

The term "bind (ing)" of an antigen or other polypeptide includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the binding of an anti-idiotypic antibody of the present invention to a receptor; the binding of an anti-anti-idiotypic antibody of the present invention to a ligand, receptor or antibody, etc.

The term "immunoglobulin" refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions.

Full-length immunoglobulin "light chains" (about 25 Kd or about 214 amino acids) are encoded by a variable region gene at the $NH_2$-terminus (about 110 amino acids) and a kappa or lambda constant region gene at the COOH-terminus. Full-length immunoglobulin "heavy chains" (about 50 Kd or about 446 amino acids), are similarly encoded by a variable region gene (about 116 amino acids) and one of the other aforementioned constant region genes (about 330 amino acids). Heavy chains are classified as gamma, mu, alpha, delta, or epsilon, and define the antibody's isotype as IgG (such as IgG1, IgG2, IgG3 and IgG4), IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd Edition, Raven Press, NY (1989)), Chapter 7 (incorporated by reference in its entirety for all purposes).

An immunoglobulin light or heavy chain variable domain or region comprises "framework regions" (FRs) interrupted by "complementarity determining regions" (CDRs). Kabat et al. (1991), *Sequences of Proteins of Immunological Interest,* 5th Edition, Public Health Service, National Institutes of Health, Bethesda, Md. (1991); Chothia et al. (1987), *J. Mol. Biol.* 196:901-917 (both of which are incorporated herein by reference). FR residues are those variable domain residues other than CDR region residues as herein defined. The sequences of the framework regions of different light or heavy chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen. Accordingly, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions—i.e., at least about 85-90%, preferably about 95% or more identical. Hence, all parts of a humanized immunoglobulin, except possibly the CDR's, are substantially identical to corresponding parts of natural human immunoglobulin sequences. Further, one or more residues in the human framework region may be back mutated to the parental sequence to retain optimal antigen-binding affinity and specificity. In this way, certain framework residues from the non-human parent antibody are retained in the humanized antibody in order to retain the binding properties of the parent antibody while minimizing its immunogenicity. The term "human framework region" as used herein includes regions with such back mutations. A "humanized antibody" is an antibody comprising a humanized light chain and a humanized heavy chain immunoglobulin. For example, a humanized antibody would not encompass a typical chimeric antibody as defined below, e.g., because the entire variable region of a chimeric antibody is non-human.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. (1984), *Proc. Natl. Acad. Sci. USA*, 81:6851-6855). Chimeric antibodies of interest herein include "primitized" antibodies comprising variable domain antigen-binding sequences derived from a non-human primate (e.g., Old World Monkey, Ape, etc.) and human constant region sequences. A variety of approaches for making chimeric antibodies have been described. See e.g., Morrison et al. (1985), *Proc. Natl. Acad. Sci. U.S.A.* 81:6851; Takeda et al. (1985), *Nature* 314:452, Cabilly et al., U.S. Pat. No. 4,816,567; Boss et al., U.S. Pat. No. 4,816,397; Tanaguchi et al., EP 0171496; EP 0173494; and GB 2177096.

The terms "human antibody" and "fully human antibody" each refer to an antibody that has an amino acid sequence of a human immunoglobulin, including antibodies isolated from human immunoglobulin libraries or from animals transgenic for one or more human immunoglobulins and that do not express endogenous immunoglobulins; for example, Xenomouse® antibodies and antibodies as described by Kucherlapati et al. in U.S. Pat. No. 5,939,598.

The term "genetically altered antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from changes to just one or a few amino acids to complete redesign of, for example, the variable and/or constant region. Changes in the constant region will, in general, be made in order to improve or alter characteristics, such as complement fixation, interaction with membranes and other effector functions, as well as manufacturability and viscosity. Changes in the variable region will be made in order to improve the antigen binding characteristics.

A "Fab fragment" is comprised of one light chain and the $C_{H1}$ and variable regions of one heavy chain. The heavy chain of a Fab molecule cannot form a disulfide bond with another heavy chain molecule.

A "Fab' fragment" contains one light chain and one heavy chain that contains more of the constant region, between the $C_{H1}$ and $C_{H2}$ domains, such that an interchain disulfide bond can be formed between two heavy chains to form a $F(ab')_2$ molecule.

A "$F(ab')_2$ fragment" contains two light chains and two heavy chains containing a portion of the constant region between the $C_{H1}$ and $C_{H2}$ domains, such that an interchain disulfide bond is formed between two heavy chains.

The terms "Fv fragment" and "single chain antibody" refer to polypeptides containing antibody variable regions from both heavy and light chains but lacking constant regions. Like a whole antibody, it is able to bind selectively to a specific antigen. With a molecular weight of only about 25 kDa, Fv fragments are much smaller than common antibodies (150-160 kD) which are composed of two heavy protein chains and two light chains, and even smaller than Fab fragments (about 50 kDa, one light chain and half a heavy chain).

A "single domain antibody" is an antibody fragment consisting of a single domain Fv unit, e.g., $V_H$ or $V_L$. Like a whole antibody, it is able to bind selectively to a specific antigen. With a molecular weight of only 12-15 kDa, single-domain antibodies are much smaller than common antibodies (150-160 kDa) which are composed of two heavy protein chains and two light chains, and even smaller than Fab fragments (.about.50 kDa, one light chain and half a heavy chain) and single-chain variable fragments (.about.25 kDa, two variable domains, one from a light and one from a heavy chain). The first single-domain antibodies were engineered from heavy-chain antibodies found in camelids. Although most research into single-domain antibodies is currently based on heavy chain variable domains, light chain variable domains and nanobodies derived from light chains have also been shown to bind specifically to target epitopes.

The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In some embodiments, an antigen binding protein of the present invention selectively inhibits the human antigen of the antibody from which it is derived. For example, the antigen binding protein having the sequence of antibody AF as substituted as described herein will selectively inhibit the antigen in FIG. 1B of antibody AF. An antibody or functional fragment thereof "selectively inhibits" a specific receptor or ligand relative to other receptors or ligands when the IC50 of the antibody in an inhibition assay of the specific receptor is at least 50-fold lower than the IC50 in an inhibition assay of another "reference" ligand or receptor. An "IC50" is the dose/concentration required to achieve 50% inhibition of a biological or biochemical function. With radioactive ligands, IC50 is the concentration of a competing ligand that displaces 50% of the specific binding of the radioactive ligand. The IC50 of any particular substance or antagonist can be determined by constructing a dose-response curve and examining the effect of different concentrations of the drug or antagonist on reversing agonist activity in a particular functional assay. IC50 values can be calculated for a given antagonist or drug by determining the concentration needed to inhibit half of the maximum biological response of the agonist. Thus, the IC50 value for any anti-PCSK9 antibody or functional fragment thereof, for example, can be calculated by determining the concentration of the antibody or fragment needed to inhibit half of the maximum biological response of PCSK9 in activating the human PCSK9 receptor in any functional assay. An antibody or functional fragment thereof that selectively inhibits a specific ligand or receptor is understood to be a neutralizing antibody or neutralizing fragment with respect to that ligand or receptor. Thus, in some embodiments, the anti-PCSK9 antibody or functional fragment is a neutralizing antibody or fragment of human PCSK9.

The substituted antigen binding proteins of the present invention can cross-block the unsubstituted antibodies from which they are derived. The terms "cross-block," "cross-blocked," and "cross-blocking" are used interchangeably herein to mean the ability of an antigen binding protein to interfere with the binding of other antigen binding proteins (e.g., antibodies or binding fragments) to a target (e.g., human PCSK9). The extent to which an antibody or binding fragment is able to interfere with the binding of another to a target and therefore whether it can be said to cross-block, can be determined using competition binding assays. In some embodiments, a cross-blocking antigen binding protein of this invention reduces binding of a reference antibody to the target antigen between about 40% and 100%, such as about 60% and about 100%, specifically preferably between about 70% and 100%, and more specifically preferably between about 80% and 100%. A particularly suitable quantitative assay for detecting cross-blocking uses a Biacore machine which measures the extent of interactions using surface plasmon resonance technology. Another suitable quantitative cross-blocking assay uses a FACS-based approach to measure competition between antibodies in terms of their binding to the target antigen.

The term "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., .alpha.-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids", which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

An "isolated nucleic acid molecule" is a nucleic acid molecule that is not integrated in the genomic DNA of an organism. For example, a DNA molecule that encodes a heavy chain of an antibody that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGchec et al. (1993), *Mol. Endocrinol.,* 7:551), cyclic AMP response elements (CREs), serum response elements (SREs; Treisman (1990), *Seminars in Cancer Biol.,* 1:47), glucocorticoid response elements (GREs), and binding sites for other transcription factors, such as CRE/ATF (O'Reilly et al. (1992), *J. Biol. Chem.,* 267:19938), AP2 (Ye et al. (1994), *J. Biol. Chem.,* 269:25728), SPI, CAMP response element binding protein (CREB; Locken (1993), *Gene Expr.,* 3:253) and octamer factors (see, in general, Watson et al. (1987), eds., *Molecular Biology of the Gene,* 4th Edition, The Benjamin/Cummings Publishing Company, Inc., and Lemaigre et al. (1994), *Biochem. J.,* 303:1). If a promoter is an inducible promoter, then the rate of transcription increases in response to an inducing agent. In contrast, the rate of transcription is not regulated by an inducing agent if the promoter is a constitutive promoter. Repressible promoters are also known.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific", "tissue-specific", or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces an antagonist of the present invention from an expression vector. In contrast, such an antagonist can be produced by a cell that is a "natural source" of said antagonist, and that lacks an expression vector.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "fusion protein" is a hybrid protein expressed by a nucleic acid molecule comprising nucleotide sequences of at least two genes. For example, a fusion protein can comprise at least part of an antibody heavy chain fused with a polypeptide that binds an affinity matrix or another target of interest.

The term "receptor" denotes a cell-associated protein that binds to a bioactive molecule termed a "ligand." This interaction mediates the effect of the ligand on the cell. Receptors can be membrane-bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor. In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increased cyclic AMP production, mobilization of cellular calcium, mobilization of membrane lipids, cell adhesion, hydrolysis of inositol lipids and hydrolysis of phospholipids.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ M$^{-1}$.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a polyhistidine tract, protein A (Nilsson et al. (1985), *EMBO J.* 4:1075; Nilsson et al. (1991), *Methods Enzymol.,* 198:3), glutathione S transferase (Smith et al. (1988), *Gene,* 67:31), Glu-Glu affinity tag (Grussenmeyer et al (1985), *Proc. Natl. Acad. Sci. USA* 82:7952), substance P, FLAG® peptide (Hopp et al. (1988), *Biotechnology* 6:1204), streptavidin binding peptide, or other antigenic epitope or binding domain. See, in general, Ford et al. (1991), *Protein Expression and Purification,* 2:95. DNA molecules encoding affinity tags are available from commercial suppliers (e.g., Pharmacia Biotech, Piscataway, N.J.).

The terms "acidic residue" and "charged negative residue" refer to amino acid residues having sidechains comprising acidic groups. Exemplary acidic or charged negative residues include D and E.

The term "amide residue" refers to amino acids having sidechains comprising amide derivatives of acidic groups. Exemplary amide residues include N and Q.

The term "aromatic residue" refers to amino acid residues having sidechains comprising aromatic groups. Exemplary aromatic residues include F, Y, and W.

The terms "basic residue" and "charged positive residue" refer to amino acid residues having sidechains comprising basic groups. Exemplary basic or charged positive residues include H, K, and R.

The terms "hydrophilic residue" and "polar uncharged residue" refer to amino acid residues having sidechains comprising polar groups. Exemplary hydrophilic or polar uncharged residues include C, S, T, N, and Q.

The terms "non-functional residue" and "small hydrophobic residue" refer to amino acid residues having sidechains that lack acidic, basic, or aromatic groups. Exemplary non-functional, small hydrophobic residues include M, G, A, V, I, L and norleucine (Nle).

One aspect of this invention concerns PCSK9 binding polypeptides. "PCSK9-binding polypeptide" means a polypeptide that binds proprotein convertase subtilisin/kexin type 9 (PCSK9) protein. In some cases, the PCSK9-binding polypeptide blocks binding of PCSK9 to low-density lipid receptors (LDLRs). Such blocking PCSK9-binding polypeptides can be monoclonal antibodies (mAbs) and can be one of the following:

a. a mAb comprising a heavy chain polypeptide having an amino acid sequence of SEQ ID NO: 136 and a light chain polypeptide having an amino acid sequence of SEQ ID NO: 134 (antibody AK, evolocumab), or an antigen-binding fragment thereof;

b. a mAb that competes with evolocumab for binding to PCSK9;

c. a mAb comprising:

i. a heavy chain polypeptide comprising the following complementarity determining regions (CDRs): a heavy chain CDR1 that is a CDR1 in SEQ ID NOs: 376 or 378; a heavy chain CDR2 that is a CDR2 in SEQ ID Nos: 376 or 378; a heavy chain CDR3 that is a CDR3 in SEQ ID NOs: 376 or 378, and ii. a light chain polypeptide comprising the following CDRs: a light chain CDR1 that is a CDR1 in SEQ ID NOs: 377 or 379; a light chain CDR2 that a CDR2 in SEQ ID NOs: 377 or 379; and a light chain CDR3 that is a CDR3 in SEQ ID NOs: 377 or 379;

d. a mAb that binds to at least one of the following residues of PCSK9, the PCSK9 comprising an amino acid sequence of SEQ ID NO: 369: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;

e. a mAb that binds to PCSK9 at an epitope on PCSK9 that overlaps with an epitope that is bound by an antibody that comprises:

i. a heavy chain variable region of the amino acid sequence in SEQ ID NO: 136; and ii. a light chain variable region of the amino acid sequence in SEQ ID NO: 134, and iii. wherein the epitope of the mAb further overlaps with a site to which binds an epidermal growth factor-like repeat A (EGF-A) domain of the low density lipoprotein receptor (LDLR) protein (Horton, Cohen, & Hobbs (2007), *Trends Biochem Sci*, 32 (2), 71-77. doi: 10.1016/j.tibs.2006.12.008; Seidah & Prat (2007), *J Mol Med* (Berl), 85 (7), 685-696;

f. a mAb that comprises a heavy chain polypeptide comprising the following complementarity determining regions (CDRs):

i. heavy chain CDR1, CDR2, and CDR3 having an amino acid sequence of SEQ ID NOs: 373, 374, and 375, respectively; and ii. light chain CDR1, CDR2, and CDR3 having an amino acid sequence of SEQ ID NOs: 369, 370, and 371, respectively; or g. a mAb that comprises the heavy chain variant region sequence of SEQ ID NO: 378 and the light chain variant region sequence of SEQ ID NO: 379.

PREFERRED EMBODIMENTS

Correlation of Global Sequence Features to Viscosity

The main goal of the study reported in Example 1 of this specification was to identify a link between viscosity and amino acid sequence, or global sequence features of IgG monoclonal antibodies with the purpose of reducing viscosity of high-concentration monoclonal antibody formulations. For that, viscosity values of 43 different monoclonal antibodies were measured at 150 mg/ml to provide a wide range of values from 5 to 33 cP (FIGS. 1A and 1B). Main global sequence features of the monoclonal antibodies, such as light and heavy chain types, their subtypes (germlines), and pI were calculated and correlated to viscosity, but did not immediately reveal significant correlations (FIGS. 1A and 1B). Polymorphisms (known as allotypes) within the IgG isotypes were described using serological reagents derived from humans (Ropartz, C., Schanfield, M. S., and Steinberg, A. G. (1976), "Review of the notation for the allotypic and related markers of human immunoglobulins," WHO meeting on human immunoglobulin allotypic markers, held 16-19 Jul. 1974, Rouen, France; report amended June 1976, *J Immunogenet*. 3, 357-362) and correlated to certain amino acid residues in several specific positions in conserved regions of heavy and light chains (Jefferis and Lefranc (2009) Human immunoglobulin allotypes: possible implications for immunogenicity, mAbs 1, 332-338.) (Vidarsson, G., Dekkers, G., and Rispens, T. (2014) IgG subclasses and allotypes: from structure to effector functions, Front Immunol. 5, 1-17). The allotypes introduce a few different residues (described below) in otherwise conserved regions of light and heavy chains. All kappa light chains used in this study were the same (3) allotype (featuring residues A153, V191 in EU numbering). All IgG2 heavy light chains were the same (n-) allotype (featuring P189). Four IgG1 heavy chain allotypes were described (including the following related residues in EU numbering): f (R214); z (K214); a (D356, L358) and x (G431) (Jefferis & Lefranc, 2009) (Vidarsson et al., 2014). IgG1 heavy chains with alternative residues in the positions E356, M358 and A431 do not constitute allotypes because these amino acid residues are present in other IgG subclasses. IgG1 allotype (x) was not present in the study; all IgG1 heavy chains had A431. IgG1 heavy chain allotypes (f), (z), (a) and related residues are shown in FIGS. 1A and 1B.

The antibodies in FIGS. 1A and 1B are sorted by viscosity. The table in FIGS. 1A and 1B includes the monoclonal antibody name, measured concentrations, measured viscosity values and global sequence parameters including type, subtype and calculated pI. IgG1 type, lambda light chains and VH1 heavy chain subtype are in boldface type.

IgG1 and IgG2 heavy chains and kappa and lambda light chains were rather evenly distributed across the viscosity range. A sequence assessment of subtypes revealed several high viscosity and low viscosity subtype pairs: VH1|1-18 and VH1|1-02; VH3|3-33 and VH3|3-07; VK3|L16 and VK3|A27 with the probability of random correlation at 0.0002; 0.076 and 0.031, respectively, correlating to viscosity residues (FIG. 2). The study looked for viscosity correlations to D and J region sequences but found no significant correlation.

FIG. 2 shows p-values, which indicate probability of random correlation to viscosity. FIG. 2 also shows residues in high viscosity subtype, positions in Aho numbering, and residues in low viscosity subtypes.

Among the fourteen IgG molecules of VH1 subtype, high viscosity was strongly associated with VH1 1-18 subtype and low viscosity with VH1 1-01 subtype with the very low probability of this being a random coincidence (FIG. 9).

In order to assess the correlation between the two subtypes and viscosity, probability of the same population mean by Student's t-test was calculated for VH1|1-02 versus VH1|1-18, VH3|3-33 versus VH3|3-07 and VK3|L16 versus VK3|A27 using t-test two-sample equal variants with a two-tailed distribution.

An association (t-test, p=0.031) of light chain VK3|L16 with high viscosity and VK3|A27 with low viscosity was detected (FIG. 2, FIG. 12, left side). VK3|L16 versus VK3|A27 and VH3|3-33 versus VH3|3-07 are discussed further in this specification. Due to the strong correlation to viscosity, VH1|1-18 and VH1|1-02 were further evaluated as follows. As the next step, 43 antibody chain sequences were aligned and assessed as follows.

Sequence Alignment and Numbering System

Several IgG numbering systems exist, including:

EU—Edelman et al. (1969), "The covalent structure of an entire gamma immunoglobulin molecule," *Proc. Natl. Acad. Sci. U.S.A.* 63, 78-85;

Kabat—Kabat et al. (1991), *Sequences of proteins of immunological interest*, Fifth Edition. NIH Publication No. 91-3242;

Chothia—Chothia et al. (1992), "Structural repertoire of the human VH segments," *J. Mol. Biol.* 227:799-817; Tomlinson et al., (1995), "The structural repertoire of the human V kappa domain. *EMBO J.* 14:4628-4638;

Aho—Hoenegger et al. (2001), "Yet another numbering scheme for immunoglobulin variable domains: an automatic modeling and analysis tool," *J. Mol. Biol.* 309, 657-670;

and others. All four numbering systems mentioned above are illustrated in FIG. 9, right side for frame region 3 of the heavy chain of VH1 subtype. The Aho scheme was built by utilizing spatial positions of amino acid residues derived from more than 400 crystal structures of variable domains of different antibodies. The Aho numbering system defined by A. Honegger (citation above) was used in this work because it is a 3D structure-based numbering system. This creates an advantage specifically for residues in CDRs: Residues with the same numbers are located in similar spatial areas and are comparable across different IgG sequences. Since residue positions in the Aho numbering scheme are related to tertiary structure, they should be more associated with biophysical and biochemical properties and, possibly, viscosity. Aho numbering is aligned and correlated with the other main numbering schemes as it is shown in several tables of this specification. Any of the four numbering systems can be interchangeably used to identify the preferred amino acid substitutions. The heavy chain variable region ends at the following residues for different numbering systems: 149 Aho, 117 EU, 113 Kabat, 113 Chothia. The light chain variable region ends at 149 Aho, 107 EU, 107 Kabat, 107 Chothia. Aho numbering allocates more numbers for CDR regions instead of using letters for CDR residues as in Kabat and Chothia (for example 82b for Kabat and Chothia). As a result, Aho numbers for the same residues are often larger. Each variable region includes three complementarity determining regions (CDRs) and four framework regions (FRs) in the following sequence: FR1-CDR1-FR2-CDR2-FR3-CDR3-FR4. While CDRs provide great sequence diversity with the purpose of binding to antigens (CDR3 regions bind most often), FR sequences are more conserved and contain only a few differences, some of which are subtype specific.

Correlation of Sequences to Viscosity

In addition to assessing the global sequence features, the variable regions' sequences were aligned to identify the residues responsible for the viscosity differences. In addition to visual observations, a software machine learning algorithm was developed and applied to identify the residues impacting viscosity the most and to predict antibodies' viscosity values from their sequences. The predictive model was constructed using charge and hydrophobicity of residues in Aho-aligned positions.

Heavy chain VH1 sequence alignment and assessment of the five sequences of high-viscosity VH1 1-18 subtype and five sequences of low-viscosity VH1 1-02 subtype molecules revealed that only 4 residues were different between the two subtypes in frames, all four located in framework 3 (FIG. 9, right side). A larger number of sequence differences were observed in CDRs, but they were left beyond the scope of the study, since CDRs are often involved in binding to the antigens, and engineering (mutating residues in) CDRs with a goal of reducing viscosity would carry a significant risk of losing potency. The subtype-related differences in viscosity and residues in FR3 indicated that the following amino acid substitutions could potentially reduce viscosity in Aho numbering: T82R, T86I, R94S and S95R. The software algorithm supported the four substitutions and also suggested that the following two substitutions correlated with reduction of viscosity: light chain G13V/L in FR1 and heavy chain S59R/K from the edge of CDR2, the latter correlation observed in VH3 subtype (FIG. 9, right side).

In Silico Assessment of Suggested Amino Acid Substitutions

VH T82R. R82 occurs with high frequency in VH1-02. IgG structure modeling indicated that heavy chain Aho position 82 is a part of the upper core of the globulin fold and does not typically contact the antigen, but it can directly contact CDR backbones according to Ewert et al. (2003), "Biophysical properties of human antibody variable domains," *J. Mol. Biol.* 325:531-553. HC82 has very conserved main chain-side chain H-bond interactions with CDR 1 and CDR2 backbone amides (Honegger et al., supra). R82 may also coordinate the backbone oxygen atoms of the CDR2 loop.

VH R94S and S95R. S94 and R95 occur with high frequency in VH1-02. These positions are located on the surface, away from the antigen binding domain and are considered a part of the lower core.

T86I. I86 occurs with high frequency in VH1-02. The data suggest substituting a hydrophobic residue (I) for hydrophilic one (T) on the surface, which can potentially lead to aggregation.

VH S59R/K—Within VH1 and VH3, a hydrophilic position 59 associates with lower viscosity. VH S59R/K position has high structural and sequence variability, is fairly solvent exposed, and is directly in between residues 58 and 60, which are part of the upper core and may affect binding. The structure will likely depend directly on the differences in residues 58 and 60 (especially 58 if it is buried). R/K59 has low frequency of occurrence (below 2%), and was not observed in VH1 according to the amino acid residue frequency analysis. All R/K59s are accommodated within the VH3 dataset except one (VH4).

VL G13V/L—This position is structurally buried and is a part of the lower core of the variable domain according to Ewert et al., supra. From this point of view, a G13V mutation to a more hydrophobic residue should make the core stronger.

To summarize, in silico sequence analysis indicated that the proposed mutations do not introduce any additional glycosylation sites or sites susceptible to rapid degradation under physiological or mildly acidic formulation conditions (NG, NS, NT, DG, DH). VH T82R, T86I, R94S and S95R mutations would provide a switch from subtype VH1-18 to VH1-02 in frame region 3, so they should not introduce any unusual or rare motifs. The addition of VH S59R and VL G13V mutations was suggested by the software from the VH3 subtype, outside of VH1. None of the mutation sites is positioned close to the binding regions, except for S59R, which is at the edge of HC CDR2 and, therefore, represents a mild risk of interfering with potency/binding. Arginine is a very low frequency residue in position 59 (R59), so prediction of its impact is difficult. T86I was identified as a high risk for aggregation and removed from the list of mutations.

Produced Mutants and their Expression, Potency, Chemical Modifications, Glycosylation and Viscosity.

Taking into account the above considerations, several mutants were produced for two IgG2 antibodies AK and AO of the high-viscosity VH1-18 subtype with the goal of reducing viscosity while maintaining potency (FIG. 9B). FIG. 9B includes monoclonal antibody mutant symbols and related mutations on the heavy and light chain.

Figures 3A, 3B, 3C:
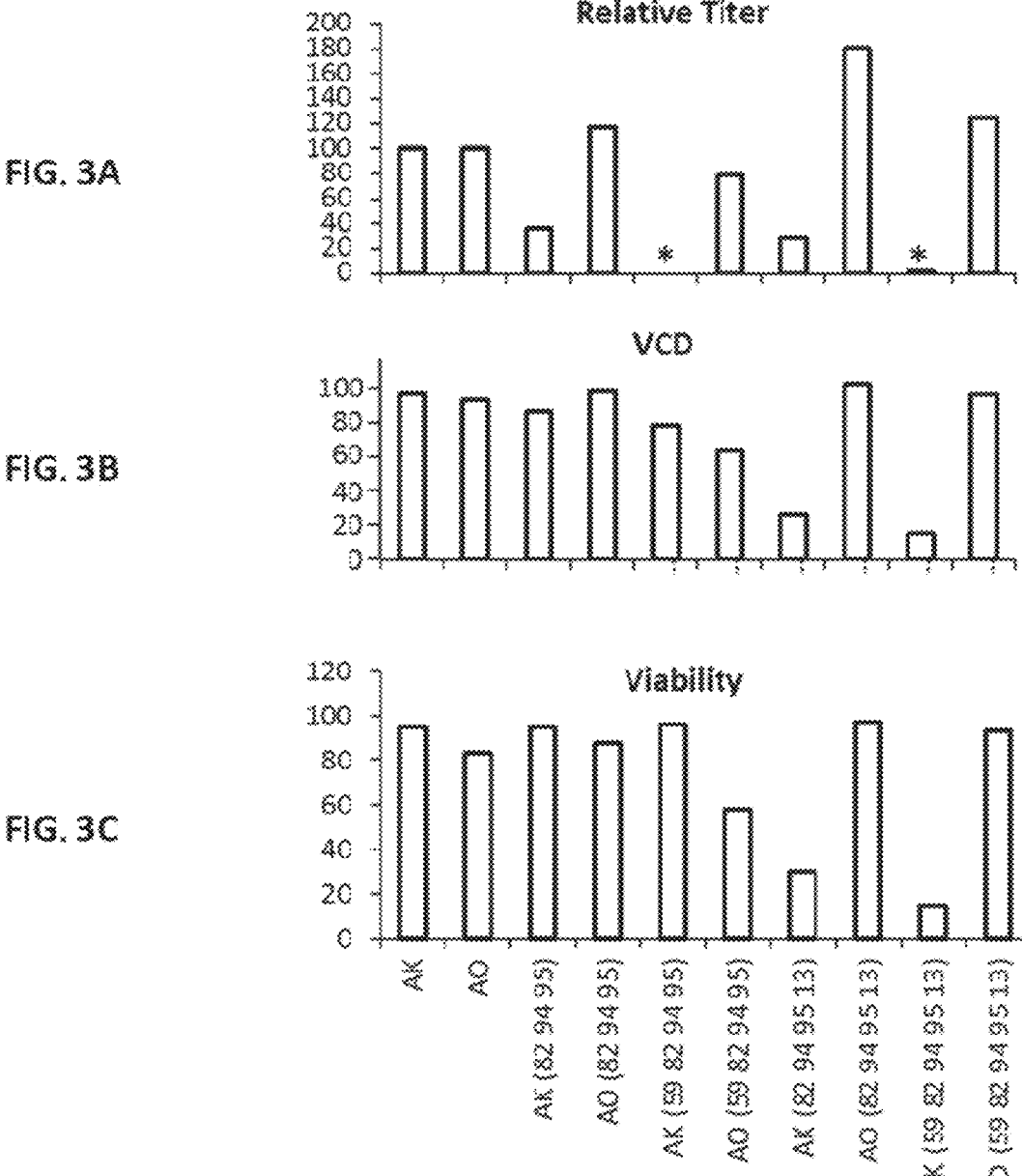
FIG. 3 shows expression results for AK and AO antibody molecules and their mutants, including relative values for titer, final viable cell density (VCD) and viability at harvest after 7 days of cell culture. AK values are at 100%.

A very low expression level was observed for both AK mutants containing the S59R substitution (marked with * on FIG. 3). Viability and viable cell density was also low for one of them, AK (59 82 94 95 13). On the other hand, antibody AO mutants containing the S59R substitution produced a titer comparable to that of the AO parent molecule. Although the statistics were not sufficient to make a general conclusion about heavy chain position 59, the case suggested that a single amino acid substitution may dramatically alter expression. Chemical modifications, including oxidation, deamidation, isomerization and the glycosylation pattern, were similar among the two parents and their mutants as measured by peptide mapping LC-MS analysis.

Figure 4:
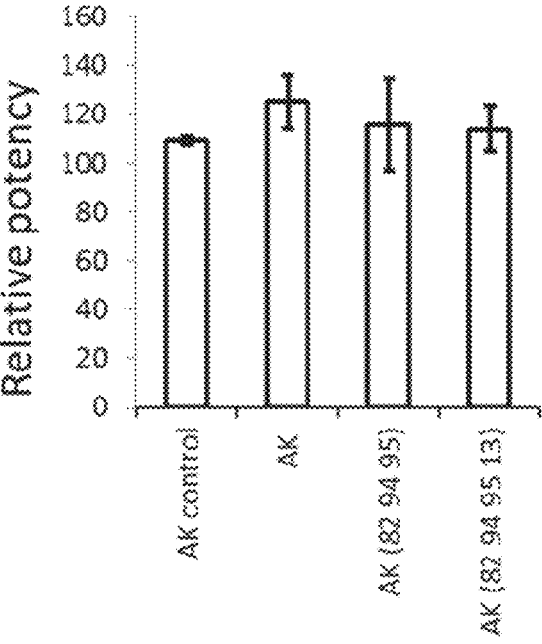
FIG. 4 shows potency of AK parent antibodies (AK control, AK) and their mutants.
Figure 5:
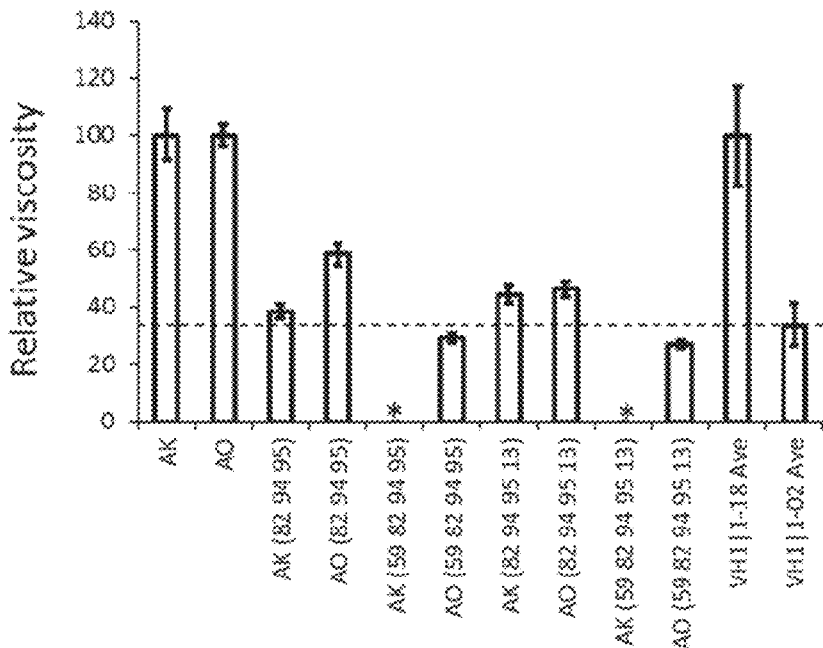
FIG. 5 shows viscosity of mutants relative to the parent AK and AO antibodies. Average viscosity values of high viscosity VH1|1-18 and low viscosity VH1|1-02 from the set of 43 antibodies are also shown for comparison.

Potency values of the parent AK antibody and the two well-expressed mutants, measured through binding to PCSK9, were similar (FIG. 4). Finally, measured viscosity values of the AK and AO mutants were significantly lower than the parents, as predicted (FIG. 5). For example, the AK (82 94 95) mutant was at only 39% of the parent's viscosity. Viscosity of both AO mutants containing the S59R substitution was even lower, at approximately 28% of the parent's viscosity (FIG. 5). The S59R mutants did not express well for the AK antibody and the viscosity could not be measured. Average viscosity values for VH1|1-18 and VH1|1-02 germline subfamilies were added for comparison. A total of 12 consistent sequence differences were identified between VH1|1-18 and VH1|1-02 subfamilies, including 8 in CDRs and 4 in frame regions (FIG. 9). Three sites, all in frame region 3, were selected for amino acid substitutions from high viscosity VH1|1-18 to low viscosity VH1|1-02. The three point mutations in frames were introduced in two mAbs of VH1|1-18 subfamily (AK and AO) to convert only these residues to the residues present in VH1|1-02. Although chances to achieve the possible 2-fold decrease in viscosity were theoretically low ($^3/_{12}$), these substitutions rather unexpectedly produced desirable outcome: with only three substitutions the viscosity decreased approximately two-fold in both antibody molecules.

Viscosity Versus pI

Figure 6:
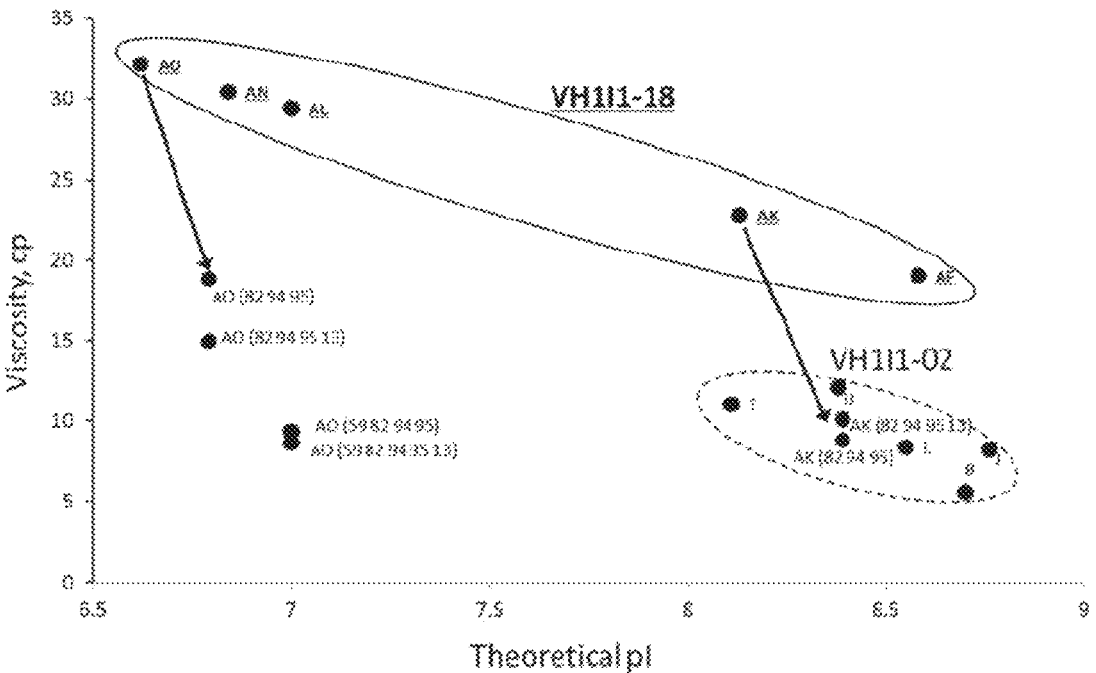
FIG. 6 shows measured viscosity values of mAbs of the high viscosity VH1|1-18 and the low viscosity VH1|1-02 subtypes versus calculated whole molecule pI values. The low-viscosity mutants of AK and AO antibodies are also shown.

Although the dependence of viscosity from pI was not clear from the whole set of the 43 mAbs, the VH1 subset clearly showed that viscosity steadily increased when pI values of the mAbs decrease from pI 8.5 to pI 6.5 in the pH 5.2 formulation (FIG. 6). The shift between the high-viscosity VH1|1-18 mAbs and low-viscosity VH1|1-02 mAbs can be also seen. As predicted, T82R, R94S and S95R mutants of AK and AO antibodies moved approximately two fold down along the viscosity scale from the VH1|1-18 to the VH1|1-02 area on the plot (FIG. 6). Mutants AO (59 82 94 95) and AO (59 82 94 95 13) moved to even lower viscosity and to slightly higher pI, indicating that the S59R substitution, adopted from outside of the VH1 group, was effective in further reducing viscosity. Unfortunately, AK mutants containing R59 were not expressed well, suggesting that appearance of the low-frequency arginine residue in position 59 may affect expression.

An increase in pI for antibodies in formulations with pH<pI (for example, the mildly acidic formulation used in this study) typically leads to a decrease in viscosity. This result can be explained by the columbic repulsion of the positively charged antibody molecules. It is known that proteins, including antibodies, show poor solubility and high precipitation, which affect viscosity, at high concentrations. It is interesting that the VH1|1-18 to VH1|1-02 substitutions in frame region 3 resulted in a two-fold decrease in viscosity and only a minor increase in antibody pI values, suggesting that not the charge increase, but rather some structural changes may be responsible for the dramatic decrease in viscosity.

After superimposing crystallography structures of hundreds of Fab domains, hydrogen bond interactions for every VH and VL position were identified (Honegger et al. (2001), "Yet another numbering scheme for immunoglobulin variable domains: an automatic modeling and analysis tool," *J. Mol. Biol.* 309:657-670). The data indicate that the identified positions may be bound to other residues through main-chain and side-chain hydrogen bond interactions (for Type III AK and AO antibody molecules). For example, 94 was bound to 77 in some VH Type III immunoglobulin structures; 95 to 18; 59 to 67, 66, 65, 61, 60 and VL13 to 146, 148. Hence, residue substitutions at these positions may change the interactions and the immunoglobulin fold. The crystal structure of AK antibody (Jackson et al., 2007), "The Crystal Structure of PCSK9: a Regulator of Plasma LDL-Cholesterol," Structure 15:545-52) suggests that all three positions 82, 94 and 95 are on the very periphery of the Fab regions and exposed to solvent and other antibody molecules. Changes in FR3 positions in VH3 (FIG. 11) and VK3 (FIG. 12) also correlate to viscosity. One explanation of their role in viscosity is that these positions in FR3 are on the periphery of the molecule and are actively engaged in the intermolecular interactions during shear stress associated with motion through the injection needles and viscosity measurements.

Figure 8:
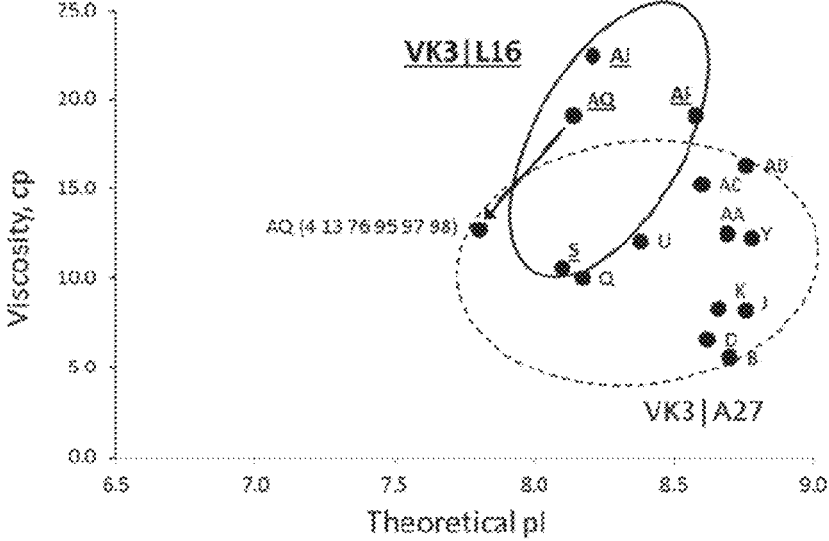
FIG. 8 shows measured viscosity values of mAbs with high viscosity VK3|L16 and VK3|L6 subfamilies and the low viscosity VK3|A27 subfamily versus calculated whole molecule pI values. The low-viscosity mutant AQ (4 13 76 95 97 98) is also shown.

Lower viscosity VK3|A27 and higher viscosity VK3|L16 antibodies showed inverse correlation between viscosity and pI (FIG. 8, FIG. 12).

Figure 7:
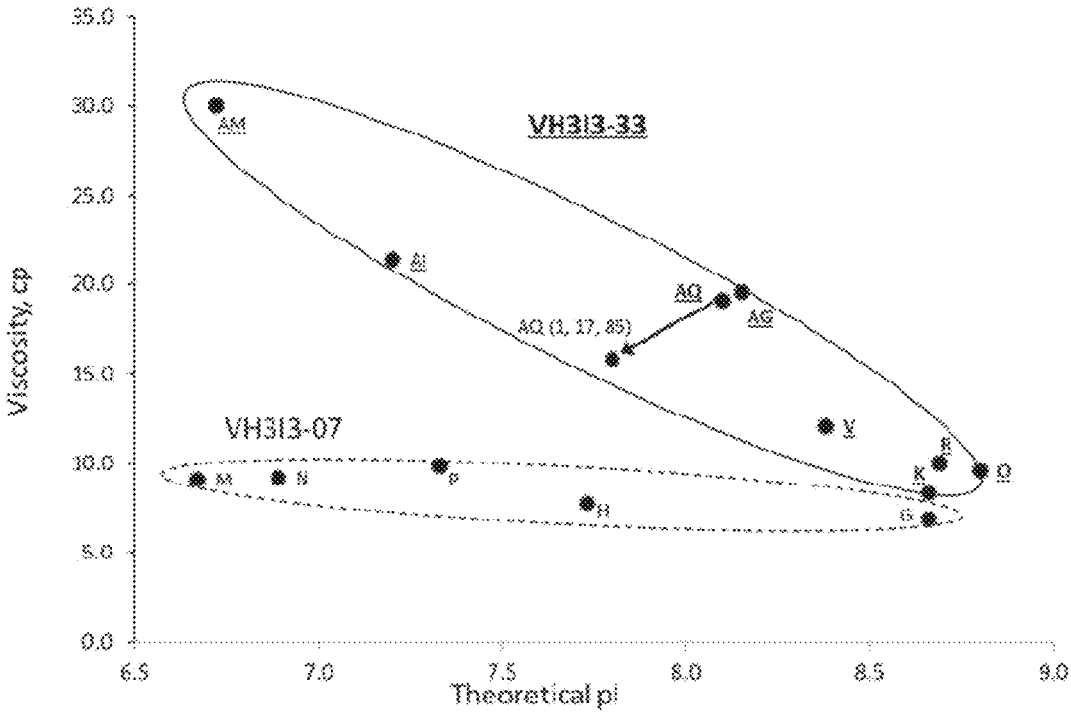
FIG. 7 shows measured viscosity values of mAbs of the high viscosity VH3|3-33 and the low viscosity VH3|3-07 subtypes versus calculated whole molecule pI. The low-viscosity mutant AQ (1, 17, 85) is also shown.

It needs to be mentioned that pI was a not very strong but in some cases useful predictor of viscosity. In general, viscosity decreased with increasing pI, and pI should be taken into account. For example, viscosity values of VH3l3-33 become lower and similar to VH3l3-07 for higher pI antibody molecules (FIG. 7). Hence, pI should be taken into account when predicting viscosity of VH3l3-33.

Proposed Viscosity Reduction for VH3 and VK3 Germline Families

High-viscosity VH3l3-33 and low-viscosity VH3l3-07 antibodies on average have a large difference in viscosity, while occupying a similar pI range (FIG. 7). Unexpectedly, on average, VH3l3-07 had lower viscosity and also lower pI, which contradicts typical behavior reported in the literature. Viscosity values of the following VH3l3-33 molecules can be reduced by the mutations: AQ, AM, AI, AG.

Monoclonal antibodies with high-viscosity VK3lL16 and low-viscosity VK3lA27 light chains also showed a large viscosity difference while showing relatively small difference in pI values, again suggesting a structural difference between subfamilies (FIG. 8). Viscosity values of the following VK3lL16 molecule can be reduced by the mutations described in FIG. 11: antibodies AQ and AF.

Figures 13A, 13B:
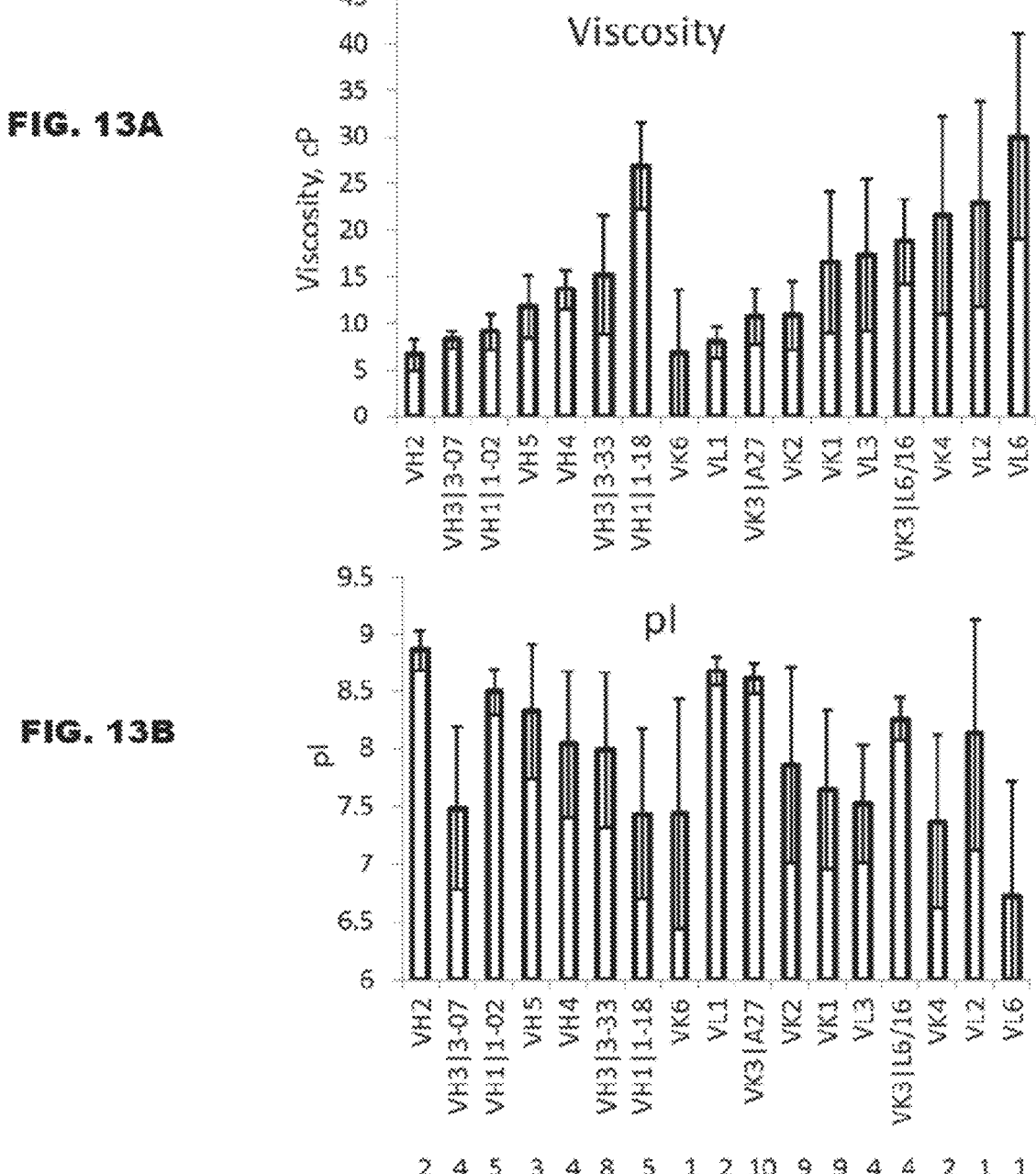
FIGS. 13A and 13B show average values for measured viscosity and calculated pI values for intact antibody molecules containing the specified heavy chain and light chain germline families and germline subfamilies of VH1, VH3 and VK3. The X-axis contains families and the number of members in each family and subfamily.
Figure 14A:
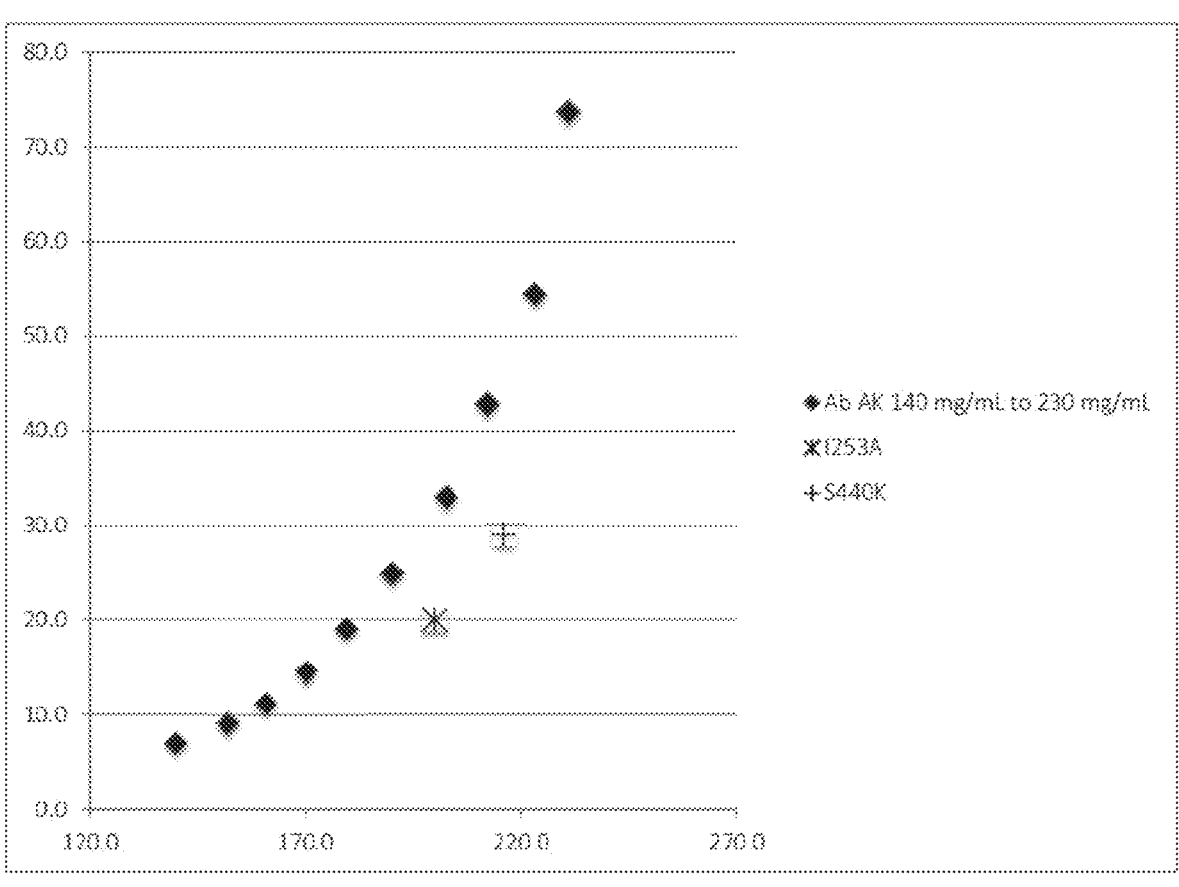
FIG. 14A shows that mutations in the Fc-Fc interaction surface can decrease solution viscosity. The viscosity of concentrations of antibody AK and antibody AK mutants I253A and S440K are shown.
Figure 14B:
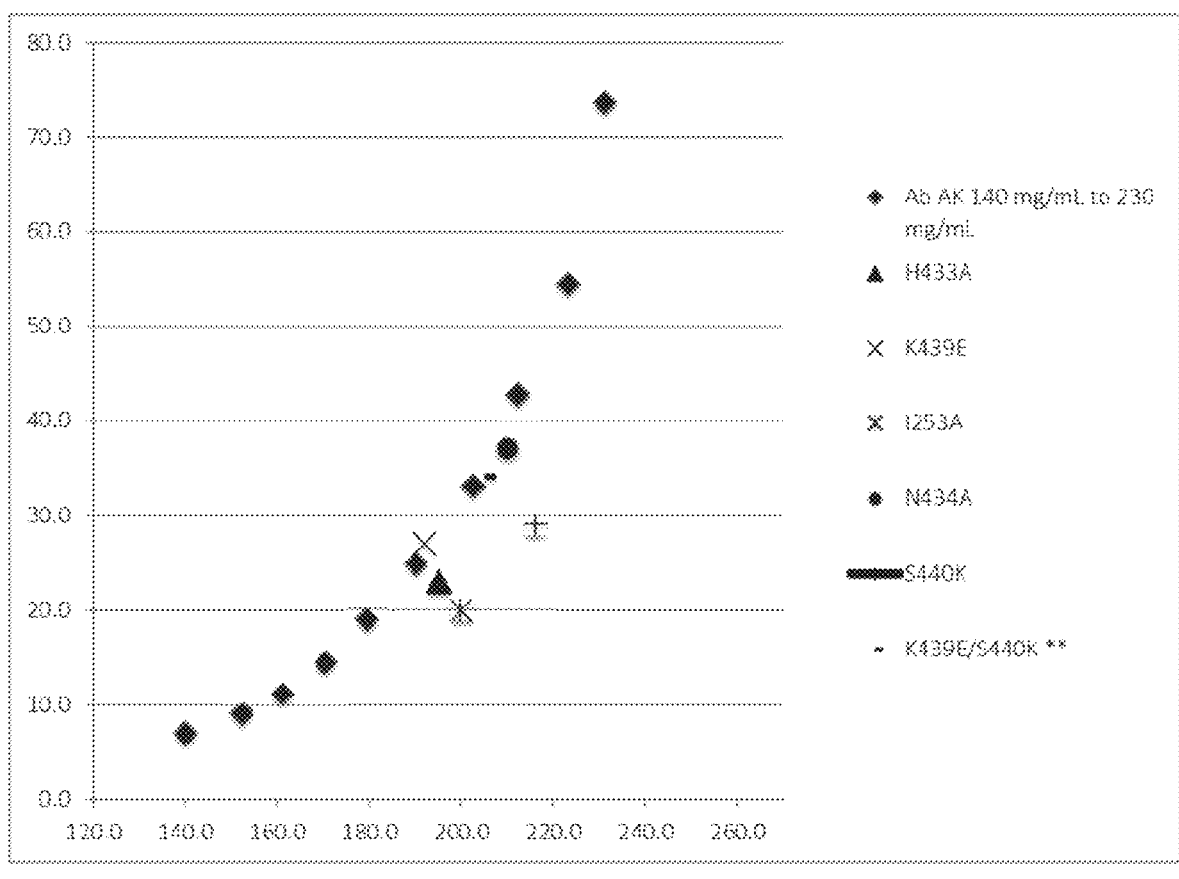

The analysis of global sequence features revealed the following high/low viscosity pairs: VH1l1-18/VH1l1-02; VK3lL16/VK3lA27; and VH3l3-33/VH3l3-07 with p-values of the correlation at 0.0002, 0.031 and 0.076, respectively (FIG. 2). Sequence positions and residues correlating to the viscosity differences were identified, and can be considered as candidates for viscosity lowering point mutations (FIG. 2). The performed above correlation of VH and VL families to viscosity indicates that theoretically antibodies with the following VH and VL combinations should have the lowest viscosity (FIGS. 13A and B): VH2, VH3l3-07, VH1l1-02 for VH and VK3, VL1, VK3lA27 for VL. Three antibodies of VH1l1-02 and VK3lA27 configuration practically occurred in our set and they indeed exhibited low viscosity values: B (5.6 cP), J (8.2 cP), Y (12.1 cP).

Chemical Cross-linking Studies

A broad survey of the potential protein-protein interactions in viscous antibody solutions was attempted using chemical cross-linking at high protein concentrations. Chemical cross-linking is a classic biochemical technique used to demonstrate that specific portions of proteins interact with each other. In this paper we describe the use of a zero length chemical cross-linking reagent to identify potential protein-protein interactions in high concentration viscous antibody solutions. The chemical cross-linking results of viscous and non-viscous antibodies are used to construct a model of potential protein-protein interactions in solution.

Chemical cross-linking with EDC reveals the presence of a common chemically cross-linkable oligomeric distribution. The chemical cross-link that results in the oligomeric pattern is surprisingly not inter-molecular but rather an intra-molecular cross-link. The intra-molecular cross-link between the top of the Fc and the bottom of a Fab results in an antibody conformation that may favor the formation of Fc-Fc mediated antibody oligomers. The 1HZH antibody crystal structure contains an antibody hexamer in the asymmetric unit that has one Fab arm pinned against the Fc domain to facilitate the Fc-Fc interaction critical to form the IgG1 hexamer. The appearance of this conformation may or may not be critical to the formation of the hexamer in the protein crystal. The increased propensity to form the hexamer in solution when the Fab-Fc intra-molecular chemical cross-link is present suggests that the Fab arm pinned to the Fc may have increased propensity to form Fc-Fc based antibody oligomers.

Decreasing Fc-Fc Interactions can Decrease Solution Viscosity

The scientific literature includes research on hexamer formation of antibodies related to interaction with Clq1 and CDC activity. Diebolder et al. found that anti-CD20 antibodies with certain Fc point mutations, including K439E and S440K, abrogated CDC activity but that the associated K439E/S440K double mutant restored CDC activity. Also I253A mutation decreased CDC activity. Diebolder et al. (2014), "Complement is Activated by IgG Hexamers Assembled at the Cell Surface," *Science* 343:1260-3. Diebolder et al. did not associate the mutants they disclose with an effect on antibody viscosity. Similarly, van den Bremer et al (2015) found that charged residues at the C-terminus of an antibody could decrease Clq1 interaction due to a decreased ability to form IgG hexamer structures. The authors did not associate the presence of charged residues at the C-terminus of IgGs to an effect on antibody solution viscosity.

The observation of a hexamer of antibodies in viscous antibody solutions suggested that the Fc-Fc interactions that are present in the antibody hexamer crystal structure as well as the structure thought to form prior to the recruitment of Clq1 (complement) are likely present in viscous antibody solutions in the absence of the chemical cross-linker EDC. In order to test whether the Fc-Fc interaction might contribute to solution viscosity, Fc mutants based on the work done by Diebolder et al. were generated at Amgen. The materials were then evaluated in anti-PCSK9 formulation buffer by cone and plate rheology. The comparison of parent anti-PCSK9 antibody AK and Fc mutant anti-PCSK9 antibodies demonstrated that decreasing the affinity of Fc for Fc does decrease the solution viscosity of the antibody. The point mutants retained FcRn binding capacity and there were no changes to bioactivity. The ability of a double mutant which restored wild-type complement activity to return to wild type viscosity demonstrates that the decrease in viscosity can be reversed if the ability of Fc-Fc interactions is restored to wild-type levels. Taken together with the observation of Fc-Fc mediated oligomeric species increasing solution viscosity, there is a common Fc-mediated protein-protein interaction that contributes to antibody solution viscosity. It needs to be noted that out of five mutations, S440K, I253A, K439E, H433A, N434A identified by Diebolder et al. as reducing CDC activity and tested for viscosity in this work, only the first two showed reduced viscosity in high concentration anti-PCSK9 formulation, while K439E, H433A and N343A did not reduce viscosity in high concentration anti-PCSK9 formulation, indicating that direct correlation does not exist and that people skilled in the art could not correctly anticipate lower viscosity from the information provided by Diebolder et al. The K439E mutant was also evaluated in a high protein concentration sucrose formulation and found to be less viscous than the parent anti-PCSK9 mutant at the same concentration. The presence of Arginine in the anti-PCSK9 formulation may have contributed to charge screening that may have decreased the effectiveness of the negative charge introduced in the K439E mutant to decrease Fc-Fc interactions. The H433A and the N434A mutants have no obvious charge screening sensitivity like the K439E mutant.

The Fc-Fc interaction may influence solution viscosity by increasing the number of potential interactions possible in two potential ways. It could increase the number of interactions per antibody from two CDR mediated interactions to two CDR mediated interactions plus 2 Fc mediated interactions per antibody or it could change the number of free CDR ends available in oligomers present in solution. Given the fact that the Fc domain of IgG1, IgG2, IgG3 and IgG4 antibodies are highly similar, it is likely that the Fc-Fc mediated interactions are present in all antibodies. The analysis of non-viscous antibodies shows that the intra-molecular cross-link which indicates the presence of an Fc-Fc interaction is absent in contrast to a viscous antibody at the same concentration. This suggests that the Fc-Fc interaction, although theoretically possible, is absent in non-viscous antibodies. The CDR next nearest neighbor interaction may influence the relative distance between Fc's as well as the relative orientation to enhance Fc-Fc interac-tion. This may explain why viscous antibodies have an Fc-Fc interaction while non-viscous antibodies do not at room temperature.

The presence of an Fc-Fc interaction also increases the likelihood that an oligomer of antibodies (dimer, trimer, tetramer, etc.) contains the maximum number of free CDR ends. The larger number of free CDR ends increases the number of CDR next nearest neighbor interactions. This in turn may increase network formation propensity and increase solution viscosity as a result of more efficient "percolation."

C-Terminal Modifications to Reduce Viscosity

Certain modifications at the antibody C-terminus interfere with C1q binding and complement-dependent cytotoxicity (CDC). Van den Bremer et al. (2015), "Human IgG is produced in a pro-form that requires clipping of C-terminal lysines for maximal complement activation," *mAbs* 7 (4): 672-80. The authors found that C-terminal lysine and C-ter-minal glutamic acid likely decreases the propensity of the Fc-Fc interactions that lead to a hexamer of antibodies that can most efficiently interact with C1q1. The authors con-structed mutants of a CD20 antibody and a CD38 antibody having PGKP, PGKKP, PGKKKP, and PGE at the C-termi-nus. They found that these mutants showed significantly reduced or completely lost CDC activity. Thus, one may conclude that the mutations blocked the hexamerization previously correlated by the authors with CDC activity. Given the present correlation of hexamerization with vis-cosity, such mutations should also reduce viscosity of anti-gen binding proteins. It is thus reasonable to conclude that placement of positively charged or negatively charged amino acids at the C-terminus, whether placed there by addition or substitution of existing C-terminal amino acids, will reduce the viscosity of an antigen binding protein.

Sequence Modification to Improve Pharmacokinetic Param-eters

This invention also includes the discovery of improved pharmacokinetic properties in antigen binding proteins hav-ing mutations that may also reduce viscosity. In particular, S440K mutations have been found to improve both Tmax (the time after dosing at which the maximum concentration was observed) and Cmax (the maximum observed concen-tration measured after dosing). Mutants of antibody AK having S440K, optionally with other mutations, have been found to have Tmax reduced by more than half that of the parental antibody AK after subcutaneous injection of the mutants and the parental antibody at the same concentration. Such mutants have also been found to have Cmax that is 28% or 42% higher after subcutaneous injection of the mutants and the parental antibody. See FIG. 22.

Nucleic Acids, Vectors, Host Cells

The invention also includes isolated nucleic acids encod-ing the bispecific antibodies of the invention, which includes, for instance, the light chain, light chain variable region, light chain constant region, heavy chain, heavy chain variable region, heavy chain constant region, linkers, and any and all components and combinations thereof of the bispecific antibodies disclosed herein. Nucleic acids of the invention include nucleic acids having at least 80%, more preferably at least about 90%, more preferably at least about 95%, and most preferably at least about 98% homology to nucleic acids of the invention. The terms "percent similar-ity", "percent identity" and "percent homology" when refer-ring to a particular sequence are used as set forth in the University of Wisconsin GCG® software program. Nucleic acids of the invention also include complementary nucleic acids. In some instances, the sequences will be fully comple-mentary (no mismatches) when aligned. In other instances, there may be up to about a 20% mismatch in the sequences. In some embodiments of the invention are provided nucleic acids encoding both a heavy chain and a light chain of an antibody of the invention.

Nucleic acids of the invention can be cloned into a vector, such as a plasmid, cosmid, bacmid, phage, artificial chro-mosome (BAC, YAC) or virus, into which another genetic sequence or element (either DNA or RNA) may be inserted so as to bring about the replication of the attached sequence or element. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfec-tion, for example.

In another embodiment, the present invention provides an expression vector comprising the following operably linked elements; a transcription promoter; a first nucleic acid molecule encoding the heavy chain of a bispecific antigen binding protein, antibody or antigen-binding fragment of the invention; a second nucleic acid molecule encoding the light chain of a bispecific antigen binding protein, antibody or antigen-binding fragment of the invention; and a transcrip-tion terminator. In another embodiment, the present inven-tion provides an expression vector comprising the following operably linked elements; a first transcription promoter; a first nucleic acid molecule encoding the heavy chain of a bispecific antigen binding protein, antibody or antigen-binding fragment of the invention; a first transcription terminator; a second transcription promoter a second nucleic acid molecule encoding the light chain of a bispecific antigen binding protein, antibody or antigen-binding frag-ment of the invention; and a second transcription terminator.

A secretory signal peptide sequence can also, optionally, be encoded by the expression vector, operably linked to the coding sequence of interest, so that the expressed polypep-tide can be secreted by the recombinant host cell, for more facile isolation of the polypeptide of interest from the cell, if desired.

Recombinant host cells comprising such vectors and expressing the heavy and light chains are also provided.

Purification

Methods of antibody purification are known in the art and can be employed with production of the antibodies and bispecific antibodies of the present invention. In some embodiments of the invention, methods for antibody puri-fication include filtration, affinity column chromatography, cation exchange chromatography, anion exchange chroma-tography, and concentration. The filtration step preferably comprises ultrafiltration, and more preferably ultrafiltration and diafiltration. Filtration is preferably performed at least about 5-50 times, more preferably 10 to 30 times, and most preferably 14 to 27 times. Affinity column chromatography, may be performed using, for example, PROSEP® Affinity Chromatography (Millipore, Billerica, Mass.). In a preferred embodiment, the affinity chromatography step comprises PROSEP®-vA column chromatography. Eluate may be washed in a solvent detergent. Cation exchange chromatography may include, for example, SP-Sepharose Cation Exchange Chromatography. Anion exchange chromatography may include, for example but not limited to, Q-Sepharose Fast Flow Anion Exchange. The anion exchange step is preferably non-binding, thereby allowing removal of contaminants including DNA and BSA. The antibody product is preferably nanofiltered, for example, using a Pall DV 20 Nanofilter. The antibody product may be concentrated, for example, using ultrafiltration and diafiltration. The method may further comprise a step of size exclusion chromatography to remove aggregates. Further parameters of purification appear in the working examples hereinafter.

The bispecific antibodies, antibodies or antigen-binding fragments may also be produced by other methods known in the art, for example by chemical coupling of antibodies and antibody fragments.

Each manuscript, research paper, review article, abstract, patent application, patent or other publication cited in this specification is hereby incorporated by reference in its entirety.

WORKING EXAMPLES

The invention is further illuminated by the following working examples, which exemplify but do not limit the scope of the invention

Example 1

Fab Mutations
Materials

A set of 43 human and humanized recombinant monoclonal antibody molecules with different targets and different sequences were produced and purified according to a standard procedure (FIGS. 1A and 1B). The set with equivalent purity of >98% by size exclusion chromatography (SEC) was collected. Samples were concentrated in a 3 mL maximum volume using Amicon Ultrafiltration Stirred Cell Model 8003 (Millipore, Billerica, MA) at 2-8° C. at a maximum pressure of 30±10 psi. They were concentrated up to 150 mg/mL according to approximate volume depletion in a formulation buffer containing 20 mM acetate, 9% sucrose at pH 5.2 (without polysorbate), and final concentrations were determined (±10%) using the protein's absorbance at 280 nm (after dilution to end up within 0.1-1 absorbance units (AU)) and a protein-specific extinction coefficient.

Several low viscosity mutants of two mAbs were produced, purified and formulated according to a similar standard procedure. They included an antibody against proprotein convertase subtilisin/kexin type 9 (PCSK9, antibody AK) and against macrophage colony-stimulating factor (M-CSF, AO).

Viscosity Measurements

Viscosity analysis was performed on a Brookfield LV-DVIII cone and plate instrument (Brookfield Engineering, Middleboro, MA, USA) using a CP-40 spindle and sample cup. All measurements were performed at 25° C., controlled by a water bath attached to the sample cup. Multiple viscosity measurements were collected, manually within a defined torque range (10-90%) by increasing the RPM of the spindle. Measurements were averaged in order to report one viscosity value per sample to simplify the resulting comparison chart Sequence Alignment A structure-based sequence alignment was performed by an Ab Initio software tool developed using Excel Macros downloaded from the Department of Biochemistry of Zürich University.

Example 2

Fc Mutations
Expression and Purification of Mutants

Materials and Methods

Anti-C-kit antibody (antibody BA, SEQ ID NOS: 174 and 176, encoded by nucleic acids of SEQ ID NOS: 173 and 175, respectively), anti-sclerostin antibody AH, and anti-PCSK9 antibody AK
Anti-streptavidin IgG1 and IgG2.
1-ethyl-3-[3-dimethylaminopropyl] carbodiimide hydrochloride (EDC)
Solubilization with n-methyl-2-pyrrolidone
Size Exclusion High Performance Liquid Chromatography (SE-HPLC) with Light Scattering (LS)
Reduced and alkylated reversed phase High Performance Liquid Chromatography (RA RP-HPLC)
Trypsin peptide map with electro spray ionization mass spectrometry (ESI-MS)
Cone and plate viscometer
Results
SE-HPLC of EDC Cross-Linking of High Concentration Monoclonal Antibody Solutions Reveals Propensity to Form Oligomers The compound 1-ethyl-3-[3-dimethylaminopropyl] carbodiimide hydrochloride (EDC) was used to chemically cross-link acidic residues in the antibody to primary amines in the antibody (N-terminus and/or Lys residues) and has been used in other studies to determine the regions of protein-protein interaction. The proximity of the carboxyl group to the primary amine is critical as an amide bond is formed between the two groups (FIG. 16). The cross-links that form are likely salt bridges that are present in solution. Carraway and Koshland, Jr. (1972). "Carbodiimide modification of proteins." *Methods Enzymol* 25:616-623. A panel of antibodies was chemically cross-linked with EDC under identical solution conditions. Previous rheological studies had determined that some of the antibodies in the panel were viscous and some were not (FIG. 17). The non-viscous antibodies had small increases in dimer content but did not contain large amounts of higher order. In contrast, the viscous antibodies contained large amounts of dimer as well as higher order oligomers. A summary is provided in FIG. 17. All of the antibodies that were identified as viscous contained EDC cross-linked species that appeared to be larger than dimer. The appearance of the larger oligomeric species is concentration dependent (antibody AH is shown in FIG. 18 as an example). In order to facilitate further analysis, chemical cross-linking conditions were changed to drive the cross-linking reaction to completion. The solutions became solids after chemical cross-linking at 200 mg/mL. The solids were re-solubilized with buffer or a buffered 3% NMP solution. SE-HPLC analysis of both samples showed that the samples were similar. The buffered 3% NMP solution solubilized the protein significantly faster with more of the material going into solution. Antibody AH was re-solubilized and analyzed further as an example.

Size Analysis by SE-HPLC with Online LS

The cross-linked antibody solutions were analyzed by SE-HPLC with online light scattering to determine the size of the eluting species. SE-HPLC was conducted with online light scattering analysis of antibody AH after EDC chemical cross-linking and resolublization with 3% NMP. SE-HPLC revealed three peaks present in the UV and RI. The first peak was identified as a species with a mass of 840.5 kD. This is close to the expected mass for a hexamer of antibody AH of 873.2 kD. Another species had a mass of 494.6 kD, which is close to the predicted mass of 436.6 kD for a trimer of antibody AH. The third species showed a mass of 139.9 kD, which is close to the predicted mass of 145.5 kD for a monomer of antibody AH.

Reduced and Alkylated Reversed Phase HPLC of EDC Cross-Linked Antibody AH

The cross-linked antibody solutions were analyzed by reduced and alkylated reversed phase high performance liquid chromatography. The recovery of the majority of both light chain (LC) and heavy chain (HC) was unexpected as it was presumed that either the HC or the LC would be cross-linked to one another to form non-native LC-HC peptides or non-native LC-LC or HC-HC peptides reflecting the cross-linked oligomers observed by SEC analysis. In the case of antibody AH, the LC eluted in the same place with the exact same mass as non-cross-linked antibody AH LC. There were changes in the HC in antibody AH that are concentration dependent. There is a small amount of HC-HC cross-linked material (eluting at about 33 minutes, FIG. 21) that had an identified mass of 100 kD. At 150 mg/mL and 200 mg/mL, the distribution of HC species is similar. At lower protein concentrations, the distribution includes more of a species that elutes at about 28.5 min. The distribution of HC species correlates with the amount of oligomer present in each sample as analyzed by SEC with the 200 mg/mL sample containing the largest amount of hexamers and the 10 mg/ml sample containing very little oligomer. The pattern was observed in other viscous antibody solutions.

Example 3

Nonhuman Primate Study of Pharmacokinetics and Pharmacodynamics (PKPD) of the Anti-PCSK9 Parent Antibody AK and Low Viscosity Mutants Materials: antibody AK and its mutants. All mutations in heavy chain.

Fab Mutant: T82(72)R, R94(84)S, S95(85)R; Aho numbering (actual numbering)

Fc Mutant S(434)K (S440K in EU numbering):

Double Mutant: T82(72)R, R94(84)S, S95(85)R; S(434)K:

Four groups of 4 male cynomolgus monkeys were used in this study. Each group received 1 subcutaneous (SC) dose of 10 mg/kg as follows. Group 1 received parent antibody AK (140 mg/ml); Group 2 received Fab mutant (210 mg/ml); Group 3 received Fc mutant (210 mg/ml); Group 4: Fab/Fc mutant (210 mg/ml). Groups 1 and 2 also had diluent control SC dose. Fab mutant included the following substitutions in positions T82(72)R, R94(84)S, S95(85)R. Fc mutant included substitution in position S(434)K.

To measure viscosity at 210 mg/ml, the parent and all mutants were formulated at 210 mg/mL in 10 mM Acetate, 155 mM N-acetyl arginine (NAR), 70 mM ArgHCl, pH 5.4, 0.01% Polysorbate 80. Viscosity was measured using ARG2 cone/plate at 1000 sec-1 and 25 C. See FIG. 15.

Study Design Outline:

4 groups of 4 male cynomolgus monkeys.

Each group received 1 SC dose (10 mg/kg) of:

Group 1: parent antibody AK (140 mg/ml)

Group 2: Fab mutant (210 mg/ml)

Group 3: Fc mutant (210 mg/ml)

Group 4: Fab/Fc mutant (210 mg/ml)

Groups 1 and 2 also had diluent control subcutaneous dose.

Skin biopsies taken at injection site 3 days after dosing.

Histopath analysis performed

Plasma LDL, HDL, total cholesterol and PK followed for 6 weeks post-dose

Study Conclusions

All 4 homologues produced marked LDL lowering

Maximal reduction 2 weeks after dosing: 1 week later than previously observed for parent The nadir of the effect was not quite as profound for the Fab/Fc mutant (~78% vs ~90%)

Return to baseline appears slightly more accelerated for the Fc mutant

PK: Mean exposures were similar (based on Cmax and AUClast) between all treatment groups (within 1.4-fold)

Fab and/or Fc mutations in anti-PCSK9 antibody AK had no significant effect on injection site reactions (ISR) or Pharmacokinetics and Pharmacodynamics (PKPD) profile in nonhuman primates (NHPs) (cynomolgus monkeys).

Fab Mutant: T82(72)R, R94(84)S, S95(85)R; Aho numbering (actual numbering).

Fc Mutant: S(434)K (S440K in EU numbering).

Example 4

Production and Characterization of Low-Viscosity Mutants of GIPR (2G10.006) Antibody AQ Cloning, Expression, Purification and High Concentration Formulation of Low Viscosity Mutants of Antibody AQ GIPR (2G10.006) AQ parent is described in U.S. Provisional Application 62/387,486 as 2G10_LC1.006 (SEQ ID NO: 74 of the cited patent application). The aforementioned US patent application is hereby incorporated by reference. Heavy chain mutant AQ (HC 1, 17, 85) with mutation sites Q1(1)E, R17(16)G, S85(75)A and light chain mutant AQ (LC 4 13 76 95 97 98) with mutation sites M4(4)L, V13 (13)L, A76(60)D, S95(77)R, Q97(79)E, S98(80)P were produced as follows. Synthetic genes for GIPR (2G10.006) (antibody AQ) low viscosity mutants were produced, digested and ligated into plasmid expression vectors. Constructs were verified by DNA sequencing. Stable cell pools were created by electroporation of a clonal CHO host cell line. The pools were cultured under selection until viability reached greater than 85%. Pools were seeding into a fed-batch production culture for 10 days and centrifuged media was harvested.

Harvested supernatants were sterile filtered and purified through a three column chromatography process consisting of Protein A, cation exchange, and anion exchange, similar to the process described earlier (Shukla et al. (2007), "Downstream processing of monoclonal antibodies—Application of platform approaches," J. Chrom. B 848:28-39). The resulting purified pools were dialyzed into formulation buffer containing 20 mM acetate and 9% sucrose at pH 5.2 (without polysorbate), achieving a final pH of ~5.2 and concentrated to approximately 150 mg/mL above 30 kDa cutoff filter via centrifugal ultrafiltration (FIG. 20A).

Potency Measurements

Potency was measured by an assay utilizing mammalian cells 293/huGIPR expressing glucose-dependent insulinotropic polyeptide receptor (GIPR). The increasing concentrations of anti-GIPR parent AQ and the low-viscosity mutants were blocking the interaction of GIP with GIPR which induced cAMP changes monitored during the assay. An application of the assay was earlier described in Tseng C. C. et al. (1996), "Postprandial stimulation of insulin release by glucose-dependent insulinotropic polypeptide (GIP). Effect of a specific glucose-dependent insulinotropic polypeptide receptor antagonist in the rat," *J. Clin. Invest.* 98:2440-2445.

Viscosity Measurements

Viscosity analysis of AQ and two low viscosity mutants was performed on an Anton Paar Rheometer using a CP25-1/TG spindle. All measurements were performed at 25° C., controlled by a water bath attached to the sample cup. Viscosity measurements were collected manually with increasing shear rate from 0-2000 rpm. 10 viscosity measurement results at shear rate 1000 1/s and 10 viscosity measurement results at shear rate 2000 1/s were collected for each sample and averaged to report one viscosity value per sample.

It needs to be noted that precision of viscosity measurements is much better that accuracy, because the viscosity measurements are sensitive to even minor changes in some parameters, such as the state of the viscometer, temperature in the room and some other minor parameters at the time of the measurements. Therefore, it is important to measure all samples of interest in one setting or, if samples of interest are measured in two settings, have the same reference standard in both settings.

Results

Anti-GIPR (2G10.006) antibody AQ belongs to high-viscosity germline subfamilies of heavy chain VH3I3-33 and light chain VK3IL16. Several mutations derived from FIGS. 11 and 12 were made in frames in the effort to reduce viscosity of AQ. The viscosity of the parent AQ and the two mutants measured in one viscometer setting revealed the following values: AQ-19.1 cP, AQ (HC 1, 17, 85)-15.8 cP, AQ (LC 4 13 76 95 97 98)-12.7 cP (FIG. 20). The heavy chain mutant AQ (HC 1, 17, 85) mutant was at 83% and the light chain mutant AQ (LC 4 13 76 95 97 98) was at 67% relative to the parent AQ. FIGS. 7 and 8 illustrate positions of the mutants on the viscosity versus pI plots for VH3 and VK3 family members. The in vitro cAMP activity was equally unaffected by viscosity mutations. The potency remained the same within the error margin of the in vitro cell-based assay (Sec FIG. 20B). To summarize, introduced mutations reduced viscosity without loss of the potency.

Example 5

GIPR Low Viscosity Mutant Light Chain V78F (LC V78F in Aho Numbering and LC V62F in Linear Numbering)

GIPR (2G10.006) antibody AQ showed a high viscosity of 23 cP at 150 mg/mL in A52Su formulation. This antibody featured a low-frequency residue V78 in Aho numbering (V62 in linear numbering) in the kappa light chain (LC V78 Aho). The frequency of occurrence of V78 is <1%, while F78 is >98% in light chain sequences related to the kappa germline. The residue LC V78 attracted attention, because it was a covariance violator. Covariance analysis allows establishing pair-wise conserved-residue positions based on the physiochemical properties of the residues in variable regions of antibodies, identifying incorrectly positioned residues (which are often non-germline residues). Covariance analysis further may suggest replacing the amino acids at the deviating positions with more common germline sequences that lead to a large conformational change uncovered by molecular-dynamics simulations (Kannan G., "Method of correlated mutational analysis to improve therapeutic antibodies," U.S. Ser. No. 61/451,929, PCT/US 2012/028596, WO 2012/125495). In an effort to eliminate the covariance violation and increase the percentage of human sequences, the LC V78F mutation was introduced in the GIPR (2G10.006) antibody AQ.

Unexpectedly, viscosity of the mutant decreased by 25%, while maintaining similar potency for human GIPR as measured in cAMP (cell-based) assays. Both sequences, the GIPR (2G10.006) AQ parent and its LC V78F mutant are described in U.S. Provisional Application 62/387,486 as 2G10_LC1.006 (SEQ ID NO: 74 of the cited application) and 2G10_LC1.003 (SEQ ID NO: 71 of the cited application), respectively. The US patent application is hereby incorporated by reference. Newly discovered in the present invention is that such substitution resulted in about 25% reduction of viscosity by LC V78F mutation. Viscosity analysis of the GIPR_2G10.006 AQ and its V78F mutant was performed at 150 mg/ml in formulation containing 20 mM acetate, 9% sucrose at pH 5.2, 0.01% polysorbate 80, 1000 shear rate and 25 C using AR-G2 Magnetic Bearing Cone and Plate Rheometer from TA Instruments-Waters LLC. Cone plate size was 20 mm in diameter, 1.988° cone angle, equipped with Steel-990918 Peltier plate and operated using the Flow Sweep procedure. The measured viscosity values were 21 cP for GIPR_2G10.006 and 15.3 cP for GIPR (2G10.003) LC V78F mutant, which is 25% decrease in viscosity.

As noted in the previous example, precision of viscosity measurements is much better that accuracy. Viscosity at 150 mg/mL with 0.01% polysorbate is typically 10% lower than without polysorbate, which was observed in case of GIPR (2G10.006). Its viscosity was 23 cP without polysorbate (as for all 43 antibodies) and 21 cP with polysorbate.

Example 6

Cynomolgus Monkey Study

The antibodies designated as AK (control, also known as AMG 145 and evolocumab) and the Fab mutant, Fc mutant, and double mutant shown in Example 3 were generated using the methodology disclosed in Examples 1 and 2. The pharmacokinetic properties of these antibodies were tested in vivo by single subcutaneous bolus injection into male cynomolgus monkeys.

Study Design

The study was conducted in male cynomolgus monkeys. The animals were 2.7 to 3.8 years old and weighted between 2.9 to 3.8 kg. The animals were acclimated to laboratory housing for 7 days before the initiation of dosing. Criteria for selection included acceptable results from the pretreatment cholesterol levels (including LDL and HDL) levels. Before the initiation of dosing, all animals were randomized and assigned to groups using a computer-based randomization procedure.

The test and control articles were administered subcutaneously into the mid-dorsal areas to the appropriate animals once on Day 1. The injection site(s) were shaved prior to administration and marked with indelible ink. The animals were temporarily restrained for dose administration and were not sedated. The dose volume for each animal was based on the most recent body weight measurement. For Groups 1 and 2, dose solutions were administered via 2 subcutaneous injections on the back of each animal (1 with test material, 1 with diluent). Injection sites were at least 5-6 cm apart. The test material was administered on the right of the spinal column for each animal. The diluent was delivered on the left of the spinal column for each animal. For Groups 3 and 4, dose solutions were administered via a single subcutaneous injection on the back of each animal. Dose levels and volumes for each group are summarized in FIG. 21.

Blood samples were collected by venipuncture into tubes containing Potassium (K2) EDTA at various time points over the duration of the in-life portion of this study (43 days). Animals were not fasted prior to serum chemistry blood collections.

Samples were chilled following blood collections, and split for preparation of cither serum or plasma. Samples were mixed gently and centrifuged. Blood samples were maintained on wet ice immediately after collection until centrifuged (1500-2000×g for approximately 10 minutes) at approximately 4° C. The resultant plasma or serum was separated and divided into 2 aliquots (primary and backup), transferred to appropriately labeled polypropylene tubes, and stored in a freezer set to maintain at −80° C. until analysis. Plasma samples were used to determine test article concentration for pharmacokinetic evaluation, serum samples were analyzed for cholesterol, HDL, and LDL.

Pharmacokinetic Evaluation

Plasma samples were analyzed for concentration of each test antibody (antibody AK, AK Fab mutant, AK S440K Fc mutant, and AK Fab/S440K double mutant) using an enzyme-linked immunosorbent assay (ELISA). The assay uses recombinant human PCSK9 as the capture reagent and a horseradish peroxidase labeled antibody to human IgG1 as the detection reagent. Standards and quality control samples (QCs) are prepared by spiking antibody AK or low viscosity homologs into 100% cynomolgus monkey K2-EDTA pool. Costar 96-well microplate wells (Corning Incorporated) are coated with recombinant human PCSK9. After a blocking step, the standards, matrix blank (NSB), QCs (QCs) and test samples are loaded into the microplate wells after pre-treating with a dilution factor of 100 in Blocker™ BLOTTO in TBS (Thermo Scientific). The antibody AK in the samples is captured by the immobilized recombinant human PCSK9 coated on the microplate. Unbound material is removed by washing the microplate wells. Following washing, mouse anti-human IgG, Ab35, HRP conjugated detection antibody is added to the microplate wells to bind the captured antibody AK. Unbound detection antibody is removed by washing the microplate wells. A onc component TMB solution is added to the microplate wells for the detection of bound mouse anti-human IgG Ab35 HRP conjugate. The TMB substrate solution reacts with peroxide and, in the presence of HRP, creates a colorimetric signal that is proportional to the amount of antibody AK, or low viscosity mutant homolog, bound by the capture reagent. The color development is stopped using 2N sulfuric acid and the intensity of the color (optical density or OD) is measured at 450 nm minus 650 nm. Data are reduced using Watson version 7.4 SP3 (or later) data reduction package using a 4 parameter (Marquardt) regression model with a weighting factor of 1.

Pharmacokinetic parameters were estimated using Win-Nonlin pharmacokinetic software. A non-compartmental approach consistent with the subcutaneous route of administration was used for parameter estimation. All parameters were generated from individual concentrations in plasma from Day 1. The following parameters were determined Tmax (the time after dosing at which the maximum observed concentration was observed), Cmax (the maximum observed concentration measured after dosing), AUC (0-t) (the area under the concentration versus time curve from the start of dose administration to the time after dosing at which the last observed quantifiable concentration using the linear or linear/log trapezoidal method), AUC (0-t)/D (the AUC (0-t) divided by the dose administered), and RAUC (the area under the curve from T1 and T2 at steady state divided by the area under the curve from T1 to T2 during the initial dosing interval).

Results and Discussion

Test article concentrations plotted versus time are shown in FIGS. 24A and 24B (mean concentrations for each test article, n=4 at each time point). Pharmacokinetic parameters for the four test articles are summarized in FIG. 22. Antibodies containing the Fc mutation S440K (both antibody AK (Fc mutant) and antibody AK (Fc and Fab double mutant)) show a reduced Tmax (0.81 and 1 days respectively versus 2.5 days) and increased Cmax (125 and 112 µg/mL respectively versus 87.8 µg/mL) relative to antibody AK (control) and antibody AK (Fab mutant) indicating antibodies containing an Fc mutation that reduces viscosity are distributing more rapidly to the circulation following subcutaneous injection.

Administration of all low viscosity homologues of antibody AK resulted in expected pharmacologic mild to moderate decreases in low density lipoprotein (LDL) associated with decreased total cholesterol concentration compared to baseline (Day-6). The magnitude of decrease for total and low density lipoprotein cholesterol following administration of AK Fab mutant and AK S440K Fc mutant was generally similar to control animals with a trend toward recovery to baseline of AK S440K Fc mutant on Day 25 and AK (control) and AK Fab mutant on Day 29. The magnitude of decrease in total and low density lipoprotein cholesterol for AK Fab/S440K double mutant was generally less pronounced compared to control (antibody AK at 10 mg/kg). There were no changes in high density lipoprotein in any AK low viscosity homologue. Percentage changes in LDL-C relative to baseline are tabulated in FIG. 23 and are plotted versus time in FIGS. 24A and 24B.

ABBREVIATIONS

Abbreviated terms used throughout this specification are defined as follows.

AEI allelic expression imbalance

ANOVA analysis of variance

AUC area under the curve

BSA bovine serum albumin

DMEM Dulbecco's Modified Eagle Medium

DMSO dimethyl sulfoxide

EDC 1-ethyl-3-[3-dimethylaminopropyl] carbodiimide hydrochloride

EDTA ethylenediaminetetraacetic acid

ELISA enzyme-linked immunosorbent assay eQTL expression quantitative trait loci

ESI-TOF electrospray ionization time of flight

FACS fluorescence-activated cell sorting

FBS fetal bovine serum

FPLC fast protein liquid chromatography
FVB a strain of mice inbred for the Friend leukemia virus
   1b (Fv1b) allele
H&E Hematoxylin and eosin
HA hypoxanthine
HIC hydrophobic interaction chromatography
HPLC high performance liquid chromatography
HRP horseradish peroxidase
HUVEC human umbilical vein epithelial cell
IBD inflammatory bowel disease
IDMEM DMEM without glutamine
IFN interferon
IL interleukin MCP monocyte chemotactic protein
MSD macromolecular structure database
PBMC peripheral blood mononuclear cell
PBS phosphate-buffered saline
PCR polymerase chain reaction
PEG polyethylene glycol
PEI polyethylenimine
QTL quantitative trait loci
RPMI media developed at Roswell Park Memorial Insti-
   tute
SNP single nucleotide polymorphism
TFA trifluoroacetic acid
TMB 3,3',5,5'-Tetramethylbenzidine

---

SEQUENCE LISTING

```
Sequence total quantity: 383
SEQ ID NO: 1               moltype = DNA  length = 705
FEATURE                    Location/Qualifiers
source                     1..705
                           mol_type = other DNA
                           organism = Homo sapiens
SEQUENCE: 1
atggaaaccc cggcgcagct gctgtttctg ctgctgctgt ggctgccgga taccaccggc  60
gaaattgtgt tgacgcagtc tccaggcacc ctgtctttgt ctccagggga cagagccacc  120
ctctcctgca gggccagtca gagtgttagt agcagctact ttgcctggta ccagcagaaa  180
cctggccagg ctcccaggct cctcatttat ggtgcatcca gtagggccac tggcatccca  240
gacaggttca gtggcagtgg gtctgggaca gacttcactc tcaccatcag cagactggag  300
cctgaagatt ttgcagtgta ttactgtcag cagtatgata ggtcacctcg gacgttcggc  360
caagggacca aggtggaaat caaacgtacg gtggctgcac catctgtctt catcttcccg  420
ccatctgatg agcagttgaa atctggaact gcctctgttg tgtgcctgct gaataacttc  480
tatcccagag aggccaaagt acagtggaag gtggataacg ccctccaatc gggtaactcc  540
caggagagtg tcacagagca ggacagcaag gacagcacct acagcctcag cagcaccctg  600
acgctgagca aagcagacta cgagaaacac aaagtctacg cctgcgaagt cacccatcag  660
ggcctgagct cgcccgtcac aaagagcttc aacaggggag agtgt              705

SEQ ID NO: 2               moltype = AA  length = 235
FEATURE                    Location/Qualifiers
source                     1..235
                           mol_type = protein
                           organism = Homo sapiens
SEQUENCE: 2
METPAQLLFL LLLWLPDTTG EIVLTQSPGT LSLSPGDRAT LSCRASQSVS SSYFAWYQQK  60
PGQAPRLLIY GASSRATGIP DRFSGSGSGT DFTLTISRLE PEDFAVYYCQ QYDRSPRTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 3               moltype = DNA  length = 1389
FEATURE                    Location/Qualifiers
source                     1..1389
                           mol_type = other DNA
                           organism = Homo sapiens
SEQUENCE: 3
atggattgga cctggcgtat tctgtttctg gtggcggcgg cgaccggcgc gcatagccag  60
gtgcagctgg tgcagtctgg ggctgaggtg aagaagcctg gggcctcagt gaaggtctcc  120
tgtaagtctt ctggatacac cttcaccggc tactatatgc actgggtgcg acaggcccct  180
ggacaagggc ttgagtggat gggatggatc aaccctaaca gtggtggcac aaactatgca  240
cagaagttta agggcagggt caccatgacc agggacacgc catcagcac agcctacatg  300
gagctgagca ggctgagatc tgacgacacg gccgtgtatt actgtgcgag agataagtgg  360
ctggacggct ttgactactg gggccaggga accctggtca ccgtctcctc agctagcacc  420
aagggcccat cggtcttccc cctggcgccc tgctccagga gcacctccga gagcacagcg  480
gccctgggct gcctggtcaa ggactacttc cccgaaccgg tgacggtgtc gtggaactca  540
ggcgctctga ccagcggcgt gcacaccttc ccagctgtcc tacagtcctc aggactctac  600
tccctcagca gcgtggtgac cgtgccctcc agcaacttcg gcacccagac ctacacctgc  660
aacgtagatc acaagcccag caacaccaag gtggacaaga cagttgagcg caaatgttgt  720
gtcgagtgcc caccgtgccc agcaccacct gtggcaggac cgtcagtctt cctcttcccc  780
ccaaaaccca aggacaccct catgatctcc cggacccctg aggtcacgtg cgtggtggtg  840
gacgtgagcc acgaagaccc cgaggtccag ttcaactggt acgtggacgg cgtggaggtg  900
cataatgcca agacaaagcc acgggaggag cagttcaaca gcacgttccg tgtggtcagc  960
gtcctcaccg ttgtgcacca ggactggctg aacggcaagg agtacaagtg caaggtctcc  1020
aacaaaggcc tcccagcccc catcgagaaa accatctcca aaaccaaagg gcagccccga  1080
gaaccacagg tgtacaccct gcccccatcc cgggaggaga tgaccaagaa ccaggtcagc  1140
ctgacctgcc tggtcaaagg cttctacccc agcgacatcg ccgtggagtg ggagagcaat  1200
gggcagccgg agaacaacta caagaccaca cctcccatgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaa                                                          1389
```

```
SEQ ID NO: 4              moltype = AA   length = 463
FEATURE                  Location/Qualifiers
source                   1..463
                         mol_type = protein
                         organism = Homo sapiens
SEQUENCE: 4
MDWTWRILFL VAAATGAHSQ VQLVQSGAEV KKPGASVKVS CKSSGYTFTG YYMHWVRQAP   60
GQGLEWMGWI NPNSGGTNYA QKFKGRVTMT RDTSISTAYM ELSRLRSDDT AVYYCARDKW  120
LDGFDYWGQG TLVTVSSAST KGPSVFPLAP CSRSTSESTA ALGCLVKDYF PEPVTVSWNS  180
GALTSGVHTF PAVLQSSGLY SLSSVVTVPS SNFGTQTYTC NVDHKPSNTK VDKTVERKCC  240
VECPPCPAPP VAGPSVFLFP PKPKDTLMIS RTPEVTCVVV DVSHEDPEVQ FNWYVDGVEV  300
HNAKTKPREE QFNSTFRVVS VLTVVHQDWL NGKEYKCKVS NKGLPAPIEK TISKTKGQPR  360
EPQVYTLPPS REEMKNQVS LTCLVKGFYP SDIAVEWESN GQPENNYKTT PPMLDSDGSF  420
FLYSKLTVDK SRWQQGNVFS CSVMHEALHN HYTQKSLSLS PGK                    463

SEQ ID NO: 5              moltype = DNA   length = 726
FEATURE                  Location/Qualifiers
source                   1..726
                         mol_type = other DNA
                         organism = Homo sapiens
SEQUENCE: 5
atggacatga gggtgcccgc tcagctcctg gggctcctgc tgctgtggct gagaggtgcg   60
cgctgtgata ttgtgatgac ccagactcca ctctccctgc ccgtcacccc tggagagccg  120
gcctccatct cctgcaggtc tagtcagagc ctcttgaata tgttgatgg aagcaccaat  180
ttggactggt atctgcagaa gccagggcag tctccacagc tcctgatcta tacgctttcc  240
tatcgggcct ctggagtccc agacaggttc agtggcagtg ggtcaggcac tgacttcaca  300
ctgaaaatca gcagggtgga ggctgaggat gttggagttt attactgcat gcaacgtata  360
gagtttccgc tcactttcgg cggagggacc aaggtggaga tcaaacgtac ggtggctgca  420
ccatctgtct tcatcttccc gccatctgat gagcagttga aatctggaac tgcctctgtt  480
gtgtgcctgc tgaataactt ctatcccaga gaggccaaag tacagtggaa ggtggataac  540
gccctccaat cgggtaactc ccaggagagt gtcacagagc aggacagcaa ggacagcacc  600
tacagcctca gcagcaccct gacgctgagc aaagcagact acgagaaaca caaagtctac  660
gcctgcgaag tcacccatca gggcctgagc tcgcccgtca caaagagctt caacagggga  720
gagtgt                                                             726

SEQ ID NO: 6              moltype = AA   length = 242
FEATURE                  Location/Qualifiers
source                   1..242
                         mol_type = protein
                         organism = Homo sapiens
SEQUENCE: 6
MDMRVPAQLL GLLLLWLRGA RCDIVMTQTP LSLPVTPGEP ASISCRSSQS LLNSVDGSTN   60
LDWYLQKPGQ SPQLLIYTLS YRASGVPDRF SGSGSGTDFT LKISRVEAED VGVYYCMQRI  120
EFPLTFGGGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
EC                                                                 242

SEQ ID NO: 7              moltype = DNA   length = 1395
FEATURE                  Location/Qualifiers
source                   1..1395
                         mol_type = other DNA
                         organism = Homo sapiens
SEQUENCE: 7
atggagttgg ggctgtgctg ggttttcctt gttgctattt tagaaggtgt ccagtgtgag   60
gtgcagctgg tggagtctgg gggaggcttg gtacagcctg ggggtccct gagactctcc  120
tgtgcagcct ctggattcac cttcagtagc tatagcatga actgggtccg ccaggctcca  180
gggaaggggc tggagtgggt ttcatacatt agtagtagtg gtagttccat atactacgca  240
gactctgtga agggccgatt caccatctcc agagacaatg ccaagaactc actgtatctg  300
caaatgaaca gcctgagaga cgaggacacg gctgtgtatt actgtgcgag agagaggtac  360
tacggtgaca cgccctttga ctactggggc cagggaaccc tggtcaccgt ctctagtgcc  420
tccaccaagg gcccatcggt cttccccctg gcgccctgct ccaggagcac ctccgagagc  480
acagcggccc tgggctgcct ggtcaaggac tacttccccg aaccggtgac ggtgtcgtgg  540
aactcaggcg ctctgaccag cggcgtgcac accttcccag ctgtcctaca gtcctcagga  600
ctctactccc tcagcagcgt ggtgaccgtg ccctccagca acttcggcac ccagacctac  660
acctgcaacg tagatcacaa gcccagcaac accaaggtgg acaagacagt tgagcgcaaa  720
tgttgtgtcg agtgcccacc gtgcccagca ccacctgtgg caggaccgtc agtcttcctc  780
ttccccccaa aacccaagga caccctcatg atctcccgga cccctgaggt cacgtgcgtg  840
gtggtggacg tgagccacga agaccccgag gtccagttca actggtacgt ggacggcgtg  900
gaggtgcata atgccaagac aaagccacgg gaggagcagt tcaacagcac gttccgtgtg  960
gtcagcgtcc tcaccgttgt gcaccaggac tggctgaacg gcaaggagta caagtgcaag 1020
gtctccaaca aaggcctccc agcccccatc gagaaaacca tctccaaaac caaagggcag 1080
ccccgagaac acaggtgta caccctgccc ccatcccggg aggagatgac caagaaccag 1140
gtcagcctga cctgcctggt caaaggcttc tacccagcg acatcgccgt ggagtgggag 1200
agcaatgggc agccggagaa caactacaag accacacctc ccatgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gtaaa                                                  1395
```

-continued

```
SEQ ID NO: 8            moltype = AA   length = 465
FEATURE                 Location/Qualifiers
source                  1..465
                        mol_type = protein
                        organism = Homo sapiens
SEQUENCE: 8
MELGLCWVFL VAILEGVQCE VQLVESGGGL VQPGGSLRLS CAASGFTFSS YSMNWVRQAP   60
GKGLEWVSYI SSSGSSIYYA DSVKGRFTIS RDNAKNSLYL QMNSLRDEDT AVYYCARERY  120
YGDTPFDYWG QGTLVTVSSA STKGPSVFPL APCSRSTSES TAALGCLVKD YFPEPVTVSW  180
NSGALTSGVH TFPAVLQSSG LYSLSSVVTV PSSNFGTQTY TCNVDHKPSN TKVDKTVERK  240
CCVECPPCPA PPVAGPSVFL FPPKPKDTLM ISRTPEVTCV VVDVSHEDPE VQFNWYVDGV  300
EVHNAKTKPR EEQFNSTFRV VSVLTVVHQD WLNGKEYKCK VSNKGLPAPI EKTISKTKGQ  360
PREPQVYTLP PSREEMTKNQ VSLTCLVKGF YPSDIAVEWE SNGQPENNYK TTPPMLDSDG  420
SFFLYSKLTV DKSRWQQGNV FSCSVMHEAL HNHYTQKSLS LSPGK                 465

SEQ ID NO: 9            moltype = DNA   length = 699
FEATURE                 Location/Qualifiers
source                  1..699
                        mol_type = other DNA
                        organism = Homo sapiens
SEQUENCE: 9
atgtcgccat cacaactcat tgggtttctg ctgctctggg ttccagcctc caggggtgaa   60
attgtgctga ctcagtctcc agactttcag tctgtgactc caaaggagaa agtcaccatc  120
acctgccggg ccagtcagag cattggtagt agcttacact ggtaccagca gaaaccagat  180
cagtctccaa agctcctcat caagtatgct tcccagtcct ctcagggggt ccctcgagag  240
ttcagtggca gtggatctgg gacagatttc accctcacca tcaatagcct ggaagctgaa  300
gatgctgcag cgtattactg tcatcagagt agtagtttac ctctcacttt cggcggaggg  360
accaaggtgg agatcaaacg aactgtggct gcaccatctg tcttcatctt cccgccatct  420
gatgagcagt tgaaatctgg aactgcctct gttgtgtgcc tgctgaataa cttctatccc  480
agagaggcca aagtacagtg gaaggtggat aacgccctcc aatcgggtaa ctcccaggag  540
agtgtcacag agcaggacag caaggacagc acctacagcc tcagcagcac cctgacgctg  600
agcaaagcag actacgagaa acacaaagtc tacgcctgcg aagtcaccca tcagggcctg  660
agctcgcccg tcacaaagag cttcaacagg ggagagtgt                        699

SEQ ID NO: 10           moltype = AA   length = 233
FEATURE                 Location/Qualifiers
source                  1..233
                        mol_type = protein
                        organism = Homo sapiens
SEQUENCE: 10
MSPSQLIGFL LLWVPASRGE IVLTQSPDFQ SVTPKEKVTI TCRASQSIGS SLHWYQQKPD   60
QSPKLLIKYA SQSFSGVPSR FSGSGSGTDF TLTINSLEAE DAAAYYCHQS SSLPLTFGGG  120
TKVEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC          233

SEQ ID NO: 11           moltype = DNA   length = 1389
FEATURE                 Location/Qualifiers
source                  1..1389
                        mol_type = other DNA
                        organism = Homo sapiens
SEQUENCE: 11
atggggtcaa ccgccatcct cgccctcctc ctggctgttc tccaaggagt ctgtgccgag   60
gtgcagctga tgcagtctgg agcagaggtg aaaaagcccg gggagtctct gaagatctcc  120
tgtaagggtt ctggatacag cttttccttc cactggatcg cctgggtgcg ccagatgccc  180
gggaaaggcc tggagtggat ggggatcatc catcctgatc cctctgatac cagatacagc  240
ccgtccttcc aaggccaggt caccatctca gccgacaact ccaacagcgc cacctacctg  300
cagtggagca gcctgaaggc ctcggacacc gccatgtatt tctgtgcgag acaaagggaa  360
ctcgactact ttgactactg gggccaggga accctggtca ccgtctctag tgcctccacc  420
aagggcccat cggtcttccc cctggcgccc tgctccagga gcacctccga gagcacagcg  480
gccctgggct gcctggtcaa ggactacttc cccgaaccgg tgacggtgtc gtggaactca  540
ggcgctctga ccagcggcgt gcacaccttc ccagctgtcc tacagtcctc aggactctac  600
tccctcagca gcgtggtgac cgtgccctcc agcaacttcg gcacccagac ctacacctgc  660
aacgtagatc acaagcccag caacaccaag gtggacaaga cagttgagcg caaatgttgt  720
gtcgagtgcc caccgtgccc agcaccacct gtggcaggac cgtcagtctt cctcttcccc  780
ccaaaaccca aggacaccct catgatctcc cggacccctg aggtcacgtg cgtggtggtg  840
gacgtgagcc acgaagaccc cgaggtccag ttcaactggt acgtggacgg cgtggaggtg  900
cataatgcca agacaaagcc acgggaggag cagttcaaca gcacgttccg tgtggtcagc  960
gtcctcaccg ttgtgcacca ggactggctg aacggcaagg agtacaagtg caaggtctcc 1020
aacaaaggcc tcccagcccc catcgagaaa accatctcca aaaccaaagg gcagccccga 1080
gaaccacagg tgtacaccct gcccccatcc cgggaggaga tgaccaagaa ccaggtcagc 1140
ctgacctgcc tggtcaaagg cttctacccc agcgacatcg ccgtggagtg ggagagcaat 1200
gggcagccgg agaacaacta caagaccaca cctcccatgc tggactccga cggctccttc 1260
ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaa                                                        1389

SEQ ID NO: 12           moltype = AA   length = 463
FEATURE                 Location/Qualifiers
source                  1..463
```

-continued

```
                          mol_type = protein
                          organism = Homo sapiens
SEQUENCE: 12
MGSTAILALL LAVLQGVCAE VQLMQSGAEV KKPGESLKIS CKGSGYSFSF HWIAWVRQMP   60
GKGLEWMGII HPGASDTRYS PSFQGQVTIS ADNSNSATYL QWSSLKASDT AMYFCARQRE  120
LDYFDYWGQG TLVTVSSAST KGPSVFPLAP CSRSTSESTA ALGCLVKDYF PEPVTVSWNS  180
GALTSGVHTF PAVLQSSGLY SLSSVVTVPS SNFGTQTYTC NVDHKPSNTK VDKTVERKCC  240
VECPPCPAPP VAGPSVFLFP PKPKDTLMIS RTPEVTCVVV DVSHEDPEVQ FNWYVDGVEV  300
HNAKTKPREE QFNSTFRVVS VLTVVHQDWL NGKEYKCKVS NKGLPAPIEK TISKTKGQPR  360
EPQVYTLPPS REEMTKNQVS LTCLVKGFYP SDIAVEWESN GQPENNYKTT PPMLDSDGSF  420
FLYSKLTVDK SRWQQGNVFS CSVMHEALHN HYTQKSLSLS PGK                    463

SEQ ID NO: 13           moltype = DNA   length = 708
FEATURE                 Location/Qualifiers
source                  1..708
                        mol_type = other DNA
                        organism = Homo sapiens
SEQUENCE: 13
atggacatga gggtccccgc tcagctcctg gggctcctgc tgctgtggct gagaggtgcg   60
cgctgtgata tccagatgac ccaatccccct tctagtctgt ccgcttctgt gggcgacagg  120
gttacaataa cttgcaaagc gagccaggac atcaacaaat atgtggcttg gtatcagcaa  180
aaacccggca aggcaccaaa attgctcatt tattacagct catggctcca gcctggtgta  240
cctagcaggt tttccggctc cggctcaggt accgacttta ctttcactat ctcctcactg  300
cagccggagg acattgccac atactactgt ctccaatatg ataacttgtt gtatactttt  360
gggcaaggaa ctaagctcga gatcaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata cgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgt               708

SEQ ID NO: 14           moltype = AA   length = 236
FEATURE                 Location/Qualifiers
source                  1..236
                        mol_type = protein
                        organism = Homo sapiens
SEQUENCE: 14
MDMRVPAQLL GLLLLWLRGA RCDIQMTQSP SSLSASVGDR VTITCKASQD INKYVAWYQQ   60
KPGKAPKLLI YYTSWLQPGV PSRFSGSGSG TDFTFTISSL QPEDIATYYC LQYDNLLYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 15           moltype = DNA   length = 1401
FEATURE                 Location/Qualifiers
source                  1..1401
                        mol_type = other DNA
                        organism = Homo sapiens
SEQUENCE: 15
atggacatga gggtgcccgc tcagctcctg gggctcctgc tgctgtggct gagaggtgcg   60
cgctgtgagg ttcagcttgt ggagtctggc ggcggcctgg tgcagccagg cggttcactc  120
aggctgagct gtgctgcatc agggttcacc ttcagcgtt actggatgaa ctgggtgcag  180
caagcacccg ggaaaggcct ggagtggggtg gctcagattc gcttgaaaag tgacaattat  240
gccactcact atgcagaaag cgtgaagggg cgctttacaa tttctagaga caacgccaaa  300
aactcactgt acctgcagat gaacagcctc agagctgagg atacagctgt gtattattgt  360
actgaggggc tcgactattg gggacagggc acgacagtga ccgtctctag tgcctccacc  420
aagggcccat cggtcttccc cctggcaccc tcctccaaga gcacctctgg gggcacagcg  480
gccctgggct gcctggtcaa ggactacttc cccgaaccgg tgacggtgtc gtggaactca  540
ggcgccctga ccagcggcgt gcacaccttc ccggctgtcc tacagtcctc aggactctac  600
tccctcagca gcgtggtgac cgtgccctcc agcagcttgg gcacccagac ctacatctgc  660
aacgtgaatc acaagcccag caacaccaag gtggacaaga agttgagcc caaatcttgt  720
gacaaaactc acacatgccc accgtgccca gcacctgaac tcctgggggg accgtcagtc  780
ttcctcttcc ccccaaaacc caaggacacc ctcatgatct cccggacccc tgaggtcaca  840
tgcgtggtgg tggacgtgag ccacgaagac cctgaggtca agttcaactg gtacgtggac  900
ggcgtggagg tgcataatgc caagacaaag ccgcgggagg agcagtacaa cagcacgtac  960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca gcctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcta tagcaagctc accgtggaca gagcaggtg gcagcagggg 1320
aacgtcttct catgctccgt gatgcatgag gctctgcaca accactacac gcagaagagc 1380
ctctccctgt ctccgggtaa a                                          1401

SEQ ID NO: 16           moltype = AA   length = 467
FEATURE                 Location/Qualifiers
source                  1..467
                        mol_type = protein
                        organism = Homo sapiens
SEQUENCE: 16
```

-continued

```
MDMRVPAQLL GLLLLWLRGA RCEVQLVESG GGLVQPGGSL RLSCAASGFT FSRYWMNWVR   60
QAPGKGLEWV AQIRLKSDNY ATHYAESVKG RFTISRDNAK NSLYLQMNSL RAEDTAVYYC   120
TEGLDYWGQG TTVTVSSAST KGPSVFPLAP SSKSTSGGTA ALGCLVKDYF PEPVTVSWNS   180
GALTSGVHTF PAVLQSSGLY SLSSVVTVPS SSLGTQTYIC NVNHKPSNTK VDKKVEPKSC   240
DKTHTCPPCP APELLGGPSV FLFPPKPKDT LMISRTPEVT CVVVDVSHED PEVKFNWYVD   300
GVEVHNAKTK PREEQYNSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPGK   467

SEQ ID NO: 17          moltype = DNA   length = 708
FEATURE                Location/Qualifiers
source                 1..708
                       mol_type = other DNA
                       organism = Homo sapiens
SEQUENCE: 17
atggacatga gggtcctcgc tcagctcctg gggctcctgc tgctctgttt cccaggtgcc   60
agatgtgaca tccagatgac ccagtctcca tcctcactgt ctgcatctgt aggagacaga   120
gtcaccatca cttgtcgggc gagtcagggt attagcaact ggttagcctg gtatcagcag   180
aaaccagaga agcccctaa gtccctgatc tatgctgcat ccagtttgca aagtggggtc   240
ccatcaaggt tcagcggcag tggatctggg acagatttca ctctcaccat cagcagcctg   300
cagcctgaag attttgcaac ttattactgc caacagtatg atagttaccc tcggacgttc   360
ggccaaggga ccaaggtgga aatcaaacga actgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgcctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga gtcacccat   660
cagggcctga gctcgcccgt cacaaagagc ttcaacaggg gagagtgt   708

SEQ ID NO: 18          moltype = AA   length = 236
FEATURE                Location/Qualifiers
source                 1..236
                       mol_type = protein
                       organism = Homo sapiens
SEQUENCE: 18
MDMRVLAQLL GLLLLCFPGA RCDIQMTQSP SSLSASVGDR VTITCRASQG ISNWLAWYQQ   60
KPEKAPKSLI YAASSLQSGV PSRFSGSGSG TDFTLTISSL QPEDFATYYC QQYDSYPRTF   120
GQGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC   236

SEQ ID NO: 19          moltype = DNA   length = 1398
FEATURE                Location/Qualifiers
source                 1..1398
                       mol_type = other DNA
                       organism = Homo sapiens
SEQUENCE: 19
atggagttgg ggctgaactg ggttttcctt gttgctattt tagaaggtgt ccactgtgag   60
gtgcagctgg tggagtctgg gggaggcttg gtccagcctg gggggtccct gagactctcc   120
tgtgcagctt ctggatttac ctttagtagt tattggatga gttgggtccg ccaggctcca   180
gggaaagggc tggagtgggt ggcctacata aagcaagatg gaaatgagaa atactatgtg   240
gactctgtga agggccgatt caccatctcc agagacaacg ccaagaactc attgtatctg   300
caaatgaaca gcctgagagc cgaggacacg ctgtgtatt actgtgcgag ggaagggata   360
ctttggttcg gggacttacc gacgttctgg ggccagggaa ccctggtcac cgtctctagt   420
gcctccacca agggcccatc ggtcttcccc ctggcgccct gctccaggag cacctccgag   480
agcacagcgc ccctgggctg cctggtcaag gactacttcc ccgaaccggt gacggtgtcg   540
tggaactcag gcgctctgac cagcggcgtg cacaccttcc cagctgtcct acagtcctca   600
ggactctact ccctcagcag cgtggtgacc gtgccctcca gcaacttcgg cacccagacc   660
tacacctgca acgtagatca caagcccagc aacaccaagg tggacaagac agttgagcgc   720
aaatgttgtg tcgagtgccc accgtgccca gcaccacctg tggcaggacc gtcagtcttc   780
ctcttccccc caaaacccaa ggacaccctc atgatctccc ggacccctga ggtcacgtgc   840
gtggtggtgg acgtgagcca cgaagacccc gaggtccagt tcaactggta cgtggacggc   900
gtggaggtgc ataatgccaa gacaaagcca cgggaggagc agttcaacag cacgttccgt   960
gtggtcagc tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaa   1398

SEQ ID NO: 20          moltype = AA   length = 466
FEATURE                Location/Qualifiers
source                 1..466
                       mol_type = protein
                       organism = Homo sapiens
SEQUENCE: 20
MELGLNWVFL VAILEGVHCE VQLVESGGGL VQPGGSLRLS CAASGFTFSS YWMSWVRQAP   60
GKGLEWVAYI KQDGNEKYYV DSVKGRFTIS RDNAKNSLYL QMNSLRAEDT AVYYCAREGI   120
LWFGDLPTFW GQGTLVTVSS ASTKGPSVFP LAPCSRSTSE STAALGCLVK DYFPEPVTVS   180
```

```
WNSGALTSGV HTFPAVLQSS GLYSLSSVVT VPSSNFGTQT YTCNVDHKPS NTKVDKTVER   240
KCCVECPPCP APPVAGPSVF LFPPKPKDTL MISRTPEVTC VVVDVSHEDP EVQFNWYVDG   300
VEVHNAKTKP REEQFNSTFR VVSVLTVVHQ DWLNGKEYKC KVSNKGLPAP IEKTISKTKG   360
QPREPQVYTL PPSREEMTKN QVSLTCLVKG FYPSDIAVEW ESNGQPENNY KTTPPMLDSD   420
GSFFLYSKLT VDKSRWQQGN VFSCSVMHEA LHNHYTQKSL SLSPGK            466

SEQ ID NO: 21            moltype = DNA   length = 723
FEATURE                  Location/Qualifiers
source                   1..723
                         mol_type = other DNA
                         organism = Homo sapiens
SEQUENCE: 21
atggacatga ggctccctgc tcagctcctg gggctgctaa tgctctgggt cccaggatcc   60
agtgggggatg ttctgatgac tcagtctcca ctctccctgc ccgtcaccct tggacagccg   120
gcctccatct cctgcaggtc tagtcaaagc atcgtacaca gtaacggaaa cacctacttg   180
gagtggtatc tgcagaggcc aggccaatct ccaaagctcc taatttataa ggtttctaac   240
cggttctctg gggtcccaga cagattcagc ggcagtgggt caggcactga tttcacactg   300
aaaatcagca gggtggaggc tgaggatgtt ggggtttatt actgcttcca aggtagccac   360
gttcctctga cgtcggcgc agggaccaag ctggaaatca aacggactgt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                        723

SEQ ID NO: 22            moltype = AA   length = 241
FEATURE                  Location/Qualifiers
source                   1..241
                         mol_type = protein
                         organism = Homo sapiens
SEQUENCE: 22
MDMRLPAQLL GLLMLWVPGS SGDVLMTQSP LSLPVTLGQP ASISCRSSQS IVHSNGNTYL   60
EWYLQRPGQS PKLLIYKVSN RFSGVPDRFS GSGSGTDFTL KISRVEADV GVYYCFQGSH   120
VPLTFGAGTK LEIKRTVAAP SVFIFPPSDE QLKSGTASVV CLLNNFYPRE AKVQWKVDNA   180
LQSGNSQESV TEQDSKDSTY SLSSTLTLSK ADYEKHKVYA CEVTHQGLSS PVTKSFNRGE   240
C                                                          241

SEQ ID NO: 23            moltype = DNA   length = 1410
FEATURE                  Location/Qualifiers
source                   1..1410
                         mol_type = other DNA
                         organism = Homo sapiens
SEQUENCE: 23
atggacacac tttgctccac gctcctgctg ctgaccatcc cttcatgggt cttgtcccag   60
gtcaccttga aggagtctgg tcctgcgctg gtgaaaccca cacagaccct cacgctgacc   120
tgcaccttct ctgggttctc actccgcact agtggaatgg gcgtgggctg gatccgtcag   180
cccccaggaa aggccctgga gtggcttgcc cacatttggt gggatgatga taagagctac   240
aacccatctc tgaagagcca gctcaccatc tctaaggaca cctccaaaaa ccaggtggtc   300
cttacaatga ccaacatgga ccctgtggac acagccacat attactgtgc acgcagaaac   360
tattactacg acgactactt cgcctactgg ggccagggca cctggtcac cgtctctagt   420
gcctccacca agggcccatc ggtcttcccc ctggcaccc cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagaa agttgagccc   720
aaatcttgtg acaaaactca cacatgccca ccgtgcccag cacctgaact cctggggggga   780
ccgtcagtct tcctcttccc cccaaaaccc aaggacaccc tcatgatctc ccggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag   1020
gagtacaagt gcaaggtctc caacaaagc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctat agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa                            1410

SEQ ID NO: 24            moltype = AA   length = 470
FEATURE                  Location/Qualifiers
source                   1..470
                         mol_type = protein
                         organism = Homo sapiens
SEQUENCE: 24
MDTLCSTLLL LTIPSWVLSQ VTLKESGPAL VKPTQTLTLT CTFSGFSLRT SGMGVGWIRQ   60
PPGKALEWLA HIWWDDDKSY NPSLKSQLTI SKDTSKNQVV LTMTNMDPVD TATYYCARRN   120
YYDDYFAYW GQGTLVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKKVEP   240
```

```
KSCDKTHTCP PCPAPELLGG PSVFLFPPKP KDTLMISRTP EVTCVVVDVS HEDPEVKFNW    300
YVDGVEVHNA KTKPREEQYN STYRVVSVLT VLHQDWLNGK EYKCKVSNKA LPAPIEKTIS    360
KAKGQPREPQ VYTLPPSRDE LTKNQVSLTC LVKGFYPSDI AVEWESNGQP ENNYKTTPPV    420
LDSDGSFFLY SKLTVDKSRW QQGNVFSCSV MHEALHNHYT QKSLSLSPGK              470

SEQ ID NO: 25          moltype = DNA   length = 705
FEATURE                Location/Qualifiers
source                 1..705
                       mol_type = other DNA
                       organism = Homo sapiens
SEQUENCE: 25
atggaaaccc cggcgcagct gctgtttctg ctgctgctgt ggctgccgga taccaccggc    60
gaaattgtgt tgacgcagtc tccaggcacc ctgtctttgt ctccagggga aagagccacc   120
ctctcctgca gggccagtca gagtgttagc agcagctact tcgcctggta ccaacagaaa   180
cctggccagg ctcccaggct cctcatctat ggtacatcca gcagggccac tggcatccca   240
gacaggttca gtggcagtgg gtctgggaca gacttcactc tcaccgtcag cagactggag   300
cctgaggatt ttgcagtgta ttactgtcag cagtatgata ggtcacctcg gacgttcggc   360
caagggacca aggtggaaat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgt                   705

SEQ ID NO: 26          moltype = AA   length = 235
FEATURE                Location/Qualifiers
source                 1..235
                       mol_type = protein
                       organism = Homo sapiens
SEQUENCE: 26
METPAQLLFL LLLWLPDTTG EIVLTQSPGT LSLSPGERAT LSCRASQSVS SSYFAWYQQK    60
PGQAPRLLIY GTSSRATGIP DRFSGSGSGT DFTLTVSRLE PEDFAVYYCQ QYDRSPRTFG   120
QGTKVEIKRT VAAPSVFIFP PSDEQLKSGT ASVVCLLNNF YPREAKVQWK VDNALQSGNS   180
QESVTEQDSK DSTYSLSSTL TLSKADYEKH KVYACEVTHQ GLSSPVTKSF NRGEC         235

SEQ ID NO: 27          moltype = DNA   length = 1389
FEATURE                Location/Qualifiers
source                 1..1389
                       mol_type = other DNA
                       organism = Homo sapiens
SEQUENCE: 27
atggattgga cctggcgtat tctgtttctg gtggcggcgg cgaccggcgc gcatagccag    60
gtgcagttgg tgcagtctgg ggctgcggtg aagaagcctg gggcctcagt gaaggtctcc   120
tgcaaggctt ctggatacac cttcaccggc tactatatac actgggtgcg acaggcccct   180
ggacaagggc ttgagtggat gggatggatc aaccctaaca gtggtggcac aaactatgca   240
caaaagtttc agggcagggt caccatgacc agggacacgt ccatcagcac agcctccatg   300
gaactgagca ggctgagatc tgacgacacg gccgtttatt tctgtgcgag agatcggtgg   360
ctggatgctt ttgatatctg gggccaaggg acaatggtca ccgtctcttc tgctagcacc   420
aagggcccat cggtcttccc cctggcgccc tgctccagga gcacctccga gagcacagcg   480
gccctgggct gcctggtcaa ggactacttc cccgaaccgg tgacggtgtc gtggaactca   540
ggcgctctga ccagcggcgt gcacaccttc ccagctgtcc tacagtcctc aggactctac   600
tccctcagca gcgtggtgac cgtgccctcc agcaacttcg gcacccagac ctacacctgc   660
aacgtagatc acaagcccag caacaccaag gtggacaaga cagttgagcg caaatgttgt   720
gtcgagtgcc caccgtgccc agcaccacct gtggcaggac cgtcagtctt cctcttcccc   780
ccaaaaccca aggacaccct catgatctcc cggacccctg aggtcacgtg cgtggtggtg   840
gacgtgagcc acgaagaccc cgaggtccag ttcaactggt acgtggacgg cgtggaggtg   900
cataatgcca agacaaagcc acgggaggag cagttcaaca gcacgttccg tgtggtcagc   960
gtcctcaccg ttgtgcacca ggactggctg aacggcaagg agtacaagtg caaggtctcc  1020
aacaaagccc tcccagcccc catcgagaaa accatctcca aaaccaaagg gcagccccga  1080
gaaccacagg tgtacaccct gcccccatcc cgggaggaga tgaccaagaa ccaggtcagc  1140
ctgacctgcc tggtcaaagg cttctacccc agcgacatcg ccgtggagtg ggagagcaat  1200
gggcagccgg agaacaacta caagaccaca cctcccatgc tggactccga cggctccttc  1260
ttcctctaca gcaagctcac cgtggacaag agcaggtggc agcaggggaa cgtcttctca  1320
tgctccgtga tgcatgaggc tctgcacaac cactacacgc agaagagcct ctccctgtct  1380
ccgggtaaa                                                          1389

SEQ ID NO: 28          moltype = AA   length = 463
FEATURE                Location/Qualifiers
source                 1..463
                       mol_type = protein
                       organism = Homo sapiens
SEQUENCE: 28
MDWTWRILFL VAAATGAHSQ VQLVQSGAAV KKPGASVKVS CKASGYTFTG YYIHWVRQAP    60
GQGLEWMGWI NPNSGGTNYA QKFQGRVTMT RDTSISTASM ELSRLRSDDT AVFYCARDRW   120
LDAFDIWGQG TMVTVSSAST KGPSVFPLAP CSRSTSESTA ALGCLVKDYF PEPVTVSWNS   180
GALTSGVHTF PAVLQSSGLY SLSSVVTVPS SNFGTQTYTC NVDHKPSNTK VDKTVERKCC   240
VECPPCPAPP VAGPSVFLFP PKPKDTLMIS RTPEVTCVVV DVSHEDPEVQ FNWYVDGVEV   300
HNAKTKPREE QFNSTFRVVS VLTVVHQDWL NGKEYKCKVS NKGLPAPIEK TISKTKGQPR   360
EPQVYTLPPS REEMTKNQVS LTCLVKGFYP SDIAVEWESN GQPENNYKTT PPMLDSDGSF   420
```

```
FLYSKLTVDK SRWQQGNVFS CSVMHEALHN HYTQKSLSLS PGK                     463

SEQ ID NO: 29          moltype = DNA   length = 705
FEATURE                Location/Qualifiers
source                 1..705
                       mol_type = other DNA
                       organism = Homo sapiens
SEQUENCE: 29
atggaaaccc cagctcagct tctcttcctc ctgctactct ggctcccaga taccaccgga   60
gaaattgtgt tgacgcagtc tccaggcacc ctgtctttgt ctccagggga aagagccacc   120
ctctcctgca gggccagtca gagtgttagc agcggctact aacctggta ccagcagaaa    180
cctggccagg ctcccagact cctcatctat ggtgcatcca gcagggccac tggcatccca   240
gacaggttca gtggcagtgg gtctgggacg gacttcactc tcaccatcag cagactggag   300
cctgaagatt ttgcagtgta ttactgtcag cagtatggta actcactgag caggtttggc   360
caggggacca agctggagat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagacta cgagaaacac aaagtctacg cctgcgaagt cacccatcag    660
ggcctgagct cgcccgtcac aaagagcttc aacaggggag agtgt                   705

SEQ ID NO: 30          moltype = AA   length = 235
FEATURE                Location/Qualifiers
source                 1..235
                       mol_type = protein
                       organism = Homo sapiens
SEQUENCE: 30
METPAQLLFL LLLWLPDTTG EIVLTQSPGT LSLSPGERAT LSCRASQSVS SGYLTWYQQK    60
PGQAPRLLIY GASSRATGIP DRFSGSGSGT DFTLTISRLE PEDFAVYYCQ QYGNSLSRFG    120
QGTKLEIKRT VAAPSVFIFP PSDEQLKSGT ASVVCLLNNF YPREAKVQWK VDNALQSGNS    180
QESVTEQDSK DSTYSLSSTL TLSKADYEKH KVYACEVTHQ GLSSPVTKSF NRGEC         235

SEQ ID NO: 31          moltype = DNA   length = 1422
FEATURE                Location/Qualifiers
source                 1..1422
                       mol_type = other DNA
                       organism = Homo sapiens
SEQUENCE: 31
atggacatga gggtgcccgc tcagctcctg gggctcctgc tgctgtggct gagaggtgcg   60
cgctgtcagg tgcagctggt gggagtctggg ggaggcgtgg tccagcctgg gaggtccctg   120
agactctcct gtgcagcgtc tggattcacc ttcagtagct atggcatgca ctgggtccgc   180
caggctccag gcaaggggct ggagtgggtg gcagttatat ggtatgatgg aagtaataaa   240
tactatgcag actccgtgaa gggccgattc atcatctcca gagataaatc caagaacacg   300
ctgtatctgc aaatgaacag cctgagagcc gaggacacgg ctgtgtatta ctgtgcgaga   360
gcggggggta tagcagcagc tggcctctac tactactacg gtatggacgt ctggggccaa   420
gggaccacgg tcaccgtctc tagtgcctcc accaagggcc catcggtctt ccccctggcg   480
cctgctccca ggagcacctc cgagagcaca gcggccctgg gctgcctggt caaggactac   540
ttccccgaac cggtgacggt gtcgtggaac tcaggcgctc tgaccagcgg cgtgcacacc   600
ttcccagctg tcctacagtc ctcaggactc tactccctca gcagcgtggt gaccgtgccc   660
tccagcaact tcggcaccca gacctacacc tgcaacgtag atcacaagcc cagcaacacc   720
aaggtggaca gacagttga gcgcaaatgt tgtgtcgagt gcccaccgtg cccagcacca   780
cctgtggcag gaccgtcagt cttcctcttc cccccaaaac ccaaggacac cctcatgatc   840
tcccggaccc ctgaggtcac gtgcgtggtg gtggacgtga gccacgaaga ccccgaggtc   900
cagttcaact ggtacgtgga cggcgtggag gtgcataatg ccaagacaaa gccacgggag   960
gagcagttca acagcacgtt ccgtgtggtc agcgtcctca ccgttgtgca ccaggactgg   1020
ctgaacggca aggagtacaa gtgcaaggtc tccaacaaag ccctcccagc ccccatcgag   1080
aaaaccatct ccaaaaccaa agggcagccc cgagaaccac aggtgtacac cctgccccca   1140
tcccgggagg agatgaccaa gaaccaggtc agcctgacct gcctggtcaa aggcttctac   1200
cccagcgaca tcgccgtgga gtgggagagc aatgggcagc cggagaacaa ctacaagacc   1260
acacctccca tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aa                      1422

SEQ ID NO: 32          moltype = AA   length = 474
FEATURE                Location/Qualifiers
source                 1..474
                       mol_type = protein
                       organism = Homo sapiens
SEQUENCE: 32
MDMRVPAQLL GLLLLWLRGA RCQVQLVESG GGVVQPGRSL RLSCAASGFT FSSYGMHWVR    60
QAPGKGLEWV AVIWYDGSNK YYADSVKGRF IISRDKSKNT LYLQMNSLRA EDTAVYYCAR    120
AGGIAAAGLY YYYGMDVWGQ GTTVTVSSAS TKGPSVFPLA PCSRSTSEST AALGCLVKDY    180
FPEPVTVSWN SGALTSGVHT FPAVLQSSGL YSLSSVVTVP SSNFGTQTYT CNVDHKPSNT    240
KVDKTVERKC CVECPPCPAP PVAGPSVFLF PPKPKDTLMI SRTPEVTCVV VDVSHEDPEV    300
QFNWYVDGVE VHNAKTKPRE EQFNSTFRVV SVLTVVHQDW LNGKEYKCKV SNKGLPAPIE    360
KTISKTKGQP REPQVYTLPP SREEMTKNQV SLTCLVKGFY PSDIAVEWES NGQPENNYKT    420
TPPMLDSDGS FFLYSKLTVD KSRWQQGNVF SCSVMHEALH NHYTQKSLSL SPGK          474

SEQ ID NO: 33          moltype = DNA   length = 806
```

```
FEATURE              Location/Qualifiers
source               1..806
                     mol_type = other DNA
                     organism = Homo sapiens
SEQUENCE: 33
atgacatcca ctttgccttt ctctccacag gtgtccactc ccaggtccaa gtttaaacgg   60
atctctagcg aattccctct agagtcgact agaccaccat ggacatgagg gtgcccgctc  120
agctcctggg gctcctgctg ctgtggctga gaggtgcgcg ctgttcttct gagctgactc  180
aggaccctac tgtgtctgtg gccttgggac agacagtcaa aatcacatgc caaggagaca  240
gcctcagaag tttttatgca agctggtacc agcagaagcc aggacaggcc cctgtacttg  300
tcttctatgg taaaaacaac cggccctcag ggatcccaga ccgattctct ggctccagct  360
caggaaacac agcttccttg accatcactg gggctcaggc ggaagatgag gctgactatt  420
attgtaattc ccgggacagc agtgtttacc atctggtact cggcggaggg accaagctga  480
ccgtcctagg tcagcccaag gccaaccca ctgtcactct gttcccgcc tcctctgagg   540
agctccaagc caacaaggcc acactagtgt gtctgatcag tgacttctac ccgggagctg  600
tgacagtggc ctggaaggca gatggcagcc ccgtcaaggc gggagtggag accaccaaac  660
cctccaaaca gagcaacaac aagtacgcgg ccagcagcta cctgagcctg acgcccgagc  720
agtggaagtc ccacagaagc tacagctgcc aggtcacgca tgaagggagc accgtggaga  780
agacagtggc ccctacagaa tgttca                                      806

SEQ ID NO: 34          moltype = AA   length = 236
FEATURE              Location/Qualifiers
source               1..236
                     mol_type = protein
                     organism = Homo sapiens
SEQUENCE: 34
MDMRVPAQLL GLLLLWLRGA RCSSELTQDP TVSVALGQTV KITCQGDSLR SFYASWYQQK   60
PGQAPVLVFY GKNNRPSGIP DRFSGSSSGN TASLTITGAQ AEDEADYYCN SRDSSVYHLV  120
LGGGTKLTVL GQPKANPTVT LFPPSSEELQ ANKATLVCLI SDFYPGAVTV AWKADGSPVK  180
AGVETTKPSK QSNNKYAASS YLSLTPEQWK SHRSYSCQVT HEGSTVEKTV APTECS      236

SEQ ID NO: 35          moltype = DNA   length = 1434
FEATURE              Location/Qualifiers
source               1..1434
                     mol_type = other DNA
                     organism = Homo sapiens
SEQUENCE: 35
atggacatga gggtgcccgc tcagctcctg gggctcctgc tgctgtggct gagaggtgcg   60
cgctgtcagg tgcagttggt gcagtctggg gctgaggtga agaagcctgg ggcctcagtg  120
aaggtctcct gcaaggcttc tggatacacc ttcaccggct actatatgca ctgggtgcga  180
caggcccctg gacaagggct tgagtggatg ggatggatca accctaacag tggtggcaca  240
aactatgcac agaagtttca gggcagggtc accatgacca gggacacgtc catcagcaca  300
gcctacatgg agctgagcag gctgagatct gacgacacgg ccgtgtattt ctgtgcgaga  360
gatcaaatga gtattattat gcttcgggga gttttttcccc cttactatta cggtatggac  420
gtctggggcc aagggaccac ggtcaccgtc tctagtgcct ccaccaaggg cccatcggtc  480
ttccccctgg cgccctgctc caggagcacc tccgagagca gcggccct gggctgcctg  540
gtcaaggact acttccccga accggtgacg gtgtcgtgga actcaggcgc tctgaccagc  600
ggcgtgcaca ccttcccagc tgtcctacag tcctcaggac tctactccct cagcagcgtg  660
gtgaccgtgc cctccagcaa cttcggcacc cagacctaca cctgcaacgt agatcacaag  720
cccagcaaca ccaaggtgga caagacagtt gagcgcaaat gttgtgtcga gtgcccaccg  780
tgcccagcac cacctgtggc aggaccgtca gtcttcctct tccccccaaa acccaaggac  840
accctcatga tctcccggac ccctgaggtc acgtgcgtgg tggtggacgt gagccacgaa  900
gaccccgagg tccagttcaa ctggtacgtg gacggcgtgg aggtgcataa tgccaagaca  960
aagccacggg aggagcagtt caacagcacg ttccgtgtgg tcagcgtcct caccgttgtg 1020
caccaggact ggctgaacgg caaggagtac aagtgcaagg tctccaacaa aggcctccca 1080
gccccccatcg agaaaaccat ctccaaaacc aaagggcagc cccgagaacc acaggtgtac 1140
accctgcccc catcccggga ggagatgacc aagaaccagg tcagcctgac ctgcctggtc 1200
aaaggcttct accccagcga catcgccgtg gagtgggaga gcaatgggca gccggagaac 1260
aactacaaga ccacacctcc catgctggac tccgacggct ccttcttcct ctacagcaag 1320
ctcaccgtgg acaagagcag gtggcagcag gggaacgtct tctcatgctc cgtgatgcat 1380
gaggctctgc acaaccacta cacgcagaag agcctctccc tgtctccggg taaa        1434

SEQ ID NO: 36          moltype = AA   length = 478
FEATURE              Location/Qualifiers
source               1..478
                     mol_type = protein
                     organism = Homo sapiens
SEQUENCE: 36
MDMRVPAQLL GLLLLWLRGA RCQVQLVQSG AEVKKPGASV KVSCKASGYT FTGYYMHWVR   60
QAPGQGLEWM GWINPNSGGT NYAQKFQGRV TMTRDTSIST AYMELSRLRS DDTAVYFCAR  120
DQMSIIMLRG VFPPYYYGMD VWGQGTTVTV SSASTKGPSV FPLAPCSRST SESTAALGCL  180
VKDYFPEPVT VSWNSGALTS GVHTFPAVLQ SSGLYSLSSV VTVPSSNFGT QTYTCNVDHK  240
PSNTKVDKTV ERKCCVECPP CPAPPVAGPS VFLFPPKPKD TLMISRTPEV TCVVVDVSHE  300
DPEVQFNWYV DGVEVHNAKT KPREEQFNST FRVVSVLTVV HQDWLNGKEY KCKVSNKGLP  360
APIEKTISKT KGQPREPQVY TLPPSREEMT KNQVSLTCLV KGFYPSDIAV EWESNGQPEN  420
NYKTTPPMLD SDGSFFLYSK LTVDKSRWQQ GNVFSCSVMH EALHNHYTQK SLSLSPGK    478

SEQ ID NO: 37          moltype = DNA   length = 723
FEATURE              Location/Qualifiers
```

-continued

```
source                  1..723
                        mol_type = other DNA
                        organism = Homo sapiens
SEQUENCE: 37
atggacatga gggtgcccgc tcagctcctg gggctcctgc tgctgtggct gagaggtgcc   60
agatgtgata ttgtgatgac tcagtctcca ctctccctgc ccgtcacccc tggagagccg  120
gcctccatct cctgcaggtc tagtcagagc ctcctgcata gtaatggata caactatttg  180
gattggtacc tgcagaagcc agggcagtct ccacagctcc tgatctattt gggttctaat  240
cgggcctccg gggtccctga caggttcagt ggcagtggat caggcacaga ttttacactg  300
aaaatcagca gagtggaggc tgaggatgtt ggggtttatt actgcatgca agctctacaa  360
actccgctca ctttcggcgg agggaccaag gtagagatca aacggactgt ggctgcacca  420
tctgtcttca tcttcccgcc atctgatgag cagttgaaat ctggaactgc ctctgttgtg  480
tgcctgctga ataacttcta tcccagagag gccaaagtac agtggaaggt ggataacgcc  540
ctccaatcgg gtaactccca ggagagtgtc acagagcagg acagcaagga cagcacctac  600
agcctcagca gcaccctgac gctgagcaaa gcagactacg agaaacacaa agtctacgcc  660
tgcgaagtca cccatcaggg cctgagctcg cccgtcacaa agagcttcaa caggggagag  720
tgt                                                                723

SEQ ID NO: 38       moltype = AA  length = 241
FEATURE             Location/Qualifiers
source              1..241
                    mol_type = protein
                    organism = Homo sapiens
SEQUENCE: 38
MDMRVPAQLL GLLLLWLRGA RCDIVMTQSP LSLPVTPGEP ASISCRSSQS LLHSNGYNYL   60
DWYLQKPGQS PQLLIYLGSN RASGVPDRFS GSGSGTDFTL KISRVEAEDV GVYYCMQALQ  120
TPLTFGGGTK VEIKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                  241

SEQ ID NO: 39       moltype = DNA  length = 1425
FEATURE             Location/Qualifiers
source              1..1425
                    mol_type = other DNA
                    organism = Homo sapiens
SEQUENCE: 39
atggacatga gggtgcccgc tcagctcctg gggctcctgc tgctgtggct gagaggtgcc   60
agatgtgagg tgcagctggt ggagtctggg ggaggcttgg tccagcctgg ggggtccctg  120
agactctcct gtgcagcctc cggattcacc tttagtagct attggatgag ctgggtccgc  180
caggctccag ggaaggggct ggagtgggtg gccagcataa aacaagatgg aagtgagaaa  240
tactatgtgg actctgtgaa gggccgattc accatctcca gagacaacgc caggaactca  300
ctgtatctgc aaatgaacag cctgagagcc gaggacacgc tgtgtatta ctgtgcgaga  360
gatcttgtat taatggtgta tgatatagac tactactact acggtatgga cgtctggggc  420
caagggacca cggtcaccgt ctcctcagcc tccaccaagg gcccatcggt cttccccctg  480
gcgccctgct ccaggagcac ctccgagagc acagcggccc tgggctgcct ggtcaaggac  540
tacttccccg aaccggtgac ggtgtcgtgg aactcaggcg ctctgaccag cggcgtgcac  600
accttcccag ctgtcctaca gtcctcagga ctctactccc tcagcagcgt ggtgaccgtg  660
ccctccagca acttcggcac ccagacctac acctgcaacg tagatcacaa gcccagcaac  720
accaaggtgg acaagacagt tgagcgcaaa tgttgtgtcg agtgcccacc gtgcccagca  780
ccacctgtgc caggaccgtc agtcttcctc ttcccccaa aacccaagga cacccctcatg  840
atctcccgga cccctgaggt cacgtgcgtg gtggtggacg tgagccacga agaccccgga  900
gtccagttca actggtacgt ggacggcgtg gaggtgcata tgccaagac aaagccacgg  960
gaggagcagt tcaacagcac gttccgtgtg gtcagcgtcc tcaccgttgt gcaccaggac  1020
tggctgaacg gcaaggagta caagtgcaag gtctccaaca aagccctccc agcccccatc  1080
gagaaaacca tctccaaaac caaagggcag ccccgagaac cacaggtgta cacccctgccc  1140
ccatcccggg aggagatgac caagaaccag gtcagcctga cctgcctggt caaaggcttc  1200
taccccagcg acatcgccgt ggagtgggag agcaatgggc agccggagaa caactacaag  1260
accacacctc ccatgctgga ctccgacggc tccttcttcc tctacagcaa gctcaccgtg  1320
gacaagagca ggtggcagca ggggaacgtc ttctcatgct ccgtgatgca tgaggctctg  1380
cacaaccact acacgcagaa gagcctctcc ctgtctccgg gtaaa                  1425

SEQ ID NO: 40       moltype = AA  length = 475
FEATURE             Location/Qualifiers
source              1..475
                    mol_type = protein
                    organism = Homo sapiens
SEQUENCE: 40
MDMRVPAQLL GLLLLWLRGA RCEVQLVESG GGLVQPGGSL RLSCAASGFT FSSYWMSWVR   60
QAPGKGLEWV ASIKQDGSEK YYVDSVKGRF TISRDNARNS LYLQMNSLRA EDTAVYYCAR  120
DLVLMVYDID YYYYGMDVWG QGTTVTVSSA STKGPSVFPL APCSRSTSES TAALGCLVKD  180
YFPEPVTVSW NSGALTSGVH TFPAVLQSSG LYSLSSVVTV PSSNFGTQTY TCNVDHKPSN  240
TKVDKTVERK CCVECPPCPA PPVAGPSVFL FPPKPKDTLM ISRTPEVTCV VVDVSHEDPE  300
VQFNWYVDGV EVHNAKTKPR EEQFNSTFRV VSVLTVVHQD WLNGKEYKCK VSNKGLPAPI  360
EKTISKTKGQ PREPQVYTLP PSREEMTKNQ VSLTCLVKGF YPSDIAVEWE SNGQPENNYK  420
TTPPMLDSDG SFFLYSKLTV DKSRWQQGNV FSCSVMHEAL HNHYTQKSLS LSPGK        475

SEQ ID NO: 41       moltype = DNA  length = 723
FEATURE             Location/Qualifiers
source              1..723
```

```
                        mol_type = other DNA
                        organism = Homo sapiens
SEQUENCE: 41
atggacatga gggtgcccgc tcagctcctg gggctcctgc tgctgtggct gagaggtgcc    60
agatgtgata ttgtgatgac tcagtctcca ctctccctgc ccgtcacccc tggagagccg   120
gcctccatct cctgcaggtc tagtcagagc ctcctgcata gtaatgggta caactatttg   180
gattggtacc tgcagaagcc agggcagtct ccacagctcc tgatctattt gggttctaat   240
cgggcctccg gggtccctga caggttcagt ggcagtggat caggcacaca tcttacactg   300
aaaatcagca gagtggaggc tgaggatgtt ggagtttatt actgcatgca aactctacaa   360
actccgctca ctttcggcgg agggaccaag gtagagatca aacggactgt ggctgcacca   420
tctgtcttca tcttcccgcc atctgatgag cagttgaaat ctggaactgc ctctgttgtg   480
tgcctgctga taacttcta tcccagagag gccaaagtac agtggaaggt ggataacgcc     540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                  723

SEQ ID NO: 42        moltype = AA  length = 241
FEATURE              Location/Qualifiers
source               1..241
                     mol_type = protein
                     organism = Homo sapiens
SEQUENCE: 42
MDMRVPAQLL GLLLLWLRGA RCDIVMTQSP LSLPVTPGEP ASISCRSSQS LLHSNGYNYL    60
DWYLQKPGQS PQLLIYLGSN RASGVPDRFS GSGSGTHLTL KISRVEAEDV GVYYCMQTLQ   120
TPLTFGGGTK VEIKRTVAAP SVFIFPPSDE QLKSGTASVV CLLNNFYPRE AKVQWKVDNA   180
LQSGNSQESV TEQDSKDSTY SLSSTLTLSK ADYEKHKVYA CEVTHQGLSS PVTKSFNRGE   240
C                                                                    241

SEQ ID NO: 43        moltype = DNA  length = 1425
FEATURE              Location/Qualifiers
source               1..1425
                     mol_type = other DNA
                     organism = Homo sapiens
SEQUENCE: 43
atggacatga gggtgcccgc tcagctcctg gggctcctgc tgctgtggct gagaggtgcc    60
agatgtgagg tgcagctggt ggagtctggg ggaggcttgg tccagcctgg ggggtccctg   120
agactctcct gtgcagcctc cggattcacc tttagtaact attggatgag ctgggtccgc   180
caggctccag ggaaggggct ggagtgggtg gccagcataa aacaagatgg aagtgagaaa   240
tactatgtgg actctgtgaa gggccgattc gccatctcca gagacaacgc caagaactca   300
ctgtttctgc aaatgaacag cctgagagcc gaggacacgg ctgtgtatta ctgtgcgaga   360
gatcttgtac taatggtgta tgatatagac tactactact acggtatgga cgtctggggc   420
caagggacca cggtcaccgt ctcctcagcc tccaccaagg gcccatcggt cttccccctg   480
gcgccctgct ccaggagcac ctccgagagc acagcggccc tgggctgcct ggtcaaggac   540
tacttccccg aaccggtgac ggtgtcgtgg aactcaggcg ctctgaccag cggcgtgcac   600
accttccag ctgtcctaca gtcctcagga ctctactccc tcagcagcgt ggtgaccgtg    660
ccctccagca cttcggcac ccagacctac acctgcaacg tagatcacaa gcccagcaac     720
accaaggtgg acaagacagt tgagcgcaaa tgttgtgtcg agtgcccacc gtgcccagca   780
ccacctgtgg caggaccgtc agtcttcctc ttcccccaa aacccaagga caccctcatg     840
atctcccgga cccctgaggt cacgtgcgtg gtggtggacg tgagccacga agaccccgag   900
gtccagttca actggtacgt ggacggcgtg gaggtgcata atgccaagac aaagccgcgg   960
gaggagcagt tcaacagcac gttccgtgtg gtcagcgtcc tcaccgttgt gcaccaggac  1020
tggctgaacg gcaaggagta caagtgcaag gtctccaaca aaggcctccc agcccccatc  1080
gagaaaacca tctccaaaac caaagggcag ccccgagaac cacaggtgta caccctgccc  1140
ccatcccggg aggagatgac caagaaccag gtcagcctga cctgcctggt caaaggcttc  1200
taccccagcg acatcgccgt ggagtgggag agcaatgggc agccggagaa caactacaag  1260
accacacctc ccatgctgga ctccgacggc tccttcttcc tctacagcaa gctcaccgtg  1320
gacaagagca ggtggcagca ggggaacgtc ttctcatgct ccgtgatgca tgaggctctg  1380
cacaaccact acacgcagaa gagcctctcc ctgtctccgg gtaaa                  1425

SEQ ID NO: 44        moltype = AA  length = 475
FEATURE              Location/Qualifiers
source               1..475
                     mol_type = protein
                     organism = Homo sapiens
SEQUENCE: 44
MDMRVPAQLL GLLLLWLRGA RCEVQLVESG GGLVQPGGSL RLSCAASGFT FSNYWMSWVR    60
QAPGKGLEWV ASIKQDGSEK YYVDSVKGRF AISRDNAKNS LFLQMNSLRA EDTAVYYCAR   120
DLVLMVYDID YYYYGMDVWG QGTTVTVSSA STKGPSVFPL APCSRSTSES TAALGCLVKD   180
YFPEPVTVSW NSGALTSGVH TFPAVLQSSG LYSLSSVVTV PSSNFGTQTY TCNVDHKPSN   240
TKVDKTVERK CCVECPPCPA PPVAGPSVFL FPPKPKDTLM ISRTPEVTCV VVDVSHEDPE   300
VQFNWYVDGV EVHNAKTKPR EEQFNSTFRV VSVLTVVHQD WLNGKEYKCK VSNKGLPAPI   360
EKTISKTKGQ PREPQVYTLP PSREEMTKNQ VSLTCLVKGF YPSDIAVEWE SNGQPENNYK   420
TTPPMLDSDG SFFLYSKLTV DKSRWQQGNV FSCSVMHEAL HNHYTQKSLS LSPGK          475

SEQ ID NO: 45        moltype = DNA  length = 705
FEATURE              Location/Qualifiers
source               1..705
                     mol_type = other DNA
```

```
                         organism = Homo sapiens
SEQUENCE: 45
atgacttgtt ctccactgct gctgactctg ctgattcatt gtactggttc ttgggcgcag   60
tctgtgttga cgcagccgcc ctcagtgtct gcggccccag gacagaaggt caccatctcc  120
tgctctggaa gcagctccaa cattgggaat aattatgtat cctggtacca gcagctccca  180
ggaacagccc ccaaactcct catttatgac aataataagc gacccctcag gattcctgac  240
cgattctctg gctccaagtc tggcacgtca accaccctgg gcatcaccgg actccagact  300
ggggacgagg ccgattatta ctgcggaaca tgggatagcc gcctgagtgc tgtggttttc  360
ggcggaggga ccaagctgac cgtcctaggt cagcccaagg ccaacccac  tgtcactctg  420
ttcccgccct cctctgagga gctccaagcc aacaaggcca cactagtgtg tctgatcagt  480
gacttctacc cgggagctgt gacagtggcc tggaaggcag atggcagccc cgtcaaggcg  540
ggagtggaga ccaccaaacc ctccaaacag agcaacaaca gtacgcggc  cagcagctac  600
ctgagcctga cgcccgagca gtggaagtcc cacagaagct acagctgcca ggtcacgcat  660
gaagggagca ccgtggagaa gacagtggcc cctacagaat gttca             705

SEQ ID NO: 46           moltype = AA  length = 235
FEATURE                 Location/Qualifiers
source                  1..235
                        mol_type = protein
                        organism = Homo sapiens
SEQUENCE: 46
MTCSPLLLTL LIHCTGSWAQ SVLTQPPSVS AAPGQKVTIS CSGSSSNIGN NYVSWYQQLP   60
GTAPKLLIYD NNKRPSGIPD RFSGSKSGTS TTLGITGLQT GDEADYYCGT WDSRLSAVVF  120
GGGTKLTVLG QPKANPTVTL FPPSSEELQA NKATLVCLIS DFYPGAVTVA WKADGSPVKA  180
GVETTKPSKQ SNNKYAASSY LSLTPEQWKS HRSYSCQVTH EGSTVEKTVA PTECS       235

SEQ ID NO: 47           moltype = DNA  length = 1425
FEATURE                 Location/Qualifiers
source                  1..1425
                        mol_type = other DNA
                        organism = Homo sapiens
SEQUENCE: 47
atggaatttg gtctgtcttg ggtatttctg gttgctctgc tgcgtggcgt gcagtgccag   60
gtgcagctgg tggaatctgg gggaggcgtg gtccagcctg gaggtccct  gagactctca  120
tgtgcagcct ctggattcac cttcagtagc tttggcatgc actgggtccg ccaggctcca  180
ggcaagggg  ctggagtggg tggcagttata tcatttgatg gaagtattaa gtattctgta  240
gactccgtga agggccgatt caccatctcc agagacaatt caaagaacac gctgtttctg  300
caaatgaaca gcctgcgagc cgaggacacg gctgtgtatt actgtgcgag agatcggctc  360
aattactatg atagtagtgg ttattatcac tacaaatact acggtatggc cgtctggggc  420
caagggacca cggtcaccgt ctctagtgcc tccaccaagg gcccatcggt cttccccctg  480
gcgccctgct ccaggagcac ctccgagagc acagcggcc  ctgggctgcct ggtcaaggac  540
tacttccccg aaccggtgac ggtgtcgtgg aactcaggcg ctctgaccag cggcgtgcac  600
accttcccag ctgtcctaca gtcctcagga ctctactccc tcagcagcgt ggtgaccgtg  660
ccctccagca acttcggcac ccagacctac acctgcaacg tagatcacaa gcccagcaac  720
accaaggtgg acaagacagt tgagcgcaaa tgttgtgtcg agtgcccacc gtgcccagca  780
ccacctgtgc caggaccgtc agtcttcctc ttcccccca  aacccaagga caccctcatg  840
atctcccgga cccctgaggt cacgtgcgtg gtggtggacg tgagccacga agaccccgga  900
gtccagttca actggtacgt ggacggcgtg gaggtgcata atgccaagac aaagccacgg  960
gaggagcagt tcaacagcac gttccgtgtg gtcagcgtcc tcaccgttgt gcaccaggac  1020
tggctgaacg gcaaggagta caagtgcaag gtctccaaca aaggcctccc agcccccatc  1080
gagaaaacca tctccaaaac caaagggcag ccccgagaac cacaggtgta cacccttgccc  1140
ccatcccggg aggagatgac caagaaccag gtcagcctga cctgcctggt caaaggcttc  1200
taccccagcg acatcgccgt ggagtgggag agcaatgggc agccggagaa caactacaag  1260
accacacctc ccatgctgga ctccgacggc tccttcttcc tctacagcaa gctcaccgtg  1320
gacaagagca ggtggcagca ggggaacgtc ttctcatgct ccgtgatgca tgaggctctg  1380
cacaaccact acacgcagaa gagcctctcc ctgtctccgg gtaaa              1425

SEQ ID NO: 48           moltype = AA  length = 475
FEATURE                 Location/Qualifiers
source                  1..475
                        mol_type = protein
                        organism = Homo sapiens
SEQUENCE: 48
MEFGLSWVFL VALLRGVQCQ VQLVESGGGV VQPGRSLRLS CAASGFTFSS FGMHWVRQAP   60
GKGLEWVAVI SFDGSIKYSV DSVKGRFTIS RDNSKNTLFL QMNSLRAEDT AVYYCARDRL  120
NYYDSSGYYH YKYYGMAVWG QGTTVTVSSA STKGPSVFPL APCSRSTSES TAALGCLVKD  180
YFPEPVTVSW NSGALTSGVH TFPAVLQSSG LYSLSSVVTV PSSNFGTQTY TCNVDHKPSN  240
TKVDKTVERK CCVECPPCPA PPVAGPSVFL FPPKPKDTLM ISRTPEVTCV VVDVSHEDPE  300
VQFNWYVDGV EVHNAKTKPR EEQFNSTFRV VSVLTVVHQD WLNGKEYKCK VSNKGLPAPI  360
EKTISKTKGQ PREPQVYTLP PSREEMTKNQ VSLTCLVKGF YPSDIAVEWE SNGQPENNYK  420
TTPPMLDSDG SFFLYSKLTV DKSRWQQGNV FSCSVMHEAL HNHYTQKSLS LSPGK       475

SEQ ID NO: 49           moltype = DNA  length = 702
FEATURE                 Location/Qualifiers
source                  1..702
                        mol_type = other DNA
                        organism = Homo sapiens
SEQUENCE: 49
atggacatga gggtgcccgc tcagctcctg gggctcctgc tgctgtggct gagaggtgcc   60
```

-continued

```
agatgttatg agctgactca gccaccctca gtgtccgtgt ccccaggaca gacagccacc    120
atcacctgct ctggagataa attggggga agatatgcgt cttggtatca gcagaggcca    180
ggccagtccc ctgtactggt catctatcaa gatatcaagc ggccctcagg gatccctgag    240
cgattctctg gctccaactc tgggaacaca gccactctga ccatcagcgg gacccaggct    300
atggatgagg ctgactattt ctgtcaggcg tggtacagca gcacaatgt gcttttcggc    360
ggagggacca agctgaccgt cctaggtcag cccaaggctg cccctcggt cactctgttc    420
ccgccctcct ctgaggagct tcaagccaac aaggccacac tggtgtgtct cataagtgac    480
ttctacccgg gagccgtgac agtggcctgg aaggcagata gcagcccgt caaggcggga    540
gtggagacca ccacccctc aaacaaagc aacaacaagt acgcggccag cagctatctg    600
agcctgacgc ctgagcagtg gaagtcccac agaagctaca gctgccaggt cacgcatgaa    660
gggagcaccg tggagaagac agtggcccct acagaatgtt ca    702

SEQ ID NO: 50          moltype = AA   length = 234
FEATURE                Location/Qualifiers
source                 1..234
                       mol_type = protein
                       organism = Homo sapiens
SEQUENCE: 50
MDMRVPAQLL GLLLLWLRGA RCYELTQPPS VSVSPGQTAT ITCSGDKLGE RYASWYQQRP    60
GQSPVLVIYQ DIKRPSGIPE RFSGSNSGNT ATLTISGTQA MDEADYFCQA WYSSTNVLFG    120
GGTKLTVLGQ PKAAPSVTLF PPSSEELQAN KATLVCLISD FYPGAVTVAW KADSSPVKAG    180
VETTTPSKQS NNKYAASSYL SLTPEQWKSH RSYSCQVTHE GSTVEKTVAP TECS    234

SEQ ID NO: 51          moltype = DNA   length = 1398
FEATURE                Location/Qualifiers
source                 1..1398
                       mol_type = other DNA
                       organism = Homo sapiens
SEQUENCE: 51
atggagtttg ggctgagctg ggttttcctc gttgctcttt taagaggtgt ccagtgtcag    60
gtgcagctgg tggagtctgg gggaggcgtg gtccagcctg ggaggtccct gagactctcc    120
tgtgcagcgt ctggattcac cttcagtagc tatggcatgc actgggtccg ccaggctcca    180
ggcaagggc tggagtgggt ggcagttata tggtatgctg aaagtaataa atactacgca    240
gactccgtga agggccgatt caccatctcc agagacaatt ccaagaacac gctgtatctg    300
caaatgaaca gcctgagagc cgaggacacg gctgtgtatt actgtgcgag agcccaggag    360
ggtatagccc ctgacgcttt tgatatctgg ggccaaggaa caatggtcac cgtctcttca    420
gcctccacca agggcccatc ggtcttcccc ctggcgccct gctccaggag cacctccgag    480
agcacagcgg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc    1020
aaggtctcca acaaaggcct cccagccccc atcgagaaaa ccatctccaa aaccaaaggg    1080
cagccccgag aaccacaggt gtacaccctg cccccatccc gggaggagat gaccaagaac    1140
caggtcagcc tgacctgcct ggtcaaaggc ttctacccca gcgacatcgc cgtggagtgg    1200
gagagcaatg ggcagccgga gaacaactac aagaccacac tcccatgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaa    1398

SEQ ID NO: 52          moltype = AA   length = 466
FEATURE                Location/Qualifiers
source                 1..466
                       mol_type = protein
                       organism = Homo sapiens
SEQUENCE: 52
MEFGLSWVFL VALLRGVQCQ VQLVESGGGV VQPGRSLRLS CAASGFTFSS YGMHWVRQAP    60
GKGLEWVAVI WYAESNKYYA DSVKGRFTIS RDNSKNTLYL QMNSLRAEDT AVYYCARQE    120
GIAPDAFDIW GQGTMVTVSS ASTKGPSVFP LAPCSRSTSE STAALGCLVK DYFPEPVTVS    180
WNSGALTSGV HTFPAVLQSS GLYSLSSVVT VPSSNFGTQT YTCNVDHKPS NTKVDKTVER    240
KCCVECPPCP APPVAGPSVF LFPPKPKDTL MISRTPEVTC VVVDVSHEDP EVQFNWYVDG    300
VEVHNAKTKP REEQFNSTFR VVSVLTVVHQ DWLNGKEYKC KVSNKGLPAP IEKTISKTKG    360
QPREPQVYTL PPSREEMTKN QVSLTCLVKG FYPSDIAVEW ESNGQPENNY KTTPPMLDSD    420
GSFFLYSKLT VDKSRWQQGN VFSCSVMHEA LHNHYTQKSL SLSPGK    466

SEQ ID NO: 53          moltype = DNA   length = 702
FEATURE                Location/Qualifiers
source                 1..702
                       mol_type = other DNA
                       organism = Homo sapiens
SEQUENCE: 53
atggggtcaa ccgccatcct tggcctcctc ctggctgtcc tgcagggagg cgcgccgaa    60
attgtgttga cgcagtctcc aggcaccctg tctttgtctc caggggaaag agccaccctc    120
tcctgcaggc ccagtcagag tgttagcagc agctacttag cctggcacca gcagaaacct    180
ggccaggctc ccaggctcct catctatggt gcatccagca gggccactgg catcccagac    240
```

-continued

```
aggttcagtg gcagtgggtc tgggacagac ttcactctca ccatcagcag actggagcct    300
gaagattttg cagtgtatta ctgtcagcag tatggtagct caccgtggac gttcggccaa    360
gggaccaagg tggaaatcaa acgtacggtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gt                      702
```

```
SEQ ID NO: 54            moltype = AA   length = 234
FEATURE                  Location/Qualifiers
source                   1..234
                         mol_type = protein
                         organism = Homo sapiens
SEQUENCE: 54
MGSTAILGLL LAVLQGGRAE IVLTQSPGTL SLSPGERATL SCRASQSVSS SYLAWHQQKP    60
GQAPRLLIYG ASSRATGIPD RFSGSGSGTD FTLTISRLEP EDFAVYYCQQ YGSSPWTFGQ   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC         234
```

```
SEQ ID NO: 55            moltype = DNA   length = 1389
FEATURE                  Location/Qualifiers
source                   1..1389
                         mol_type = other DNA
                         organism = Homo sapiens
SEQUENCE: 55
atggggtcaa ccgccatcct tggcctcctc ctggctgtcc tgcagggagg gcgcgccgag     60
gtgcagctat ggagtctggg gggaggcttg gtacagcctg gggggtccct gagactctcc    120
tgtgcagcct ctggattcac ctttagcacc tatgtcatga gctgggtccg ccaggctcca    180
gggaaggggc tggagtgggt ctcaagtatt agtggtagtg gtcttggctc atactacgca    240
gactccgtga agggccggtt caccatctcc agagacaatt ccaagaacac gctgtatctg    300
caaatgaaca gcctgagagc cgaggacacg gccgtatatt actgtgcgaa agaggcccat    360
cggggggccct tgactactg gggccaggga accctggtca ccgtctcctc agctagcacc    420
aagggcccat cggtcttccc cctggcgccc tgctccagga gcacctccga gagcacagcc    480
gccctgggct gcctggtcaa ggactacttc cccgaaccgg tgacggtgtc gtggaactca    540
ggcgctctga ccagcggcgt gcacaccttc ccagctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttgagcg caaatgttgt    720
gtcgagtgcc caccgtgccc agcaccacct gtggcaggac cgtcagtctt cctcttcccc    780
ccaaaaccca aggacaccct catgatctcc cggacccctg aggtcacgtg cgtggtggtg    840
gacgtgagcc acgaagaccc cgaggtccag ttcaactggt acgtggacgg cgtggaggtg    900
cataatgcca agacaaagcc acgggaggag cagttcaaca gcacgttccg tgtggtcagc    960
gtcctcaccg ttgtgcacca ggactggctg aacggcaagg agtacaagtg caaggtctcc   1020
aacaaaggcc tcccagcccc catcgagaaa accatctcca aaaccaaagg gcagcccga   1080
gaaccacagg tgtacaccct gccccatcc gggaggaga tgaccaagaa ccaggtcagc   1140
ctgacctgcc tggtcaaagg cttctacccc agcgacatcg ccgtggagtg ggagagcaat   1200
gggcagccgg agaacaacta caagaccaca cctcccatgc tggactccga cggctccttc   1260
ttcctctaca gcaagctcac cgtggacaag agcaggtggc agcaggggaa cgtcttctca   1320
tgctccgtga tgcatgaggc tctgcacaac cactacacgc agaagagcct ctccctgtct   1380
ccgggtaaa                                                          1389
```

```
SEQ ID NO: 56            moltype = AA   length = 463
FEATURE                  Location/Qualifiers
source                   1..463
                         mol_type = protein
                         organism = Homo sapiens
SEQUENCE: 56
MGSTAILGLL LAVLQGGRAE VQLLESGGGL VQPGGSLRLS CAASGFTFST YVMSWVRQAP    60
GKGLEWVSSI SGSGLGSYYA DSVKGRFTIS RDNSKNTLYL QMNSLRAEDT AVYYCAKEAH   120
RGPFDYWGQG TLVTVSSAST KGPSVFPLAP CSRSTSESTA ALGCLVKDYF PEPVTVSWNS   180
GALTSGVHTF PAVLQSSGLY SLSSVVTVPS SNFGTQTYTC NVDHKPSNTK VDKTVERKCC   240
VECPPCPAPP VAGPSVFLFP PKPKDTLMIS RTPEVTCVVV DVSHEDPEVQ FNWYVDGVEV   300
HNAKTKPREE QFNSTFRVVS VLTVVHQDWL NGKEYKCKVS NKGLPAPIEK TISKTKGQPR   360
EPQVYTLPPS REEMTKNQVS LTCLVKGFYP SDIAVEWESN GQPENNYKTT PPMLDSDGSF   420
FLYSKLTVDK SRWQQGNVFS CSVMHEALHN HYTQKSLSLS PGK                    463
```

```
SEQ ID NO: 57            moltype = DNA   length = 721
FEATURE                  Location/Qualifiers
source                   1..721
                         mol_type = other DNA
                         organism = Homo sapiens
SEQUENCE: 57
atgaggctcc ttgctcagct tctggggctg ctaatgctct gggtccctgg atccagtggg     60
gatattgtga tgacccagac tccactctcc tcacctgtca cccttggaca gccggcctcc    120
atctcctgca ggtctagtca aagcctcgta cacagtgatg gaaacaccta cttgagttgg    180
cttcagcaga ggccaggcca gcctccaaga ctcctaattt ataagaaatt taaccggttc    240
tctggggtcc cagacagatt cagtggcagt ggggcaggga cagatttcac actgaaaatc    300
agcagggtgg aagctgagga tgtcggggtt tattactgca tgcaagctac acaaattcct    360
ctcactttcg gccctgggac caaagtggat atcaaacgaa ctgtggctgc accatctgtc    420
```

```
ttcatcttcc cgccatctga tgagcagttg aaatctggaa ctgcctctgt tgtgtgcctg   480
ctgaataact tctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgttga   720
g                                                                   721
```

SEQ ID NO: 58            moltype = AA  length = 239
FEATURE                  Location/Qualifiers
source                   1..239
                         mol_type = protein
                         organism = Homo sapiens
SEQUENCE: 58
```
MRLLAQLLGL LMLWVPGSSG DIVMTQTPLS SPVTLGQPAS ISCRSSQSLV HSDGNTYLSW   60
LQQRPGQPPR LLIYKKFNRF SGVPDRFSGS GAGTDFTLKI SRVEAEDVGV YYCMQATQIP   120
LTFGPGTKVD IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239
```

SEQ ID NO: 59            moltype = DNA  length = 1416
FEATURE                  Location/Qualifiers
source                   1..1416
                         mol_type = other DNA
                         organism = Homo sapiens
SEQUENCE: 59
```
atggagtttg ggctgagctg ggttttcctc gttgctcttt taagaggtgt ccagtgtcag   60
gtgcagctgg tggagtctgg gggaggcgtg gtccagcctg ggaggtccct gagactctcc   120
tgtgcagcgt ctggattcac cttcagtttc tatggcatgc actgggtccg ccaggctcca   180
ggcaaggggc tggagtgggt ggcagttata tggtatgatg gaagtaataa atactatgca   240
gactccgtga agggccgatt caccatctcc agagacaatt ccaagaacac gctgtatctg   300
caaatgaaca gcctgagagc cgaggacacg gctgtgtatt actgtgcgag aggggggttat   360
gattacgttt gggggagtta tcgccgtaac tccgactttg actactgggg ccagggaacc   420
ctggtcaccg tctctagtgc ctccaccaag ggcccatcgg tcttccccct ggcgccctgc   480
tccaggagca cctccgagag cacagcggcc ctgggctgcc tggtcaagga ctacttcccc   540
gaaccggtga cggtgtcgtg gaactcaggc gctctgacca gcggcgtgca caccttccca   600
gctgtcctac agtcctcagg actctactcc ctcagcagcg tggtgaccgt gccctccagc   660
aacttcggca cccagaccta cacctgcaac gtagatcaca agcccagcaa caccaaggtg   720
gacaagacag ttgagcgcaa atgttgtgtc gagtgcccac cgtgcccagc accacctgtg   780
gcaggaccgt cagtcttcct cttccccca aaacccaagg acaccctcat gatctcccgg   840
accectgagg tcacgtgcgt ggtggtggac gtgagccacg aagaccccga ggtccagttc   900
aactggtacg tggacggcgt ggaggtgcat aatgccaaga caaagccacg ggaggagcag   960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct   1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga gagcctctc cctgtctccg ggtaaa                              1416
```

SEQ ID NO: 60            moltype = AA  length = 472
FEATURE                  Location/Qualifiers
source                   1..472
                         mol_type = protein
                         organism = Homo sapiens
SEQUENCE: 60
```
MEFGLSWVFL VALLRGVQCQ VQLVESGGGV VQPGRSLRLS CAASGFTFSF YGMHWVRQAP   60
GKGLEWVAVI WYDGSNKYYA DSVKGRFTIS RDNSKNTLYL QMNSLRAEDT AVYYCARGGY   120
DYVWGSYRRN SDFDYWGQGT LVTVSSASTK GPSVFPLAPC SRSTSESTAA LGCLVKDYFP   180
EPVTVSWNSG ALTSGVHTFP AVLQSSGLYS LSSVVTVPSS NFGTQTYTCN VDHKPSNTKV   240
DKTVERKCCV ECPPCPAPPV AGPSVFLFPP KPKDTLMISR TPEVTCVVVD VSHEDPEVQF   300
NWYVDGVEVH NAKTKPREEQ FNSTFRVVSV LTVVHQDWLN GKEYKCKVSN KGLPAPIEKT   360
ISKTKGQPRE PQVYTLPPSR EEMTKNQVSL TCLVKGFYPS DIAVEWESNG QPENNYKTTP   420
PMLDSDGSFF LYSKLTVDKS RWQQGNVFSC SVMHEALHNH YTQKSLSLSP GK           472
```

SEQ ID NO: 61            moltype = DNA  length = 705
FEATURE                  Location/Qualifiers
source                   1..705
                         mol_type = other DNA
                         organism = Homo sapiens
SEQUENCE: 61
```
atggaagccc cagctcagct tctcttcctc ctgctactct ggctcccaga taccactgga   60
gaaatagtga tgacgcagtc tccagccacc ctgtctgtgt ctccagggga aagagccacc   120
ctctcctgca gggccagtca gagtgttgac agcaacttag cctggtaccg gcagaaacct   180
ggccaggctc ccaggctcct catctatggt gcatccacca gggccactgg tatcccagcc   240
aggttcagtg gcagtgggtc tgggactgag ttcactctca ccatcagcag cctgcagtct   300
gaagattttg cagtttatta ctgtcagcag tatattaact ggcctccgat caccttcggc   360
caagggacac gactggagat taaacgaact gtggctgcac catctgtctt catcttcccg   420
ccatctgatg agcagttgaa atctggaact gcctctgttg tgtgcctgct gaataacttc   480
tatcccagag gccaaagt acagtggaag gtggataacg ccctccaatc gggtaactcc   540
```

-continued

```
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgt                   705

SEQ ID NO: 62              moltype = AA  length = 235
FEATURE                   Location/Qualifiers
source                    1..235
                          mol_type = protein
                          organism = Homo sapiens
SEQUENCE: 62
MEAPAQLLFL LLLWLPDTTG EIVMTQSPAT LSVSPGERAT LSCRASQSVD SNLAWYRQKP    60
GQAPRLLIYG ASTRATGIPA RFSGSGSGTE FTLTISSLQS EDFAVYYCQQ YINWPPITFG    120
QGTRLEIKRT VAAPSVFIFP PSDEQLKSGT ASVVCLLNNF YPREAKVQWK VDNALQSGNS    180
QESVTEQDSK DSTYSLSSTL TLSKADYEKH KVYACEVTHQ GLSSPVTKSF NRGEC         235

SEQ ID NO: 63              moltype = DNA  length = 1395
FEATURE                   Location/Qualifiers
source                    1..1395
                          mol_type = other DNA
                          organism = Homo sapiens
SEQUENCE: 63
atgaaacacc tgtggttctt ccttctcctg gtggcagctc ccagatgggg cctgtcccag    60
gtgcagctgc aggagtcggg cccaggactg gtgaagcctt cggagaccct gtccctcacc   120
tgcactgtct ctggtggctc catcagtatt tactactgga gctggatccg gcagccccca   180
gggaagggac tggagtggat tgggtatgtc tattacagtg ggagcaccaa ttacaacccc   240
tccctcaaga gtcgagtcac catatcagta gacacgtcca agaaccagtt ctccctgaag   300
ctgaactctg tgaccgctgc ggacacggcc gtgtattact gtgcgagagg gggatacgat   360
ttttggagtg gttattttga ctactggggc cagggaaccc tggtcaccgt ctctagtgcc   420
tccaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca acttcggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac cacaggtgta caccctgccc ccatcccggg aggagatgac caagaaccag  1140
gtcagcctga cctgcctggt caaaggcttc taccccagcg acatcgccgt ggagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                                    1395

SEQ ID NO: 64              moltype = AA  length = 465
FEATURE                   Location/Qualifiers
source                    1..465
                          mol_type = protein
                          organism = Homo sapiens
SEQUENCE: 64
MKHLWFFLLL VAAPRWVLSQ VQLQESGPGL VKPSETLSLT CTVSGGSISI YYWSWIRQPP    60
GKGLEWIGYV YYSGSTNYNP SLKSRVTISV DTSKNQFSLK LNSVTAADTA VYYCARGGYD   120
FWSGYFDYWG QGTLVTVSSA STKGPSVFPL APCSRSTSES TAALGCLVKD YFPEPVTVSW   180
NSGALTSGVH TFPAVLQSSG LYSLSSVVTV PSSNFGTQTY TCNVDHKPSN TKVDKTVERK   240
CCVECPPCPA PPVAGPSVFL FPPKPKDTLM ISRTPEVTCV VVDVSHEDPE VQFNWYVDGV   300
EVHNAKTKPR EEQFNSTFRV VSVLTVVHQD WLNGKEYKCK VSNKGLPAPI EKTISKTKGQ   360
PREPQVYTLP PSREEMTKNQ VSLTCLVKGF YPSDIAVEWE SNGQPENNYK TTPPMLDSDG   420
SFFLYSKLTV DKSRWQQGNV FSCSVMHEAL HNHYTQKSLS LSPGK                   465

SEQ ID NO: 65              moltype = DNA  length = 723
FEATURE                   Location/Qualifiers
source                    1..723
                          mol_type = other DNA
                          organism = Homo sapiens
SEQUENCE: 65
atggtgcgtgc agacccaggt gtttattagc ctgctgctgt ggattagcgg cgcgtatggc    60
gacatcgtgc tgacccagtc tccagactcc ctggctgtgt ctctgggcga gagggccacc   120
atcaactgca gtccagcca gagtatttta tacagctcca gcaatgagaa cttcttaact   180
tggtaccagc agaaaccagg acagcctcct aagctgctca tttactgggc atctacccgg   240
gaatccgggg tccctgaccg attcagtggc agcgggtctg ggacagattt cactctcacc   300
atcagcagcc tgcagcctga agatgtggca gtttattact gtcagcaata ttttagtgtt   360
tttcggacgt tcggccaagg gaccaaggtg gaaatcaaac gtacggtggc tgcaccatct   420
gtcttcatct tcccgccatc tgatgagcag ttgaaatctg gaactgcctc tgttgtgtgcc   480
ctgctgaata acttctatcc cagagaggcc aaagtacagt ggaaggtgga taacgccctc   540
caatcgggta actcccagga gagtgtcaca gagcaggaca gcaaggacag cacctacagc   600
ctcagcagca ccctgacgct gagcaaagca gactacgaga acacaaagt ctacgcctgc   660
gaagtcaccc atcaggggct gagctcgccc gtcacaaaga gcttcaacag gggagagtgt   720
```

-continued

```
tag                                                          723

SEQ ID NO: 66          moltype = AA  length = 240
FEATURE                Location/Qualifiers
source                 1..240
                       mol_type = protein
                       organism = Homo sapiens
SEQUENCE: 66
MVLQTQVFIS LLLWISGAYG DIVLTQSPDS LAVSLGERAT INCKSSQSIL YSSSNENFLT  60
WYQQKPGQPP KLLIYWASTR ESGVPDRFSG SGSGTDFTLT ISSLQPEDVA VYYCQQYFSV  120
FRTFGQGTRV EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240

SEQ ID NO: 67          moltype = DNA  length = 1395
FEATURE                Location/Qualifiers
source                 1..1395
                       mol_type = other DNA
                       organism = Homo sapiens
SEQUENCE: 67
atggattgga cctggcgtat tctgtttctg gtggcggcgg cgaccggcgc gcatagccag  60
gtgcagctgg tgcagtctgg ggctgaggtg aagaagcctg gggcctcagt gaaggtctcc  120
tgcaaggctt ctggatacac cttcaccggc tactatatac actgggtgca acaggcccct  180
ggacaagggc ttgagtggat gggatggatc aaccctaaca gtggtggcac aaactctgca  240
cagaagtttc ggggcagggt caccatgacc agggacacgt ccatcagcac agcctacatg  300
gagctgagca ggctgagatc tgacgacacg gccgtgtatt actgtgcgcg agaggtggga  360
tacagctatg gttactttga ctactggggc cagggaaccc tggtcaccgt ctcctcagct  420
agcaccaagg gcccatcggt cttcccccctg cgcgccctgct ccaggagcac ctccgagagc  480
acagcggccc tgggctgcct ggtcaaggac tacttccccg aaccggtgac ggtgtcgtgg  540
aactcaggcg ctctgaccag cggcgtgcac accttcccag ctgtcctaca gtcctcagga  600
ctctactccc tcagcagcgt ggtgaccgtg ccctccagca gcttgggcac ccagacctac  660
acctgcaacg tagatcacaa gcccagcaac accaaggtgg acaagacagt tgagcgcaaa  720
tgttgtgtcg agtgcccacc gtgcccagca ccacctgtgg caggaccgtc agtcttcctc  780
ttccccccaa aacccaagga caccctcatg atctcccgga cccctgaggt cacgtgcgtg  840
gtggtggacg tgagccacga agaccccgag gtccagttca actggtacgt ggacggcgtg  900
gaggtgcata atgccaagac aaagccacgg gaggagcagt tcaacagcac gttccgtgtg  960
gtcagcgtcc tcaccgttgt gcaccaggac tggctgaacg gcaaggagta caagtgcaag  1020
gtctccaaca aaggcctccc agcccccatc gagaaaacca tctccaaaac caaagggcag  1080
ccccgagaac cacaggtgta caccctgccc ccatcccggg aggagatgac caagaaccag  1140
gtcagcctga cctgcctggt caaaggcttc tacccatccga catcgccgtg gagtgggag  1200
agcaatgggc agccggagaa caactacaag accacacctc ccatgctgga ctccgacggc  1260
tccttcttcc tctacagcaa gctcaccgtg gacaagagca ggtggcagca ggggaacgtc  1320
ttctcatgct ccgtgatgca tgaggctctg cacaaccact acacgcagaa gagcctctcc  1380
ctgtctccgg gtaaa                                             1395

SEQ ID NO: 68          moltype = AA  length = 465
FEATURE                Location/Qualifiers
source                 1..465
                       mol_type = protein
                       organism = Homo sapiens
SEQUENCE: 68
MDWTWRILFL VAAATGAHSQ VQLVQSGAEV KKPGASVKVS CKASGYTFTG YYIHWVRQAP  60
GQGLEWMGWI NPNSGGTNSA QKFRGRVTMT RDTSISTAYM ELSRLRSDDT AVYYCAREGG  120
YSYGYFDYWG QGTLVTVSSA STKGPSVFPL APCSRSTSES TAALGCLVKD YFPEPVTVSW  180
NSGALTSGVH TFPAVLQSSG LYSLSSVVTV PSSNFGTQTY TCNVDHKPSN TKVDKTVERK  240
CCVECPPCPA PPVAGPSVFL FPPKPKDTLM ISRTPEVTCV VVDVSHEDPE VQFNWYVDGV  300
EVHNAKTKPR EEQFNSTFRV VSVLTVVHQD WLNGKEYKCK VSNKGLPAPI EKTISKTKGQ  360
PREPQVYTLP PSREEMTKNQ VSLTCLVKGF YPSDIAVEWE SNGQPENNYK TTPPMLDSDG  420
SFFLYSKLTV DKSRWQQGNV FSCSVMHEAL HNHYTQKSLS LSPGK              465

SEQ ID NO: 69          moltype = DNA  length = 708
FEATURE                Location/Qualifiers
source                 1..708
                       mol_type = other DNA
                       organism = Homo sapiens
SEQUENCE: 69
atggacatga gggtccccgc tcagctcctg gggctcctgc tgctctggtt cccaggtgcc  60
aggtgtgaca tccagatgac ccagtctcca tcctccctgt ctgcatctgt aggagacaga  120
gtcaccatca cttgccgggc aagtcagggc attagaaatg atttaggctg gtatcagcag  180
aaaccaggga aagcccctaa gcgcctgatc tatgctgcat ccagtttgca aagtggggtc  240
ccatcaaggt tcagcggcag tggatctggg acagaattca ctctcacaat cagcagtgtg  300
cagcctgaag attttgtaac ttattactgt ctacagcata atagtaaccc tctcactttc  360
ggcggaggga ccaaggtgga gatcaaacga actgtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata acgccctcca atcggggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgt            708

SEQ ID NO: 70          moltype = AA  length = 236
```

```
FEATURE                 Location/Qualifiers
source                  1..236
                        mol_type = protein
                        organism = Homo sapiens
SEQUENCE: 70
MDMRVPAQLL GLLLLWFPGA RCDIQMTQSP SSLSASVGDR VTITCRASQG IRNDLGWYQQ  60
KPGKAPKRLI YAASSLQSGV PSRFSGSGSG TEFTLTISSV QPEDFVTYYC LQHNSNPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC       236

SEQ ID NO: 71           moltype = DNA   length = 1419
FEATURE                 Location/Qualifiers
source                  1..1419
                        mol_type = other DNA
                        organism = Homo sapiens
SEQUENCE: 71
atggagtttg ggctgagctg ggttttcctc gttgctcttt taagaggtgt ccagtgtcag  60
gtgcagctgg tggagtctgg gggaggcgtg gtccagcctg ggaggtccct gagactctcc  120
tgtgcagcgt ctggattcac cttcagtagc tatggcatgc actgggtccg ccaggctcca  180
ggcaagggc tggagtgggt ggcagttatg tggtatgatg gaagtaataa agactatgta  240
gactccgtga agggccgatt caccatctcc agagacaatt ccaagaacac gctgtatctg  300
caaatgaacc gcctgagagc cgaggacacg gctgtgtatt actgtgcgag agaaaaagat  360
cattacgaca ttttgactgg ttataactac tactacggtc tggacgtctg gggccaaggg  420
accacggtca ccgtctcctc agcctccacc aagggcccat cggtcttccc cctggcgccc  480
tgctccagga gcacctccga gagcacagcg ccctgggct gcctggtcaa ggactacttc  540
cccgaaccgg tgacggtgtc gtggaactca ggcgctctga ccagcggcgt gcacaccttc  600
ccagctgtcc tacagtcctc aggactctac tccctcagca gcgtggtgac cgtgccctcc  660
agcaacttcg gcacccagac ctacacctgc aacgtagatc acaagcccag caacaccaag  720
gtggacaaga cagttgagcg caaatgttgt gtcgagtgcc caccgtgccc agcaccacct  780
gtggcaggac cgtcagtctt cctcttcccc ccaaaaccca aggacaccct catgatctcc  840
cggacccctg aggtcacgtg cgtggtggtg gacgtgagcc acgaagaccc cgaggtccag  900
ttcaactggt acgtggacgg cgtggaggtg cataatgcca agacaaagcc acgggaggag  960
cagttcaaca gcacgttccg tgtggtcagc gtcctcaccg ttgtgcacca ggactggctg  1020
aacggcaagg agtacaagtg caaggtctcc aacaaaggcc tcccagcccc catcgagaaa  1080
accatctcca aaaccaaagg gcagccccga gaaccacagg tgtacaccct gcccccatcc  1140
cgggaggaga tgaccaagaa ccaggtcagc ctgacctgcc tggtcaaagg cttctacccc  1200
agcgacatcg ccgtggagtg ggagagcaat gggcagccgg agaacaacta caagaccaca  1260
cctcccatgc tggactccga cggctccttc ttcctctaca gcaagctcac cgtggacaag  1320
agcaggtggc agcaggggaa cgtcttctca tgctccgtga tgcatgaggc tctgcacaac  1380
cactacacgc agaagagcct ctccctgtct ccgggtaaa                          1419

SEQ ID NO: 72           moltype = AA   length = 473
FEATURE                 Location/Qualifiers
source                  1..473
                        mol_type = protein
                        organism = Homo sapiens
SEQUENCE: 72
MEFGLSWVFL VALLRGVQCQ VQLVESGGGV VQPGRSLRLS CAASGFTFSS YGMHWVRQAP  60
GKGLEWVAVM WYDGSNKDYV DSVKGRFTIS RDNSKNTLYL QMNRLRAEDT AVYYCAREKD  120
HYDILTGYNY YYGLDVWGQG TTVTVSSAST KGPSVFPLAP CSRSTSESTA ALGCLVKDYF  180
PEPVTVSWNS GALTSGVHTF PAVLQSSGLY SLSSVVTVPS SNFGTQTYTC NVDHKPSNTK  240
VDKTVERKCC VECPPCPAPP VAGPSVFLFP PKPKDTLMIS RTPEVTCVVV DVSHEDPEVQ  300
FNWYVDGVEV HNAKTKPREE QFNSTFRVVS VLTVVHQDWL NGKEYKCKVS NKGLPAPIEK  360
TISKTKGQPR EPQVYTLPPS REEMTKNQVS LTCLVKGFYP SDIAVEWESN GQPENNYKTT  420
PPMLDSDGSF FLYSKLTVDK SRWQQGNVFS CSVMHEALHN HYTQKSLSLS PGK          473

SEQ ID NO: 73           moltype = DNA   length = 705
FEATURE                 Location/Qualifiers
source                  1..705
                        mol_type = other DNA
                        organism = Homo sapiens
SEQUENCE: 73
atggaaaccc cggcgcagct gctgtttctg ctgctgctgt ggctgccgga taccaccggc  60
gaaattgtgt tgacgcagtc tccaggcacc ctgtctttgt ctccagggga aagagccacc  120
ctctcctgca gggccagtca gtatattagc aacaccatt agcctggtt ccagcagaaa  180
cctggccagg ctcccaggct cctcatctat ggtgcagcca ccagggccac tggcatccca  240
gacaggttca gtggcagtgg gtctgggaca gacttcactt tcaccatcag cagactggag  300
cctgaagatt ttgcagtgta ttactgtcag cagtatggta gctcaccgtg gacgttcggc  360
caagggacca cggtggaaat caaacgtacg gtggctgcac catctgtctt catcttcccg  420
ccatctgatg agcagttgaa atctggaact gcctctgttg tgtgcctgct gaataacttc  480
tatcccagag aggccaaagt acagtggaag gtggataacg ccctccaatc gggtaactcc  540
caggagagtg tcacagagca ggacagcaag gacagcacct acagcctcag cagcaccctg  600
acgctgagca aagcagacta cgagaaacac aaagtctacg cctgcgaagt cacccatcag  660
ggcctgagct cgcccgtcac aaagagcttc aacaggggag agtgt                    705

SEQ ID NO: 74           moltype = AA   length = 235
FEATURE                 Location/Qualifiers
source                  1..235
                        mol_type = protein
```

-continued

```
                        organism = Homo sapiens
SEQUENCE: 74
METPAQLLFL LLLWLPDTTG EIVLTQSPGT LSLSPGERAT LSCRASQYIS NTYLAWFQQK   60
PGQAPRLLIY GAATRATGIP DRFSGSGSGT DFTFTISRLE PEDFAVYYCQ QYGSSPWTFG  120
QGTTVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC        235

SEQ ID NO: 75          moltype = DNA   length = 1389
FEATURE                Location/Qualifiers
source                 1..1389
                       mol_type = other DNA
                       organism = Homo sapiens
SEQUENCE: 75
atggattgga cctggcgtat tctgtttctg gtggcggcgg cgaccggcgc gcatagccag   60
gtgcagttgg tgcagtctgg ggctgaggtg aagaagcctg gggcctcagt gaaggtctcc  120
tgcaaggctt ctggatacac cttcaccggc tactatatgc actgggtgcg acaggcccct  180
ggacaagggc ttgagtggat gggatggatc aaccctaaca gtggtggcac aaactatgca  240
cagaggtttc ggggcagggt caccatgacc agggacacgt ccatcagcac agcctacatg  300
gaactgagca ggctgagatc tgacgacacg gccgtgtatt actgtgcgag agccccgtat  360
gactggacct ttgactactg gggccaggga accctggtca ccgtctcctc agctagcacc  420
aagggcccat cggtcttccc cctggcgccc tgctccagga gcacctccga gagcacagcg  480
gccctgggct gcctggtcaa ggactacttc cccgaaccgg tgacggtgtc gtggaactca  540
ggcgctctga ccagcggcgt gcacaccttc ccagctgtcc tacagtcctc aggactctac  600
tccctcagca gcgtggtgac cgtgccctcc agcaacttcg gcacccagac ctacacctgc  660
aacgtagatc acaagcccag caacaccaag gtggacaaga cagttgagcg caaatgttgt  720
gtcgagtgcc caccgtgccc agcaccacct gtggcaggac cgtcagtctt cctcttcccc  780
ccaaaaccca aggacaccct catgatctcc cggacccctg aggtcacgtg cgtggtggtg  840
gacgtgagcc acgaagaccc cgaggtccag ttcaactggt acgtggacgg cgtggaggtg  900
cataatgcca agacaaagcc acgggaggag cagttcaaca gcacgttccg tgtggtcagc  960
gtcctcaccg ttgtgcacca ggactggctg aacggcaagg agtacaagtg caaggtctcc 1020
aacaaaggcc tcccagcccc catcgagaaa accatctcca aaaccaaagg cagcccccga 1080
gaaccacagg tgtacaccct gcccccatcc cgggaggaga tgaccaagaa ccaggtcagc 1140
ctgacctgcc tggtcaaagg cttctacccc agcgacatcg ccgtggagtg ggagagcaat 1200
gggcagccgg agaacaacta caagaccaca cctcccatgc tggactccga cggctccttc 1260
ttcctctaca gcaagctcac cgtggacaag agcaggtggc agcaggggaa cgtcttctca 1320
tgctccgtga tgcatgaggc tctgcacaac cactacacgc agaagagcct ctccctgtct 1380
ccgggtaaa                                                         1389

SEQ ID NO: 76          moltype = AA   length = 463
FEATURE                Location/Qualifiers
source                 1..463
                       mol_type = protein
                       organism = Homo sapiens
SEQUENCE: 76
MDWTWRILFL VAAATGAHSQ VQLVQSGAEV KKPGASVKVS CKASGYTFTG YYMHWVRQAP   60
GQGLEWMGWI NPNSGGTNYA QRFRGRVTMT RDTSISTAYM ELSRLRSDDT AVYYCARAPY  120
DWTFDYWGQG TLVTVSSAST KGPSVFPLAP CSRSTSESTA ALGCLVKDYF PEPVTVSWNS  180
GALTSGVHTF PAVLQSSGLY SLSSVVTVPS SNFGTQTYTC NVDHKPSNTK VDKTVERKCC  240
VECPPCPAPP VAGPSVFLFP PKPKDTLMIS RTPEVTCVVV DVSHEDPEVQ FNWYVDGVEV  300
HNAKTKPREE QFNSTFRVVS VLTVVHQDWL NGKEYKCKVS NKGLPAPIEK TISKTKGQPR  360
EPQVYTLPPS REEMTKNQVS LTCLVKGFYP SDIAVEWESN GQPENNYKTT PPMLDSDGSF  420
FLYSKLTVDK SRWQQGNVFS CSVMHEALHN HYTQKSLSLS PGK                    463

SEQ ID NO: 77          moltype = DNA   length = 708
FEATURE                Location/Qualifiers
source                 1..708
                       mol_type = other DNA
                       organism = Homo sapiens
SEQUENCE: 77
atggacatga gggtgcccgc tcagctcctg gggctcctgc tgctgtggct gagaggtgcg   60
cgctgtgaca tccagatgac ccagtctcca tcttccgtgt ctgcatctgt aggagacaga  120
gtcaccatca cttgtcgggc gagtcagggt attagcaact ggttagcctg gtatcagcag  180
aaaccaggga gcccctaa actcctgatc tatgctgcat ccagtttgca aagtggggtc  240
ccatcaaggt tcagcggcag tggatctggg acagatttca ctctcaccat cagcagcctg  300
cagcctgaag attttgcaac ttactattgt caacaggcta cagtttccc attcactttc  360
ggccctggga ccaaagtgga tatcaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata cgccctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga agtcacccat  660
cagggcctga gctcgcccgt cacaaagagc ttcaacaggg gagagtgt              708

SEQ ID NO: 78          moltype = AA   length = 236
FEATURE                Location/Qualifiers
source                 1..236
                       mol_type = protein
                       organism = Homo sapiens
SEQUENCE: 78
MDMRVPAQLL GLLLLWLRGA RCDIQMTQSP SSVSASVGDR VTITCRASQG ISNWLAWYQQ   60
```

-continued

```
KPGTAPKLLI YAASSLQSGV PSRFSGSGSG TDFTLTISSL QPEDFATYYC QQANSFPPTF 120
GPGTKVDIKR TVAAPSVFIF PPSDEQLKSG TASVVCLLNN FYPREAKVQW KVDNALQSGN 180
SQESVTEQDS KDSTYSLSST LTLSKADYEK HKVYACEVTH QGLSSPVTKS FNRGEC      236

SEQ ID NO: 79            moltype = DNA  length = 1407
FEATURE                  Location/Qualifiers
source                   1..1407
                         mol_type = other DNA
                         organism = Homo sapiens
SEQUENCE: 79
atggacatga gggtgcccgc tcagctcctg gggctcctgc tgctgtggct gagaggtgcg  60
cgctgtcagg tgcagttggt gcagtctggg actgaggtga agaagcctgg ggcctcaatg 120
aaggtttcct gcaaggcatc tggatacacc ttcaccagct attatatgca ctgggtgcga 180
caggcccctg gacaagggct tgagtggatg ggaataatca accctagtgg tgatagcaca 240
agctacgcac agaagttcca gggcagagtc accatgacca gggacacgtc cacgaacaca 300
gtctacatgg agctgagcag cctgagatct gaggacacgg ccatgtatta ctgtgcgaga 360
gatgtagagg ttcgggggaat ttctcacttt gactactggg gccagggaac cctggtcacc 420
gtctctagtg cctccaccaa gggcccatcg gtcttccccc tggcgccctg ctccaggagc 480
acctccgaga gcacagcggc cctgggctgc ctggtcaagg actacttccc cgaaccggtg 540
acggtgtcgt ggaactcagg cgctctgacc agcggcgtgc acaccttccc agctgtccta 600
cagtcctcag gactctactc cctcagcagc gtggtgaccg tgccctccag caacttcggc 660
acccagacct acacctgcaa cgtagatcac aagcccagca acaccaaggt ggacaagaca 720
gttgagcgca aatgttgtgt cgagtgccca ccgtgcccag caccacctgt ggcaggacca 780
tcagtcttcc tcttcccccc aaaacccaag gacaccctca tgatctcccg gacccctgag 840
gtcacgtgcg tggtggtgga cgtgagccac gaagaccccg aggtccagtt caactggtac 900
gtggacggcg tggaggtgca taatgccaag acaaagccac gggaggagca gttcaacagc 960
acgttccgtg tggtcagcgt cctcaccgtt gtgcaccagg actggctgaa cggcaaggag 1020
tacaagtgca aggtctccaa caaaggcctc ccagccccca tcgagaaaac catctccaaa 1080
accaaagggc agccccgaga accacaggtg tacaccctgc ccccatcccg ggaggagatg 1140
accaagaacc aggtcagcct gacctgcctg gtcaaaggct tctaccccag cgacatcgcc 1200
gtggagtggg agagcaatgg gcagccggag aacaactaca agaccacacc tcccatgctg 1260
gactccgacg gctccttctt cctctacagc aagctcaccg tggacaagag caggtggcag 1320
caggggaact cttctcatg ctccgtgatg catgaggctc tgcacaacca ctacacgcag 1380
aagagcctct ccctgtctcc gggtaaa                                     1407

SEQ ID NO: 80            moltype = AA  length = 469
FEATURE                  Location/Qualifiers
source                   1..469
                         mol_type = protein
                         organism = Homo sapiens
SEQUENCE: 80
MDMRVPAQLL GLLLLWLRGA RCQVQLVQSG TEVKKPGASM KVSCKASGYT FTSYYMHWVR  60
QAPGQGLEWM GIINPSGDST SYAQKFQGRV TMTRDTSTNT VYMELSSLRS EDTAMYYCAR 120
DVEVRGISHF DYWGQGTLVT VSSASTKGPS VFPLAPCSRS TSESTAALGC LVKDYFPEPV 180
TVSWNSGALT SGVHTFPAVL QSSGLYSLSS VVTVPSSNFG TQTYTCNVDH KPSNTKVDKT 240
VERKCCVECP PCPAPPVAGP SVFLFPPKPK DTLMISRTPE VTCVVVDVSH EDPEVQFNWY 300
VDGVEVHNAK TKPREEQFNS TFRVVSVLTV VHQDWLNGKE YKCKVSNKGL PAPIEKTISK 360
TKGQPREPQV YTLPPSREEM TKNQVSLTCL VKGFYPSDIA VEWESNGQPE NNYKTTPPML 420
DSDGSFFLYS KLTVDKSRWQ QGNVFSCSVM HEALHNHYTQ KSLSLSPGK              469

SEQ ID NO: 81            moltype = DNA  length = 714
FEATURE                  Location/Qualifiers
source                   1..714
                         mol_type = other DNA
                         organism = Homo sapiens
SEQUENCE: 81
atgggatgga gctgtatcat cctcttcttg gtagcaacag ctacaggtgt ccactccgac  60
atccagctga cccagtctcc atcatctctg agcgcatctg ttggagatag ggtcactatg 120
agctgtaagt ccagtcaaag tgttttatac agtgcaaatc acaagaacta cttggcctgg 180
taccagcaga aaccagggaa agcacctaaa ctgctgatct actgggcatc cactagggaa 240
tctggtgtcc cttcgcgatt ctctggcagc ggatctggga cagatttTac tttcaccatc 300
agctctcttc aaccagaaga cattgcaaca tattattgtc accaatacct cctcgtgg   360
acgttcggtg agggaccaa ggtgcagatc aaacgaactg tggctgcacc atctgtcttc 420
atcttcccgc catctgatga gcagttgaaa tctggaactg cctctgttgt gtgcctgctg 480
aataacttct atcccagaga ggccaaagta cagtggaagg tggataacgc cctccaatcg 540
ggtaactccc aggagagtgt cacagagcag gacagcaagg acagcaccta cagcctcagc 600
agcaccctga cgctgagcaa agcagactac gagaaacaca agtctacgc ctgcgaagtc 660
acccatcagg gcctgagctc gcccgtcaca aagagcttca caggggagag tgt          714

SEQ ID NO: 82            moltype = AA  length = 238
FEATURE                  Location/Qualifiers
source                   1..238
                         mol_type = protein
                         organism = Homo sapiens
SEQUENCE: 82
MGWSCIILFL VATATGVHSD IQLTQSPSSL SASVGDRVTM SCKSSQSVLY SANHKNYLAW  60
YQQKPGKAPK LLIYWASTRE SGVPSRFSGS GSGTDFTFTI SSLQPEDIAT YYCHQYLSSW 120
TFGGGTKVQI KRTVAAPSVF IFPPSDEQLK SGTASVVCLL NNFYPREAKV QWKVDNALQS 180
GNSQESVTEQ DSKDSTYSLS STLTLSKADY EKHKVYACEV THQGLSSPVT KSFNRGEC    238
```

-continued

```
SEQ ID NO: 83           moltype = DNA  length = 1395
FEATURE                 Location/Qualifiers
source                  1..1395
                        mol_type = other DNA
                        organism = Homo sapiens
SEQUENCE: 83
atgggatgga gctgtatcat cctcttcttg gtagcaacag ctacaggtgt ccactcccag      60
gtccagctgg tccaatcagg ggctgaagtc aagaaacctg ggtcatcagt gaaggtctcc     120
tgcaaggctt ctggctacac ctttactagc tactggctgc actgggtcag gcaggcacct     180
ggacagggtc tggaatggat tggatacatt aatcctagga atgattatac tgagtacaat     240
cagaacttca aggacaaggc cacaataact gcagacgaat ccaccaatac agcctacatg     300
gagctgagca gcctgaggtc tgaggacacg gcattttatt tttgtgcaag aagggatatt     360
actacgttct actgggggcca aggcaccacg gtcaccgtct cctcagcctc caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttccgggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagagagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agcccccatc gagaaaacca tctccaaagc caaagggcag    1080
ccccgagaac cacaggtgta caccctgccc ccatcccggg aggagatgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctatagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                    1395

SEQ ID NO: 84           moltype = AA  length = 465
FEATURE                 Location/Qualifiers
source                  1..465
                        mol_type = protein
                        organism = Homo sapiens
SEQUENCE: 84
MGWSCIILFL VATATGVHSQ VQLVQSGAEV KKPGSSVKVS CKASGYTFTS YWLHWVRQAP      60
GQGLEWIGYI NPRNDYTEYN QNFKDKATIT ADESTNTAYM ELSSLRSEDT AFYFCARRDI     120
TTFYWGQGTT VTVSSASTKG PSVFPLAPSS KSTSGGTAAL GCLVKDYFPE PVTVSWNSGA     180
LTSGVHTFPA VLQSSGLYSL SSVVTVPSSS LGTQTYICNV NHKPSNTKVD KRVEPKSCDK     240
THTCPPCPAP ELLGGPSVFL FPPKPKDTLM ISRTPEVTCV VVDVSHEDPE VKFNWYVDGV     300
EVHNAKTKPR EEQYNSTYRV VSVLTVLHQD WLNGKEYKCK VSNKALPAPI EKTISKAKGQ     360
PREPQVYTLP PSREEMTKNQ VSLTCLVKGF YPSDIAVEWE SNGQPENNYK TTPPVLDSDG     420
SFFLYSKLTV DKSRWQQGNV FSCSVMHEAL HNHYTQKSLS LSPGK                    465

SEQ ID NO: 85           moltype = DNA  length = 705
FEATURE                 Location/Qualifiers
source                  1..705
                        mol_type = other DNA
                        organism = Homo sapiens
SEQUENCE: 85
atggaaaccc cagctcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact agcctggta ccagcagaaa      180
cctggccagg ctcccaggct cctcatatat ggtgcatcca gcagggccac tggcatccca     240
gacaggttca gtggcagtgg gtctgggaca gacttcactc tcaccatcag cagactggag     300
cctgaagatt ttgcagtgta ttactgtcag cggtctggtg gctcatcatt cacttttcggc     360
cctgggacca aagtggatat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgt                    705

SEQ ID NO: 86           moltype = AA  length = 235
FEATURE                 Location/Qualifiers
source                  1..235
                        mol_type = protein
                        organism = Homo sapiens
SEQUENCE: 86
METPAQLLFL LLLWLPDTTG EIVLTQSPGT LSLSPGERAT LSCRASQSVS SSYLAWYQQK      60
PGQAPRLLIY GASSRATGIP DRFSGSGSGT DFTLTISRLE PEDFAVYYCQ RSGGSSFTFG     120
PGTKVDIKRT VAAPSVFIFP PSDEQLKSGT ASVVCLLNNF YPREAKVQWK VDNALQSGNS     180
QESVTEQDSK DSTYSLSSTL TLSKADYEKH KVYACEVTHQ GLSSPVTKSF NRGEC          235

SEQ ID NO: 87           moltype = DNA  length = 1398
FEATURE                 Location/Qualifiers
```

```
source                  1..1398
                        mol_type = other DNA
                        organism = Homo sapiens
SEQUENCE: 87
atggggtcaa ccgccatcct cgccctcctc ctggctgttc tccaaggagt ctgtgccgag    60
gtgcagctgg tacagtctgg agcagaggtg aaaaagcccg gggagtctct gaagatctcc   120
tgtaagggtt ctggatacaa ctttaccagc tactggatcg gctgggtgcg ccagatgccc   180
gggaaaggcc tggagttgat ggggatcatc tatcctggtg actctgatac cagatacagc   240
ccgtccttcc aaggccaggt caccatctca gccgacaagt ccatcagcac cgcctacctg   300
cagtggagca gcctgaaggc ctcggacacc gccatgtatt actgtggttc ggggagctac   360
ttttacttcg atctctgggg ccgtggcacc ctggtcaccg tctctagtgc ctccaccaag   420
ggcccatcgg tcttccccct ggcaccctcc tccaagagca cctctggggg cacagcggcc   480
ctgggctgcc tggtcaagga ctacttcccc gaaccggtga cggtgtcgtg gaactcaggc   540
gccctgacca gcggcgtgca caccttcccg gctgtcctac agtcctcagg actctactcc   600
ctcagcagcg tggtgaccgt gccctccagc agcttgggca cccagaccta catctgcaac   660
gtgaatcaca agcccagcaa caccaaggtg gacaagaaag ttgagcccaa atcttgtgac   720
aaaactcaca catgcccacc gtgcccagca cctgaactcc tggggggacc gtcagtcttc   780
ctcttccccc caaaacccaa ggacaccctc atgatctccc ggacccctga ggtcacatgc   840
gtggtggtgg acgtgagcca cgaagaccct gaggtcaagt tcaactggta cgtggacggc   900
gtggaggtgc ataatgccaa gacaaagccg cgggaggagc agtacaacag cacgtaccgt   960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggatgagct gaccaagaac  1140
caggtcagcc tgacctgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctatag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaa                                                 1398

SEQ ID NO: 88           moltype = AA  length = 466
FEATURE                 Location/Qualifiers
source                  1..466
                        mol_type = protein
                        organism = Homo sapiens
SEQUENCE: 88
MGSTAILALL LAVLQGVCAE VQLVQSGAEV KKPGESLKIS CKGSGYNFTS YWIGWVRQMP    60
GKGLELMGII YPGDSDTRYS PSFQGQVTIS ADKSISTAYL QWSSLKASDT AMYYCGSGSY   120
FYFDLWGRGT LVTVSSASTK GPSVFPLAPS SKSTSGGTAA LGCLVKDYFP EPVTVSWNSG   180
ALTSGVHTFP AVLQSSGLYS LSSVVTVPSS SLGTQTYICN VNHKPSNTKV DKKVEPKSCD   240
KTHTCPPCPA PELLGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSRDELTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK                   466

SEQ ID NO: 89           moltype = DNA  length = 723
FEATURE                 Location/Qualifiers
source                  1..723
                        mol_type = other DNA
                        organism = Homo sapiens
SEQUENCE: 89
atggacatga gggtccccgc tcagctcctg gggctcctgc tgctgtggct gagaggtgcg    60
cgctgtgata ttgtgatgac tcagtctcca ctctccctgc ccgtcacccc tggagagccg   120
gcctccatct cctgcaggtc tagtcagagc ctcctgcata gtcatggata caactatttg   180
gattggtacc tgcagaagcc agggcagtct ccacagctcc tgatctattt gggttctaat   240
cgggcctccg gggtccctga caggttcagt ggcagtggat caggcacaga ttttacactg   300
aaaatcagca gagtggaggc tgaggatgtt ggggtttatt actgcatgca aggtacacac   360
tggcctccga cttttggcca ggggaccaag ctggagatca aacgtacggt ggctgcacca   420
tctgtcttca tcttcccgcc atctgatgag cagttgaaat ctggaactgc ctctgttgtg   480
tgcctgctga ataacttcta tcccagagag gccaaagtac agtggaaggt ggataacgcc   540
ctccaatcgg gtaactccca ggagagtgtc acagagcagg acagcaagga cagcacctac   600
agcctcagca gcaccctgac gctgagcaaa gcagactacg agaaacacaa agtctacgcc   660
tgcgaagtca cccatcaggg cctgagctcg cccgtcacaa agagcttcaa caggggagag   720
tgt                                                                 723

SEQ ID NO: 90           moltype = AA  length = 241
FEATURE                 Location/Qualifiers
source                  1..241
                        mol_type = protein
                        organism = Homo sapiens
SEQUENCE: 90
MDMRVPAQLL GLLLLWLRGA RCDIVMTQSP LSLPVTPGEP ASISCRSSQS LLHSHGYNYL    60
DWYLQKPGQS PQLLIYLGSN RASGVPDRFS GSGSGTDFTL KISRVEAEDV GVYYCMQGTH   120
WPPTFGQGTK LEIKRTVAAP SVFIFPPSDE QLKSGTASVV CLLNNFYPRE AKVQWKVDNA   180
LQSGNSQESV TEQDSKDSTY SLSSTLTLSK ADYEKHKVYA CEVTHQGLSS PVTKSFNRGE   240
C                                                                    241

SEQ ID NO: 91           moltype = DNA  length = 1410
FEATURE                 Location/Qualifiers
source                  1..1410
```

```
                         mol_type = other DNA
                         organism = Homo sapiens
SEQUENCE: 91
atggacatga gggtgcccgc tcagctcctg gggctcctgc tgctgtggct gagaggtgcg    60
cgctgtgagg tccagctggt gcagtctggg ggaggcgtgg tccagcctgg gaggtccctg   120
agactctcct gtgcagccgtc tggattcacc ttcagtagct atggcatgca ctgggtccgc   180
caggctccag gcaagggggct ggagtggggtt tcatacatta gtagtagtgg tagtaccata   240
tactacgcag actctgtgaa gggccgattc accatctcca gggacaacgc caagaactca   300
ctatatctgc aaatgaacag cctgagagcc gaggacacgg ccgtgtatta ctgtgcgaga   360
gatctgttag attacgatct gttgactggt tatggctact ggggccaggg aaccctggtc   420
accgtctcta gtgcctccac caagggccca tcggtcttcc ccctggcgcc ctgctccagg   480
agcacctccg agagcacagc ggccctgggc tgcctggtca aggactactt ccccgaaccg   540
gtgacggtgt cgtggaactc aggcgctctg accagcggcg tgcacacctt cccagctgtc   600
ctacagtcct caggactcta ctccctcagc agcgtggtga ccgtgccctc cagcaacttc   660
ggcacccaga cctacacctg caacgtagat cacaagccca gcaacaccaa ggtggacaag   720
acagttgagc gcaaatgttg tgtcgagtgc ccaccgtgcc cagcaccacc tgtggcagga   780
ccgtcagtct tcctcttccc cccaaaaccc aaggacaccc tcatgatctc ccggaccct   840
gaggtcacgt gcgtggtggt ggacgtgagc cacgaagacc ccgaggtcca gttcaactgg   900
tacgtggacg gcgtggaggt gcataatgcc aagacaaagc cacgggagga gcagttcaac   960
agcacgttcc gtgtggtcag cgtcctcacc gttgtgcacc aggactggct gaacggcaag  1020
gagtacaagt gcaaggtctc caacaaaggc ctcccagccc ccatcgagaa aaccatctcc  1080
aaaaccaaag ggcagccccg agaaccacag gtgtacaccc tgcccccatc ccgggaggag  1140
atgaccaaga accaggtcag cctgacctgc ctggtcaaag gcttctaccc cagcgacatc  1200
gccgtggagt gggagagcaa tgggcagccg gagaacaact acaagaccac acctcccatg  1260
ctggactccg acggctcctt cttcctctac agcaagctca ccgtggacaa gagcaggtgg  1320
cagcagggga acgtcttctc atgctccgtg atgcatgagg ctctgcacaa ccactacacg  1380
cagaagagcc tctccctgtc tccgggtaaa                                   1410

SEQ ID NO: 92           moltype = AA  length = 470
FEATURE                 Location/Qualifiers
source                  1..470
                        mol_type = protein
                        organism = Homo sapiens
SEQUENCE: 92
MDMRVPAQLL GLLLLWLRGA RCEVQLVQSG GGVVQPGRSL RLSCAASGFT FSSYGMHWVR    60
QAPGKGLEWV SYISSSGSTI YYADSVKGRF TISRDNAKNS LYLQMNSLRA EDTAVYYCAR   120
DLLDYDLLTG YGYWGQGTLV TVSSASTKGP SVFPLAPCSR STSESTAALG CLVKDYFPEP   180
VTVSWNSGAL TSGVHTFPAV LQSSGLYSLS SVVTVPSSNF GTQTYTCNVD HKPSNTKVDK   240
TVERKCCVEC PPCPAPPVAG PSVFLFPPKP KDTLMISRTP EVTCVVVDVS HEDPEVQFNW   300
YVDGVEVHNA KTKPREEQFN STFRVVSVLT VVHQDWLNGK EYKCKVSNKG LPAPIEKTIS   360
KTKGQPREPQ VYTLPPSREE MTKNQVSLTC LVKGFYPSDI AVEWESNGQP ENNYKTTPPM   420
LDSDGSFFLY SKLTVDKSRW QQGNVFSCSV MHEALHNHYT QKSLSLSPGK              470

SEQ ID NO: 93           moltype = DNA  length = 705
FEATURE                 Location/Qualifiers
source                  1..705
                        mol_type = other DNA
                        organism = Homo sapiens
SEQUENCE: 93
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gggtattagt agaagctact tagcctggta ccagcagaaa   180
cctggccagg ctcccagcct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcaa caatttggt gttcaccgtg gacgttcggc   360
caagggacca aggtggaaat caaacgaact gtggctgcac catctgtctt catcttcccg   420
ccatctgatg agcagttgaa atctggaact gctagcgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca agcagacta cgagaaacac aaagtctacg cctgcgaagt cacccatcag   660
ggcctgagct cgcccgtcac aaagagcttc aacaggggag agtgt                  705

SEQ ID NO: 94           moltype = AA  length = 235
FEATURE                 Location/Qualifiers
source                  1..235
                        mol_type = protein
                        organism = Homo sapiens
SEQUENCE: 94
METPAQLLFL LLLWLPDTTG EIVLTQSPGT LSLSPGERAT LSCRASQGIS RSYLAWYQQK    60
PGQAPSLLIY GASSRATGIP DRFSGSGSGT DFTLTISRLE PEDFAVYYCQ QFGSSPWTFG   120
QGTKVEIKRT VAAPSVFIFP PSDEQLKSGT ASVVCLLNNF YPREAKVQWK VDNALQSGNS   180
QESVTEQDSK DSTYSLSSTL TLSKADYEKH KVYACEVTHQ GLSSPVTKSF NRGEC        235

SEQ ID NO: 95           moltype = DNA  length = 1413
FEATURE                 Location/Qualifiers
source                  1..1413
                        mol_type = other DNA
                        organism = Homo sapiens
SEQUENCE: 95
```

```
atgaagcatc tgtggttctt cctcctgctg gtggcagctc ccagatgggt cctgtcccag   60
gtgcagctgc aggagtcggg cccaggactg gtgaagcctt cacagaccct gtccctcacc   120
tgcactgtct ctggtggctc catcagcagt ggtgattact tctggagctg gatccgccag   180
ctcccaggga agggcctgga gtggattggg cacatccata acagtgggac cacctactac   240
aatccgtccc tcaagagtcg agttaccata tcagtagaca cgtctaagaa ccagttctcc   300
ctgaggctga gttctgtgac tgccgcggac acggccgtat attactgtgc gagagatcga   360
gggggtgact actactatgg tatggacgtc tggggccaag ggaccacggt caccgtctcc   420
tcagcctcca ccaagggccc atccgtcttc cccctggcac cctcctccaa gagcacctct   480
gggggcacag cggccctggg ctgcctggtc aaggactact ccccgaacc ggtgacggtg   540
tcgtggaact caggcgccct gaccagcggc gtgcacacct tcccggctgt cctacagtcc   600
tcaggactct actccctcag cagcgtggtg accgtgccct ccagcagctt gggcacccag   660
acctacatct gcaacgtgaa tcacaagccc agcaacacca aggtggacaa gagagttgag   720
cccaaatctt gtgacaaaac tcacacatgc ccaccgtgcc cagcacctga actcctgggg   780
ggaccgtcag tcttcctctt ccccccaaaa cccaaggaca ccctcatgat ctcccggacc   840
cctgaggtca catgcgtggt ggtggacgtg agccacgaag accctgaggt caagttcaac   900
tggtacgtgg acggcgtgga ggtgcataat gccaagacaa agccgcggga ggagcagtac   960
aacagcacgt accgtgtggt cagcgtcctc accgtcctgc accaggactg gctgaatggc   1020
aaggagtaca agtgcaaggt ctccaacaaa gccctcccag cccccatcga gaaaaccatc   1080
tccaaagcca aagggcagcc ccgagaacca caggtgtaca ccctgccccc atcccgggga   1140
gagatgacca gaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tatagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaa   1413
```

```
SEQ ID NO: 96           moltype = AA   length = 471
FEATURE                 Location/Qualifiers
source                  1..471
                        mol_type = protein
                        organism = Homo sapiens
SEQUENCE: 96
MKHLWFFLLL VAAPRWVLSQ VQLQESGPGL VKPSQTLSLT CTVSGGSISS GDYFWSWIRQ   60
LPGKGLEWIG HIHNSGTTYY NPSLKSRVTI SVDTSKKQFS LRLSSVTAAD TAVYYCARDR   120
GGDYYYGMDV WGQGTTVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K   471
```

```
SEQ ID NO: 97           moltype = DNA   length = 708
FEATURE                 Location/Qualifiers
source                  1..708
                        mol_type = other DNA
                        organism = Homo sapiens
SEQUENCE: 97
atggacatga gggtccctgc tcagctcctg gggctcctgc tgctctggct ctcaggtgcc   60
agatgtgaca tccagatgac ccagtctcca tcctccctgt ctgcatctgt aggagacaga   120
gtcaccatca cttgccaggc gagtcaggac atcagcaact atttaaattg gtatcagcag   180
aaaccaggga aagcccctaa actcctgatc tacgatgcat ccaatttgga aacaggggtc   240
ccatcaaggt tcagtggaag tggatctggg acagatttta ctttcaccat cagcagcctg   300
cagcctgaag atattgcaac atatttctgt caacactttg atcatctccc gctcgctttc   360
ggcggaggga ccaaggtgga gatcaaacga actgtggctg caccatcgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagc cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt   708
```

```
SEQ ID NO: 98           moltype = AA   length = 236
FEATURE                 Location/Qualifiers
source                  1..236
                        mol_type = protein
                        organism = Homo sapiens
SEQUENCE: 98
MDMRVPAQLL GLLLLWLSGA RCDIQMTQSP SSLSASVGDR VTITCQASQD ISNYLNWYQQ   60
KPGKAPKLLI YDASNLETGV PSRFSGSGSG TDFTFTISSL QPEDIATYFC QHFDHLPLAF   120
GGGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC   236
```

```
SEQ ID NO: 99           moltype = DNA   length = 1392
FEATURE                 Location/Qualifiers
source                  1..1392
                        mol_type = other DNA
                        organism = Homo sapiens
SEQUENCE: 99
atgaaacacc tgtggttctt cctcctcctg gtggcagctc ccagatgggt cctgtcccag   60
gtacagctgc aggagtcggg cccaggactg gtgaagcctt cggagaccct gtccctcacc   120
tgcactgtct ctggtggctc cgtcagcagt ggtgattact actggacctg gatccggcag   180
```

-continued

```
tccccaggga agggactgga gtggattgga cacatctatt acagtgggaa caccaattat   240
aacccctccc tcaagagtcg actcaccata tcaattgaca cgtccaagac tcagttctcc   300
ctgaagctga gttctgtgac cgctgcggac acggccattt attactgtgt gcgagatcga   360
gtgactggtg cttttgatat ctggggccaa gggacaatgg tcaccgtctc ttcagctagc   420
accaagggcc catcggtctt ccccctggcg ccctgctcca ggagcacctc cgagagcaca   480
gcggccctgg gctgcctggt caaggactac ttccccgaac cggtgacggt gtcgtggaac   540
tcaggcgctc tgaccagcgg cgtgcacacc ttcccagctg tcctacagtc ctcaggactc   600
tactccctca gcagcgtggt gaccgtgccc tccagcaact cggcacccca gacctacacc   660
tgcaacgtag atcacaagcc cagcaacacc aaggtggaca gacagttgga gcgcaaatgt   720
tgtgtcgagt gcccaccgtg cccagcacca cctgtggcag gaccgtcagt cttcctcttc   780
cccccaaaac ccaaggacac cctcatgatc tcccggaccc ctgaggtcac gtgcgtggtg   840
gtggacgtga gccacgaaga ccccgaggtc cagttcaact ggtacgtgga cggcgtggag   900
gtgcataatg ccaagacaaa gccacgggag gagcagttca acagcacgtt ccgtgtggtc   960
agcgtcctca ccgttgtgca ccaggactgg ctgaacggca aggagtacaa gtgcaaggtc   1020
tccaacaaag gcctcccagc ccccatcgag aaaaccatct ccaaaaccaa agggcagccc   1080
cgagaaccac aggtgtacac cctgcccca tcccgggagg agatgaccaa gaaccaggtc   1140
agcctgacct gcctggtcaa aggcttctac cccagcgaca tcgccgtgga gtgggagagc   1200
aatgggcagc cggagaacaa ctacaagacc acacctcca tgctggactc cgacggctcc   1260
ttcttcctct acagcaagct caccgtggac aagagcaggt ggcagcaggg gaacgtcttc   1320
tcatgctccg tgatgcatga ggctctgcac aaccactaca cgcagaagag cctctccctg   1380
tctccgggta aa                                                      1392
```

```
SEQ ID NO: 100          moltype = AA   length = 464
FEATURE                 Location/Qualifiers
source                  1..464
                        mol_type = protein
                        organism = Homo sapiens
SEQUENCE: 100
MKHLWFFLLL VAAPRWVLSQ VQLQESGPGL VKPSETLSLT CTVSGGSVSS GDYYWTWIRQ   60
SPGKGLEWIG HIYYSGNTNY NPSLKSRLTI SIDTSKTQFS LKLSSVTAAD TAIYYCVRDR   120
VTGAFDIWGQ GTMVTVSSAS TKGPSVFPLA PCSRSTSEST AALGCLVKDY FPEPVTVSWN   180
SGALTSGVHT FPAVLQSSGL YSLSSVVTVP SSNFGTQTYT CNVDHKPSNT KVDKTVERKC   240
CVECPPCPAP PVAGPSVFLF PPKPKDTLMI SRTPEVTCVV VDVSHEDPEV QFNWYVDGVE   300
VHNAKTKPRE EQFNSTFRVV SVLTVVHQDW LNGKEYKCKV SNKGLPAPIE KTISKTKGQP   360
REPQVYTLPP SREEMTKNQV SLTCLVKGFY PSDIAVEWES NGQPENNYKT TPPMLDSDGS   420
FFLYSKLTVD KSRWQQGNVF SCSVMHEALH NHYTQKSLSL SPGK                   464
```

```
SEQ ID NO: 101          moltype = DNA   length = 708
FEATURE                 Location/Qualifiers
source                  1..708
                        mol_type = other DNA
                        organism = Homo sapiens
SEQUENCE: 101
atggaaaccc cagcgcagct tctcttcctc ctgctactct ggctcccaga taccgctagc   60
gaaattgtgt tgacgcagtc tccaggcacc ctgtctttgt ctccagggga aagagccacc   120
ctctcctgca gggccagtca gagtgttagc aacagctact tagcctggta ccagcagaaa   180
cctggccagg ctcccaggct cctcatctat ggtgcatcca gcagggccac tggcatccca   240
gacaggttca gtggcagtgg gtctgggaca gacttcactc tcaccatcag cagactggag   300
cctgaagatt ttgcagtgta ttactgtcag cagtatgatc actcagcagg tggacgttc   360
ggccaaggga ccaaggtgga gatcaaacgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt                708
```

```
SEQ ID NO: 102          moltype = AA   length = 236
FEATURE                 Location/Qualifiers
source                  1..236
                        mol_type = protein
                        organism = Homo sapiens
SEQUENCE: 102
METPAQLLFL LLLWLPDTAS EIVLTQSPGT LSLSPGERAT LSCRASQSVS NSYLAWYQQK   60
PGQAPRLLIY GASSRAPGIP DRFSGSGSGT DFTLTISRLE PEDFAVYYCQ QYDHSAGWTF   120
GQGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGEC       236
```

```
SEQ ID NO: 103          moltype = DNA   length = 1680
FEATURE                 Location/Qualifiers
source                  1..1680
                        mol_type = other DNA
                        organism = Homo sapiens
SEQUENCE: 103
atggggtcaa ccgccatcct tggcctcctc ctggctgttc tccaaggagt cgctagcgag   60
gttcagctgg tggagtctgg gggaggcttg gtacagcctg gggggtccct gagactctcc   120
tgtgcagcct ctggattcac cttcagtaga aatgctatgt ctggggttcg ccaggctcca   180
ggaaaaggtc tggagtgggt atcaggtatt ggtactggtg gtgccacaag ctatgcagac   240
tccgtgaagg gccgattcac catctccaga gacaatgcca gaactccttt gtatcttcaa   300
atgaacagcc tgagagccga ggacacggct gtgtattact gtgcaagagg gaggtactac   360
```

-continued

```
ttcccgtggt gggccaggg aaccctggtc accgtctcct cagcctccac caagggccca    420
tcggtcttcc ccctggcgcc ctgctccagg agcacctccg agagcacagc ggccctgggc    480
tgcctggtca aggactactt ccccgaaccg gtgacggtgt cgtggaactc aggcgctctg    540
accagcggcg tgcacacctt cccggctgtc ctacagtcct caggactcta ctccctcagc    600
agcgtggtga ccgtgccctc cagcaacttc ggcacccaga cctacacctg caacgtagat    660
cacaagccca gcaacaccaa ggtggacaag acagttggtg agaggccagc tcagggaggg    720
agggtgtctg ctggaagcca ggctcagccc tcctgcctgg acgcacccCg gctgtgcagc    780
cccagcccag ggcagcaagg caggccccat ctgtctcctc acccggaggc ctctgcccgc    840
cccactcatg ctcagggaga gggtcttctg gctttttcca ccaggctcca ggcaggcaca    900
ggctgggtgc ccctacccca ggcccttcac acacaggggc aggtgcttgg ctcagacctg    960
ccaaaagcca tatccgggag gaccctgccc ctgaccgagc gcaaatgttg tgtcgagtgc   1020
ccaccgtgcc cagcacccac ctgtggcagga ccgtcagtct tcctcttccc cccaaaaccc   1080
aaggacaccc tcatgatctc ccggacccct gaggtcacgt gcgtggtggt ggacgtgagc   1140
cacgaagacc ccgaggtcca gttcaactgg tacgtggacg gcgtggaggt gcataatgac   1200
aagacaaagc cacgggagga gcagttcaac agcacgttcc gtgtggtcag cgtcctcacc   1260
gtcgtgcacc aggactggct gaacggcaag gagtacaagt gcaaggtctc caacaaaggc   1320
ctcccagccc ccatcgagaa aaccatctcc aaaaccaaag gcagccccg agaaccacag   1380
gtgtacaccc tgcccccatc ccgggaggag atgaccaaga accaggtcag cctgacctgc   1440
ctggtcaaag gcttctaccc cagcgacatc gccgtggagt gggagagcaa tgggcagccg   1500
gagaacaact acaagaccac acctcccatg ctggactccg acggctcctt cttcctctac   1560
agcaagctca ccgtggacaa gagcaggtgg cagcagggga acgtcttctc atgctccgtg   1620
atgcatgagg ctctgcacaa ccactacacg cagaagagcc tctccctgtc tccgggtaaa   1680
```

```
SEQ ID NO: 104          moltype = AA  length = 460
FEATURE                 Location/Qualifiers
source                  1..460
                        mol_type = protein
                        organism = Homo sapiens
SEQUENCE: 104
MGSTAILGLL LAVLQGVASE VQLVESGGGL VQPGGSLRLS CAASGFTFSR NAMFWVRQAP    60
GKGLEWVSGI GTGGATSYAD SVKGRFTISR DNAKNSLYLQ MNSLRAEDTA VYYCARGRYY   120
FPWWGQGTLV TVSSASTKGP SVFPLAPCSR STSESTAALG CLVKDYFPEP VTVSWNSGAL   180
TSGVHTFPAV LQSSGLYSLS SVVTVPSSNF GTQTYTCNVD HKPSNTKVDK TVERKCCVEC   240
PPCPAPPVAG PSVFLFPPKP KDTLMISRTP EVTCVVVDVS HEDPEVQFNW YVDGVEVHNA   300
KTKPREEQFN STFRVVSVLT VVHQDWLNGK EYKCKVSNKG LPAPIEKTIS KTKGQPREPQ   360
VYTLPPSREE MTKNQVSLTC LVKGFYPSDI AVEWESNGQP ENNYKTTPPM LDSDGSFFLY   420
SKLTVDKSRW QQGNVFSCSV MHEALHNHYT QKSLSLSPGK                          460
```

```
SEQ ID NO: 105          moltype = DNA  length = 702
FEATURE                 Location/Qualifiers
source                  1..702
                        mol_type = other DNA
                        organism = Homo sapiens
SEQUENCE: 105
atggaaaccc cagcgcagct tctcttcctc ctgctactct ggctcccaga taccaccgga    60
gaaattgtgt tgacgcagtc tccaggcacc ctgtctttgt ctccagggga aagagccacc   120
ctctcctgca gggccagtca gagtgttagc agcagctact tagcctggta ccagcagaaa   180
cctggccagg ctcccaggct cctcatctat ggtgcatccc gcaggggcac tggcatccca   240
gacaggttca gtggcagtgg gtctgggaca gacttcactc tcaccatcag cagactggag   300
cctgaagatt ttgcagtgta ttactgtcag cggtatggta gctcacacac ttttggccag   360
gggaccaagc tggagatcag ccgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                       702
```

```
SEQ ID NO: 106          moltype = AA  length = 234
FEATURE                 Location/Qualifiers
source                  1..234
                        mol_type = protein
                        organism = Homo sapiens
SEQUENCE: 106
METPAQLLFL LLLWLPDTTG EIVLTQSPGT LSLSPGERAT LSCRASQSVS SSYLAWYQQK    60
PGQAPRLLIY GASRRATGIP DRFSGSGSGT DFTLTISRLE PEDFAVYYCQ RYGSSHTFGQ   120
GTKLEISRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC          234
```

```
SEQ ID NO: 107          moltype = DNA  length = 1401
FEATURE                 Location/Qualifiers
source                  1..1401
                        mol_type = other DNA
                        organism = Homo sapiens
SEQUENCE: 107
atggggtcaa ccgccatcct cgccctcctc ctggctgttc tccaaggagt ctgtgccgag    60
gtgcagctgg tgcagtctgg agcagaggtg aaaaagcccg ggagtctct gaagatctcc    120
tgtaaggttt ctggatactt ctttaccacc tactggatcg gctgggtgcg ccagatgccc    180
gggaaaggcc tggagtatat ggggatcatc tatcctggtg actctgatac cagatacagc    240
ccgtccttcc aaggccaggt caccatctca gccgacaagt ccatcagcac cgcctacctg    300
```

```
cagtggagca gcctgaaggc ctcggacacc gccatgtatt actgtgcgag agggggtaac    360
tggaactgct ttgactactg gggccaggga accctggtca ccgtctcctc agcctccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggatga gctgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320
aacgtcttct catgctccgt gatgcatgag gctctgcaca ccactacac gcagaagagc   1380
ctctccctgt ctccgggtaa a                                            1401
```

SEQ ID NO: 108          moltype = AA  length = 467
FEATURE                 Location/Qualifiers
source                  1..467
                        mol_type = protein
                        organism = Homo sapiens
SEQUENCE: 108
MGSTAILALL LAVLQGVCAE VQLVQSGAEV KKPGESLKIS CKVSGYFFTT YWIGWVRQMP     60
GKGLEYMGII YPGDSDTRYS PSFQGQVTIS ADKSISTAYL QWSSLKASDT AMYYCARGGN    120
WNCFDYWGQG TLVTVSSAST KGPSVFPLAP SSKSTSGGTA ALGCLVKDYF PEPVTVSWNS    180
GALTSGVHTF PAVLQSSGLY SLSSVVTVPS SSLGTQTYIC NVNHKPSNTK VDKRVEPKSC    240
DKTHTCPPCP APELLGGPSV FLFPPKPKDT LMISRTPEVT CVVVDVSHED PEVKFNWYVD    300
GVEVHNAKTK PREEQYNSTY RVVSVLTVLH QDWLNGKEYK CKVSNKALPA PIEKTISKAK    360
GQPREPQVYT LPPSRDELTK NQVSLTCLVK GFYPSDIAVE WESNGQPENN YKTTPPVLDS    420
DGSFFLYSKL TVDKSRWQQG NVFSCSVMHE ALHNHYTQKS LSLSPGK                  467

SEQ ID NO: 109          moltype = DNA  length = 723
FEATURE                 Location/Qualifiers
source                  1..723
                        mol_type = other DNA
                        organism = Homo sapiens
SEQUENCE: 109
atggacatga gggtgcccgc tcagctcctg gggctcctgc tgctgtggct gagaggtgcc     60
agatgtgatg ttgtgatgac tcagtctcca ctctccctgc ccgtcacccc tggagagccg    120
gcctccatct cctgcaggtc tagtcagagc ctcctgcata gtaatggata caactatttg    180
gattggtacc tgcagaagcc agggcagtct ccacagctcc tgatctattt gggttctaat    240
cgggcctccg gggtccctga caggttcagt ggcagtggat caggcacaga tttttacactg    300
aaaatcagca gggtggaggc tgaggatgtt ggggtttatt actgcatgca aggtacacac    360
tggcctctga cgttcggcca agggaccaag gtggagatca aacgaactgt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgt                                                                  723

SEQ ID NO: 110          moltype = AA  length = 241
FEATURE                 Location/Qualifiers
source                  1..241
                        mol_type = protein
                        organism = Homo sapiens
SEQUENCE: 110
MDMRVPAQLL GLLLLWLRGA RCDVVMTQSP LSLPVTPGEP ASISCRSSQS LLHSNGYNYL     60
DWYLQKPGQS PQLLIYLGSN RASGVPDRFS GSGSGTDFTL KISRVEAEDV GVYYCMQGTH    120
WPLTFGQGTK VEIKRTVAAP SVFIFPPSDE QLKSGTASVV CLLNNFYPRE AKVQWKVDNA    180
LQSGNSQESV TEQDSKDSTY SLSSTLTLSK ADYEKHKVYA CEVTHQGLSS PVTKSFNRGE    240
C                                                                    241

SEQ ID NO: 111          moltype = DNA  length = 1413
FEATURE                 Location/Qualifiers
source                  1..1413
                        mol_type = other DNA
                        organism = Homo sapiens
SEQUENCE: 111
atggacatga gggtgcccgc tcagctcctg gggctcctgc tgctgtggct gagaggtgcc     60
agatgtcagg tgcagctgca ggagtcgggc ccaggactgg tgaagccttc ggggaccctg    120
tccctcacct gcgctgtctc tggtggctcc atcagcagta gtaactggtg gagttgggtc    180
cgccagcccc cagggaaggg gctggagtgg attggggaaa tctatcatag tgggagcacc    240
aactacaacc cgtccctcaa gagtcgagtc accatatcag tagacaagtc caagaaccag    300
ttctccctga agctgagctc tgtgaccgcc gcggacacgg ccgtgtatta ctgtgcgaga    360
```

-continued

```
tggaccgggc gtactgatgc ttttgatatc tggggccaag ggacaatggt caccgtctct    420
agtgcctcca ccaagggccc atcggtcttc cccctggcac cctcctccaa gagcacctct    480
gggggcacag cggccctggg ctgcctggtc aaggactact tccccgaacc ggtgacggtg    540
tcgtggaact caggcgccct gaccagcggc gtgcacacct tcccggctgt cctacagtcc    600
tcaggactct actccctcag cagcgtggtg accgtgccct ccagcagctt gggcacccag    660
acctacatct gcaacgtgaa tcacaagccc agcaacacca aggtggacaa gaaagttgag    720
cccaaatctt gtgacaaaac tcacacatgc ccaccgtgcc cagcacctga actcctgggg    780
ggaccgtcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccgcggga ggagcagtac    960
aacagcacgt accgtgtggt cagcgtcctc accgtcctgc accaggactg gctgaatggc   1020
aaggagtaca agtgcaaggt ctccaacaaa gccctcccag cccccatcga gaaaaccatc   1080
tccaaagcca aagggcagcc ccgagaacca caggtgtaca ccctgccccc atcccgggat   1140
gagctgacca agaaccaggt cagcctgacc tgcctggtca aaggcttcta tcccagcgac   1200
atcgccgtgg agtgggagag caatgggcag ccggagaaca actacaagac cacgcctccc   1260
gtgctggact ccgacggctc cttcttcctc tatagcaagc tcaccgtgga caagagcagg   1320
tggcagcagg ggaacgtctt ctcatgctcc gtgatgcatg aggctctgca caaccactac   1380
acgcagaaga gcctctccct gtctccgggt aaa                                 1413
```

SEQ ID NO: 112            moltype = AA  length = 471
FEATURE                   Location/Qualifiers
source                    1..471
                          mol_type = protein
                          organism = Homo sapiens
SEQUENCE: 112
```
MDMRVPAQLL GLLLLWLRGA RCQVQLQESG PGLVKPSGTL SLTCAVSGGS ISSSNWWSWV    60
RQPPGKGLEW IGEIYHSGST NYNPSLKSRV TISVDKSKNQ FSLKLSSVTA ADTAVYYCAR   120
WTGRTDAFDI WGQGTMVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKKVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRD ELTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471
```

SEQ ID NO: 113            moltype = DNA  length = 702
FEATURE                   Location/Qualifiers
source                    1..702
                          mol_type = other DNA
                          organism = Homo sapiens
SEQUENCE: 113
```
atggaagcgc cggcgcagct tctcttcctc ctgctactct ggctcccaga taccactgga    60
gaaatagtga tgacgcagtc tccagccacc ctgtctgtgt ctcctgggga aagagccacc   120
ctctcctgca gggccagtca gagtgttagc agcaacttag cctggttcca gcagaaacct   180
ggccaggctc ccaggcccct catctatgat gcatccacca gggccactgg tgtcccagcc   240
aggttcagtg gcagtgggtc tgggacagac ttcactctca ccatcagcag cctgcagtct   300
gaagattttg cagtttatta ctgtcagcag tatgataact ggccgctcac tttcggcgga   360
gggaccaagg tggagatcaa acgtacggtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gt                       702
```

SEQ ID NO: 114            moltype = AA  length = 234
FEATURE                   Location/Qualifiers
source                    1..234
                          mol_type = protein
                          organism = Homo sapiens
SEQUENCE: 114
```
MEAPAQLLFL LLLWLPDTTG EIVMTQSPAT LSVSPGERAT LSCRASQSVS SNLAWFQQKP    60
GQAPRPLIYD ASTRATGVPA RFSGSGSGTD FTLTISSLQS EDFAVYYCQQ YDNWPLTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC          234
```

SEQ ID NO: 115            moltype = DNA  length = 1383
FEATURE                   Location/Qualifiers
source                    1..1383
                          mol_type = other DNA
                          organism = Homo sapiens
SEQUENCE: 115
```
atggagtgga cctggagggt cctttttctt gtggcagcag caacaggtgc ccactcccag    60
gttcagctgt tgcagtctgg agctgaggtg aagaagcctg ggcctcagt gaaggtctcc   120
tgcaaggctt ctggttacac ctttaccaga tatggtatca gctgggtgcg acaggcccct   180
ggacaagggc ttgagtggat gggatggatc agcacttacg gtggtaacac aaactatgca   240
cagaagctcc agggcagagt caccatgacc acagacacat ccacgagcac agcctacatg   300
gagctgagga gcctgagatc tgacgacacg gccgtgtatt actgtgcgag acggcagctt   360
tactttgact actggggcca gggaaccctg gtcaccgtct cctcagctag caccaagggc   420
ccatcggtct tccccctggc gccctgctcc aggagcacct ccgagagcac agcggccctg   480
ggctgcctgg tcaaggacta cttccccgaa ccggtgacgg tgtcgtggaa ctcaggcgct   540
```

```
ctgaccagcg gcgtgcacac cttccagct gtcctacagt cctcaggact ctactccctc  600
agcagcgtgg tgaccgtgcc ctccagcaac ttcggcaccc agacctacac ctgcaacgta  660
gatcacaagc ccagcaacac caaggtggac aagacagttg agcgcaaatg ttgtgtcgag  720
tgcccaccgt gcccagcacc acctgtggca ggaccgtcag tcttcctctt cccccccaaa  780
cccaaggaca ccctcatgat ctcccggacc cctgaggtca cgtgcgtggt ggtggacgtg  840
agccacgaag accccgaggt ccagttcaac tggtacgtgg acggcgtgga ggtgcataat  900
gccaagacaa agccacggga ggagcagttc aacagcacgt tccgtgtggt cagcgtcctc  960
accgttgtgc accaggactg gctgaacggc aaggagtaca agtgcaaggt ctccaacaaa  1020
ggcctcccag ccccatcga gaaaaccatc tccaaaacca aagggcagcc ccgagaacca  1080
caggtgtaca ccctgcccccc atccgggag gagatgacca agaaccaggt cagcctgacc  1140
tgcctggtca aaggcttcta ccccagcgac atcgccgtgg agtgggagag caatgggcag  1200
ccggagaaca actacaagac cacacctccc atgctggact ccgacggctc cttcttcctc  1260
tacagcaagc tcaccgtgga caagagcagg tggcagcagg ggaacgtctt ctcatgctcc  1320
gtgatgcatg aggctctgca caaccactac acgcagaaga gcctctccct gtctccgggt  1380
aaa                                                                 1383

SEQ ID NO: 116        moltype = AA   length = 461
FEATURE               Location/Qualifiers
source                1..461
                      mol_type = protein
                      organism = Homo sapiens
SEQUENCE: 116
MEWTWRVLFL VAAATGAHSQ VQLVQSGAEV KKPGASVKVS CKASGYTFTR YGISWVRQAP  60
GQGLEWMGWI STYSGNTNYA QKLQGRVTMT TDTSTSTAYM ELRSLRSDDT AVYYCARRQL  120
YFDYWGQGTL VTVSSASTKG PSVFPLAPCS RSTSESTAAL GCLVKDYFPE PVTVSWNSGA  180
LTSGVHTFPA VLQSSGLYSL SSVVTVPSSN FGTQTYTCNV DHKPSNTKVD KTVERKCCVE  240
CPPCPAPPVA GPSVFLFPPK PKDTLMISRT PEVTCVVVDV SHEDPEVQFN WYVDGVEVHN  300
AKTKPREEQF NSTFRVVSVL TVVHQDWLNG KEYKCKVSNK GLPAPIEKTI SKTKGQPREP  360
QVYTLPPSRE EMTKNQVSLT CLVKGFYPSD IAVEWESNGQ PENNYKTTPP MLDSDGSFFL  420
YSKLTVDKSR WQQGNVFSCS VMHEALHNHY TQKSLSLSPG K                       461

SEQ ID NO: 117        moltype = DNA   length = 717
FEATURE               Location/Qualifiers
source                1..717
                      mol_type = other DNA
                      organism = Homo sapiens
SEQUENCE: 117
atgaggctcc ctgctcagct cctggggctg ctaatgctct ggatacctgg atccagtgca  60
gatattgtga tgacccagac tccactctct ctgtccgtca ccctgggaca gccggcctcc  120
atctcctgca agtctggtca gagcctcctg catagtgatg gaaagaccta tttgtattgg  180
tacctgcaga agccaggcca gcctccacag ttcctgatct atgaagtttc caaccggttc  240
tctagagtgc cagataggtt cagtggcagc gggtcaggga cagatttcac actgagaatc  300
agccggtgag aggctgagga tgttggaatt tattactgca tgcaaagtat acagcttccg  360
tggacgttcg gccaagggac ccaggtggaa atcaaacgaa ctgtggctgc accatctgtc  420
ttcatcttcc cgccatctga tgagcagttg aaatctggaa ctgcctctgt tgtgtgcctg  480
ctgaataact tctatcccag agaggccaaa gtacagtgga aggtggataa cgccctccaa  540
tcgggtaact cccaggagag tgtcacagag caggacagca ctacagcctc  600
agcagcaccc tgacgctgag caaagcagac tacgagaaac acaaagtcta cgcctgcgaa  660
gtcacccatc agggcctgag ctcgcccgtc acaaagagct tcaacagggg agagtgt     717

SEQ ID NO: 118        moltype = AA   length = 239
FEATURE               Location/Qualifiers
source                1..239
                      mol_type = protein
                      organism = Homo sapiens
SEQUENCE: 118
MRLPAQLLGL LMLWIPGSSA DIVMTQTPLS LSVTPGQPAS ISCKSGQSLL HSDGKTYLYW  60
YLQKPGQPPQ FLIYEVSNRF SRVPDRFSGS GSGTDFTLRI SRVEAEDVGI YYCMQSIQLP  120
WTFGQGTQVE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 119        moltype = DNA   length = 1377
FEATURE               Location/Qualifiers
source                1..1377
                      mol_type = other DNA
                      organism = Homo sapiens
SEQUENCE: 119
atggagtttg ggctgagctg ggttttcctc gttgctcttt taagaggtgt ccagtgtcag  60
gtgcagctgg tggagtctgg gggaggcgtg gtccagcctg ggaggtccct gagactctcc  120
tgtgcagcct ctggattcac cttcagtggc tatggcatgc actgggtccg ccaggctcca  180
ggcaaggggc tggagtgggt ggcagttata tcatatgatg gaaatgataa atactatgca  240
gactccgtga agggccgatt caccatctcc agagacaatg ccaagaacac gctgtatctg  300
caaatgaaca gcctgagagc tgaggacacg gctgtgtatt actgtgcgag agagctacgg  360
gtcctctggg gccagggaac cctggtcacc gtctctagtg cctccaccaa gggcccatcg  420
gtcttccccc tggcgccctg ctccaggagc acctccgaga gcacagcggc cctgggctgc  480
ctggtcaagg actacttccc cgaaccggtg acggtgtcgt ggaactcagg cgctctgacc  540
agcggcgtgc acaccttccc agctgtccta cagtcctcag gactctactc cctcagcagc  600
gtggtgaccg tgccctccag caacttcggc acccagacct acacctgcaa cgtagatcac  660
aagcccagca acaccaaggt ggacaagaca gttgagcgca aatgttgtgt cgagtgccca  720
```

```
ccgtgcccag caccacctgt ggcaggaccg tcagtcttcc tcttcccccc aaaacccaag   780
gacaccctca tgatctcccg gacccctgag gtcacgtgcg tggtggtgga cgtgagccac   840
gaagaccccg aggtccagtt caactggtac gtggacggcg tggaggtgca taatgccaag   900
acaaagccac gggaggagca gttcaacagc acgttccgtg tggtcagcgt cctcaccgtt   960
gtgcaccagg actggctgaa cggcaaggag tacaagtgca aggtctccaa caaaggcctc  1020
ccagcccca tcgagaaaac catctccaaa accaaagggc agccccgaga accacaggtg   1080
tacaccctgc ccccatcccg ggaggagatg accaagaacc aggtcagcct gacctgcctg  1140
gtcaaaggct tctaccccag cgacatcgcc gtggagtggg agagcaatgg gcagccggag  1200
aacaactaca agaccacacc tcccatgctg gactccgacg gctccttctt cctctacagc  1260
aagctcaccg tggacaagag caggtggcag caggggaacg tcttctcatg ctccgtgatg  1320
catgaggctc tgcacaacca ctacacgcag aagagcctct ccctgtctcc gggtaaa     1377

SEQ ID NO: 120           moltype = AA   length = 459
FEATURE                  Location/Qualifiers
source                   1..459
                         mol_type = protein
                         organism = Homo sapiens
SEQUENCE: 120
MEFGLSWVFL VALLRGVQCQ VQLVESGGGV VQPGRSLRLS CAASGFTFSG YGMHWVRQAP    60
GKGLEWVAVI SYDGNDKYYA DSVKGRFTIS RDNAKNTLYL QMNSLRAEDT AVYYCARELR   120
VLWGQGTLVT VSSASTKGPS VFPLAPCSRS TSESTAALGC LVKDYFPEPV TVSWNSGALT   180
SGVHTFPAVL QSSGLYSLSS VVTVPSSNFG TQTYTCNVDH KPSNTKVDKT VERKCCVECP   240
PCPAPPVAGP SVFLFPPKPK DTLMISRTPE VTCVVVDVSH EDPEVQFNWY VDGVEVHNAK   300
TKPREEQFNS TFRVVSVLTV VHQDWLNGKE YKCKVSNKGL PAPIEKTISK TKGQPREPQV   360
YTLPPSREEM TKNQVSLTCL VKGFYPSDIA VEWESNGQPE NNYKTTPPML DSDGSFFLYS   420
KLTVDKSRWQ QGNVFSCSVM HEALHNHYTQ KSLSLSPGK                          459

SEQ ID NO: 121           moltype = DNA   length = 705
FEATURE                  Location/Qualifiers
source                   1..705
                         mol_type = other DNA
                         organism = Homo sapiens
SEQUENCE: 121
atggacatga gggtgcccgc tcagctcctg gggctcctgc tgctgtggct gagaggtgcc    60
agatgtgaca tccagatgac ccagtctcca tcctccctgt ctgcatctgt aggtgaccgt   120
gtcaccatca cttgccgcgc aagtcaggat attagcagct atttaaattg gtatcagcag   180
aaaccaggga aagcccctaa gctcctgatc tattctactt cccgtttgaa tagtggggtc   240
ccatcacgct tcagtggcag tggctctggg acagatttca ctctcaccat cagcagtctg   300
caacctgaag attttgcaac ttactactgt caacaggata ttaaacacc tacgttcggt   360
caaggcacca aggtggagat caaacgtacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct cacgcctgag cagcaccctg   600
acgctgagca agcagactac gagaaaacac aaagtctacg cctgcgaagt cacccatcag   660
ggcctgagct cgcccgtcac aaagagcttc aacaggggag agtgt                   705

SEQ ID NO: 122           moltype = AA   length = 235
FEATURE                  Location/Qualifiers
source                   1..235
                         mol_type = protein
                         organism = Homo sapiens
SEQUENCE: 122
MDMRVPAQLL GLLLLWLRGA RCDIQMTQSP SSLSASVGDR VTITCRASQD ISSYLNWYQQ    60
KPGKAPKLLI YSTSRLNSGV PSRFSGSGSG TDFTLTISSL QPEDFATYYC QQDIKHPTFG   120
QGTKVEIKRT VAAPSVFIFP PSDEQLKSGT ASVVCLLNNF YPREAKVQWK VDNALQSGNS   180
QESVTEQDSK DSTYSLSSTL TLSKADYEKH KVYACEVTHQ GLSSPVTKSF NRGEC          235

SEQ ID NO: 123           moltype = DNA   length = 1395
FEATURE                  Location/Qualifiers
source                   1..1395
                         mol_type = other DNA
                         organism = Homo sapiens
SEQUENCE: 123
atggactgga cctggaggat cctcttcttg gtggcagcag ccacaggagc ccactccgag    60
gtgcagctgg tgcagtctgg ggctgaggtg aagaagcctg gtcctcggt gaaggtctcc    120
tgcaaggctt ctggttttac cttcaccgac tatattatgc actgggtgcg tcaggcccct   180
ggtcaagggc ttgagtggat gggctatatc aaccctatat atgatgacac cgaatacaac   240
gagaagttca gagggccgtg tcacgattac cgcggacaaat ccacgagcac agcctacatg   300
gagctgagca gcctgcgctc tgaggacacg gccgtgtatt actgtgcgcg ttcgatttat   360
tactacgatg ccccgtttgc ttactggggc caagggactc tggtcaccgt ctctagtgcc   420
tccaccaagg gcccatcggt cttccccctg gcgccctgct ccaggagcac ctccgagagc   480
acagcggccc tgggctgcct ggtcaaggac tacttccccg aaccggtgac ggtgtcgtgg   540
aactcaggcg ctctgaccag cggcgtgcac accttcccag ctgtcctaca gtcctcagga   600
ctctactccc tcagcagcgt ggtgaccgtg ccctccagca gcttgggcac ccagacctac   660
acctgcaacg tagatcacaa gcccagcaac accaaggtgg acaagacagt tgagcgcaaa   720
tgttgtgtcg agtgcccacc gtgcccagca ccacctgtgg caggaccgtc agtcttcctc   780
ttccccccaa aacccaagga caccctcatg atctcccgga cccctgaggt cacgtgcgtg   840
gtggtggacg tgagccacga agaccccgag gtccagttca actggtacgt ggacggcgtg   900
gaggtgcata atgccaagac aaagccacgg gaggagcagt tcaacagcac gttccgtgtg   960
```

-continued

```
gtcagcgtcc tcaccgttgt gcaccaggac tggctgaacg gcaaggagta caagtgcaag   1020
gtctccaaca aaggcctccc agcccccatc gagaaaacca tctccaaaac caaagggcag   1080
ccccgagaac cacaggtgta caccctgccc ccatcccggg aggagatgac caagaaccag   1140
gtcagcctga cctgcctggt caaaggcttc taccccagcg acatcgccgt ggagtgggag   1200
agcaatgggc agccggagaa caactacaag accacgcctc ccatgctgga ctccgacggc   1260
tccttcttcc tctacagcaa gctcaccgtg gacaagagca ggtggcagca ggggaacgtc   1320
ttctcatgct ccgtgatgca tgaggctctg cacaaccact acacgcagaa gagcctctcc   1380
ctgtctccgg gtaaa                                                    1395
```

```
SEQ ID NO: 124            moltype = AA  length = 465
FEATURE                   Location/Qualifiers
source                    1..465
                          mol_type = protein
                          organism = Homo sapiens
SEQUENCE: 124
MDWTWRILFL VAAATGAHSE VQLVQSGAEV KKPGSSVKVS CKASGFTFTD YIMHWVRQAP   60
GQGLEWMGYI NPYNDDTEYN EKFKGRVTIT ADKSTSTAYM ELSSLRSEDT AVYYCARSIY   120
YYDAPFAYWG QGTLVTVSSA STKGPSVFPL APCSRSTSES TAALGCLVKD YFPEPVTVSW   180
NSGALTSGVH TFPAVLQSSG LYSLSSVVTV PSSNFGTQTY TCNVDHKPSN TKVDKTVERK   240
CCVECPPCPA PPVAGPSVFL FPPKPKDTLM ISRTPEVTCV VVDVSHEDPE VQFNWYVDGV   300
EVHNAKTKPR EEQFNSTFRV VSVLTVVHQD WLNGKEYKCK VSNKGLPAPI EKTISKTKGQ   360
PREPQVYTLP PSREEMTKNQ VSLTCLVKGF YPSDIAVEWE SNGQPENNYK TTPPMLDSDG   420
SFFLYSKLTV DKSRWQQGNV FSCSVMHEAL HNHYTQKSLS LSPGK               465
```

```
SEQ ID NO: 125            moltype = DNA  length = 699
FEATURE                   Location/Qualifiers
source                    1..699
                          mol_type = other DNA
                          organism = Homo sapiens
SEQUENCE: 125
atggggtcaa ccgccatcct tggcctcctc ctggctgtcc tgcagggagg gcgcgcctcc   60
tatgtgctga ctcagccacc ctcggtgtca gtggcccag gacagacggc caggattacc    120
tgtgggggaa acaaccttgg aagtaaaagt gtgcactggt accagcagaa gccaggccag   180
gcccctgtgc tggtcgtcta tgatgatagc gaccggccct catggatccc tgagcgattc   240
tctggctcca actctgggaa cacggccacc ctgaccatca gcggggtcga agccggggat   300
gaggccgact attactgtca ggtgtgggat agtagtagtg atcatgtggt attcggcgga   360
gggaccaagc tgaccgtcct aggccaaccg aaagcggcgc cctcggtcac tctgttcccg   420
ccctcctctg aggagcttca agccaacaag gccacactgg tgtgtctcat aagtgacttc   480
tacccgggag ccgtgacagt ggcctggaag gcagatagca gccccgtcaa ggcgggagtg   540
gagaccacca caccctccaa acaaagcaac aacaagtacg cggccagcag ctatctgagc   600
ctgacgcctg agcagtggaa gtcccacaga agctacagct gccaggtcac gcatgaaggg   660
agcaccgtgg agaagacagt ggcccctaca gaatgttca                         699
```

```
SEQ ID NO: 126            moltype = AA  length = 233
FEATURE                   Location/Qualifiers
source                    1..233
                          mol_type = protein
                          organism = Homo sapiens
SEQUENCE: 126
MGSTAILGLL LAVLQGGRAS YVLTQPPSVS VAPGQTARIT CGGNNLGSKS VHWYQQKPGQ   60
APVLVVYDDS DRPSWIPERF SGSNSGNTAT LTISRGEAGD EADYYCQVWD SSSDHVVFGG   120
GTKLTVLGQP KAAPSVTLFP PSSEELQANK ATLVCLISDF YPGAVTVAWK ADSSPVKAGV   180
ETTTPSKQSN NKYAASSYLS LTPEQWKSHR SYSCQVTHEG STVEKTVAPT ECS          233
```

```
SEQ ID NO: 127            moltype = DNA  length = 1401
FEATURE                   Location/Qualifiers
source                    1..1401
                          mol_type = other DNA
                          organism = Homo sapiens
SEQUENCE: 127
atggggtcaa ccgccatcct tggcctcctc ctggctgtcc tgcagggagg gcgcgcccag   60
atgcagctgt tggagtctgg gggaggcgtg gtccagcctg gaggtccct gagactctcc    120
tgtgcagcgt ctggattcac cttcagaacc tatggcatgc actgggtccg ccaggctcca   180
ggcaagggac tggagtgggt ggcagttata tggtatgatg gaagtaataa acactatgca   240
gactccgtga agggccgatt caccatcacc agagacaatt ccaagaacac tctgaatctg   300
caaatgaaca gcctgagagc cgaggacacg gctgtgtatt actgtgcgag agcccctcag   360
tgggagctag ttcatgaagc ttttgatatc tggggccaag gacaatggt caccgtctct    420
tcagctagca ccaagggccc atcggtcttc cccctggcgc cctgctccag gagcacctcc   480
gagagcacag cggccctggg ctgcctggtc aaggactact cccccgaacc ggtgacggtg   540
tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc ccccaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtggtca gcgtcctcac cgttgtgcac caggactggc tgaacggcaa ggagtacaag   1020
tgcaaggtct ccaacaaagg cctcccagcc cccatcgaga aaccatctc caaaaccaaa    1080
gggcagcccc gagaaccaca ggtgtacacc ctgcccccat cccgggagga gatgaccaag   1140
```

```
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctccctgt ctccgggtaa a                                             1401

SEQ ID NO: 128          moltype = AA   length = 467
FEATURE                 Location/Qualifiers
source                  1..467
                        mol_type = protein
                        organism = Homo sapiens
SEQUENCE: 128
MGSTAILGLL LAVLQGGRAQ MQLVESGGGV VQPGRSLRLS CAASGFTFRT YGMHWVRQAP   60
GKGLEWVAVI WYDGSNKHYA DSVKGRFTIT RDNSKNTLNL QMNSLRAEDT AVYYCARAPQ   120
WELVHEAFDI WGQGTMVTVS SASTKGPSVF PLAPCSRSTS ESTAALGCLV KDYFPEPVTV   180
SWNSGALTSG VHTFPAVLQS SGLYSLSSVV TVPSSNFGTQ TYTCNVDHKP SNTKVDKTVE   240
RKCCVECPPC PAPPVAGPSV FLFPPKPKDT LMISRTPEVT CVVVDVSHED PEVQFNWYVD   300
GVEVHNAKTK PREEQFNSTF RVVSVLTVVH QDWLNGKEYK CKVSNKGLPA PIEKTISKTK   360
GQPREPQVYT LPPSREEMTK NQVSLTCLVK GFYPSDIAVE WESNGQPENN YKTTPPMLDS   420
DGSFFLYSKL TVDKSRWQQG NVFSCSVMHE ALHNHYTQKS LSLSPGK               467

SEQ ID NO: 129          moltype = DNA   length = 702
FEATURE                 Location/Qualifiers
source                  1..702
                        mol_type = other DNA
                        organism = Homo sapiens
SEQUENCE: 129
atgggtgtgc ctactcatct cctgggtttg ttgctgctct ggattacaca tgccatatgt   60
gatatccgga tgacacagtc tccagcttcc ctgtctgcat ctctgggaga aactgtcaac   120
atcgaatgtc tagcaagtga ggacatttac agtgatttag catggtatca gcagaagcca   180
gggaaatctc ctcagctcct gatctataat gcaaatagct tgcaaaatgg ggtcccttca   240
cggtttagtg gcagtggatc tggcacacag tattctctaa aaataaacag cctgcaatct   300
gaagatgtcg cgacttattt ctgtcaacaa tataacaatt atcctccgac gttcggtgga   360
ggcaccaagc tggaattgaa acgggctgat gctgcaccaa ctgtatctat cttcccacca   420
tccacggaac agttagcaac tggaggtgcc tcagtcgtgt gcctcatgaa caacttctat   480
cccagagaca tcagtgtcaa gtggaagatt gatggcactg aacgacgaga tggtgtcctg   540
gacagtgtta ctgatcagga cagcaaagac agcacgtaca gcatgagcag caccctctcg   600
ttgaccaagg ctgactatga aagtcataac ctctatacct gtgaggttgt tcataagaca   660
tcatcctcac ccgtcgtcaa gagcttcaac aggaatgagt gt                      702

SEQ ID NO: 130          moltype = AA   length = 234
FEATURE                 Location/Qualifiers
source                  1..234
                        mol_type = protein
                        organism = Homo sapiens
SEQUENCE: 130
MGVPTHLLGL LLLWITHAIC DIRMTQSPAS LSASLGETVN IECLASEDIY SDLAWYQQKP   60
GKSPQLLIYN ANSLQNGVPS RFSGSGSGTQ YSLKINSLQS EDVATYFCQQ YNNYPPTFGG   120
GTKLELKRAD AAPTVSIFPP STEQLATGGA SVVCLMNNFY PRDISVKWKI DGTERRDGVL   180
DSVTDQDSKD STYSMSSTLS LTKADYESHN LYTCEVVHKT SSSPVVKSFN RNEC         234

SEQ ID NO: 131          moltype = DNA   length = 1395
FEATURE                 Location/Qualifiers
source                  1..1395
                        mol_type = other DNA
                        organism = Homo sapiens
SEQUENCE: 131
atggacatca ggctcagctt ggctttcctt gtccttttca taaaaggtgt ccagtgtgag   60
gtacagctgt tggagtctgg cggaggattg gtacagcctg caaactccct gaaactctcc   120
tgtgcagcct caggattcac tttcagtgac tatgccatgc cctgggtccg ccagtctcca   180
aagaagggtc tggagtgggt cgcaaccatt atttatgatg gtagtagcac ttactatcga   240
gactccgtga agggccgatt cactatctcc agagataatg caaaaagcac cctatacctg   300
caaatggaca gtctgaggtc tgaggacacg gccacttatt actgtgcaac aggtctgggt   360
atagctacgg actactttga ttactggggc caaggagtcc tggtcacagt ctcctcagct   420
gaaacaacag ccccatctgt ctatccactg gctcctggaa ctgctctcaa aagtaactcc   480
atggtgaccc tgggatgcct ggtcaagggc tatttccctg agccagtcac cgtgacctgg   540
aactctggag ccctgtccag cggtgtgcac accttccag ctgtcctgca gtctgggctc    600
tacactctca ccagctcagt gactgtaccc tccagcacct ggcccagcca gaccgtcacc   660
tgcaacgtag cccacccggc cagcagcacc aaggtggaca agaaaattgt gcccagaaac   720
tgtggaggtg attgcaagcc ttgtatatgt acaggctcag aagtatcatc tgtcttcatc   780
ttcccccca agcccaaaga tgtgctcacc atcactctga ctcctaaggt cacgtgtgtt    840
gtggtagaca ttagccagga cgatcccgag gtccatttca gctggtttgt agatgacgtg   900
gaagtccaca cagctcagac tcgaccacca gaggagcagt tcaacagcac tttccgctca   960
gtcagtgaac tccccatcct gcaccaggac tggctgcaatg gcaaggacgtt cagatgcaaa   1020
gtcaccagtg cagctttccc atcccccatc gagaaaacca tctccaaacc cgaaggcaga   1080
acacaagttc cgcatgtata caccatgtca cctaccaagg aagagatgac ccagaatgaa   1140
gtcagtatca cctgcatggt aaaaggcttc tatcccccag acatttatgt gggagtggcag   1200
atgaacgggc agccacagga aaactacaag aacactccac ctacgatgga cacagatggg   1260
agttacttcc tctacagcaa gctcaatgtg aagaaggaaa atggcagca gggaaacacg    1320
```

```
ttcacgtgtt ctgtgctgca tgaaggcctg cacaaccacc atactgagaa gagtctctcc   1380
cactctccgg gtaaa                                                     1395

SEQ ID NO: 132          moltype = AA   length = 465
FEATURE                 Location/Qualifiers
source                  1..465
                        mol_type = protein
                        organism = Homo sapiens
SEQUENCE: 132
MDIRLSLAFL VLFIKGVQCE VQLVESGGGL VQPANSLKLS CAASGFTFSD YAMAWVRQSP    60
KKGLEWVATI IYDGSSTYYR DSVKGRFTIS RDNAKSTLYL QMDSLRSEDT ATYYCATGLG   120
IATDYFDYWG QGVLVTVSSA ETTAPSVYPL APGTALKSNS MVTLGCLVKG YFPEPVTVTW   180
NSGALSSGVH TFPAVLQSGL YTLTSSVTVP SSTWPSQTVT CNVAHPASST KVDKKIVPRN   240
CGGDCKPCIC TGSEVSSVFI FPPKPKDVLT ITLTPKVTCV VVDISQDDPE VHFSWFVDDV   300
EVHTAQTRPP EEQFNSTFRS VSELPILHQD WLNGRTFRCK VTSAAFPSPI EKTISKPEGR   360
TQVPHVYTMS PTKEEMTQNE VSITCMVKGF YPPDIYVEWQ MNGQPQENYK NTPPTMDTDG   420
SYFLYSKLNV KKEKWQQGNT FTCSVLHEGL HNHHTEKSLS HSPGK                   465

SEQ ID NO: 133          moltype = DNA   length = 711
FEATURE                 Location/Qualifiers
source                  1..711
                        mol_type = other DNA
                        organism = Homo sapiens
SEQUENCE: 133
atggacatga gggtgcccgc tcagctcctg gggctcctgc tgctgtggct gagaggtgcc    60
agatgtgagt ctgccctgac tcagcctgcc tccgtgtctg ggtctcctgg acagtcgatc   120
accatctcct gcactggaac cagcagtgac gttggtggtt ataactctgt ctcctggtac   180
caacagcacc caggcaaagc ccccaaactc atgatttatg aggtcagtaa tcggccctca   240
ggggtttcta atcgcttctc tggctccaag tctggcaaca cggcctccct gaccatctct   300
gggctccagg ctgaggacga ggctgattat tactgcaatt catatacaag caccagcatg   360
gtattcggcg gagggaccaa gctgaccgtc ctaggtcagc ccaaggctgc ccctcggtc    420
actctgttcc cgccctcctc tgaggagctt caagccaaca aggccacact ggtgtgtctc   480
ataagtgact ctacccgggg agccgtgaca gtggcctgga aggcagatag cagccccgtc   540
aaggcgggag tggagaccac cacaccctcc aaacaaagca acaacaagta cgcggccagc   600
agctatctga gcctgacgcc tgagcagtgg aagtcccaca gaagctacag ctgccaggtc   660
acgcatgaag ggagcaccgt ggagaagaca gtggccccta cagaatgttc a            711

SEQ ID NO: 134          moltype = AA   length = 237
FEATURE                 Location/Qualifiers
source                  1..237
                        mol_type = protein
                        organism = Homo sapiens
SEQUENCE: 134
MDMRVPAQLL GLLLLWLRGA RCESALTQPA SVSGSPGQSI TISCTGTSSD VGGYNSVSWY    60
QQHPGKAPKL MIYEVSNRPS GVSNRFSGSK SGNTASLTIS GLQAEDEADY YCNSYTSTSM   120
VFGGGTKLTV LGQPKAAPSV TLFPPSSEEL QANKATLVCL ISDFYPGAVT VAWKADSSPV   180
KAGVETTTPS KQSNNKYAAS SYLSLTPEQW KSHRSYSCQV THEGSTVEKT VAPTECS      237

SEQ ID NO: 135          moltype = DNA   length = 1380
FEATURE                 Location/Qualifiers
source                  1..1380
                        mol_type = other DNA
                        organism = Homo sapiens
SEQUENCE: 135
atggactgga cctggaggat ccttttcttg gtggcagcag ccacaggtgt ccactccgag    60
gttcagctgg tgcagtctgg agctgaggtg aagaagcctg gggcctcagt gaaggtctcc   120
tgcaaggctt ctggttacac cttaaccagc tatggtatca gctgggtgcg acaggcccct   180
ggacaagggc ttgagtggat gggatgggtc agtttttata atggtaacac aaactatgca   240
cagaagctcc agggcagagg caccatgacc acagaccctc caagcgagca gccctacatg   300
gagctgagga gcctgagatc tgacgacacg gccgtgtatt actgtgcgag aggctacgat   360
atggacgtct ggggccaagg gaccacggtc accgtctcct ctgcctccac caagggccca   420
tcggtcttcc cctggcgccc ctgctccagg agcacctccg agagcacagc ggccctgggc   480
tgcctggtca aggactactt ccccgaaccg gtgacggtgt cgtggaactc aggcgctctg   540
accagcggcg tgcacacctt cccagctgtc ctacagtcct caggactcta ctccctcagc   600
agcgtggtga ccgtgccctc cagcaacttc ggcacccaga cctacacctg caacgtagat   660
cacaagccca gcaacaccaa ggtggacaag acagttgagc gcaaatgttg tgtcgagtgc   720
ccaccgtgcc cagcaccacc tgtggcagga ccgtcagtct tcctcttccc cccaaaaccc   780
aaggacaccc tcatgatctc ccggacccct gaggtcacgt gcgtggtggt ggacgtgagc   840
cacgaagacc ccgaggtcca gttcaactgg tacgtggacg gcgtggaggt gcataatgcc   900
aagacaaagc cacgggagga gcagttcaac agcacgttcc gtgtggtcag cgtcctcacc   960
gttgtgcacc aggactggct gaacggcaag gagtacaagt gcaaggtctc caacaaaggc  1020
ctcccagccc ccatcgagaa aaccatctcc aaaaccaaag gcagccccg agaaccacag   1080
gtgtacaccc tgcccccatc ccgggaggag atgaccaaga ccaggtcag cctgacctgc   1140
ctggtcaaag gcttctaccc cagcgacatc gccgtggagt gggagagcaa tgggcagccg  1200
gagaacaact acaagaccac acctcccatg ctggactccg acggctcctt cttcctctac  1260
agcaagctca ccgtggacaa gagcaggtgg cagcagggga acgtcttctc atgctccgtg  1320
atgcatgagg ctctgcacaa ccactacacg cagaagagcc tctccctgtc tccgggtaaa  1380

SEQ ID NO: 136          moltype = AA   length = 460
```

-continued

```
FEATURE                 Location/Qualifiers
source                  1..460
                        mol_type = protein
                        organism = Homo sapiens
SEQUENCE: 136
MDWTWRILFL VAAATGVHSE VQLVQSGAEV KKPGASVKVS CKASGYTLTS YGISWVRQAP    60
GQGLEWMGWV SFYNGNTNYA QKLQGRGTMT TDPSTSTAYM ELRSLRSDDT AVYYCARGYG   120
MDVWGQGTTV TVSSASTKGP SVFPLAPCSR STSESTAALG CLVKDYFPEP VTVSWNSGAL   180
TSGVHTFPAV LQSSGLYSLS SVVTVPSSNF GTQTYTCNVD HKPSNTKVDK TVERKCCVEC   240
PPCPAPPVAG PSVFLFPPKP KDTLMISRTP EVTCVVVDVS HEDPEVQFNW YVDGVEVHNA   300
KTKPREEQFN STFRVVSVLT VVHQDWLNGK EYKCKVSNKG LPAPIEKTIS KTKGQPREPQ   360
VYTLPPSREE MTKNQVSLTC LVKGFYPSDI AVEWESNGQP ENNYKTTPPM LDSDGSFFLY   420
SKLTVDKSRW QQGNVFSCSV MHEALHNHYT QKSLSLSPGK                         460

SEQ ID NO: 137          moltype = DNA   length = 693
FEATURE                 Location/Qualifiers
source                  1..693
                        mol_type = other DNA
                        organism = Homo sapiens
SEQUENCE: 137
atggcatgga tccctctctt cctcggcgtc cttgcttact gcacaggatc cgtggcctcc    60
tatgaggtga ctcaggcacc ctcagtgtcc gtgtccccag gacagacagc cagcatcacc   120
tgctctggag ataaattggg ggataaaatat gcttgttggt atcagcagaa gccaggccag   180
tcccctgtgc tggtcatcta tcaagatagc aagcggccct cagggatccc tgagcgattc   240
tctggctcca actctggaaa cacagccact ctgaccatca gcgggaccca ggctatggat   300
gaggctgact attactgtca ggcgtgggac agcagcactg cggtattcgg cggagggacc   360
aagctgaccg tcctaggtca gcccaaggct gcccctcgg tcactctgtt cccgccctcc    420
tctgaggagc ttcaagccaa caaggccaca ctggtgtgtc tcataagtga cttctacccg   480
ggagccgtga cagtggcctg gaaggcagat agcagccccg tcaaggcggg agtggagacc   540
accacaccct ccaaacaaag caacaacaag tacgcggcca gcagctatct gagcctgacg   600
cctgagcagt ggaagtccca cagaagctac agctgccagg tcacgcatga agggagcacc   660
gtggagaaga cagtggcccc tacagaatgt tca                                693

SEQ ID NO: 138          moltype = AA   length = 231
FEATURE                 Location/Qualifiers
source                  1..231
                        mol_type = protein
                        organism = Homo sapiens
SEQUENCE: 138
MAWIPLFLGV LAYCTGSVAS YEVTQAPSVS VSPGQTASIT CSGDKLGDKY ACWYQQKPGQ    60
SPVLVIYQDS KRPSGIPERF SGSNSGNTAT LTISGTQAMD EADYYCQAWD SSTAVFGGGT   120
KLTVLGQPKA APSVTLFPPS SEELQANKAT LVCLISDFYP GAVTVAWKAD SSPVKAGVET   180
TTPSKQSNNK YAASSYLSLT PEQWKSHRSY SCQVTHEGST VEKTVAPTEC S            231

SEQ ID NO: 139          moltype = DNA   length = 1401
FEATURE                 Location/Qualifiers
source                  1..1401
                        mol_type = other DNA
                        organism = Homo sapiens
SEQUENCE: 139
atggactgga cctggagcat ccttttcttg gtggcagcag caacaggtgc ccactcccag    60
gttcagctgg tgcagtctgg agctgaggtg aagaagcctg gggcctcagt gaaggtctcc   120
tgcaaggctt ctggttacac ctttaccagt tatggtctca gctgggtgcg acaggcccct   180
ggacaagggc ttgagtggat gggatggatc atcccttaca tggtaacac aaactctgca    240
cagaaactcc agggcagagt caccatgacc acagacacat ccacgagcac agcctacatg    300
gagctgagga gcctgagatc tgacgacacg gccgtgtatt tctgtgcgag agacagggac   360
tacggtgtca attatgatgc ttttgatatc tggggccaag gacaatggt caccgtctct    420
tcagcctcca ccaagggccc atcggtcttc ccctggcgc cctgctccag gagcacctcc    480
gagagcacag cggccctggg ctgcctggtc aaggactact ccccgaacc ggtgacggtg    540
tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc ccccaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtggtca gcgtcctcac cgttgtgcac caggactggc tgaacggcaa ggagtacaag   1020
tgcaaggtct ccaacaaagg cctcccagcc cccatcgaga aaaccatctc caaaaccaaa   1080
gggcagcccc gagaaccaca ggtgtacacc ctgcccccat cccgggagga tgatgaccag   1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca gagcaggtg gcagcagggg    1320
aacgtcttct catgctccgt gatgcatgag gctctgcaca accactacac gcagaagagc   1380
ctctccctgt ctccgggtaa a                                            1401

SEQ ID NO: 140          moltype = AA   length = 467
FEATURE                 Location/Qualifiers
source                  1..467
                        mol_type = protein
``` organism = Homo sapiens
SEQUENCE: 140
MDWTWSILFL VAAATGAHSQ VQLVQSGAEV KKPGASVKVS CKASGYTFTS YGLSWVRQAP      60
GQGLEWMGWI IPYNGNTNSA QKLQGRVTMT TDTSTSTAYM ELRSLRSDDT AVYFCARDRD     120
YGVNYDAFDI WGQGTMVTVS SASTKGPSVF PLAPCSRSTS ESTAALGCLV KDYFPEPVTV     180
SWNSGALTSG VHTFPAVLQS SGLYSLSSVV TVPSSNFGTQ TYTCNVDHKP SNTKVDKTVE     240
RKCCVECPPC PAPPVAGPSV FLFPPKPKDT LMISRTPEVT CVVVDVSHED PEVQFNWYVD     300
GVEVHNAKTK PREEQFNSTF RVVSVLTVVH QDWLNGKEYK CKVSNKGLPA PIEKTISKTK     360
GQPREPQVYT LPPSREEMTK NQVSLTCLVK GFYPSDIAVE WESNGQPENN YKTTPPMLDS     420
DGSFFLYSKL TVDKSRWQQG NVFSCSVMHE ALHNHYTQKS LSLSPGK                   467

SEQ ID NO: 141          moltype = DNA   length = 705
FEATURE                 Location/Qualifiers
source                  1..705
                        mol_type = other DNA
                        organism = Homo sapiens
SEQUENCE: 141
atggcctggg ctccactact tctcacccts ctcgctcact gcacaggttc ttgggccaat      60
tttatgctga ctcagcccca ctctgtgtcg gagtctccgg ggaagacggt ggccatctcc     120
tgcacccgca acagtggcag cattgccagc aactctgtgc agtggtacca gcagcgcccg     180
ggcagttccc ccaccactgt gatctttgag gataaccaaa gaccctctgg ggtccctgat     240
cggttctctg gctccatcga cagctcctcc aactctgcct ccctcaccat tctggtctg      300
aagactgagg acgaggctga ctactactgt cagtcttatg atagcaacaa ttgggtgttc     360
ggcggaggga ccaaactgac cgtcctaggt cagcccaagg ccaaccccac tgtcactctg     420
ttcccgccct cctctgagga gctccaagcc aacaaggcca cactagtgtg tctgatcagt     480
gacttctacc cgggagctgt gacagtggcc tggaaggcag atggcagccc cgtcaaggcg     540
ggagtggaga ccaccaaacc ctccaaacag agcaacaaca gtacgcggc cagcagctac     600
ctgagcctga cgcccgagca gtggaagtcc cacagaagct acagctgcca ggtcacgcat     660
gaagggagca ccgtggagaa gacagtggcc cctacagaat gttca                    705

SEQ ID NO: 142          moltype = AA   length = 235
FEATURE                 Location/Qualifiers
source                  1..235
                        mol_type = protein
                        organism = Homo sapiens
SEQUENCE: 142
MAWAPLLLTL LAHCTGSWAN FMLTQPHSVS ESPGKTVAIS CTRNSGSIAS NSVQWYQQRP      60
GSSPTTVIFE DNQRPSGVPD RFSGSIDSSS NSASLTISGL KTEDEADYYC QSYDSNNWVF     120
GGGTKLTVLG QPKANPTVTL FPPSSEELQA NKATLVCLIS DFYPGAVTVA WKADGSPVKA     180
GVETTKPSKQ SNNKYAASSY LSLTPEQWKS HRSYSCQVTH EGSTVEKTVA PTECS          235

SEQ ID NO: 143          moltype = DNA   length = 1410
FEATURE                 Location/Qualifiers
source                  1..1410
                        mol_type = other DNA
                        organism = Homo sapiens
SEQUENCE: 143
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtagc tatgtcatgc actgggtccg ccaggctcca     180
ggcaaggggc tggagtgggt ggctgttata tggtatgatg gaagtaataa atactatgca     240
gactccgtga agggccgatt caccatctcc agagacaatt ccaagaacac gctgtatctg     300
caaatgaaca gcctgagagc cgaggacacg gctgtgtatt actgtgcgag agaggggtat     360
gactacggta agactacta ctactacggt atggacgtct ggggccaagg gaccacggtc     420
accgtctcta gtgcctccac caagggccca tcggtcttcc cctggcgcc ctgctccagg     480
agcacctccg agagcacagc ggccctgggc tgcctggtca aggactactt ccccgaaccg     540
gtgacggtgt cgtggaactc aggcgctctg accagcggcg tgcacacctt cccagctgtc     600
ctacagtcct caggactcta ctccctcagc agcgtggtga ccgtgccctc cagcaacttc     660
ggcacccaga cctacacctg caacgtagat cacaagccca gcaacaccaa ggtggacaag     720
acagttgagc gcaaatgttg tgtcgagtgc ccaccgtgcc cagcaccacc tgtggcagga     780
ccgtcagtct tcctcttccc cccaaaaccc aaggacaccc tcatgatctc ccggacccct     840
gaggtcacgt gcgtggtggt ggacgtgagc cacgaagacc ccgaggtcca gttcaactgg     900
tacgtggacg gcgtggaggt gcataatgcc aagacaaagc cacgggagga gcagttcaac     960
agcacgttcc gtgtggtcag cgtcctcacc gttgtgcacc aggactggct gaacggcaag    1020
gagtacaagt gcaaggtctc caacaaaggc ctcccagccc ccatcgagaa aaccatctcc    1080
aaaaccaaag ggcagccccg agaaccacag gtgtacaccc tgcccccatc ccgggaggag    1140
atgaccaaga accaggtcag cctgacctgc ctggtcaaag gcttctaccc cagcgacatc    1200
gccgtggagt gggagagcaa tgggcagccg gagaacaact acaagaccac acctcccatg    1260
ctggactccg acggctcctt cttcctctac agcaagctca ccgtggacaa gagcaggtgg    1320
cagcaggga acgtcttctc atgctccgtg atgcatgagg ctctgcacaa ccactacacg    1380
cagaagagcc tctccctgtc tccgggtaaa                                     1410

SEQ ID NO: 144          moltype = AA   length = 470
FEATURE                 Location/Qualifiers
source                  1..470
                        mol_type = protein
                        organism = Homo sapiens
SEQUENCE: 144
MEFGLSWVFL VALLRGVQCQ VQLVESGGGV VQPGRSLRLS CAASGFTFSS YVMHWVRQAP      60

```
GKGLEWVAVI WYDGSNKYYA DSVKGRFTIS RDNSKNTLYL QMNSLRAEDT AVYYCAREGY  120
DYGEDYYYG MDVWGQGTTV TVSSASTKGP SVFPLAPCSR STSESTAALG CLVKDYFPEP  180
VTVSWNSGAL TSGVHTFPAV LQSSGLYSLS SVVTVPSSNF GTQTYTCNVD HKPSNTKVDK  240
TVERKCCVEC PPCPAPPVAG PSVFLFPPKP KDTLMISRTP EVTCVVVDVS HEDPEVQFNW  300
YVDGVEVHNA KTKPREEQFN STFRVVSVLT VVHQDWLNGK EYKCKVSNKG LPAPIEKTIS  360
KTKGQPREPQ VYTLPPSREE MTKNQVSLTC LVKGFYPSDI AVEWESNGQP ENNYKTTPPM  420
LDSDGSFFLY SKLTVDKSRW QQGNVFSCSV MHEALHNHYT QKSLSLSPGK            470

SEQ ID NO: 145        moltype = DNA   length = 708
FEATURE               Location/Qualifiers
source                1..708
                      mol_type = other DNA
                      organism = Homo sapiens
SEQUENCE: 145
atggacatga gggtccccgc tcagctcctg gggctcctgc tactctggct ccgaggtgcc  60
agatgtgaca tccagatgac ccagtctcca tcctccctct ccgcatccgt aggcgaccgc  120
gtaaccataa catgtagagc atctcaagat atttccaact atttgaattg gtaccaacaa  180
aaacccggca aagcacctaa actcctcatt tactatacat caagactcct ctccggcgtt  240
ccatcacgat tctcaggctc cggctccggc acagatttca cactcactat ttcctccctc  300
caaccagaag attttgcaac ctattactgt caacaaggcg atacactccc atacacattc  360
ggcggcggca caaaagttga aattaaacgt acggtggctg caccatctgt cttcatcttc  420
ccgccatctg atgagcagtt gaaatctgga actgcctctg ttgtgtgcct gctgaataac  480
ttctatccca gagaggccaa agtacagtgg aaggtggata cgcctcca atcgggtaac  540
tcccaggaga gtgtcacaga gcaggacagc aaggacagca cctacagcct cagcagcacc  600
ctgacgctga gcaaagcaga ctacgagaaa cacaaagtct acgcctgcga gtcacccat  660
cagggcctga gctcgcccgt cacaaagagc ttcaacaggg gagagtgt            708

SEQ ID NO: 146        moltype = AA   length = 236
FEATURE               Location/Qualifiers
source                1..236
                      mol_type = protein
                      organism = Homo sapiens
SEQUENCE: 146
MDMRVPAQLL GLLLLWLRGA RCDIQMTQSP SSLSASVGDR VTITCRASQD ISNYLNWYQQ  60
KPGKAPKLLI YYTSRLLSGV PSRFSGSGSG TDFTLTISSL QPEDFATYYC QQGDTLPYTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 147        moltype = DNA   length = 1404
FEATURE               Location/Qualifiers
source                1..1404
                      mol_type = other DNA
                      organism = Homo sapiens
SEQUENCE: 147
atggactgga cctggaggat cctcttcttg gtggcagcag ccacaggagc ccactccgag  60
gtgcagctgt gcagagcgg cgccgaggta aaaaaaccag gagcaagcgt taaagtttct  120
tgtaaagcaa gcgcgatatac atttacagat tacaacatgc attgggtagg acaagcgcca  180
ggacaaggat tggaatggat gggcgaaatt aaccctaata gtggaggagc aggctacaat  240
caaaaattca aagggagagt tacaatgaca acagacacaa gcacttcaac agcatatatg  300
gaactgcgat cacttagaag cgacgataca gctgtatact attgcgcacg acttgggtat  360
gatgatatat atgatgactg gtatttcgat gtttggggcc agggaacaac agttaccgtc  420
tctagtgcct ccaccaaggg cccatcggtc ttccccctgg cgccctgctc caggagcacc  480
tccgagagca gcgggccct gggctgcctg gtcaaggact acttccccga accggtgacg  540
gtgtcgtgga actcaggcgc tctgaccagc ggcgtgcaca ccttcccagc tgtcctacag  600
tcctcaggac tctactccct cagcagcgtg gtgaccgtgc cctccagcaa cttcggcacc  660
cagacctaca cctgcaacgt agatcacaag cccagcaaca ccaaggtgga caagacagtt  720
gagcgcaaat gttgtgtcga gtgcccaccg tgcccagcac cacctgtggc aggaccgtca  780
gtcttcctct ccccccaaaa acccaaggac accctcatga tctcccggac ccctgaggtc  840
acgtgcgtgg tggtggacgt gagccacgaa gaccccgagg tccagttcaa ctggtacgtg  900
gacggcgtgg aggtgcataa tgccaagaca aagccgcggg aggagcagtt caacagcacg  960
ttccgtgtgg tcagcgtcct caccgttgtg caccaggact ggctgaacgg caaggagtac  1020
aagtgcaagg tctccaacaa aggcctccca gcccccatcg agaaaaccat ctccaaaacc  1080
aaagggcagc cccgagaacc acaggtgtac accctgcccc catcccggga ggagatgacc  1140
aagaaccagg tcagcctgac ctgcctggtc aaaggcttct accccagcga catcgccgtg  1200
gagtgggaga gcaatgggca gccggagaac aactacaaga ccacacctcc catgctggac  1260
tccgacggct ccttcttcct ctacagcaag ctcaccgtgg acaagagcag gtggcagcag  1320
gggaacgtct tctcatgctc cgtgatgcat gaggctctgc acaaccacta cacgcagaag  1380
agcctctccc tgtctccggg taaa                                        1404

SEQ ID NO: 148        moltype = AA   length = 468
FEATURE               Location/Qualifiers
source                1..468
                      mol_type = protein
                      organism = Homo sapiens
SEQUENCE: 148
MDWTWRILFL VAAATGAHSE VQLVQSGAEV KKPGASVKVS CKASGYTFTD YNMHWVRQAP  60
GQGLEWMGEI NPNSGGAGYN QKFKGRVTMT TDTSTSTAYM ELRSLRSDDT AVYYCARLGY  120
DDIYDDWYFD VWGQGTTVTV SSASTKGPSV FPLAPCSRST SESTAALGCL VKDYFPEPVT  180
VSWNSGALTS GVHTFPAVLQ SSGLYSLSSV VTVPSSNFGT QTYTCNVDHK PSNTKVDKTV  240
```

```
ERKCCVECPP CPAPPVAGPS VFLFPPPKPKD TLMISRTPEV TCVVVDVSHE DPEVQFNWYV    300
DGVEVHNAKT KPREEQFNST FRVVSVLTVV HQDWLNGKEY KCKVSNKGLP APIEKTISKT    360
KGQPREPQVY TLPPSREEMT KNQVSLTCLV KGFYPSDIAV EWESNGQPEN NYKTTPPMLD    420
SDGSFFLYSK LTVDKSRWQQ GNVFSCSVMH EALHNHYTQK SLSLSPGK                 468

SEQ ID NO: 149            moltype = DNA   length = 720
FEATURE                   Location/Qualifiers
source                    1..720
                          mol_type = other DNA
                          organism = Homo sapiens
SEQUENCE: 149
atggtgttgc agacccaggt cttcatttct ctgttgctct ggatctctgg tgcctacggg    60
gacatcgtga tgacccagtc tccagactcc ctggctgtgt ctctgggcga gagggccacc    120
atcaactgca agtccagcca gagtgtttta gacagctccg acaataagaa ctacttagct    180
tggtaccagc agaaaccagg acagcctcct aagctgctca tttactgggc atctaaccgg    240
gaatccgggg tccctgaccg attcagtggc agcgggtctg ggacagattt cactctcacc    300
atcagcagcc tgcaggctga agatgtggca gtttattact gtcagcaata ttatagtgat    360
ccattcactt tcggccctgg gaccaaagtg gatatcaaac gtacggtggc tgcaccatct    420
gtcttcatct tcccgccatc tgatgagcag ttgaaatctg gaactgcctc tgttgtgtgc    480
ctgctgaata acttctatcc cagagaggcc aaagtacagt ggaaggtgga taacgccctc    540
caatcgggta actcccagga gagtgtcaca gagcaggaca gcaaggacag cacctacagc    600
ctcagcagca ccctgacgct gagcaaagca gactacgagaa aacacaaagt ctacgcctgc    660
gaagtcaccc atcagggcct gagctcgccc gtcacaaaga gcttcaacag gggagagtgt    720

SEQ ID NO: 150            moltype = AA   length = 240
FEATURE                   Location/Qualifiers
source                    1..240
                          mol_type = protein
                          organism = Homo sapiens
SEQUENCE: 150
MVLQTQVFIS LLLWISGAYG DIVMTQSPDS LAVSLGERAT INCKSSQSVL DSSDNKNYLA    60
WYQQKPGQPP KLLIYWASNR ESGVPDRFSG SGSGTDFTLT ISSLQAEDVA VYYCQQYYSD    120
PFTFGPGTKV DIKRTVAAPS VFIFPPSDEQ LKSGTASVVC LLNNFYPREA KVQWKVDNAL    180
QSGNSQESVT EQDSKDSTYS LSSTLTLSKA DYEKHKVYAC EVTHQGLSSP VTKSFNRGEC    240

SEQ ID NO: 151            moltype = DNA   length = 1395
FEATURE                   Location/Qualifiers
source                    1..1395
                          mol_type = other DNA
                          organism = Homo sapiens
SEQUENCE: 151
atggactgga cctggagcat cctttttcttg gtggcagcac aacaggtgc ccactcccag    60
gttcagctgg tgcagtctgg agctgaggtg aagaagcctg gggcctcagt gaaggtctcc    120
tgcaaggctt ctggttacac ctttaccagc tatggtatca gctgggtgcg acaggcccct    180
ggacaagggc ttgagtggat gggatggatc agcgcttaca atggtaacac aaaactatgca    240
cagaagctcc agggcagagt caccatgacc acagacacat ccacgagcac agcctacatg    300
gagctgagga gcctgagatc tgacgacacg gccgtgtatt actgtgcgag agagtcgtgg    360
ttcggggagg tattctttga ctactgggc cagggaaccc tggtcaccgt ctcctcagct    420
agcaccaagg gcccatcggt cttcccctg cgcccctgct ccaggagcac ctccgagagc    480
acagcggccc tgggctgcct ggtcaaggac tacttcccg aaccggtgac ggtgtcgtgg    540
aactcaggcg ctctgaccag cggcgtgcac accttccag ctgtcctaca gtcctcaggga    600
ctctactccc tcagcagcgt ggtgaccgtg ccctccagca acttcggcac ccagacctac    660
acctgcaacg tagatcacaa gcccagcaac accaaggtgg acaagacagt tgagcgcaaa    720
tgttgtgtcg agtgcccacc gtgcccagca ccacctgtgg caggaccgtc agtcttcctc    780
ttcccccaa aacccaagga caccctcatg atctcccgga cccctgaggt cacgtgcgtg    840
gtggtggacg tgagccacga agaccccgag gtccagttca actggtacgt ggacggcgtg    900
gaggtgcata atgccaagac aaagccacgg gaggagcagt tcaacagcac gttccgtgtg    960
gtcagcgtcc tcaccgttgt gcaccaggac tggctgaacg gcaaggagta caagtgcaag    1020
gtctccaaca aaggcctccc agcccccatc gagaaaacca tctccaaaac caaagggcag    1080
ccccgagaac acaggtgta caccctgccc ccatcccggg aggagatgac caagaaccag    1140
gtcagcctga cctgcctggt caaaggcttc taccccagcg acatcgccgt ggagtgggag    1200
agcaatgggc agccggagaa caactacaag accacacctc ccatgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaa                                                    1395

SEQ ID NO: 152            moltype = AA   length = 465
FEATURE                   Location/Qualifiers
source                    1..465
                          mol_type = protein
                          organism = Homo sapiens
SEQUENCE: 152
MDWTWSILFL VAAPTGAHSQ VQLVQSGAEV KKPGASVKVS CKASGYTFTS YGISWVRQAP    60
GQGLEWMGWI SAYNGNTNYA QKLQGRVTMT TDTSTSTAYM ELRSLRSDDT AVYYCARESW    120
FGEVFFDYWG QGTLVTVSSA STKGPSVFPL APCSRSTSES TAALGCLVKD YFPEPVTVSW    180
NSGALTSGVH TFPAVLQSSG LYSLSSVVTV PSSNFGTQTY TCNVDHKPSN TKVDKTVERK    240
CCVECPPCPA PPVAGPSVFL FPPKPKDTLM ISRTPEVTCV VVDVSHEDPE VQFNWYVDGV    300
EVHNAKTKPR EEQFNSTFRV VSVLTVVHQD WLNGKEYKCK VSNKGLPAPI EKTISKTKGQ    360
PREPQVYTLP PSREEMTKNQ VSLTCLVKGF YPSDIAVEWE SNGQPENNYK TTPPMLDSDG    420
```

```
SFFLYSKLTV DKSRWQQGNV FSCSVMHEAL HNHYTQKSLS LSPGK                          465

SEQ ID NO: 153          moltype = DNA   length = 708
FEATURE                 Location/Qualifiers
source                  1..708
                        mol_type = other DNA
                        organism = Homo sapiens
SEQUENCE: 153
atggacatga gggtgcccgc tcagctcctg gggctcctgc tgctgtggct gagaggtgcg        60
cgctgtgaca tccagatgac ccagtctcca tcttccgtgt ctgcatctgt aggagacaga       120
gtcaccatca cttgtcgggc gagtcagggg attagcagct ggttagcctg gtatcaacag       180
aaaccaggga aagcccctaa gctcctgatc tatggtgcat ccaatttgga aagtggggtc       240
ccatcaaggt tcagcggcag tggatctggg acagatttca ctctcaccat cagcagcctg       300
cagcctgaag attttgcaaa ttactattgt caacaggcta cagtttccc gtggacgttc        360
ggccaaggga ccaaggtgga aatcaaacgt acggtggctg caccatctgt cttcatcttc       420
ccgccatctg atgagcagtt gaaatctgga actgcctctg ttgtgtgcct gctgaataac       480
ttctatccca gagaggccaa agtacagtgg aaggtggata acgccctcca atcgggtaac       540
tcccaggaga gtgtcacaga gcaggacagc aaggacagca cctacagcct cagcagcacc       600
ctgacgctga gcaaagcaga ctacgagaaa cacaaagtct acgcctgcga agtcacccat       660
caggggcctga gctcgcccgt cacaaagagc ttcaacaggg gagagtgt                   708

SEQ ID NO: 154          moltype = AA   length = 236
FEATURE                 Location/Qualifiers
source                  1..236
                        mol_type = protein
                        organism = Homo sapiens
SEQUENCE: 154
MDMRVPAQLL GLLLLWLRGA RCDIQMTQSP SSVSASVGDR VTITCRASQG ISSWLAWYQQ        60
KPGKAPKLLI YGASNLESGV PSRFSGSGSG TDFTLTISSL QPEDFANYYC QQANSFPWTF       120
GQGTKVEIKR TVAAPSVFIF PPSDEQLKSG TASVVCLLNN FYPREAKVQW KVDNALQSGN       180
SQESVTEQDS KDSTYSLSST LTLSKADYEK HKVYACEVTH QGLSSPVTKS FNRGEC           236

SEQ ID NO: 155          moltype = DNA   length = 1398
FEATURE                 Location/Qualifiers
source                  1..1398
                        mol_type = other DNA
                        organism = Homo sapiens
SEQUENCE: 155
atggacatga gggtgcccgc tcagctcctg gggctcctgc tgctgtggct gagaggtgcg        60
cgctgtcagg tccagctggt acagtctggg gctgaggtga agaagcctgg ggcctcagtg       120
aaggtctcct gcaaggtttc cggatacacc ctcagtgatt tatccatcca ctgggtgcga       180
caggctcctg gaaaagggct tgagtggatg ggaggttttg atcctcaaga tggtgaaaca       240
atctacgcac agaagttcca gggcagagtc accatgaccg aagacacatc tacagacaca       300
gcctacatgg agctgagcag cctgaaatct gaggacacgg ccgtgtatta ctgcgcaacg       360
gggagcagc cgtcctggtt cgaccccctgg ggccagggaa ccctggtcac cgtctctagt       420
gcctccacca agggcccatc ggtcttcccc ctggcgccct gctccaggag cacctccgag       480
agcacagcgg ccctgggctg cctggtcaag gactacttcc ccgaaccggt gacggtgtcg       540
tggaactcag gcgctctgac cagcggcgtg cacaccttcc cagctgtcct acagtcctca       600
ggactctact ccctcagcag cgtggtgacc gtgccctcca gcaacttcgg cacccagacc       660
tacacctgca acgtagatca caagcccagc aacaccaagg tggacaagac agttgagcgc       720
aaatgttgtg tcgagtgccc accgtgccca gcaccacctg tggcaggacc gtcagtcttc       780
ctcttccccc caaaacccaa ggacaccctc atgatctccc ggaccccctga ggtcacgtgc       840
gtggtggtgg acgtgagcca cgaagacccc gaggtccagt tcaactggta cgtggacggc       900
gtggaggtgc ataatgccaa gacaaagcca cgggaggagc agttcaacag cacgttccgt       960
gtggtcagcg tcctcaccgt tgtgcaccag gactggctga acggcaagga gtacaagtgc      1020
aaggtctcca acaaaggcct cccagccccc atcgagaaaa ccatctccaa aaccaaaggg      1080
cagccccgag aaccacaggt gtacaccctg cccccatccc gggaggagat gaccaagaac      1140
caggtcagcc tgacctgcct ggtcaaaggc ttctacccca gcgacatcgc cgtggagtgg      1200
gagagcaatg ggcagccgga gaacaactac aagaccacac ctcccatgct ggactccgac      1260
ggctccttct tcctctacag caagctcacc gtggacaaga gcaggtggca gcagggggaac      1320
gtcttctcat gctccgtgat gcatgaggct ctgcacaacc actacacgca gaagagcctc      1380
tccctgtctc cgggtaaa                                                    1398

SEQ ID NO: 156          moltype = AA   length = 466
FEATURE                 Location/Qualifiers
source                  1..466
                        mol_type = protein
                        organism = Homo sapiens
SEQUENCE: 156
MDMRVPAQLL GLLLLWLRGA RCQVQLVQSG AEVKKPGASV KVSCKVSGYT LSDLSIHWVR        60
QAPGKGLEWM GGFDPQDGET IYAQKFQGRV TMTEDTSTDT AYMELSSLKS EDTAVYYCAT       120
GSSSSWFDPW GQGTLVTVSS ASTKGPSVFP LAPCSRSTSE STAALGCLVK DYFPEPVTVS       180
WNSGALTSGV HTFPAVLQSS GLYSLSSVVT VPSSNFGTQT YTCNVDHKPS NTKVDKTVER       240
KCCVECPPCP APPVAGPSVF LFPPKPKDTL MISRTPEVTC VVVDVSHEDP EVQFNWYVDG       300
VEVHNAKTKP REEQFNSTFR VVSVLTVVHQ DWLNGKEYKC KVSNKGLPAP IEKTISKTKG       360
QPREPQVYTL PPSREEMTKN QVSLTCLVKG FYPSDIAVEW ESNGQPENNY KTTPPMLDSD       420
GSFFLYSKLT VDKSRWQQGN VFSCSVMHEA LHNHYTQKSL SLSPGK                      466

SEQ ID NO: 157          moltype = DNA   length = 702
```

```
FEATURE                 Location/Qualifiers
source                  1..702
                        mol_type = other DNA
                        organism = Homo sapiens
SEQUENCE: 157
atggagaccc ctgcccagct gctgttcctg ctgctgctgt ggctgcccga cacaaccggc   60
gaaatcgtca tgacacagag ccctgccaca ctgtccgtga ccctggaga  gagggctacc  120
ctgagctgca gggcttccca gagcgtgagc agcaacctgg cctggtacca acagaagcct  180
ggccaggccc ctaggctgct gatctacggc gctgctcca  gggccaccgg tattcctgcc  240
agggtgtccg gctccggatc cggcaccgag tttaccctga ccatcagcag cctgcagagc  300
gaggacttcg ccgtgtacta ctgtcagcaa tacaacaact ggcccctgac ctttggcggc  360
ggcaccaagg tggagatcaa gaggacagtg gccgccccca gcgtgttcat cttccctccc  420
agcgacgagc agctgaagag cggcaccgcc agcgtggtgt gtctgctgaa caacttctac  480
cccagggagg ccaaggtgca gtggaaggtg gacaacgcc  tgcagtccgg caactcccag  540
gagtccgtga ccgagcagga ctccaaggac tccacctact ccctgtcctc cacctgacc   600
ctgtccaagg ccgactacga gaagcacaag gtgtacgcct gcgaggtgac ccaccagggc  660
ctgtcctccc ctgtgaccaa gagcttcaac aggggcgagt gc                      702

SEQ ID NO: 158          moltype = AA  length = 234
FEATURE                 Location/Qualifiers
source                  1..234
                        mol_type = protein
                        organism = Homo sapiens
SEQUENCE: 158
METPAQLLFL LLLWLPDTTG EIVMTQSPAT LSVSPGERAT LSCRASQSVS SNLAWYQQKP   60
GQAPRLLIYG AATRATGIPA RVSGSGSGTE FTLTISSLQS EDFAVYYCQQ YNNWPLTFGG  120
GTKVEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC         234

SEQ ID NO: 159          moltype = DNA  length = 1416
FEATURE                 Location/Qualifiers
source                  1..1416
                        mol_type = other DNA
                        organism = Homo sapiens
SEQUENCE: 159
atggatatgc gggtccctgc tcagctgctg ggactgctgc tgctgtggct gaggggcgcc   60
aggtgtcagg tgcagctggt cgaaagcgga ggaggagtgg tgcagcccgg aaggtccctg  120
aggctgtcct gcgccgctag cggcttcacc ttttccaact acggcatgca ctgggtgagg  180
caagccctg  gagagggcct ggaatgggtg gctgctatct ggttcgacgc cagcgacaag  240
tactatgccg acgctgtgaa gggccggttc accatcagca gggacaacag caagaacacc  300
ctctacctgc agatgaacag cctccggggc gaggacaccg ctgtctatta ctgtgccagg  360
gaccaggcca tcttcggagt ggtccccgat tactgggggcc agggaaccct ggtgaccgtg  420
tcctccgctt ccacaaaggg acctagcgtg ttccctctgg cccctagcag caagtccaca  480
agcggaggaa cagccgccct gggctgtctc gtgaaggact attttcccga gcccgtgacc  540
gtgtcctgga actccggagc cctgacctcc ggcgtgcata cattcccgc  tgtcctgcag  600
tccagcggcc tctactccct gtcctccgtg gtcaccgtgc ctagcagcag cctgggcacc  660
cagacataca tctgcaacgt caaccacaag ccttccaacc caaggtgga  caagaaggtg  720
gagcccaagt cctgtgacaa gacccacacc tgtcctccct gtcctgctcc tgagctgctg  780
ggaggcccct ccgtcttcct gttccctccc aagcccaagg acaccctgat gatctccagg  840
acccctgaag tgacatgtgt ggtggtggat gtgagccacg aagatcccga ggtgaagttc  900
aactggtacg tggacggcgt ggaggtgcac aacgctaaa  caaagccctg cgaggagcag  960
tacggatcca cctacaggtg cgtgtccgtg ctcaccgtgc tccatcagga ctggctgaac  1020
ggaaaagagt acaagtgcaa agtcagcaat aaggccctgc ccgcccctat cgagaaaacc  1080
atcagcaagg ccaaaggcca gcccagggag cctcaggtgt ataccctgcc tccctccagg  1140
gaggagatga caagaacca  ggtgagcctg acctgcctcg tgaagggctt ttatccctcc  1200
gacatcgctg tggagtggga gagcaatggc cagcctgaaa acaactacaa aaccacccc   1260
cctgtgctgg atagcgacgg cagcttcttc ctctactcca agctgaccgt cgataagtcc  1320
cggtggcagc agggcaacgt gtttagctgc agcgtgatgc acgaagccct gcataaccac  1380
tacacccaga gagcctgag  cctcagcccc ggaaag                             1416

SEQ ID NO: 160          moltype = AA  length = 472
FEATURE                 Location/Qualifiers
source                  1..472
                        mol_type = protein
                        organism = Homo sapiens
SEQUENCE: 160
MDMRVPAQLL GLLLLWLRGA RCQVQLVESG GGVVQPGRSL RLSCAASGFT FSNYGMHWVR   60
QAPGEGLEWV AAIWFDASDK YYADAVKGRF TISRDNSKNT LYLQMNSLRA EDTAVYYCAR  120
DQAIFGVVPD YWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSCDKTHT CPPCPAPELL GGPSVFLFPP KPKDTLMISR TPEVTCVVVD VSHEDPEVKF  300
NWYVDGVEVH NAKTKPCEEQ YGSTYRCVSV LTVLHQDWLN GKEYKCKVSN KALPAPIEKT  360
ISKAKGQPRE PQVYTLPPSR EEMTKNQVSL TCLVKGFYPS DIAVEWESNG QPENNYKTTP  420
PVLDSDGSFF LYSKLTVDKS RWQQGNVFSC SVMHEALHNH YTQKSLSLSP GK           472

SEQ ID NO: 161          moltype = DNA  length = 702
FEATURE                 Location/Qualifiers
source                  1..702
                        mol_type = other DNA
```

-continued

```
                           organism = Homo sapiens
SEQUENCE: 161
atggagaccc ctgcccagct gctgttcctg ctgctgctgt ggctgcccga cacaaccggc    60
gaaatcgtcc tgacacagag ccctgccaca ctgtccctga ccctggaga gagggctacc     120
ctgagctgca gggcttccca gagcgtgagc agcaacctgg cctggtacca acagaagcct    180
ggccaggccc ctaggctgct gatctacggc gctgctacca gggccaccgg tattcctgac    240
agggtgtccg gctccggatc cggcaccgag tttaccctga ccatcagccg cctggagccc    300
gaggacttcg ccgtgtacta ctgtcagcaa tacaacaact ggcccctgac ctttggcggc    360
ggcaccaagg tggagatcaa gaggacagtg gccgccccca gcgtgttcat cttccctcca    420
agcgacgagc agctgaagag cggcaccgcc agcgtggtgt gtctgctgaa caacttctac    480
cccagggagg ccaaggtgca gtggaaggtg gacaacgccc tgcagtccgg caactcccag    540
gagtccgtga ccgagcagga ctccaaggac tccacctact ccctgtcctc caccctgacc    600
ctgtccaagg ccgactacga gaagcacaag gtgtacgcct gcgaggtgac caccagggc     660
ctgtcctccc ctgtgaccaa gagcttcaac aggggcgagt gc                       702

SEQ ID NO: 162        moltype = AA   length = 234
FEATURE               Location/Qualifiers
source                1..234
                      mol_type = protein
                      organism = Homo sapiens
SEQUENCE: 162
METPAQLLFL LLLWLPDTTG EIVLTQSPAT LSLSPGERAT LSCRASQSVS SNLAWYQQKP     60
GQAPRLLIYG AATRATGIPD RVSGSGSGTE FTLTISRLEP EDFAVYYCQQ YNNWPLTFGG    120
GTKVEIKRTV AAPSVFIFPP SDEQLKSGTA SVVCLLNNFY PREAKVQWKV DNALQSGNSQ    180
ESVTEQDSKD STYSLSSTLT LSKADYEKHK VYACEVTHQG LSSPVTKSFN RGEC          234

SEQ ID NO: 163        moltype = DNA   length = 1416
FEATURE               Location/Qualifiers
source                1..1416
                      mol_type = other DNA
                      organism = Homo sapiens
SEQUENCE: 163
atggatatgc gggtccctgc tcagctgctg ggactgctgc tgctgtggct gaggggcgcc     60
aggtgtgagg tgcagctggt cgaaagcgga ggaggagtgg tgcagcccgg agggtccctg    120
aggctgtcct gcgccgctag cggcttcacc ttttccaact acggcatgca ctgggtgagg    180
caagccctg gagagggcct ggaatgggtg gctgctatct ggttcgacgc cagcgacaag     240
tactatgccg acgctgtgaa gggccggttc accatcagca gggacaacgc caagaacacc    300
ctctacctgc agatgaacag cctccgggcc gaggacaccg ctgtctatta ctgtgccagg    360
gaccaggcca tcttcggagt ggtccccgat tactggggcc agggaaccct ggtgaccgtg    420
tcctccgctt ccacaaaggg acctagcgtg ttccctctgg ccctagcag caagtccaca     480
agcggaggaa cagccgccct gggctgtctc gtgaaggact attttcccga gcccgtgacc    540
gtgtcctgga actccggagc cctgacctcc ggcgtgcata cattccccgc tgtcctgcag    600
tccagcggcc tctactccct gtcctccgtg gtcaccgtgc ctagcagcag cctgggcacc    660
cagacataca tctgcaacgt caaccacaag ccttccaaca ccaaggtgga caagaaggtg    720
gagcccaagt cctgtgacaa gacccacacc tgtcctcct gtcctgctcc tgagctgctg    780
ggaggcccct ccgtcttcct gttccctccc aagcccaagg acaccctgat gatctccagg    840
acccctgaag tgacatgtgt ggtggtggat gtgagccacg aagatcccga ggtgaagttc    900
aactggtacg tggacggcgt ggaggtgcac aacgctaaaa caaagcccg cgaggagcag     960
tacgatcca cctacaggtg cgtgtccgtg ctcaccgtgc tccatcagga ctggctgaac    1020
ggaaaagagt acaagtgcaa agtcagcaat aaggccctgc ccgcccctat cgagaaaacc   1080
atcagcaagg ccaaagggca gcccagggag cctcaggtgt atacccctgcc tccctccagg   1140
gaggagatga ccaagaacca ggtgagcctg acctgcctcg tgaagggctt ttatccctcc   1200
gacatcgctg tggagtggga gagcaatggc cagcctgaaa acaactacaa aaccacccccc   1260
cctgtgctgg atagcgacgg cagcttcttc ctctactcca agctgaccgt cgataagtcc   1320
cggtggcagc agggcaacgt gtttagctgc agcgtgatgc acgaagccct gcataaccac   1380
tacacccaga gagcctgag cctcagcccc ggaaag                               1416

SEQ ID NO: 164        moltype = AA   length = 472
FEATURE               Location/Qualifiers
source                1..472
                      mol_type = protein
                      organism = Homo sapiens
SEQUENCE: 164
MDMRVPAQLL GLLLLWLRGA RCEVQLVESG GGVVQPGGSL RLSCAASGFT FSNYGMHWVR     60
QAPGEGLEWV AAIWFDASDK YYADAVKGRF TISRDNAKNT LYLQMNSLRA EDTAVYYCAR    120
DQAIFGVVPD YWGQGTLVTV SSASTKGPSV FPLAPSSKST SGGTAALGCL VKDYFPEPVT    180
VSWNSGALTS GVHTFPAVLQ SSGLYSLSSV VTVPSSSLGT QTYICNVNHK PSNTKVDKKV    240
EPKSCDKTHT CPPCPAPELL GGPSVFLFPP KPKDTLMISR TPEVTCVVVD VSHEDPEVKF    300
NWYVDGVEVH NAKTKPCEEQ YGSTYRCVSV LTVLHQDWLN GKEYKCKVSN KALPAPIEKT    360
ISKAKGQPRE PQVYTLPPSR EEMTKNQVSL TCLVKGFYPS DIAVEWESNG QPENNYKTTP    420
PVLDSDGSFF LYSKLTVDKS RWQQGNVFSC SVMHEALHNH YTQKSLSLSP GK            472

SEQ ID NO: 165        moltype = DNA   length = 717
FEATURE               Location/Qualifiers
source                1..717
                      mol_type = other DNA
                      organism = Homo sapiens
SEQUENCE: 165
atgaggctcc ctgctcagct cctgggggctg ctaatgctct gggtccctgg atccagtggg     60
```

```
gatattgtga tgacccagac tccactctcc tcacctgtca cccttggaca gccggcctcc   120
atctcctgca ggtctagtca aagcctcgta cacagtgatg gaaacaccta cttgaattgg   180
cttcagcaga ggccaggcca gcctccaaga ctcctaattt ataagatttc taaccggttc   240
tctggggtcc cagacagatt cactggcagt ggggcaggga cagatttcac actgaaaatc   300
agcagggtgg aagctgagga tgtcgggggtt tatacctgca tgcaagttac acaatttcct   360
ctcaccttcg gccaagggac acgactggag attaaacgaa ctgtggctgc accatctgtc   420
ttcatcttcc cgccatctga tgagcagttg aaatctggaa ctgcctctgt tgtgtgcctg   480
ctgaataact ctatcccag agaggccaaa gtacagtgga aggtggataa cgccctccaa   540
tcgggtaact cccaggagag tgtcacagag caggacagca aggacagcac ctacagcctc   600
agcagcaccc tgacgctgag caaagcagac tacgagaaac acaaagtcta cgcctgcgaa   660
gtcacccatc agggcctgag ctcgcccgtc acaaagagct tcaacagggg agagtgt     717
```

```
SEQ ID NO: 166          moltype = AA   length = 239
FEATURE                 Location/Qualifiers
source                  1..239
                        mol_type = protein
                        organism = Homo sapiens
SEQUENCE: 166
MRLPAQLLGL LMLWVPGSSG DIVMTQTPLS SPVTLGQPAS ISCRSSQSLV HSDGNTYLNW   60
LQQRPGQPPR LLIYKISNRF SGVPDRFTGS GAGTDFTLKI SRVEAEDVGV YTCMQVTQFP   120
LTFGQGTRLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239
```

```
SEQ ID NO: 167          moltype = DNA   length = 1410
FEATURE                 Location/Qualifiers
source                  1..1410
                        mol_type = other DNA
                        organism = Homo sapiens
SEQUENCE: 167
atggacacac tttgctacac actcctgctg ctgaccaccc cttcctgggt cttgtcccag   60
gtcaccttga aggagtctgg tcctgtgctg ctgaaaccca cagagaccct cacgctgacc   120
tgcaccgtct ctgggttctc actcagcaat gctagaatgg gtgtgagctg gatccgtcag   180
cccccaggga aggccctgga gtggcttgca cattttttt cgaatgacga aaaatcctac   240
atcacatctc tgaagagcag gctcaccatc tccaaggaca cctccaaaag ccaggtggtc   300
cttaccatga ccaacatgga ccctgtggac acagccacat attactgtgc acggataccc   360
ctacgatccc cgggtgcttt tgatatctgg ggccaaggga caatggtcac cgtctcttca   420
gcctccacca agggcccatc ggtcttcccc ctggcaccct cctccaagag cacctctggg   480
ggcacagcgg ccctgggctg cctggtcaag gactacttcc ccgaaccggt gacggtgtcg   540
tggaactcag gcgccctgac cagcggcgtg cacaccttcc cggctgtcct acagtcctca   600
ggactctact ccctcagcag cgtggtgacc gtgccctcca gcagcttggg cacccagacc   660
tacatctgca acgtgaatca caagcccagc aacaccaagg tggacaagag agttgagccc   720
aaatcttgtg acaaaactca cacatgccca ccgtgcccag cacctgaact cctggggggga   780
ccgtcagtct tcctcttccc cccaaaaccc aaggacaccc tcatgatctc cgggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggaggag   1140
atgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctat agcaagctca ccgtggacaa gagcaggtgg   1320
cagcagggga acgtcttctc atgctccgtg atgcatgagg ctctgcacaa ccactacacg   1380
cagaagagcc tctcactgtc tccgggtaaa                                    1410
```

```
SEQ ID NO: 168          moltype = AA   length = 470
FEATURE                 Location/Qualifiers
source                  1..470
                        mol_type = protein
                        organism = Homo sapiens
SEQUENCE: 168
MDTLCYTLLL LTTPSWVLSQ VTLKESGPVL LKPTETLTLT CTVSGFSLSN ARMGVSWIRQ   60
PPGKALEWLA HIFSNDEKSY ITSLKSRLTI SKDTSKSQVV LTMTNMDPVD TATYYCARIP   120
LRSPGAFDIW GQGTMVTVSS ASTKGPSVFP LAPSSKSTSG GTAALGCLVK DYFPEPVTVS   180
WNSGALTSGV HTFPAVLQSS GLYSLSSVVT VPSSSLGTQT YICNVNHKPS NTKVDKRVEP   240
KSCDKTHTCP PCPAPELLGG PSVFLFPPKP KDTLMISRTP EVTCVVVDVS HEDPEVKFNW   300
YVDGVEVHNA KTKPREEQYN STYRVVSVLT VLHQDWLNGK EYKCKVSNKA LPAPIEKTIS   360
KAKGQPREPQ VYTLPPSREE MTKNQVSLTC LVKGFYPSDI AVEWESNGQP ENNYKTTPPV   420
LDSDGSFFLY SKLTVDKSRW QQGNVFSCSV MHEALHNHYT QKSLSLSPGK            470
```

```
SEQ ID NO: 169          moltype = DNA   length = 705
FEATURE                 Location/Qualifiers
source                  1..705
                        mol_type = other DNA
                        organism = Homo sapiens
SEQUENCE: 169
atggaaaccc cagcgcagct tctcttcctc ctgctactct ggctcccaga taccaccgga   60
gaaattgtgt tgacgcagtc tccaggcacc ctgtctttgt ctccagggga aagagccacc   120
ctctcctgta gggccagtca gagtgttcgg ggcaggtact agcctggta ccagcagaaa   180
cctggccagg ctcccaggct cctcatctat ggtgcatcca gcagggccac tggcatccca   240
```

```
gacaggttca gtggcagtgg gtctgggaca gacttcactc tcaccatcag cagactggag   300
cctgaagatt ttgcagtgtt ttactgtcag cagtatggta gttcacctcg gacgttcggc   360
caagggacca aggtggaaat caaacgaact gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgt               705

SEQ ID NO: 170           moltype = AA  length = 235
FEATURE                  Location/Qualifiers
source                   1..235
                         mol_type = protein
                         organism = Homo sapiens
SEQUENCE: 170
METPAQLLFL LLLWLPDTTG EIVLTQSPGT LSLSPGERAT LSCRASQSVR GRYLAWYQQK   60
PGQAPRLLIY GASSRATGIP DRFSGSGSGT DFTLTISRLE PEDFAVFYCQ QYGSSPRTFG   120
QGTKVEIKRT VAAPSVFIFP PSDEQLKSGT ASVVCLLNNF YPREAKVQWK VDNALQSGNS   180
QESVTEQDSK DSTYSLSSTL TLSKADYEKH KVYACEVTHQ GLSSPVTKSF NRGEC        235

SEQ ID NO: 171           moltype = DNA  length = 1401
FEATURE                  Location/Qualifiers
source                   1..1401
                         mol_type = other DNA
                         organism = Homo sapiens
SEQUENCE: 171
atggagtttg ggctgagctg gctttttctt gtggctattt taaaaggtgt ccagtgtgag   60
gtgcagctgt tggagtctgg gggaggcttg gtacagcctg ggggtccct gagactctcc   120
tgtgcagcct ctggattcac ctttagcagc tatgccatga gctgggtccg ccaggctcca   180
gggaaggggc tggagtgggt ctcaggtatt actgggagtg gtggtagtac atactacgca   240
gactccgtga agggccggtt caccatctcc agagacaatt ccaagaacac gctgtatctg   300
caaatgaaca gcctgagagc cgaggacacg gccgtatatt actgtgcgaa agatccaggg   360
actacggtga ttatgagttg gttcgacccc tggggccagg gaaccctggt caccgtctcc   420
tcagcctcca ccaagggccc atcggtcttc ccctggcgc cctgctccag gagcacctcc   480
gagagcacag cggcccctggg ctgcctggtc aaggactact tccccgaacc ggtgacggtg   540
tcgtggaact caggcgctct gaccagcggc gtgcacacct tcccagctgt cctacagtcc   600
tcaggactct actccctcag cagcgtggtg accgtgccct ccagcaactt cggcacccag   660
acctacacct gcaacgtaga tcacaagccc agcaacacca aggtggacaa gacagttgag   720
cgcaaatgtt gtgtcgagtg cccaccgtgc ccagcaccac ctgtggcagg accgtcagtc   780
ttcctcttcc ccccaaaacc caaggacacc ctcatgatct cccggacccc tgaggtcacg   840
tgcgtggtgg tggacgtgag ccacgaagac cccgaggtcc agttcaactg gtacgtggac   900
ggcgtggagg tgcataatgc caagacaaag ccacgggagg agcagttcaa cagcacgttc   960
cgtgtgtca gcgtcctcac cgttgtgcac caggactggc tgaacggcaa ggagtacaag   1020
tgcaaggtct ccaacaaagg cctcccagcc cccatcgaga aaaccatctc caaaaccaaa   1080
gggcagcccc gagaaccaca ggtgtacacc ctgcccccat cccgggagga gatgaccaag   1140
aaccaggtca gcctgacctg cctggtcaaa ggcttctacc ccagcgacat cgccgtggag   1200
tgggagagca atgggcagcc ggagaacaac tacaagacca cacctcccat gctggactcc   1260
gacggctcct tcttcctcta cagcaagctc accgtggaca agagcaggtg gcagcagggg   1320
aacgtcttct catgctccgt gatgcatgag gctctgcaca accactacac gcagaagagc   1380
ctctcctgt ctccgggtaa a                                           1401

SEQ ID NO: 172           moltype = AA  length = 467
FEATURE                  Location/Qualifiers
source                   1..467
                         mol_type = protein
                         organism = Homo sapiens
SEQUENCE: 172
MEFGLSWLFL VAILKGVQCE VQLLESGGGL VQPGGSLRLS CAASGFTFSS YAMSWVRQAP   60
GKGLEWVSGI TGSGGSTYYA DSVKGRFTIS RDNSKNTLYL QMNSLRAEDT AVYYCAKDPG   120
TTVIMSWFDP WGQGTLVTVS SASTKGPSVF PLAPCSRSTS ESTAALGCLV KDYFPEPVTV   180
SWNSGALTSG VHTFPAVLQS SGLYSLSSVV TVPSSNFGTQ TYTCNVDHKP SNTKVDKTVE   240
RKCCVECPPC PAPPVAGPSV FLFPPKPKDT LMISRTPEVT CVVVDVSHED PEVQFNWYVD   300
GVEVHNAKTK PREEQFNSTF RVVSVLTVVH QDWLNGKEYK CKVSNKGLPA PIEKTISKTK   360
GQPREPQVYT LPPSREEMTK NQVSLTCLVK GFYPSDIAVE WESNGQPENN YKTTPPMLDS   420
DGSFFLYSKL TVDKSRWQQG NVFSCSVMHE ALHNHYTQKS LSLSPGK             467

SEQ ID NO: 173           moltype = DNA  length = 714
FEATURE                  Location/Qualifiers
source                   1..714
                         mol_type = other DNA
                         organism = Homo sapiens
SEQUENCE: 173
atggtgttgc agacccaggt cttcatttct ctgttgctct ggatctctgg tgcctacggg   60
gacatcgtga tgacccagtc tccagactcc ctggctgtgt ctctgggcga gagggccacc   120
atcaactgca agccagtga aagtgttgat atttatggca atagtttat gcactggtac   180
cagcagaaac aggacagcc tcctaagctg ctcatttacc ttgcatccaa cctagaatct   240
ggggtccctg accgattcag tggcagcggg tctgggacag atttcactct caccatcagc   300
agcctgcagg ctgaagatgt ggcagtttat tactgtcagc aaaataatga ggatccgtac   360
acgttcggag gtgggaccaa ggtggaaata aaacgtacgg tggctgcacc atctgtcttc   420
```

```
atcttcccgc catctgatga gcagttgaaa tctggaactg cctctgttgt gtgcctgctg   480
aataacttct atcccagaga ggccaaagta cagtggaagg tggataacgc cctccaatcg   540
ggtaactccc aggagagtgt cacagagcag gacagcaagg acagcaccta cagcctcagc   600
agcaccctga cgctgagcaa agcagactac gagaaacaca aagtctacgc ctgcgaagtc   660
acccatcagg gcctgagctc gcccgtcaca aagagcttca caggggagag gtgt           714

SEQ ID NO: 174             moltype = AA   length = 238
FEATURE                    Location/Qualifiers
source                     1..238
                           mol_type = protein
                           organism = Homo sapiens
SEQUENCE: 174
MVLQTQVFIS LLLWISGAYG DIVMTQSPDS LAVSLGERAT INCRASESVD IYGNSFMHWY   60
QQKPGQPPKL LIYLASNLES GVPDRFSGSG SGTDFTLTIS SLQAEDVAVY YCQQNNEDPY  120
TFGGGTKVEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 175             moltype = DNA   length = 1398
FEATURE                    Location/Qualifiers
source                     1..1398
                           mol_type = other DNA
                           organism = Homo sapiens
SEQUENCE: 175
atggactgga cctggagggt cttctgcttg ctggcagtgg ccccaggtgc ccactcccag   60
gtgcagctgt tgcagtctgg ggctgaggtg aagaagcctg gggcctcagt gaaggtctcc  120
tgcaaggctt ctggatacac cttcaccagt tacaatatgc actgggtgcg ccaggcccct  180
ggacaagggc ttgagtggat gggagttatt tattcaggaa atggtgatac ttcctacaat  240
cagaagttca aaggcagggt caccattacc gctgacaaat ccaccagcac agcctacatg  300
gagctgagca gcctgagatc tgaggacacg gccgtgtatt actgtgcgag agagagggat  360
actcgttttg gtaactgggg ccaagggact ctggtcactg tctctagtgc ctccaccaag  420
ggcccatcgg tcttccccct ggcaccctcc tccaagagca cctctggggg cacagcggcc  480
ctgggctgcc tggtcaagga ctacttcccc gaaccggtga cggtgtcgtg gaactcaggc  540
gccctgacca gcggcgtgca caccttcccg gctgtcctac agtcctcagg actctactcc  600
ctcagcagcg tggtgaccgt gccctccagc agcttgggca cccagaccta catctgcaac  660
gtgaatcaca agcccagcaa caccaaggtg gacaagaaag ttgagcccaa atcttgtgac  720
aaaactcaca catgcccacc gtgcccagca cctgaactcc tggggggacc gtcagtcttc  780
ctcttccccc caaaacccaa ggacaccctc atgatctccc ggacccctga ggtcacatgc  840
gtggtggtgg acgtgagcca cgaagaccct gaggtcaagt tcaactggta cgtggacggc  900
gtggaggtgc ataatgccaa gacaaagccg cgggaggagc agtaccagag cacgtaccgt  960
gtggtcagcg tcctcaccgt cctgcaccag gactggctga atggcaagga gtacaagtgc  1020
aaggtctcca acaaagccct cccagccccc atcgagaaaa ccatctccaa agccaaaggg  1080
cagccccgag aaccacaggt gtacaccctg cccccatccc gggatgagct gaccaagaac  1140
caggtcagcc tgacctgcct ggtcaaaggc ttctatccca gcgacatcgc cgtggagtgg  1200
gagagcaatg ggcagccgga gaacaactac aagaccacgc ctcccgtgct ggactccgac  1260
ggctccttct tcctctatag caagctcacc gtggacaaga gcaggtggca gcaggggaac  1320
gtcttctcat gctccgtgat gcatgaggct ctgcacaacc actacacgca gaagagcctc  1380
tccctgtctc cgggtaaa                                                 1398

SEQ ID NO: 176             moltype = AA   length = 466
FEATURE                    Location/Qualifiers
source                     1..466
                           mol_type = protein
                           organism = Homo sapiens
SEQUENCE: 176
MDWTWRVFCL LAVAPGAHSQ VQLVQSGAEV KKPGASVKVS CKASGYTFTS YNMHWVRQAP   60
GQGLEWMGVI YSGNGDTSYN QKFKGRVTIT ADKSTSTAYM ELSSLRSEDT AVYYCARERD  120
TRFGNWQQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSCD  240
KTHTCPPCPA PELLGGPSVF LFPPKPKDTL MISRTPEVTC VVVDVSHEDP EVKFNWYVDG  300
VEVHNAKTKP REEQYQSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK                  466

SEQ ID NO: 177             moltype = DNA   length = 705
FEATURE                    Location/Qualifiers
source                     1..705
                           mol_type = other DNA
                           organism = Homo sapiens
SEQUENCE: 177
atggcctggg ctctgctgct cctcactctc ctcactcagg acacagggtc ctgggcccag   60
tctgtgctga ctcagtcacc ctcagcgtct gggacccccg ggcagagagt caccatctct  120
tgttctggaa gcagctccaa catcggcagt aattatgtat actggtacca gcagctccca  180
ggagcggccc caaaactcct catccttagg aataatcagc ggcctcagg ggtccctgac   240
cgattctctg gctccaagtc tggcacctca gcctccctgg ccatcagtgg gctccggtcc  300
gaggatgagg ctgactatta ttgtgcagca tgggatgaca gcctgagtgg ttgggtgttc  360
ggcggaggga ccaagctgac cgtcctaggt cagcccaagg ccaacccccac tgtcactctg  420
ttcccgccct cctctgagga gctccaagcc aacaaggcca cactagtgtg tctgatcagt  480
gacttctacc cgggagctgt gacagtggcc tggaaggcag atggcagccc cgtcaaggcg  540
ggagtggaga ccaccaaacc ctccaaacag agcaacaaca gtacgcggc cagcagctac  600
```

```
ctgagcctga cgcccgagca gtggaagtcc cacagaagct acagctgcca ggtcacgcat    660
gaagggagca ccgtggagaa gacagtggcc cctacagaat gttca                    705

SEQ ID NO: 178        moltype = AA  length = 235
FEATURE               Location/Qualifiers
source                1..235
                      mol_type = protein
                      organism = Homo sapiens
SEQUENCE: 178
MAWALLLLTL LTQDTGSWAQ SVLTQSPSAS GTPGQRVTIS CSGSSSNIGS NYVYWYQQLP    60
GAAPKLLILR NNQRPSGVPD RFSGSKSGTS ASLTISGLRS EDEADYYCAA WDDSLSGWVF    120
GGGTKLTVLG QPKANPTVTL FPPSSEELQA NKATLVCLIS DFYPGAVTVA WKADGSPVKA    180
GVETTKPSKQ SNNKYAASSY LSLTPEQWKS HRSYSCQVTH EGSTVEKTVA PTECS         235

SEQ ID NO: 179        moltype = DNA  length = 1437
FEATURE               Location/Qualifiers
source                1..1437
                      mol_type = other DNA
                      organism = Homo sapiens
SEQUENCE: 179
atggacatga gggtgcccgc tcagctcctg gggctcctgc tgctgtggct gagaggtgcg    60
cgctgtgagg tgcagctggt ggagtctggg ggaggcttgg taaagcctgg ggggtccctt    120
agactctcct gtgcagcctc tggattcact ttcagtaacg cctggatgag ctgggtccgc    180
caggctccag ggaaggggct ggagtgggtt ggccgtatta aaagcaaaac tgatggtggg    240
acaacagact acactgcacc cgtgaaaggc agattcacca tctcaagaga tgattcaaaa    300
aacacgctgt atctgcaaat gaatagcctg aaagccgagg acacagccgt gtattactgt    360
accacagatc ggaccgggta tagcatcagc tggtctagtt actactacta ctacggtatg    420
gacgtctggg gccaagggac cacggtcacc gtctctagtg cctccaccaa gggcccatcg    480
gtcttccccc tggcgccctg ctccaggagc acctccgaga gcacagcggc cctgggctgc    540
ctggtcaagg actacttccc cgaaccggtg acggtgtcgt ggaactcagg cgctctgacc    600
agcggcgtgc acaccttccc agctgtccta cagtcctcag gactctactc cctcagcagc    660
gtggtgaccg tgccctccag caacttcggc acccagacct acacctgcaa cgtagatcac    720
aagcccagca acaccaaggt ggacaagaca gttgagcgca aatgttgtgt cgagtgccca    780
ccgtgcccag caccacctgt ggcaggaccg tcagtcttcc tcttcccccc aaaacccaag    840
gacaccctca tgatctcccg gacccctgag gtcacgtgcg tggtggtgga cgtgagccac    900
gaagaccccg aggtccagtt caactggtac gtggacggcg tggaggtgca taatgccaag    960
acaaagccac gggaggagca gttcaacagc acgttccgtg tggtcagcgt cctcaccgtt    1020
gtgcaccagg actggctgaa cggcaaggag tacaagtgca aggtctccaa caaaggcctc    1080
ccagcccccat cgagaaaaac catctccaaa accaaaggac agccccgaga accacaggtg    1140
tacaccctgc ccccatcccg ggaggagatg accaagaacc aggtcagcct gacctgcctg    1200
gtcaaaggct tctaccccag cgacatcgcc gtggagtggg agagcaatgg gcagccggag    1260
aacaactaca agaccacacc tcccatgctg gactccgacg gctccttctt cctctacagc    1320
aagctcaccg tggacaagag caggtggcag caggggaacg tcttctcatg ctccgtgatg    1380
catgaggctc tgcacaacca ctacacgcag aagagcctct ccctgtctcc gggtaaa      1437

SEQ ID NO: 180        moltype = AA  length = 479
FEATURE               Location/Qualifiers
source                1..479
                      mol_type = protein
                      organism = Homo sapiens
SEQUENCE: 180
MDMRVPAQLL GLLLLWLRGA RCEVQLVESG GGLVKPGGSL RLSCAASGFT FSNAWMSWVR    60
QAPGKGLEWV GRIKSKTDGG TTDYTAPVKG RFTISRDDSK NTLYLQMNSL KAEDTAVYYC    120
TTDRTGYSIS WSSYYYYGM DVWGQGTTVT VSSASTKGPS VFPLAPCSRS TSESTAALGC    180
LVKDYFPEPV TVSWNSGALT SGVHTFPAVL QSSGLYSLSS VVTVPSSNFG TQTYTCNVDH    240
KPSNTKVDKT VERKCCVECP PCPAPPVAGP SVFLFPPKPK DTLMISRTPE VTCVVVDVSH    300
EDPEVQFNWY VDGVEVHNAK TKPREEQFNS TFRVVSVLTV VHQDWLNGKE YKCKVSNKGL    360
PAPIEKTISK TKGQPREPQV YTLPPSREEM TKNQVSLTCL VKGFYPSDIA VEWESNGQPE    420
NNYKTTPPML DSDGSFFLYS KLTVDKSRWQ QGNVFSCSVM HEALHNHYTQ KSLSLSPGK    479

SEQ ID NO: 181        moltype = AA  length = 23
FEATURE               Location/Qualifiers
source                1..23
                      mol_type = protein
                      organism = Homo sapiens
SEQUENCE: 181
EIVMTQSPAT LSVSPGERAT LSC                                            23

SEQ ID NO: 182        moltype = AA  length = 15
FEATURE               Location/Qualifiers
source                1..15
                      mol_type = protein
                      organism = Homo sapiens
SEQUENCE: 182
WYRQKPGQAP RLLIY                                                     15

SEQ ID NO: 183        moltype = AA  length = 32
FEATURE               Location/Qualifiers
source                1..32
```

-continued

```
                              mol_type = protein
                              organism = Homo sapiens
SEQUENCE: 183
GIPARFSGSG SGTEFTLTIS SLQSEDFAVY YC                              32

SEQ ID NO: 184            moltype = AA  length = 10
FEATURE                   Location/Qualifiers
source                    1..10
                          mol_type = protein
                          organism = Homo sapiens
SEQUENCE: 184
FGQGTRLEIK                                                       10

SEQ ID NO: 185            moltype = AA  length = 23
FEATURE                   Location/Qualifiers
source                    1..23
                          mol_type = protein
                          organism = Homo sapiens
SEQUENCE: 185
EIVLTQSPDF QSVTPKEKVT ITC                                        23

SEQ ID NO: 186            moltype = AA  length = 15
FEATURE                   Location/Qualifiers
source                    1..15
                          mol_type = protein
                          organism = Homo sapiens
SEQUENCE: 186
WYQQKPDQSP KLLIK                                                 15

SEQ ID NO: 187            moltype = AA  length = 32
FEATURE                   Location/Qualifiers
source                    1..32
                          mol_type = protein
                          organism = Homo sapiens
SEQUENCE: 187
GVPSRFSGSG SGTDFTLTIN SLEAEDAAAY YC                              32

SEQ ID NO: 188            moltype = AA  length = 10
FEATURE                   Location/Qualifiers
source                    1..10
                          mol_type = protein
                          organism = Homo sapiens
SEQUENCE: 188
FGGGTKVEIK                                                       10

SEQ ID NO: 189            moltype = AA  length = 23
FEATURE                   Location/Qualifiers
source                    1..23
                          mol_type = protein
                          organism = Homo sapiens
SEQUENCE: 189
DIVMTQTPLS SPVTLGQPAS ISC                                        23

SEQ ID NO: 190            moltype = AA  length = 15
FEATURE                   Location/Qualifiers
source                    1..15
                          mol_type = protein
                          organism = Homo sapiens
SEQUENCE: 190
WLQQRPGQPP RLLIY                                                 15

SEQ ID NO: 191            moltype = AA  length = 32
FEATURE                   Location/Qualifiers
source                    1..32
                          mol_type = protein
                          organism = Homo sapiens
SEQUENCE: 191
GVPDRFTGSG AGTDFTLKIS RVEAEDVGVY TC                              32

SEQ ID NO: 192            moltype = AA  length = 10
FEATURE                   Location/Qualifiers
source                    1..10
                          mol_type = protein
                          organism = Homo sapiens
SEQUENCE: 192
FGQGTRLEIK                                                       10

SEQ ID NO: 193            moltype = AA  length = 23
FEATURE                   Location/Qualifiers
```

-continued

```
source                  1..23
                        mol_type = protein
                        organism = Homo sapiens
SEQUENCE: 193
EIVLTQSPGT LSLSPGERAT LSC                                         23

SEQ ID NO: 194          moltype = AA  length = 15
FEATURE                 Location/Qualifiers
source                  1..15
                        mol_type = protein
                        organism = Homo sapiens
SEQUENCE: 194
WYQQKPGQAP RLLIY                                                  15

SEQ ID NO: 195          moltype = AA  length = 32
FEATURE                 Location/Qualifiers
source                  1..32
                        mol_type = protein
                        organism = Homo sapiens
SEQUENCE: 195
GIPDRFSGSG SGTDFTLTIS RLEPEDFAVF YC                               32

SEQ ID NO: 196          moltype = AA  length = 10
FEATURE                 Location/Qualifiers
source                  1..10
                        mol_type = protein
                        organism = Homo sapiens
SEQUENCE: 196
FGQGTKVEIK                                                        10

SEQ ID NO: 197          moltype = AA  length = 23
FEATURE                 Location/Qualifiers
source                  1..23
                        mol_type = protein
                        organism = Homo sapiens
SEQUENCE: 197
EIVLTQSPGT LSLSPGDRAT LSC                                         23

SEQ ID NO: 198          moltype = AA  length = 32
FEATURE                 Location/Qualifiers
source                  1..32
                        mol_type = protein
                        organism = Homo sapiens
SEQUENCE: 198
GIPDRFSGSG SGTDFTLTIS RLEPEDFAVY YC                               32

SEQ ID NO: 199          moltype = AA  length = 15
FEATURE                 Location/Qualifiers
source                  1..15
                        mol_type = protein
                        organism = Homo sapiens
SEQUENCE: 199
WHQQKPGQAP RLLIY                                                  15

SEQ ID NO: 200          moltype = AA  length = 15
FEATURE                 Location/Qualifiers
source                  1..15
                        mol_type = protein
                        organism = Homo sapiens
SEQUENCE: 200
WHQQKPGQAP RLLIY                                                  15

SEQ ID NO: 201          moltype = AA  length = 32
FEATURE                 Location/Qualifiers
source                  1..32
                        mol_type = protein
                        organism = Homo sapiens
SEQUENCE: 201
GIPDRFSGSG SGTDFTLTVS RLEPEDFAVY YC                               32

SEQ ID NO: 202          moltype = AA  length = 15
FEATURE                 Location/Qualifiers
source                  1..15
                        mol_type = protein
                        organism = Homo sapiens
SEQUENCE: 202
WFQQKPGQAP RLLIY                                                  15

SEQ ID NO: 203          moltype = AA  length = 32
```

-continued

```
FEATURE                Location/Qualifiers
source                 1..32
                       mol_type = protein
                       organism = Homo sapiens
SEQUENCE: 203
GIPDRFSGSG SGTDFTFTIS RLEPEDFAVY YC                              32

SEQ ID NO: 204         moltype = AA  length = 10
FEATURE                Location/Qualifiers
source                 1..10
                       mol_type = protein
                       organism = Homo sapiens
SEQUENCE: 204
FGQGTTVEIK                                                       10

SEQ ID NO: 205         moltype = AA  length = 23
FEATURE                Location/Qualifiers
source                 1..23
                       mol_type = protein
                       organism = Homo sapiens
SEQUENCE: 205
DIQMTQSPSS LSASVGDRVT ITC                                        23

SEQ ID NO: 206         moltype = AA  length = 15
FEATURE                Location/Qualifiers
source                 1..15
                       mol_type = protein
                       organism = Homo sapiens
SEQUENCE: 206
WYQQKPGKAP KLLIY                                                 15

SEQ ID NO: 207         moltype = AA  length = 32
FEATURE                Location/Qualifiers
source                 1..32
                       mol_type = protein
                       organism = Homo sapiens
SEQUENCE: 207
GVPSRFSGSG SGTDFTLTIS SLQPEDFATY YC                              32

SEQ ID NO: 208         moltype = AA  length = 23
FEATURE                Location/Qualifiers
source                 1..23
                       mol_type = protein
                       organism = Homo sapiens
SEQUENCE: 208
DIQMTQSPSS VSASVGDRVT ITC                                        23

SEQ ID NO: 209         moltype = AA  length = 32
FEATURE                Location/Qualifiers
source                 1..32
                       mol_type = protein
                       organism = Homo sapiens
SEQUENCE: 209
GVPSRFSGSG SGTDFTLTIS SLQPEDFANY YC                              32

SEQ ID NO: 210         moltype = AA  length = 23
FEATURE                Location/Qualifiers
source                 1..23
                       mol_type = protein
                       organism = Homo sapiens
SEQUENCE: 210
DIVMTQSPDS LAVSLGERAT INC                                        23

SEQ ID NO: 211         moltype = AA  length = 15
FEATURE                Location/Qualifiers
source                 1..15
                       mol_type = protein
                       organism = Homo sapiens
SEQUENCE: 211
WYQQKPGQPP KLLIY                                                 15

SEQ ID NO: 212         moltype = AA  length = 32
FEATURE                Location/Qualifiers
source                 1..32
                       mol_type = protein
                       organism = Homo sapiens
SEQUENCE: 212
GVPDRFSGSG SGTDFTLTIS SLQAEDVAVY YC                              32
```

-continued

```
SEQ ID NO: 213            moltype = AA   length = 32
FEATURE                   Location/Qualifiers
source                    1..32
                          mol_type = protein
                          organism = Homo sapiens
SEQUENCE: 213
GVPDRFSGSG AGTDFTLKIS RVEAEDVGVY YC                                         32

SEQ ID NO: 214            moltype = AA   length = 10
FEATURE                   Location/Qualifiers
source                    1..10
                          mol_type = protein
                          organism = Homo sapiens
SEQUENCE: 214
FGPGTKVDIK                                                                  10

SEQ ID NO: 215            moltype = AA   length = 23
FEATURE                   Location/Qualifiers
source                    1..23
                          mol_type = protein
                          organism = Homo sapiens
SEQUENCE: 215
DIVLTQSPDS LAVSLGERAT INC                                                   23

SEQ ID NO: 216            moltype = AA   length = 32
FEATURE                   Location/Qualifiers
source                    1..32
                          mol_type = protein
                          organism = Homo sapiens
SEQUENCE: 216
GVPDRFSGSG SGTDFTLTIS SLQPEDVAVY YC                                         32

SEQ ID NO: 217            moltype = AA   length = 10
FEATURE                   Location/Qualifiers
source                    1..10
                          mol_type = protein
                          organism = Homo sapiens
SEQUENCE: 217
FGQGTRVEIK                                                                  10

SEQ ID NO: 218            moltype = AA   length = 23
FEATURE                   Location/Qualifiers
source                    1..23
                          mol_type = protein
                          organism = Homo sapiens
SEQUENCE: 218
DIQLTQSPSS LSASVGDRVT MSC                                                   23

SEQ ID NO: 219            moltype = AA   length = 32
FEATURE                   Location/Qualifiers
source                    1..32
                          mol_type = protein
                          organism = Homo sapiens
SEQUENCE: 219
GVPSRFSGSG SGTDFTFTIS SLQPEDIATY YC                                         32

SEQ ID NO: 220            moltype = AA   length = 10
FEATURE                   Location/Qualifiers
source                    1..10
                          mol_type = protein
                          organism = Homo sapiens
SEQUENCE: 220
FGGGTKVQIK                                                                  10

SEQ ID NO: 221            moltype = AA   length = 32
FEATURE                   Location/Qualifiers
source                    1..32
                          mol_type = protein
                          organism = Homo sapiens
SEQUENCE: 221
GVPSRFSGSG SGTDFTFTIS SLQPEDIATY FC                                         32

SEQ ID NO: 222            moltype = AA   length = 15
FEATURE                   Location/Qualifiers
source                    1..15
                          mol_type = protein
                          organism = Homo sapiens
SEQUENCE: 222
WYQQKPGKAP KRLIY                                                            15
```

-continued

```
SEQ ID NO: 223              moltype = AA  length = 32
FEATURE                     Location/Qualifiers
source                      1..32
                            mol_type = protein
                            organism = Homo sapiens
SEQUENCE: 223
GVPSRFSGSG SGTEFTLTIS SVQPEDFVTY YC                               32

SEQ ID NO: 224              moltype = AA  length = 23
FEATURE                     Location/Qualifiers
source                      1..23
                            mol_type = protein
                            organism = Homo sapiens
SEQUENCE: 224
DVVMTQSPLS LPVTPGEPAS ISC                                        23

SEQ ID NO: 225              moltype = AA  length = 15
FEATURE                     Location/Qualifiers
source                      1..15
                            mol_type = protein
                            organism = Homo sapiens
SEQUENCE: 225
WYLQKPGQSP QLLIY                                                 15

SEQ ID NO: 226              moltype = AA  length = 32
FEATURE                     Location/Qualifiers
source                      1..32
                            mol_type = protein
                            organism = Homo sapiens
SEQUENCE: 226
GVPDRFSGSG SGTDFTLKIS RVEAEDVGVY YC                              32

SEQ ID NO: 227              moltype = AA  length = 23
FEATURE                     Location/Qualifiers
source                      1..23
                            mol_type = protein
                            organism = Homo sapiens
SEQUENCE: 227
DIVMTQSPLS LPVTPGEPAS ISC                                        23

SEQ ID NO: 228              moltype = AA  length = 32
FEATURE                     Location/Qualifiers
source                      1..32
                            mol_type = protein
                            organism = Homo sapiens
SEQUENCE: 228
GVPDRFSGSG SGTHLTLKIS RVEAEDVGVY YC                              32

SEQ ID NO: 229              moltype = AA  length = 15
FEATURE                     Location/Qualifiers
source                      1..15
                            mol_type = protein
                            organism = Homo sapiens
SEQUENCE: 229
WYQQKPEKAP KSLIY                                                 15

SEQ ID NO: 230              moltype = AA  length = 10
FEATURE                     Location/Qualifiers
source                      1..10
                            mol_type = protein
                            organism = Homo sapiens
SEQUENCE: 230
FGQGTKLEIS                                                       10

SEQ ID NO: 231              moltype = AA  length = 10
FEATURE                     Location/Qualifiers
source                      1..10
                            mol_type = protein
                            organism = Homo sapiens
SEQUENCE: 231
FGQGTKLEIK                                                       10

SEQ ID NO: 232              moltype = AA  length = 15
FEATURE                     Location/Qualifiers
source                      1..15
                            mol_type = protein
                            organism = Homo sapiens
SEQUENCE: 232
```

-continued

```
WFQQKPGQAP RPLIY                                                15

SEQ ID NO: 233          moltype = AA   length = 32
FEATURE                 Location/Qualifiers
source                  1..32
                        mol_type = protein
                        organism = Homo sapiens
SEQUENCE: 233
GVPARFSGSG SGTDFTLTIS SLQSEDFAVY YC                             32

SEQ ID NO: 234          moltype = AA   length = 32
FEATURE                 Location/Qualifiers
source                  1..32
                        mol_type = protein
                        organism = Homo sapiens
SEQUENCE: 234
GIPARVSGSG SGTEFTLTIS SLQSEDFAVY YC                             32

SEQ ID NO: 235          moltype = AA   length = 23
FEATURE                 Location/Qualifiers
source                  1..23
                        mol_type = protein
                        organism = Homo sapiens
SEQUENCE: 235
DVLMTQSPLS LPVTLGQPAS ISC                                       23

SEQ ID NO: 236          moltype = AA   length = 15
FEATURE                 Location/Qualifiers
source                  1..15
                        mol_type = protein
                        organism = Homo sapiens
SEQUENCE: 236
WYLQRPGQSP KLLIY                                                15

SEQ ID NO: 237          moltype = AA   length = 10
FEATURE                 Location/Qualifiers
source                  1..10
                        mol_type = protein
                        organism = Homo sapiens
SEQUENCE: 237
FGAGTKLEIK                                                      10

SEQ ID NO: 238          moltype = AA   length = 23
FEATURE                 Location/Qualifiers
source                  1..23
                        mol_type = protein
                        organism = Homo sapiens
SEQUENCE: 238
EIVLTQSPAT LSLSPGERAT LSC                                       23

SEQ ID NO: 239          moltype = AA   length = 32
FEATURE                 Location/Qualifiers
source                  1..32
                        mol_type = protein
                        organism = Homo sapiens
SEQUENCE: 239
GIPARFSGSG SGTDFTLTIS SLEPEDFAVY YC                             32

SEQ ID NO: 240          moltype = AA   length = 23
FEATURE                 Location/Qualifiers
source                  1..23
                        mol_type = protein
                        organism = Homo sapiens
SEQUENCE: 240
DIVMTQTPLS LSVTPGQPAS ISC                                       23

SEQ ID NO: 241          moltype = AA   length = 15
FEATURE                 Location/Qualifiers
source                  1..15
                        mol_type = protein
                        organism = Homo sapiens
SEQUENCE: 241
WYLQKPGQPP QFLIY                                                15

SEQ ID NO: 242          moltype = AA   length = 32
FEATURE                 Location/Qualifiers
source                  1..32
                        mol_type = protein
                        organism = Homo sapiens
```

-continued

```
SEQUENCE: 242
RVPDRFSGSG SGTDFTLRIS RVEAEDVGIY YC                                 32

SEQ ID NO: 243          moltype = AA  length = 10
FEATURE                 Location/Qualifiers
source                  1..10
                        mol_type = protein
                        organism = Homo sapiens
SEQUENCE: 243
FGQGTQVEIK                                                          10

SEQ ID NO: 244          moltype = AA  length = 32
FEATURE                 Location/Qualifiers
source                  1..32
                        mol_type = protein
                        organism = Homo sapiens
SEQUENCE: 244
GIPDRVSGSG SGTEFTLTIS RLEPEDFAVY YC                                 32

SEQ ID NO: 245          moltype = AA  length = 15
FEATURE                 Location/Qualifiers
source                  1..15
                        mol_type = protein
                        organism = Homo sapiens
SEQUENCE: 245
WYQQKPGTAP KLLIY                                                    15

SEQ ID NO: 246          moltype = AA  length = 23
FEATURE                 Location/Qualifiers
source                  1..23
                        mol_type = protein
                        organism = Homo sapiens
SEQUENCE: 246
DIVMTQTPLS LPVTPGEPAS ISC                                           23

SEQ ID NO: 247          moltype = AA  length = 22
FEATURE                 Location/Qualifiers
source                  1..22
                        mol_type = protein
                        organism = Homo sapiens
SEQUENCE: 247
ESALTQPASV SGSPGQSITI SC                                            22

SEQ ID NO: 248          moltype = AA  length = 15
FEATURE                 Location/Qualifiers
source                  1..15
                        mol_type = protein
                        organism = Homo sapiens
SEQUENCE: 248
WYQQHPGKAP KLMIY                                                    15

SEQ ID NO: 249          moltype = AA  length = 32
FEATURE                 Location/Qualifiers
source                  1..32
                        mol_type = protein
                        organism = Homo sapiens
SEQUENCE: 249
GVSNRFSGSK SGNTASLTIS GLQAEDEADY YC                                 32

SEQ ID NO: 250          moltype = AA  length = 10
FEATURE                 Location/Qualifiers
source                  1..10
                        mol_type = protein
                        organism = Homo sapiens
SEQUENCE: 250
FGGGTKLTVL                                                          10

SEQ ID NO: 251          moltype = AA  length = 22
FEATURE                 Location/Qualifiers
source                  1..22
                        mol_type = protein
                        organism = Homo sapiens
SEQUENCE: 251
SYVLTQPPSV SVAPGQTARI TC                                            22

SEQ ID NO: 252          moltype = AA  length = 15
FEATURE                 Location/Qualifiers
source                  1..15
                        mol_type = protein
```

-continued

```
                                 organism = Homo sapiens
SEQUENCE: 252
WYQQKPGQAP VLVVY                                                        15

SEQ ID NO: 253         moltype = AA   length = 32
FEATURE                Location/Qualifiers
source                 1..32
                       mol_type = protein
                       organism = Homo sapiens
SEQUENCE: 253
WIPERFSGSN SGNTATLTIS RGEAGDEADY YC                                     32

SEQ ID NO: 254         moltype = AA   length = 22
FEATURE                Location/Qualifiers
source                 1..22
                       mol_type = protein
                       organism = Homo sapiens
SEQUENCE: 254
QSVLTQPPSV SAAPGQKVTI SC                                                22

SEQ ID NO: 255         moltype = AA   length = 15
FEATURE                Location/Qualifiers
source                 1..15
                       mol_type = protein
                       organism = Homo sapiens
SEQUENCE: 255
WYQQLPGTAP KLLIY                                                        15

SEQ ID NO: 256         moltype = AA   length = 32
FEATURE                Location/Qualifiers
source                 1..32
                       mol_type = protein
                       organism = Homo sapiens
SEQUENCE: 256
GIPDRFSGSK SGTSTTLGIT GLQTGDEADY YC                                     32

SEQ ID NO: 257         moltype = AA   length = 22
FEATURE                Location/Qualifiers
source                 1..22
                       mol_type = protein
                       organism = Homo sapiens
SEQUENCE: 257
QSVLTQSPSA SGTPGQRVTI SC                                                22

SEQ ID NO: 258         moltype = AA   length = 15
FEATURE                Location/Qualifiers
source                 1..15
                       mol_type = protein
                       organism = Homo sapiens
SEQUENCE: 258
WYQQLPGAAP KLLIL                                                        15

SEQ ID NO: 259         moltype = AA   length = 32
FEATURE                Location/Qualifiers
source                 1..32
                       mol_type = protein
                       organism = Homo sapiens
SEQUENCE: 259
GVPDRFSGSK SGTSASLTIS GLRSEDEADY YC                                     32

SEQ ID NO: 260         moltype = AA   length = 22
FEATURE                Location/Qualifiers
source                 1..22
                       mol_type = protein
                       organism = Homo sapiens
SEQUENCE: 260
SYEVTQAPSV SVSPGQTASI TC                                                22

SEQ ID NO: 261         moltype = AA   length = 15
FEATURE                Location/Qualifiers
source                 1..15
                       mol_type = protein
                       organism = Homo sapiens
SEQUENCE: 261
WYQQKPGQSP VLVIY                                                        15

SEQ ID NO: 262         moltype = AA   length = 32
FEATURE                Location/Qualifiers
source                 1..32
```

-continued

```
                                        mol_type = protein
                                        organism = Homo sapiens
SEQUENCE: 262
GIPERFSGSN SGNTATLTIS GTQAMDEADY YC                                          32

SEQ ID NO: 263          moltype = AA  length = 22
FEATURE                 Location/Qualifiers
source                  1..22
                        mol_type = protein
                        organism = Homo sapiens
SEQUENCE: 263
CYELTQPPSV SVSPGQTATI TC                                                     22

SEQ ID NO: 264          moltype = AA  length = 15
FEATURE                 Location/Qualifiers
source                  1..15
                        mol_type = protein
                        organism = Homo sapiens
SEQUENCE: 264
WYQQRPGQSP VLVIY                                                            15

SEQ ID NO: 265          moltype = AA  length = 32
FEATURE                 Location/Qualifiers
source                  1..32
                        mol_type = protein
                        organism = Homo sapiens
SEQUENCE: 265
GIPERFSGSN SGNTATLTIS GTQAMDEADY FC                                          32

SEQ ID NO: 266          moltype = AA  length = 22
FEATURE                 Location/Qualifiers
source                  1..22
                        mol_type = protein
                        organism = Homo sapiens
SEQUENCE: 266
SSELTQDPTV SVALGQTVKI TC                                                     22

SEQ ID NO: 267          moltype = AA  length = 15
FEATURE                 Location/Qualifiers
source                  1..15
                        mol_type = protein
                        organism = Homo sapiens
SEQUENCE: 267
WYQQKPGQAP VLVFY                                                            15

SEQ ID NO: 268          moltype = AA  length = 32
FEATURE                 Location/Qualifiers
source                  1..32
                        mol_type = protein
                        organism = Homo sapiens
SEQUENCE: 268
GIPDRFSGSS SGNTASLTIT GAQAEDEADY YC                                          32

SEQ ID NO: 269          moltype = AA  length = 10
FEATURE                 Location/Qualifiers
source                  1..10
                        mol_type = protein
                        organism = Homo sapiens
SEQUENCE: 269
LGGGTKLTVL                                                                  10

SEQ ID NO: 270          moltype = AA  length = 22
FEATURE                 Location/Qualifiers
source                  1..22
                        mol_type = protein
                        organism = Homo sapiens
SEQUENCE: 270
NFMLTQPHSV SESPGKTVAI SC                                                     22

SEQ ID NO: 271          moltype = AA  length = 15
FEATURE                 Location/Qualifiers
source                  1..15
                        mol_type = protein
                        organism = Homo sapiens
SEQUENCE: 271
WYQQRPGSSP TTVIF                                                            15

SEQ ID NO: 272          moltype = AA  length = 34
FEATURE                 Location/Qualifiers
```

-continued

```
source                  1..34
                        mol_type = protein
                        organism = Homo sapiens
SEQUENCE: 272
GVPDRFSGSI DSSSNSASLT ISGLKTEDEA DYYC                                34

SEQ ID NO: 273          moltype = AA  length = 30
FEATURE                 Location/Qualifiers
source                  1..30
                        mol_type = protein
                        organism = Homo sapiens
SEQUENCE: 273
QVQLQESGPG LVKPSETLSL TCTVSGGSIS                                     30

SEQ ID NO: 274          moltype = AA  length = 14
FEATURE                 Location/Qualifiers
source                  1..14
                        mol_type = protein
                        organism = Homo sapiens
SEQUENCE: 274
WIRQPPGKGL EWIG                                                      14

SEQ ID NO: 275          moltype = AA  length = 32
FEATURE                 Location/Qualifiers
source                  1..32
                        mol_type = protein
                        organism = Homo sapiens
SEQUENCE: 275
RVTISVDTSK NQFSLKLNSV TAADTAVYYC AR                                  32

SEQ ID NO: 276          moltype = AA  length = 11
FEATURE                 Location/Qualifiers
source                  1..11
                        mol_type = protein
                        organism = Homo sapiens
SEQUENCE: 276
WGQGTLVTVS S                                                         11

SEQ ID NO: 277          moltype = AA  length = 30
FEATURE                 Location/Qualifiers
source                  1..30
                        mol_type = protein
                        organism = Homo sapiens
SEQUENCE: 277
EVQLMQSGAE VKKPGESLKI SCKGSGYSFS                                     30

SEQ ID NO: 278          moltype = AA  length = 14
FEATURE                 Location/Qualifiers
source                  1..14
                        mol_type = protein
                        organism = Homo sapiens
SEQUENCE: 278
WVRQMPGKGL EWMG                                                      14

SEQ ID NO: 279          moltype = AA  length = 32
FEATURE                 Location/Qualifiers
source                  1..32
                        mol_type = protein
                        organism = Homo sapiens
SEQUENCE: 279
QVTISADNSN SATYLQWSSL KASDTAMYFC AR                                  32

SEQ ID NO: 280          moltype = AA  length = 30
FEATURE                 Location/Qualifiers
source                  1..30
                        mol_type = protein
                        organism = Homo sapiens
SEQUENCE: 280
QVTLKESGPV LLKPTETLTL TCTVSGFSLS                                     30

SEQ ID NO: 281          moltype = AA  length = 14
FEATURE                 Location/Qualifiers
source                  1..14
                        mol_type = protein
                        organism = Homo sapiens
SEQUENCE: 281
WIRQPPGKAL EWLA                                                      14

SEQ ID NO: 282          moltype = AA  length = 32
```

-continued

```
FEATURE              Location/Qualifiers
source               1..32
                     mol_type = protein
                     organism = Homo sapiens
SEQUENCE: 282
RLTISKDTSK SQVVLTMTNM DPVDTATYYC AR                         32

SEQ ID NO: 283       moltype = AA  length = 11
FEATURE              Location/Qualifiers
source               1..11
                     mol_type = protein
                     organism = Homo sapiens
SEQUENCE: 283
WGQGTMVTVS S                                                11

SEQ ID NO: 284       moltype = AA  length = 30
FEATURE              Location/Qualifiers
source               1..30
                     mol_type = protein
                     organism = Homo sapiens
SEQUENCE: 284
EVQLVQSGAE VKKPGASVKV SCKASGYTLT                            30

SEQ ID NO: 285       moltype = AA  length = 14
FEATURE              Location/Qualifiers
source               1..14
                     mol_type = protein
                     organism = Homo sapiens
SEQUENCE: 285
WVRQAPGQGL EWMG                                             14

SEQ ID NO: 286       moltype = AA  length = 32
FEATURE              Location/Qualifiers
source               1..32
                     mol_type = protein
                     organism = Homo sapiens
SEQUENCE: 286
RGTMTTDPST STAYMELRSL RSDDTAVYYC AR                         32

SEQ ID NO: 287       moltype = AA  length = 11
FEATURE              Location/Qualifiers
source               1..11
                     mol_type = protein
                     organism = Homo sapiens
SEQUENCE: 287
WGQGTTVTVS S                                                11

SEQ ID NO: 288       moltype = AA  length = 30
FEATURE              Location/Qualifiers
source               1..30
                     mol_type = protein
                     organism = Homo sapiens
SEQUENCE: 288
QMQLVESGGG VVQPGRSLRL SCAASGFTFR                            30

SEQ ID NO: 289       moltype = AA  length = 14
FEATURE              Location/Qualifiers
source               1..14
                     mol_type = protein
                     organism = Homo sapiens
SEQUENCE: 289
WVRQAPGKGL EWVA                                             14

SEQ ID NO: 290       moltype = AA  length = 32
FEATURE              Location/Qualifiers
source               1..32
                     mol_type = protein
                     organism = Homo sapiens
SEQUENCE: 290
RFTITRDNSK NTLNLQMNSL RAEDTAVYYC AR                         32

SEQ ID NO: 291       moltype = AA  length = 30
FEATURE              Location/Qualifiers
source               1..30
                     mol_type = protein
                     organism = Homo sapiens
SEQUENCE: 291
EVQLLESGGG LVQPGGSLRL SCAASGFTFS                            30
```

-continued

```
SEQ ID NO: 292          moltype = AA  length = 14
FEATURE                 Location/Qualifiers
source                  1..14
                        mol_type = protein
                        organism = Homo sapiens
SEQUENCE: 292
WVRQAPGKGL EWVS                                                    14

SEQ ID NO: 293          moltype = AA  length = 32
FEATURE                 Location/Qualifiers
source                  1..32
                        mol_type = protein
                        organism = Homo sapiens
SEQUENCE: 293
RFTISRDNSK NTLYLQMNSL RAEDTAVYYC AK                                32

SEQ ID NO: 294          moltype = AA  length = 30
FEATURE                 Location/Qualifiers
source                  1..30
                        mol_type = protein
                        organism = Homo sapiens
SEQUENCE: 294
EVQLVQSGAE VKKPGSSVKV SCKASGFTFT                                   30

SEQ ID NO: 295          moltype = AA  length = 32
FEATURE                 Location/Qualifiers
source                  1..32
                        mol_type = protein
                        organism = Homo sapiens
SEQUENCE: 295
RVTITADKST STAYMELSSL RSEDTAVYYC AR                                32

SEQ ID NO: 296          moltype = AA  length = 30
FEATURE                 Location/Qualifiers
source                  1..30
                        mol_type = protein
                        organism = Homo sapiens
SEQUENCE: 296
QVQLVQSGAE VKKPGASVKV SCKVSGYTLS                                   30

SEQ ID NO: 297          moltype = AA  length = 14
FEATURE                 Location/Qualifiers
source                  1..14
                        mol_type = protein
                        organism = Homo sapiens
SEQUENCE: 297
WVRQAPGKGL EWMG                                                    14

SEQ ID NO: 298          moltype = AA  length = 32
FEATURE                 Location/Qualifiers
source                  1..32
                        mol_type = protein
                        organism = Homo sapiens
SEQUENCE: 298
RVTMTEDTST DTAYMELSSL KSEDTAVYYC AT                                32

SEQ ID NO: 299          moltype = AA  length = 30
FEATURE                 Location/Qualifiers
source                  1..30
                        mol_type = protein
                        organism = Homo sapiens
SEQUENCE: 299
QVQLVQSGAE VKKPGASVKV SCKASGYTFT                                   30

SEQ ID NO: 300          moltype = AA  length = 30
FEATURE                 Location/Qualifiers
source                  1..30
                        mol_type = protein
                        organism = Homo sapiens
SEQUENCE: 300
QVQLVQSGAE VKKPGASVKV SCKSSGYTFT                                   30

SEQ ID NO: 301          moltype = AA  length = 32
FEATURE                 Location/Qualifiers
source                  1..32
                        mol_type = protein
                        organism = Homo sapiens
SEQUENCE: 301
RVTMTRDTSI STAYMELSRL RSDDTAVYYC AR                                32
```

-continued

```
SEQ ID NO: 302          moltype = AA   length = 30
FEATURE                 Location/Qualifiers
source                  1..30
                        mol_type = protein
                        organism = Homo sapiens
SEQUENCE: 302
QVQLVESGGG VVQPGRSLRL SCAASGFTFS                                    30

SEQ ID NO: 303          moltype = AA   length = 33
FEATURE                 Location/Qualifiers
source                  1..33
                        mol_type = protein
                        organism = Homo sapiens
SEQUENCE: 303
RFTISRDNSK NTLYLQMNSL RAEDTAVYYC ARG                                33

SEQ ID NO: 304          moltype = AA   length = 30
FEATURE                 Location/Qualifiers
source                  1..30
                        mol_type = protein
                        organism = Homo sapiens
SEQUENCE: 304
EVQLVESGGG LVQPGGSLRL SCAASGFTFS                                    30

SEQ ID NO: 305          moltype = AA   length = 32
FEATURE                 Location/Qualifiers
source                  1..32
                        mol_type = protein
                        organism = Homo sapiens
SEQUENCE: 305
RFTISRDNAK NSLYLQMNSL RAEDTAVYYC AR                                 32

SEQ ID NO: 306          moltype = AA   length = 32
FEATURE                 Location/Qualifiers
source                  1..32
                        mol_type = protein
                        organism = Homo sapiens
SEQUENCE: 306
RFTISRDNSK NTLFLQMNSL RAEDTAVYYC AR                                 32

SEQ ID NO: 307          moltype = AA   length = 30
FEATURE                 Location/Qualifiers
source                  1..30
                        mol_type = protein
                        organism = Homo sapiens
SEQUENCE: 307
QVQLVQSGAE VKKPGSSVKV SCKASGYTFT                                    30

SEQ ID NO: 308          moltype = AA   length = 14
FEATURE                 Location/Qualifiers
source                  1..14
                        mol_type = protein
                        organism = Homo sapiens
SEQUENCE: 308
WVRQAPGQGL EWIG                                                     14

SEQ ID NO: 309          moltype = AA   length = 32
FEATURE                 Location/Qualifiers
source                  1..32
                        mol_type = protein
                        organism = Homo sapiens
SEQUENCE: 309
KATITADEST NTAYMELSSL RSEDTAFYFC AR                                 32

SEQ ID NO: 310          moltype = AA   length = 32
FEATURE                 Location/Qualifiers
source                  1..32
                        mol_type = protein
                        organism = Homo sapiens
SEQUENCE: 310
RFTISRDNSK NTLYLQMNRL RAEDTAVYYC AR                                 32

SEQ ID NO: 311          moltype = AA   length = 30
FEATURE                 Location/Qualifiers
source                  1..30
                        mol_type = protein
                        organism = Homo sapiens
SEQUENCE: 311
```

```
QVQLQESGPG LVKPSGTLSL TCAVSGGSIS                             30

SEQ ID NO: 312          moltype = AA  length = 14
FEATURE                 Location/Qualifiers
source                  1..14
                        mol_type = protein
                        organism = Homo sapiens
SEQUENCE: 312
WVRQPPGKGL EWIG                                             14

SEQ ID NO: 313          moltype = AA  length = 32
FEATURE                 Location/Qualifiers
source                  1..32
                        mol_type = protein
                        organism = Homo sapiens
SEQUENCE: 313
RVTISVDKSK NQFSLKLSSV TAADTAVYYC AR                         32

SEQ ID NO: 314          moltype = AA  length = 32
FEATURE                 Location/Qualifiers
source                  1..32
                        mol_type = protein
                        organism = Homo sapiens
SEQUENCE: 314
RFAISRDNAK NSLFLQMNSL RAEDTAVYYC AR                         32

SEQ ID NO: 315          moltype = AA  length = 32
FEATURE                 Location/Qualifiers
source                  1..32
                        mol_type = protein
                        organism = Homo sapiens
SEQUENCE: 315
RFTISRDNAR NSLYLQMNSL RAEDTAVYYC AR                         32

SEQ ID NO: 316          moltype = AA  length = 30
FEATURE                 Location/Qualifiers
source                  1..30
                        mol_type = protein
                        organism = Homo sapiens
SEQUENCE: 316
EVQLVESGGG LVKPGGSLRL SCAASGFTFS                             30

SEQ ID NO: 317          moltype = AA  length = 14
FEATURE                 Location/Qualifiers
source                  1..14
                        mol_type = protein
                        organism = Homo sapiens
SEQUENCE: 317
WVRQAPGKGL EWVG                                             14

SEQ ID NO: 318          moltype = AA  length = 32
FEATURE                 Location/Qualifiers
source                  1..32
                        mol_type = protein
                        organism = Homo sapiens
SEQUENCE: 318
RFTISRDDSK NTLYLQMNSL KAEDTAVYYC TT                         32

SEQ ID NO: 319          moltype = AA  length = 30
FEATURE                 Location/Qualifiers
source                  1..30
                        mol_type = protein
                        organism = Homo sapiens
SEQUENCE: 319
QVQLQESGPG LVKPSQTLSL TCTVSGGSIS                             30

SEQ ID NO: 320          moltype = AA  length = 14
FEATURE                 Location/Qualifiers
source                  1..14
                        mol_type = protein
                        organism = Homo sapiens
SEQUENCE: 320
WIRQLPGKGL EWIG                                             14

SEQ ID NO: 321          moltype = AA  length = 32
FEATURE                 Location/Qualifiers
source                  1..32
                        mol_type = protein
                        organism = Homo sapiens
```

```
SEQUENCE: 321
RVTISVDTSK KQFSLRLSSV TAADTAVYYC AR                                              32

SEQ ID NO: 322           moltype = AA  length = 30
FEATURE                  Location/Qualifiers
source                   1..30
                         mol_type = protein
                         organism = Homo sapiens
SEQUENCE: 322
EVQLVQSGAE VKKPGESLKI SCKVSGYFFT                                                 30

SEQ ID NO: 323           moltype = AA  length = 14
FEATURE                  Location/Qualifiers
source                   1..14
                         mol_type = protein
                         organism = Homo sapiens
SEQUENCE: 323
WVRQMPGKGL EYMG                                                                  14

SEQ ID NO: 324           moltype = AA  length = 32
FEATURE                  Location/Qualifiers
source                   1..32
                         mol_type = protein
                         organism = Homo sapiens
SEQUENCE: 324
QVTISADKSI STAYLQWSSL KASDTAMYYC AR                                              32

SEQ ID NO: 325           moltype = AA  length = 32
FEATURE                  Location/Qualifiers
source                   1..32
                         mol_type = protein
                         organism = Homo sapiens
SEQUENCE: 325
RVTMTTDTST STAYMELRSL RSDDTAVYFC AR                                              32

SEQ ID NO: 326           moltype = AA  length = 30
FEATURE                  Location/Qualifiers
source                   1..30
                         mol_type = protein
                         organism = Homo sapiens
SEQUENCE: 326
EVQLVQSGGG VVQPGRSLRL SCAASGFTFS                                                 30

SEQ ID NO: 327           moltype = AA  length = 30
FEATURE                  Location/Qualifiers
source                   1..30
                         mol_type = protein
                         organism = Homo sapiens
SEQUENCE: 327
EVQLVQSGAE VKKPGASVKV SCKASGYTFT                                                 30

SEQ ID NO: 328           moltype = AA  length = 32
FEATURE                  Location/Qualifiers
source                   1..32
                         mol_type = protein
                         organism = Homo sapiens
SEQUENCE: 328
RVTMTTDTST STAYMELRSL RSDDTAVYYC AR                                              32

SEQ ID NO: 329           moltype = AA  length = 30
FEATURE                  Location/Qualifiers
source                   1..30
                         mol_type = protein
                         organism = Homo sapiens
SEQUENCE: 329
EVQLVQSGAE VKKPGESLKI SCKGSGYNFT                                                 30

SEQ ID NO: 330           moltype = AA  length = 14
FEATURE                  Location/Qualifiers
source                   1..14
                         mol_type = protein
                         organism = Homo sapiens
SEQUENCE: 330
WVRQMPGKGL ELMG                                                                  14

SEQ ID NO: 331           moltype = AA  length = 32
FEATURE                  Location/Qualifiers
source                   1..32
                         mol_type = protein
```

-continued

```
                              organism = Homo sapiens
SEQUENCE: 331
QVTISADKSI STAYLQWSSL KASDTAMYYC GS                                  32

SEQ ID NO: 332        moltype = AA  length = 11
FEATURE               Location/Qualifiers
source                1..11
                      mol_type = protein
                      organism = Homo sapiens
SEQUENCE: 332
WGRGTLVTVS S                                                         11

SEQ ID NO: 333        moltype = AA  length = 30
FEATURE               Location/Qualifiers
source                1..30
                      mol_type = protein
                      organism = Homo sapiens
SEQUENCE: 333
QVTLKESGPA LVKPTQTLTL TCTFSGFSLR                                     30

SEQ ID NO: 334        moltype = AA  length = 32
FEATURE               Location/Qualifiers
source                1..32
                      mol_type = protein
                      organism = Homo sapiens
SEQUENCE: 334
QLTISKDTSK NQVVLTMTNM DPVDTATYYC AR                                  32

SEQ ID NO: 335        moltype = AA  length = 30
FEATURE               Location/Qualifiers
source                1..30
                      mol_type = protein
                      organism = Homo sapiens
SEQUENCE: 335
QVQLQESGPG LVKPSETLSL TCTVSGGSVS                                     30

SEQ ID NO: 336        moltype = AA  length = 14
FEATURE               Location/Qualifiers
source                1..14
                      mol_type = protein
                      organism = Homo sapiens
SEQUENCE: 336
WIRQSPGKGL EWIG                                                      14

SEQ ID NO: 337        moltype = AA  length = 32
FEATURE               Location/Qualifiers
source                1..32
                      mol_type = protein
                      organism = Homo sapiens
SEQUENCE: 337
RLTISIDTSK TQFSLKLSSV TAADTAIYYC VR                                  32

SEQ ID NO: 338        moltype = AA  length = 32
FEATURE               Location/Qualifiers
source                1..32
                      mol_type = protein
                      organism = Homo sapiens
SEQUENCE: 338
RFIISRDKSK NTLYLQMNSL RAEDTAVYYC AR                                  32

SEQ ID NO: 339        moltype = AA  length = 32
FEATURE               Location/Qualifiers
source                1..32
                      mol_type = protein
                      organism = Homo sapiens
SEQUENCE: 339
RVTMTRDTSI STAYMELSRL RSDDTAVYFC AR                                  32

SEQ ID NO: 340        moltype = AA  length = 30
FEATURE               Location/Qualifiers
source                1..30
                      mol_type = protein
                      organism = Homo sapiens
SEQUENCE: 340
EVQLVQSGGG LVQPGGSLRL SCTASGFTFS                                     30

SEQ ID NO: 341        moltype = AA  length = 32
FEATURE               Location/Qualifiers
source                1..32
```

-continued

```
                            mol_type = protein
                            organism = Homo sapiens
SEQUENCE: 341
RFTISRDNAK NTLYLQMNSL RAEDTAVYYC AR                           32

SEQ ID NO: 342         moltype = AA  length = 14
FEATURE                Location/Qualifiers
source                 1..14
                       mol_type = protein
                       organism = Homo sapiens
SEQUENCE: 342
WVRQAPGEGL EWVA                                               14

SEQ ID NO: 343         moltype = AA  length = 30
FEATURE                Location/Qualifiers
source                 1..30
                       mol_type = protein
                       organism = Homo sapiens
SEQUENCE: 343
EVQLVESGGG VVQPGGSLRL SCAASGFTFS                              30

SEQ ID NO: 344         moltype = AA  length = 30
FEATURE                Location/Qualifiers
source                 1..30
                       mol_type = protein
                       organism = Homo sapiens
SEQUENCE: 344
QVQLVQSGAA VKKPGASVKV SCKASGYTFT                              30

SEQ ID NO: 345         moltype = AA  length = 32
FEATURE                Location/Qualifiers
source                 1..32
                       mol_type = protein
                       organism = Homo sapiens
SEQUENCE: 345
RVTMTRDTSI STASMELSRL RSDDTAVYFC AR                           32

SEQ ID NO: 346         moltype = AA  length = 32
FEATURE                Location/Qualifiers
source                 1..32
                       mol_type = protein
                       organism = Homo sapiens
SEQUENCE: 346
RFTISRDNAK NSLYLQMNSL RAEDTAVYYC TE                           32

SEQ ID NO: 347         moltype = AA  length = 30
FEATURE                Location/Qualifiers
source                 1..30
                       mol_type = protein
                       organism = Homo sapiens
SEQUENCE: 347
QVQLVQSGTE VKKPGASMKV SCKASGYTFT                              30

SEQ ID NO: 348         moltype = AA  length = 32
FEATURE                Location/Qualifiers
source                 1..32
                       mol_type = protein
                       organism = Homo sapiens
SEQUENCE: 348
RVTMTRDTST NTVYMELSSL RSEDTAMYYC AR                           32

SEQ ID NO: 349         moltype = AA  length = 32
FEATURE                Location/Qualifiers
source                 1..32
                       mol_type = protein
                       organism = Homo sapiens
SEQUENCE: 349
RFTISRDNAK NSLYLQMNSL RDEDTAVYYC AR                           32

SEQ ID NO: 350         moltype = AA  length = 441
FEATURE                Location/Qualifiers
source                 1..441
                       mol_type = protein
                       organism = Homo sapiens
SEQUENCE: 350
EVQLVQSGAE VKKPGASVKV SCKASGYTLT SYGISWVRQA PGQGLEWMGW VSFYNGNTNY  60
AQKLQGRGTM TTDPSTSTAY MELRSLRSDD TAVYYCARGY GMDVWGQGTT VTVSSASTKG  120
PSVFPLAPCS RSTSESTAAL GCLVKDYFPE PVTVSWNSGA LTSGVHTFPA VLQSSGLYSL  180
SSVVTVPSSN FGTQTYTCNV DHKPSNTKVD KTVERKCCVE CPPCPAPPVA GPSVFLFPPK  240
```

-continued

```
PKDTLMISRT PEVTCVVVDV SHEDPEVQFN WYVDGVEVHN AKTKPREEQF NSTFRVVSVL    300
TVVHQDWLNG KEYKCKVSNK GLPAPIEKTI SKTKGQPREP QVYTLPPSRE EMTKNQVSLT    360
CLVKGFYPSD IAVEWESNGQ PENNYKTTPP MLDSDGSFFL YSKLTVDKSR WQQGNVFSCS    420
VMHEALHNHY TQKSLSLSPG K                                              441

SEQ ID NO: 351            moltype = AA  length = 215
FEATURE                   Location/Qualifiers
source                    1..215
                          mol_type = protein
                          organism = Homo sapiens
SEQUENCE: 351
ESALTQPASV SGSPGQSITI SCTGTSSDVG GYNSVSWYQQ HPGKAPKLMI YEVSNRPSGV     60
SNRFSGSKSG NTASLTISGL QAEDEADYYC NSYTSTSMVF GGGTKLTVLG QPKAAPSVTL    120
FPPSSEELQA NKATLVCLIS DFYPGAVTVA WKADSSPVKA GVETTTPSKQ SNNKYAASSY    180
LSLTPEQWKS HRSYSCQVTH EGSTVEKTVA PTECS                               215

SEQ ID NO: 352            moltype = AA  length = 441
FEATURE                   Location/Qualifiers
source                    1..441
                          mol_type = protein
                          organism = Homo sapiens
SEQUENCE: 352
EVQLVQSGAE VKKPGASVKV SCKASGYTLT SYGISWVRQA PGQGLEWMGW VSFYNGNTNY     60
AQKLQGRGTM TRDPSTSTAY MELSRLRSDD TAVYYCARGY GMDVWGQGTT VTVSSASTKG    120
PSVFPLAPCS RSTSESTAAL GCLVKDYFPE PVTVSWNSGA LTSGVHTFPA VLQSSGLYSL    180
SSVVTVPSSN FGTQTYTCNV DHKPSNTKVD KTVERKCCVE CPPCPAPPVA GPSVFLFPPK    240
PKDTLMISRT PEVTCVVVDV SHEDPEVQFN WYVDGVEVHN AKTKPREEQF NSTFRVVSVL    300
TVVHQDWLNG KEYKCKVSNK GLPAPIEKTI SKTKGQPREP QVYTLPPSRE EMTKNQVSLT    360
CLVKGFYPSD IAVEWESNGQ PENNYKTTPP MLDSDGSFFL YSKLTVDKSR WQQGNVFSCS    420
VMHEALHNHY TQKSLSLSPG K                                              441

SEQ ID NO: 353            moltype = AA  length = 441
FEATURE                   Location/Qualifiers
source                    1..441
                          mol_type = protein
                          organism = Homo sapiens
SEQUENCE: 353
EVQLVQSGAE VKKPGASVKV SCKASGYTLT SYGISWVRQA PGQGLEWMGW VSFYNGNTNY     60
AQKLQGRGTM TTDPSTSTAY MELRSLRSDD TAVYYCARGY GMDVWGQGTT VTVSSASTKG    120
PSVFPLAPCS RSTSESTAAL GCLVKDYFPE PVTVSWNSGA LTSGVHTFPA VLQSSGLYSL    180
SSVVTVPSSN FGTQTYTCNV DHKPSNTKVD KTVERKCCVE CPPCPAPPVA GPSVFLFPPK    240
PKDTLMISRT PEVTCVVVDV SHEDPEVQFN WYVDGVEVHN AKTKPREEQF NSTFRVVSVL    300
TVVHQDWLNG KEYKCKVSNK GLPAPIEKTI SKTKGQPREP QVYTLPPSRE EMTKNQVSLT    360
CLVKGFYPSD IAVEWESNGQ PENNYKTTPP MLDSDGSFFL YSKLTVDKSR WQQGNVFSCS    420
VMHEALHNHY TQKKLSLSPG K                                              441

SEQ ID NO: 354            moltype = AA  length = 441
FEATURE                   Location/Qualifiers
source                    1..441
                          mol_type = protein
                          organism = Homo sapiens
SEQUENCE: 354
EVQLVQSGAE VKKPGASVKV SCKASGYTLT SYGISWVRQA PGQGLEWMGW VSFYNGNTNY     60
AQKLQGRGTM TRDPSTSTAY MELSRLRSDD TAVYYCARGY GMDVWGQGTT VTVSSASTKG    120
PSVFPLAPCS RSTSESTAAL GCLVKDYFPE PVTVSWNSGA LTSGVHTFPA VLQSSGLYSL    180
SSVVTVPSSN FGTQTYTCNV DHKPSNTKVD KTVERKCCVE CPPCPAPPVA GPSVFLFPPK    240
PKDTLMISRT PEVTCVVVDV SHEDPEVQFN WYVDGVEVHN AKTKPREEQF NSTFRVVSVL    300
TVVHQDWLNG KEYKCKVSNK GLPAPIEKTI SKTKGQPREP QVYTLPPSRE EMTKNQVSLT    360
CLVKGFYPSD IAVEWESNGQ PENNYKTTPP MLDSDGSFFL YSKLTVDKSR WQQGNVFSCS    420
VMHEALHNHY TQKKLSLSPG K                                              441

SEQ ID NO: 355            moltype = AA  length = 220
FEATURE                   Location/Qualifiers
source                    1..220
                          mol_type = protein
                          organism = Homo sapiens
SEQUENCE: 355
DIVMTQSPDS LAVSLGERAT INCKSSQSVL DSSDNKNYLA WYQQKPGQPP KLLIYWASNR     60
ESGVPDRFSG SGSGTDFTLT ISSLQAEDVA VYYCQQYYSD PFTFGPGTKV DIKRTVAAPS    120
VFIFPPSDEQ LKSGTASVVC LLNNFYPREA KVQWKVDNAL QSGNSQESVT EQDSKDSTYS    180
LSSTLTLSKA DYEKHKVYAC EVTHQGLSSP VTKSFNRGEC                          220

SEQ ID NO: 356            moltype = AA  length = 446
FEATURE                   Location/Qualifiers
source                    1..446
                          mol_type = protein
                          organism = Homo sapiens
SEQUENCE: 356
QVQLVQSGAE VKKPGASVKV SCKASGYTFT SYGISWVRQA PGQGLEWMGW ISAYNGNTNY     60
```

```
AQKLQGRVTM TTDTSTSTAY MELRSLRSDD TAVYYCARES WFGEVFFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                       446

SEQ ID NO: 357          moltype = AA  length = 446
FEATURE                 Location/Qualifiers
source                  1..446
                        mol_type = protein
                        organism = Homo sapiens
SEQUENCE: 357
QVQLVQSGAE VKKPGASVKV SCKASGYTFT SYGISWVRQA PGQGLEWMGW ISAYNGNTNY  60
AQKLQGRVTM TRDTSTSTAY MELSRLRSDD TAVYYCARES WFGEVFFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                       446

SEQ ID NO: 358          moltype = AA  length = 446
FEATURE                 Location/Qualifiers
source                  1..446
                        mol_type = protein
                        organism = Homo sapiens
SEQUENCE: 358
QVQLVQSGAE VKKPGASVKV SCKASGYTFT SYGISWVRQA PGQGLEWMGW IKAYNGNTNY  60
AQKLQGRVTM TRDTSTSTAY MELSRLRSDD TAVYYCARES WFGEVFFDYW GQGTLVTVSS  120
ASTKGPSVFP LAPCSRSTSE STAALGCLVK DYFPEPVTVS WNSGALTSGV HTFPAVLQSS  180
GLYSLSSVVT VPSSNFGTQT YTCNVDHKPS NTKVDKTVER KCCVECPPCP APPVAGPSVF  240
LFPPKPKDTL MISRTPEVTC VVVDVSHEDP EVQFNWYVDG VEVHNAKTKP REEQFNSTFR  300
VVSVLTVVHQ DWLNGKEYKC KVSNKGLPAP IEKTISKTKG QPREPQVYTL PPSREEMTKN  360
QVSLTCLVKG FYPSDIAVEW ESNGQPENNY KTTPPMLDSD GSFFLYSKLT VDKSRWQQGN  420
VFSCSVMHEA LHNHYTQKSL SLSPGK                                       446

SEQ ID NO: 359          moltype = AA  length = 450
FEATURE                 Location/Qualifiers
source                  1..450
                        mol_type = protein
                        organism = Homo sapiens
SEQUENCE: 359
QVQLVESGGG VVQPGRSLRL SCAASGFTFS NYGMHWVRQA PGEGLEWVAA IWFDASDKYY  60
ADAVKGRFTI SRDNSKNTLY LQMNSLRAED TAVYYCARDQ AIFGVVPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSLT  VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 360          moltype = AA  length = 214
FEATURE                 Location/Qualifiers
source                  1..214
                        mol_type = protein
                        organism = Homo sapiens
SEQUENCE: 360
EIVMTQSPAT LSVSPGERAT LSCRASQSVS SNLAWYQQKP GQAPRLLIYG AATRATGIPA  60
RVSGSGSGTE FTLTISSLQS EDFAVYYCQQ YNNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 361          moltype = AA  length = 450
FEATURE                 Location/Qualifiers
source                  1..450
                        mol_type = protein
                        organism = Homo sapiens
SEQUENCE: 361
EVQLVESGGG VVQPGGSLRL SCAASGFTFS NYGMHWVRQA PGEGLEWVAA IWFDASDKYY  60
ADAVKGRFTI SRDNAKNTLY LQMNSLRAED TAVYYCARDQ AIFGVVPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSLT  VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450
```

```
SEQ ID NO: 362          moltype = AA   length = 450
FEATURE                 Location/Qualifiers
source                  1..450
                        mol_type = protein
                        organism = Homo sapiens
SEQUENCE: 362
QVQLVESGGG VVQPGRSLRL SCAASGFTFS NYGMHWVRQA PGEGLEWVAA IWFDASDKYY   60
ADAVKGRFTI SRDNSKNTLY LQMNSLRAED TAVYYCARDQ AIFGVVPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 363          moltype = AA   length = 214
FEATURE                 Location/Qualifiers
source                  1..214
                        mol_type = protein
                        organism = Homo sapiens
SEQUENCE: 363
EIVMTQSPAT LSVSPGERAT LSCRASQSVS SNLAWYQQKP GQAPRLLIYG AATRATGIPD   60
RVSGSGSGTE FTLTISRLEP EDFAVYYCQQ YNNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 364          moltype = AA   length = 450
FEATURE                 Location/Qualifiers
source                  1..450
                        mol_type = protein
                        organism = Homo sapiens
SEQUENCE: 364
EVQLVESGGG VVQPGGSLRL SCAASGFTFS NYGMHWVRQA PGEGLEWVAA IWFDASDKYY   60
ADAVKGRFTI SRDNAKNTLY LQMNSLRAED TAVYYCARDQ AIFGVVPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 365          moltype = AA   length = 214
FEATURE                 Location/Qualifiers
source                  1..214
                        mol_type = protein
                        organism = Homo sapiens
SEQUENCE: 365
EIVMTQSPAT LSVSPGERAT LSCRASQSVS SNLAWYQQKP GQAPRLLIYG AATRATGIPD   60
RVSGSGSGTE FTLTISRLEP EDFAVYYCQQ YNNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 366          moltype = AA   length = 441
FEATURE                 Location/Qualifiers
source                  1..441
                        mol_type = protein
                        organism = Homo sapiens
SEQUENCE: 366
EVQLVQSGAE VKKPGASVKV SCKASGYTLT SYGISWVRQA PGQGLEWMGW VSFYNGNTNY   60
AQKLQGRGTM TTDPSTSTAY MELRSLRSDD TAVYYCARGY GMDVWGQGTT VTVSSASTKG  120
PSVFPLAPCS RSTSESTAAL GCLVKDYFPE PVTVSWNSGA LTSGVHTFPA VLQSSGLYSL  180
SSVVTVPSSN FGTQTYTCNV DHKPSNTKVD KTVERKCCVE CPPCPAPPVA GPSVFLFPPK  240
PKDTLMISRT PEVTCVVVDV SHEDPEVQFN WYVDGVEVHN AKTKPREEQF NSTFRVVSVL  300
TVVHQDWLNG KEYKCKVSNK GLPAPIEKTI SKTKGQPREP QVYTLPPSRE EMTKNQVSLT  360
CLVKGFYPSD IAVEWESNGQ PENNYKTTPP MLDSDGSFFL YSKLTVDKSR WQQGNVFSCS  420
VMHEALHNHY TQKKLSLSPG K                                            441

SEQ ID NO: 367          moltype = AA   length = 214
FEATURE                 Location/Qualifiers
source                  1..214
                        mol_type = protein
                        organism = Homo sapiens
SEQUENCE: 367
EIVMTQSPAT LSVSPGERAT LSCRASQSVS SNLAWYQQKP GQAPRLLIYG AATRATGIPA   60
RVSGSGSGTE FTLTISSLQS EDFAVYYCQQ YNNWPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 368          moltype = AA   length = 450
```

-continued

```
FEATURE              Location/Qualifiers
source               1..450
                     mol_type = protein
                     organism = Homo sapiens
SEQUENCE: 368
QVQLVESGGG VVQPGRSLRL SCAASGFTFS NYGMHWVRQA PGEGLEWVAA IWFDASDKYY  60
ADAVKGRFTI SRDNSKNTLY LQMNSLRAED TAVYYCARDQ AIFGVVPDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPCEEQYG  300
STYRCVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKKLSLSPGK                                   450

SEQ ID NO: 369          moltype = AA  length = 692
FEATURE              Location/Qualifiers
source               1..692
                     mol_type = protein
                     organism = Homo sapiens
SEQUENCE: 369
MGTVSSRRSW WPLPLLLLLL LLLGPAGARA QEDEDGDYEE LVLALRSEED GLAEAPEHGT  60
TATFHRCAKD PWRLPGTYVV VLKEETHLSQ SERTARRLQA QAARRGYLTK ILHVFHGLLP  120
GFLVKMSGDL LELALKLPHV DYIEEDSSVF AQSIPWNLER ITPPRYRADE YQPPDGGSLV  180
EVYLLDTSIQ SDHREIEGRV MVTDFENVPE EDGTRFHRQA SKCDSHGTHL AGVVSGRDAG  240
VAKGASMRSL RVLNCQGKGT VSGTLIGLEF IRKSQLVQPV GPLVVLLPLA GGYSRVLNAA  300
CQRLARAGVV LVTAAGNFRD DACLYSPASA PEVITVGATN AQDQPVTLGT LGTNFGRCVD  360
LFAPGEDIIG ASSDCSTCFV SQSGTSQAAA HVAGIAAMML SAEPELTLAE LRQRLIHFSA  420
KDVINEAWFP EDQRVLTPNL VAALPPSTHG AGWQLFCRTV WSAHSGPTRM ATAIARCAPD  480
EELLSCSSFS RSGKRRGERM EAQGGKLVCR AHNAFGGEGV YAIARCCLLP QANCSVHTAP  540
PAEASMGTRV HCHQQGHVLT GCSSHWEVED LGTHKPPVLR PRGQPNQCVG HREASIHASC  600
CHAPGLECKV KEHGIPAPQG QVTVACEEGW TLTGCSALPG TSHVLGAYAV DNTCVVRSRD  660
VSTTGSTSEE AVTAVAICCR SRHLAQASQE LQ                                692

SEQ ID NO: 370          moltype = AA  length = 14
FEATURE              Location/Qualifiers
source               1..14
                     mol_type = protein
                     organism = Homo sapiens
SEQUENCE: 370
TGTSSDVGGY NSVS                                                    14

SEQ ID NO: 371          moltype = AA  length = 7
FEATURE              Location/Qualifiers
source               1..7
                     mol_type = protein
                     organism = Homo sapiens
SEQUENCE: 371
EVSNRPS                                                            7

SEQ ID NO: 372          moltype = AA  length = 9
FEATURE              Location/Qualifiers
source               1..9
                     mol_type = protein
                     organism = Homo sapiens
SEQUENCE: 372
NSYTSTSMV                                                          9

SEQ ID NO: 373          moltype = AA  length = 10
FEATURE              Location/Qualifiers
source               1..10
                     mol_type = protein
                     organism = Homo sapiens
SEQUENCE: 373
GYTLTSYGIS                                                         10

SEQ ID NO: 374          moltype = AA  length = 16
FEATURE              Location/Qualifiers
source               1..16
                     mol_type = protein
                     organism = Homo sapiens
SEQUENCE: 374
WVSFYNGNTN YAQKLQ                                                  16
```

-continued

```
SEQ ID NO: 375              moltype = AA   length = 6
FEATURE                     Location/Qualifiers
source                      1..6
                            mol_type = protein
                            organism = Homo sapiens
SEQUENCE: 375
GYGMDV                                                            6

SEQ ID NO: 376              moltype = AA   length = 115
FEATURE                     Location/Qualifiers
source                      1..115
                            mol_type = protein
                            organism = Homo sapiens
SEQUENCE: 376
QVQLVQSGAE VKKPGASVKV SCKASGYTLT SYGISWVRQA PGQGLEWMGW VSFYNGNTNY   60
AQKLQGRGTM TTDPSTSTAY MELRSLRSDD TAVYYCARGY GMDVWGQGTT VTVSS        115

SEQ ID NO: 377              moltype = AA   length = 109
FEATURE                     Location/Qualifiers
source                      1..109
                            mol_type = protein
                            organism = Homo sapiens
SEQUENCE: 377
QSALTQPASV SGSPGQSITI SCTGTSSDVG GYNSVSWYQQ HPGKAPKLMI YEVSNRPSGV   60
SNRFSGSKSG NTASLTISGL QAEDEADYYC NSYTSTSMVF GGGTKLTVL              109

SEQ ID NO: 378              moltype = AA   length = 115
FEATURE                     Location/Qualifiers
source                      1..115
                            mol_type = protein
                            organism = Homo sapiens
SEQUENCE: 378
QVQLVQSGAE VKKPGASVKV SCKASGYTLT SYGISWVRQA PGQGLEWMGW VSFYNGNTNY   60
AQKLQGRGTM TTDPSTSTAY MELRSLRSDD TAVYYCARGY GMDVWGQGTT VTVSS        115

SEQ ID NO: 379              moltype = AA   length = 109
FEATURE                     Location/Qualifiers
source                      1..109
                            mol_type = protein
                            organism = Homo sapiens
SEQUENCE: 379
QSALTQPASV SGSPGQSITI SCTGTSSDVG GYNSVSWYQQ HPGKAPKLMI YEVSNRPSGV   60
SNRFSGSKSG NTASLTISGL QAEDEADYYC NSYTSTSMVF GGGTKLTVL              109

SEQ ID NO: 380              moltype = AA   length = 4
FEATURE                     Location/Qualifiers
source                      1..4
                            mol_type = protein
                            organism = Homo sapiens
SEQUENCE: 380
KKKP                                                              4

SEQ ID NO: 381              moltype = AA   length = 4
FEATURE                     Location/Qualifiers
source                      1..4
                            mol_type = protein
                            organism = Homo sapiens
SEQUENCE: 381
PGKP                                                              4

SEQ ID NO: 382              moltype = AA   length = 5
FEATURE                     Location/Qualifiers
source                      1..5
                            mol_type = protein
                            organism = Homo sapiens
SEQUENCE: 382
PGKKP                                                             5

SEQ ID NO: 383              moltype = AA   length = 6
FEATURE                     Location/Qualifiers
source                      1..6
                            mol_type = protein
                            organism = Homo sapiens
SEQUENCE: 383
PGKKKP                                                            6
```

What is claimed is:

1. A method of reducing the viscosity of an antibody of the VH3I3-33 germline subfamily, which comprises making viscosity- reducing substitutions 1X$^4$, 17X$^5$, and 85X$^6$ in the VH3 amino acid sequence of the antibody wherein X$^4$ is selected from D and E, X$^5$ is selected from G, A, V, I, L, and M, and W, and X$^6$ is selected from G, A, V, I, L, and M; and
wherein the amino acids are numbered according to the Aho numbering system.

2. The method of claim 1, wherein the viscosity-reducing substitutions comprise 1E, 17G, and 85A.

3. The method of claim 1, wherein the antibody comprises a heavy chain amino acid sequence comprising SEQ ID NO: 160, except for substitutions 1E, 17G, and 85A, and a light chain amino acid sequence comprising SEQ ID NO: 158.

4. The method of claim 1, wherein the antibody comprises a heavy chain amino acid sequence comprising SEQ ID NO: 144, except for substitutions 1E, 17G, and 85A, and a light chain amino acid sequence comprising SEQ ID NO: 142.

5. The method of claim 1, wherein the antibody comprises a heavy chain amino acid sequence comprising SEQ ID NO: 128, except for substitutions 1E, 17G, and 85A, and a light chain amino acid sequence comprising SEQ ID NO: 126.

6. The method of claim 1, wherein the antibody comprises a heavy chain amino acid sequence comprising SEQ ID NO: 120, except for substitutions 1E, 17G, and 85A, and a light chain amino acid sequence comprising SEQ ID NO: 118.

7. An antibody of the VH3I3-33 germline subfamily, which comprises
a VH3 sequence comprising viscosity- reducing substitutions 1X$^4$, 17X$^5$, and 85X$^6$, wherein X$^4$ is selected from D and E, X$^5$ is selected from G, A, V, I, L, and M, and X$^6$ is selected from G, A, V, I, L, and M;
wherein the amino acids in subparagraphs a, b, and e are numbered according to the Aho numbering system.

8. The antibody of claim 7, wherein the viscosity-reducing substitutions comprise 1E, 17G, and 85A.

9. The antibody of claim 7, comprising a heavy chain amino acid sequence comprising SEQ ID NO: 160, except for substitutions 1E, 17G, and 85A, and a light chain amino acid sequence comprising SEQ ID NO: 158.

10. The antibody of claim 7, comprising a heavy chain amino acid sequence comprising SEQ ID NO: 144, except for substitutions 1E, 17G, and 85A, and a light chain amino acid sequence comprising SEQ ID NO: 142.

11. The antibody of claim 7, comprising a heavy chain amino acid sequence comprising SEQ ID NO: 128, except for substitutions 1E, 17G, and 85A, and a light chain amino acid sequence comprising SEQ ID NO: 126.

12. The antibody of claim 7, comprising a heavy chain amino acid sequence comprising SEQ ID NO: 120, except for substitutions 1E, 17G, and 85A, and a light chain amino acid sequence comprising SEQ ID NO: 118.

* * * * *